US007887661B2

(12) United States Patent
Chiu et al.

(10) Patent No.: US 7,887,661 B2
(45) Date of Patent: Feb. 15, 2011

(54) INFUSION TREATMENT AGENTS, CATHETERS, FILTER DEVICES, AND OCCLUSION DEVICES, AND USE THEREOF

(75) Inventors: Jessica G. Chiu, Belmont, CA (US); Gregory Waimong Chan, Mountain View, CA (US); Gabriel Asongwe, San Jose, CA (US); Robert C. Esselstein, Fallbrook, CA (US); Douglas Gesswein, Temecula, CA (US); Srinivasan Sridharan, Morgan Hill, CA (US); Nianjiong Joan Bei, Foster City, CA (US); William E. Webler, Escondido, CA (US); Stephen G. Schaible, Anaheim, CA (US); Mina Chow, Campbell, CA (US); Yan Shen, Sunnyvale, CA (US); Hongzhi Bai, Menlo Park, CA (US); Mark J. Bly, Saint Paul, MN (US); Thomas R. Hatten, Los Altos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 695 days.

(21) Appl. No.: 11/923,258

(22) Filed: Oct. 24, 2007

(65) Prior Publication Data

US 2008/0041516 A1 Feb. 21, 2008

Related U.S. Application Data

(60) Division of application No. 10/800,323, filed on Mar. 11, 2004, now abandoned, and a continuation-in-part of application No. 10/387,048, filed on Mar. 12, 2003, now Pat. No. 7,250,041.

(60) Provisional application No. 60/467,402, filed on May 1, 2003.

(51) Int. Cl.
*B32B 37/00* (2006.01)

(52) U.S. Cl. ............... 156/194; 156/173; 156/175; 156/191; 156/187; 156/308.2; 604/96.01

(58) Field of Classification Search .............. 156/173, 156/175, 187, 194, 191, 308.2, 309.6; 604/96.01
See application file for complete search history.

(56) References Cited

U.S. PATENT DOCUMENTS 4,171,698 A  10/1979  Genese (Continued)

FOREIGN PATENT DOCUMENTS

| CH | 671883 | 10/1989 |
| DE | 195 26 784 | 1/1997 |
| EP | 0 841 073 | 5/1998 |

(Continued)

OTHER PUBLICATIONS

Al-Khadra, A., et al., "The Role of Electroporation in Defibrillation", Circulation Research, vol. 87, American Heart Association, Inc. (Oct. 27, 2000) pp. 797-804.

(Continued)

*Primary Examiner*—Jeff H Aftergut
(74) *Attorney, Agent, or Firm*—Blakely Sokoloff Taylor & Zafman LLP

(57) ABSTRACT

Embodiments include an infusion-occlusion system having a delivery catheter, a guide catheter adapted to receive the delivery catheter, and a guidewire with an occlusion device adapted to be received within the guide catheter. The guide catheter of the catheter kit may be provided with an occlusion device at the distal end of the guide catheter. The delivery catheter may have an accessory lumen, coaxial or co-linear lumen, a supporting mandrel, or an occlusion device at its distal end. Moreover, according to some embodiments, occlusion devices may be a single material or a composite balloon having an inner liner and an outer layer of different materials, a high compliance low pressure balloon, or a filter device that restricts particles from passing through but does not restrict fluid, such as blood. An inflation device with a large volume and low volume syringe can be used to inflate the balloon.

9 Claims, 60 Drawing Sheets

U.S. PATENT DOCUMENTS

| | | |
|---|---|---|
| 4,313,440 A | 2/1982 | Ashley |
| 4,424,057 A | 1/1984 | House |
| 4,459,977 A | 7/1984 | Pizon et al. |
| 4,465,476 A | 8/1984 | Gahwiler |
| 4,516,969 A | 5/1985 | Kintner |
| 4,581,016 A | 4/1986 | Gettig |
| 4,636,195 A | 1/1987 | Wolinsky |
| 4,642,102 A | 2/1987 | Ohmori |
| 4,685,910 A | 8/1987 | Schwieizer |
| 4,689,041 A | 8/1987 | Corday et al. |
| 4,693,706 A | 9/1987 | Ennis, III |
| 4,702,737 A | 10/1987 | Pizzino |
| 4,772,273 A | 9/1988 | Alchas |
| 4,850,969 A | 7/1989 | Jackson |
| 4,927,412 A | 5/1990 | Menasche |
| 5,021,045 A | 6/1991 | Buckberg et al. |
| 5,024,668 A | 6/1991 | Peters et al. |
| 5,032,117 A | 7/1991 | Motta |
| 5,033,998 A | 7/1991 | Corday et al. |
| 5,053,008 A | 10/1991 | Bajaj |
| 5,059,178 A | 10/1991 | Ya |
| 5,092,841 A | 3/1992 | Spears |
| 5,147,377 A | 9/1992 | Sahota |
| 5,181,909 A | 1/1993 | McFarlane |
| 5,226,427 A | 7/1993 | Buckberg et al. |
| 5,265,622 A | 11/1993 | Barbere |
| 5,324,266 A | 6/1994 | Ambrisco et al. |
| 5,328,471 A | 7/1994 | Slepian |
| 5,370,617 A | 12/1994 | Sahota |
| 5,374,250 A | 12/1994 | Dixon |
| 5,385,548 A | 1/1995 | Williams et al. |
| 5,395,331 A | 3/1995 | O'Neill et al. |
| 5,423,744 A | 6/1995 | Gencheff et al. |
| 5,433,735 A | 7/1995 | Zanakis et al. |
| 5,460,611 A | 10/1995 | Alexander |
| 5,464,395 A | 11/1995 | Faxon et al. |
| 5,533,957 A | 7/1996 | Aldea |
| 5,575,773 A | 11/1996 | Song et al. |
| 5,597,377 A | 1/1997 | Aldea |
| 5,620,418 A | 4/1997 | O'Neill et al. |
| 5,662,607 A | 9/1997 | Booth et al. |
| 5,662,609 A | 9/1997 | Slepian |
| 5,674,195 A | 10/1997 | Truthan |
| 5,674,287 A | 10/1997 | Slepian et al. |
| 5,702,368 A | 12/1997 | Stevens et al. |
| 5,707,358 A | 1/1998 | Wright |
| 5,720,726 A | 2/1998 | Marcadis et al. |
| 5,720,727 A | 2/1998 | Alexander et al. |
| 5,749,922 A | 5/1998 | Slepian et al. |
| 5,762,633 A | 6/1998 | Whisson |
| 5,769,812 A | 6/1998 | Stevens et al. |
| 5,779,685 A | 7/1998 | Thompson et al. |
| 5,785,662 A | 7/1998 | Alexander |
| 5,795,325 A | 8/1998 | Valley et al. |
| 5,800,538 A | 9/1998 | Slepian et al. |
| 5,807,326 A | 9/1998 | O'Neill et al. |
| 5,814,016 A | 9/1998 | Valley et al. |
| 5,814,022 A | 9/1998 | Antanavich et al. |
| 5,814,064 A | 9/1998 | Daniel et al. |
| 5,814,097 A | 9/1998 | Sterman et al. |
| 5,833,659 A | 11/1998 | Kranys |
| 5,846,228 A | 12/1998 | Alexander |
| 5,858,990 A | 1/1999 | Walsh |
| 5,865,801 A | 2/1999 | Houser |
| 5,879,336 A | 3/1999 | Brinon |
| 5,879,499 A | 3/1999 | Corvi |
| 5,895,399 A | 4/1999 | Barbut et al. |
| 5,913,842 A | 6/1999 | Boyd et al. |
| 5,916,193 A | 6/1999 | Stevens et al. |
| 5,944,710 A | 8/1999 | Dev et al. |
| 5,947,977 A | 9/1999 | Slepian et al. |
| 5,964,735 A | 10/1999 | Alexander |
| 5,967,988 A | 10/1999 | Briscoe et al. |
| 5,968,013 A | 10/1999 | Smith et al. |
| 5,989,237 A | 11/1999 | Fowles et al. |
| 5,993,418 A | 11/1999 | Alexander |
| 6,007,476 A | 12/1999 | Wascher et al. |
| 6,010,531 A | 1/2000 | Donlon et al. |
| 6,015,402 A | 1/2000 | Sahota |
| 6,019,750 A | 2/2000 | Fowles et al. |
| 6,022,339 A | 2/2000 | Fowles et al. |
| 6,024,739 A | 2/2000 | Ponzi et al. |
| 6,027,476 A | 2/2000 | Sterman et al. |
| 6,043,273 A | 3/2000 | Duhaylongsod |
| 6,045,531 A | 4/2000 | Davis |
| 6,063,068 A | 5/2000 | Fowles et al. |
| 6,071,270 A | 6/2000 | Fowles et al. |
| 6,071,271 A | 6/2000 | Baker et al. |
| 6,083,215 A | 7/2000 | Milavetz |
| 6,087,394 A | 7/2000 | Duhaylongsod |
| 6,090,091 A | 7/2000 | Fowles et al. |
| 6,090,092 A | 7/2000 | Fowles et al. |
| 6,090,096 A | 7/2000 | St. Goar et al. |
| 6,101,412 A | 8/2000 | Duhaylongsod |
| 6,113,583 A | 9/2000 | Fowles et al. |
| 6,123,084 A | 9/2000 | Jandak et al. |
| 6,127,410 A | 10/2000 | Duhaylongsod |
| 6,141,589 A | 10/2000 | Duhaylongsod |
| 6,159,192 A | 12/2000 | Fowles et al. |
| 6,161,731 A | 12/2000 | Sigg |
| 6,186,972 B1 | 2/2001 | Nelson et al. |
| 6,234,996 B1 | 5/2001 | Bagaoisan et al. |
| 6,241,699 B1 | 6/2001 | Suresh et al. |
| 6,283,127 B1 | 9/2001 | Sterman et al. |
| 6,287,320 B1 | 9/2001 | Slepian |
| 6,287,430 B1 | 9/2001 | Matsumoto et al. |
| 6,340,356 B1 | 1/2002 | Navia et al. |
| 6,346,098 B1 | 2/2002 | Yock et al. |
| 6,361,545 B1 | 3/2002 | Macoviak et al. |
| 6,414,018 B1 | 7/2002 | Duhaylongsod |
| 6,423,031 B1 | 7/2002 | Donlon |
| 6,443,926 B1 | 9/2002 | Kletschka |
| 6,443,941 B1 | 9/2002 | Slepian et al. |
| 6,458,096 B1 | 10/2002 | Briscoe et al. |
| 6,458,323 B1 | 10/2002 | Boekstegers |
| 6,482,171 B1 | 11/2002 | Corvi et al. |
| 6,485,500 B1 | 11/2002 | Kokish et al. |
| 6,500,145 B1 | 12/2002 | Bicakci et al. |
| 6,534,641 B2 | 3/2003 | Falb et al. |
| 6,569,145 B1 | 5/2003 | Shmulewitz et al. |
| 6,575,932 B1 | 6/2003 | O'Brien et al. |
| 6,582,415 B1 | 6/2003 | Fowles et al. |
| 6,610,040 B1 | 8/2003 | Fowles et al. |
| 6,626,862 B1 | 9/2003 | Duchon et al. |
| 6,641,562 B1 | 11/2003 | Peterson |
| 6,685,672 B1 | 2/2004 | Forman |
| 6,695,810 B2 | 2/2004 | Peacock et al. |
| 6,805,860 B1 | 10/2004 | Alt |
| 7,195,638 B1 * | 3/2007 | Sridharan ............... 606/194 |
| 2001/0025187 A1 | 9/2001 | Okada |
| 2001/0031986 A1 | 10/2001 | Hauck |
| 2001/0041864 A1 | 11/2001 | Sweezer |
| 2001/0044624 A1 | 11/2001 | Seraj et al. |
| 2002/0010492 A1 | 1/2002 | Donovan et al. |
| 2002/0022863 A1 | 2/2002 | Hauck |
| 2002/0026228 A1 | 2/2002 | Schauerte |
| 2002/0049402 A1 | 4/2002 | Peacock et al. |
| 2003/0187411 A1 | 10/2003 | Constantz |

FOREIGN PATENT DOCUMENTS

| | | |
|---|---|---|
| EP | 1 118 348 | 7/2001 |
| EP | 1 208 867 | 5/2002 |
| WO | WO-95/16476 | 6/1995 |

| | | |
|---|---|---|
| WO | WO-96/30073 | 10/1996 |
| WO | WO-96/40346 | 12/1996 |
| WO | WO-98/38930 | 9/1998 |
| WO | WO-99/04836 | 2/1999 |
| WO | WO-00/10631 | 3/2000 |
| WO | WO-01/00268 | 1/2001 |
| WO | WO-01/10313 | 2/2001 |
| WO | WO-01/13983 | 3/2001 |
| WO | WO-02/05887 | 1/2002 |

OTHER PUBLICATIONS

Angelos, M. G., et al., "Left Ventricular Myocardial Adenosine Triphosphate Changes During Reperfusion of Ventricular Fibrillation: The Influence of Flow and Epinephrine", Critical Care Medicine, vol. 28, No. 5 (May 2000), 12 pages.

Boekstegers, P., et al., "Myocardial gene transfer by selective pressure-regulated retroinfusion of coronary veins", Circulation, Abstract (Jun. 6, 2000) 1 page.

Boekstegers, P., et al., "Selective suction and pressure-regulated retroinfusion: an effective and safe approach to retrograde protection against myocardial ischemia in patients undergoing normal and high risk percutaneous transluminal coronary angioplasty", J. Am. Coll. Cardiol., Abstract (Jun. 31, 1998) 2 pages.

Braunwald, E., et al., Heart Disease—A Textbook of Cardiovascular Medicine, 6th Edition (2001).

Gerber, T. C., et al., "The Coronary Venous System: An Alternate Portal to the Myocardium for Diagnostic and Therapeutic Procedures in Invasive Cardiology", Current Interventional Cardiology Reports, vol. 2 (2000) pp. 27-37.

Kanno, S., et al., "Establishment of a Simple and Practical Procedure Applicable to Therapeutic Angiogenesis", Circulation, vol. 99, American Heart Association, Inc. (May 25, 1999) pp. 2682-2687.

Labhasetwar, V., et al., "Iontophoresis for modulation of cardiac drug delivery in dogs", Proc. Natl. Acad. Sci. USA, Medical Sciences, vol. 92 (Mar. 1995) pp. 2612-2626.

Lebherz, C., et al., "Therapeutic Angiogenesis/Arteriogenesis in the Chronic Ischemic Rabbit Hindlimb: Effect of Venous Basic Fibroblast Growth Factor Retroinfusion", Endothelium, Abstract, vol. 10, No. 4-5 (Jul.-Oct. 2003) 2 pages.

Novalija, E., et al., "Sevoflurane Mimics Ischemic Preconditioning Effects on Coronary Flow and Nitric Oxide Release in Isolated Hearts", Anesthesiology, vol. 91, No. 3 (Sep. 1, 1999) pp. 701-712.

PCT Search report dated Oct. 29, 2004 of PCT/US2004/007735, filed Mar. 12, 2004.

Raake, P., et al., "Myocardial Gene Transfer by Selective Pressure-Regulated Retroinfusion of Coronary Veins", Journal of the American College of Cardiology, vol. 44, No. 5 (2004) pp. 1124-1129.

Raake, P., et al., "Percutaneous approach to a stent-based ventricle to coronary vein bypass (venous VPASS™): comparison to catheter-based selective pressure-regulated retro-infusion of the coronary vein", European Heart Journal, The European Society of Cardiology (Feb. 25, 2005) 10 pages.

Verma, S., et al., "Fundamentals of Reperfusion Injury for the Clinical Cardiologist", Circulation, vol. 105 (2002) pp. 2332-2336.

Von Degenfeld, G., et al., "Selective Pressure-Regulated Retroinfusion of Fibroblast Growth Factor-2 Into the Coronary Vein Enhances Regional Myocardial Blood Flow and Function in Pigs with Chronic Myocardial Ischemia", Journal of the American College of Cardiology, vol. 42, No. 6 (2003) pp. 1120-1128.

Yost, C. S., et al., "Anesthetic Considerations for Minimally Invasive Cardiovascular Procedures", Anesthesiology Clinics of North America, vol. 17, No. 2 (Jun. 1999), 16 pages.

Abbott Cardiovascular Systems, Non final office action dated Dec. 30, 2009 for U.S. Appl. No. 11/923,332.

Abbott Cardiovascular Systems, Final office action dated Jan. 20, 2010 for U.S. Appl. No. 10/800,323.

Abbott Cardiovascular Systems, Non-final office action dated Oct. 2, 2009 for U.S. Appl. No. 11/923,411.

Abbott Cardiovascular Systems, Non Final Office Action mailed Jul. 25, 2007; U.S. Appl. No. 10/800,323.

Abbott Cardiovascular Systems, Final Office Action mailed Jan. 10, 2008; U.S. Appl. No. 10/800,323.

Abbott Cardiovascular Systems, Non Final office Action mailed Mar. 31, 2008; U.S. Appl. No. 10/800,323.

Abbott Cardiovascular Systems, Final office Action mailed Oct. 14, 2008; U.S. Appl. No. 10/800,323.

Abbott Cardiovascular Systems, Non-final office action dated Feb. 5, 2009 for U.S. Appl. No. 10/800,323.

Abbott Cardiovascular Systems, Non-final office action dated Aug. 4, 2009 for U.S. Appl. No. 10/800,323.

Giuseppe, A., et al., "New insights into pathophysiology of AMI", American Heart Journal, vol. 138, No. 2, Abstract, (Aug. 1999), 10 pages.

Mathur, S., et al., "Cardioprotective effects of propofol and sevoflurane in ischemic and reperfused rat hearts: role of K(ATP) channels and interaction with the sodium-hydrogen exchange inhibitor HOE 642 (cariporide)", Anethesiology, 91(5); Abstract, (Nov. 1, 1999), 1349-60.

McPherson, BC, et al., "Signal transduction of opioid-induced cardioprotection in ischemia-reperfusion", Anethesiology, 94(6), (Jun. 1, 2001), 1082-8.

* cited by examiner

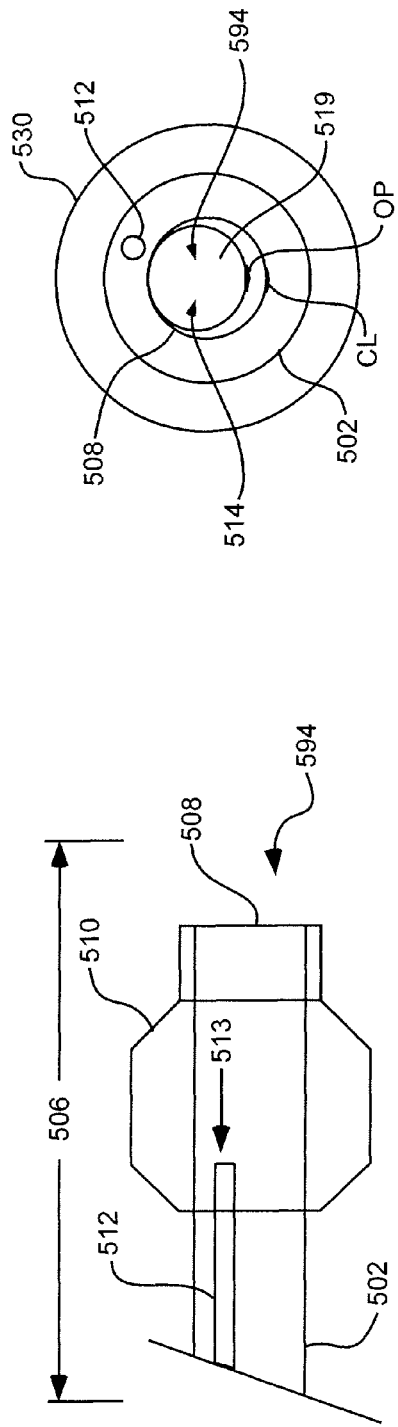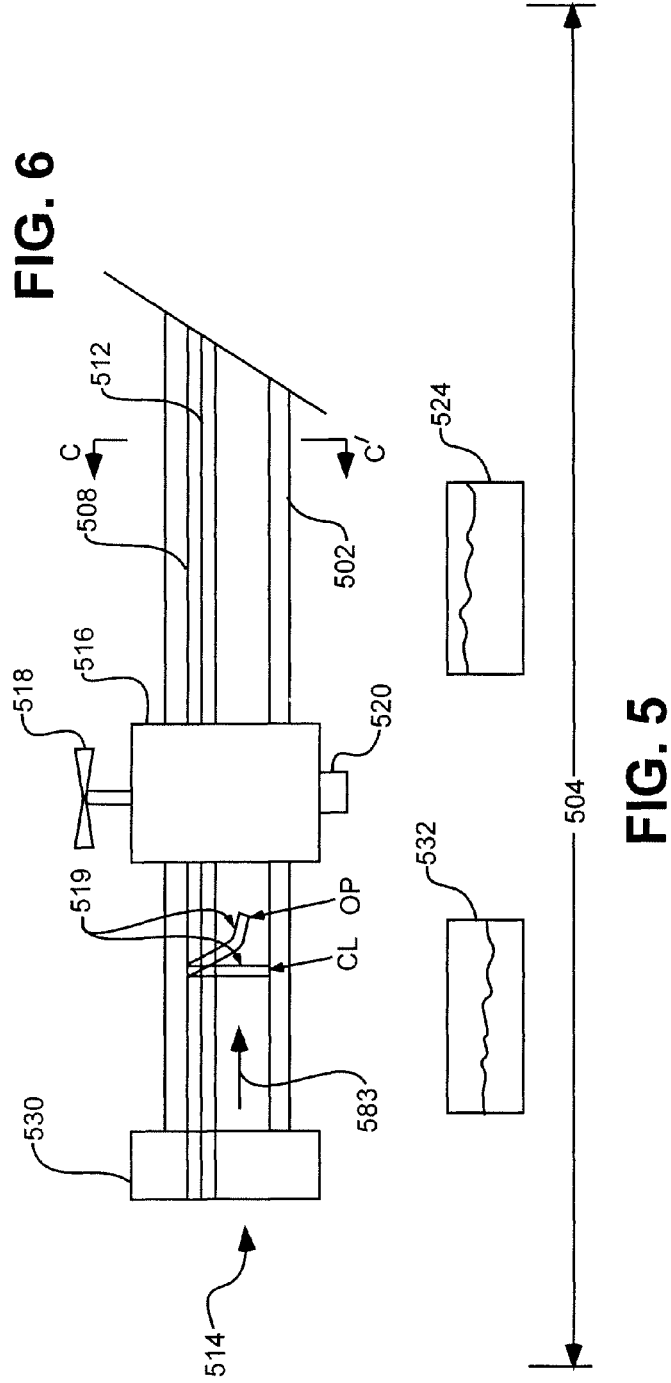

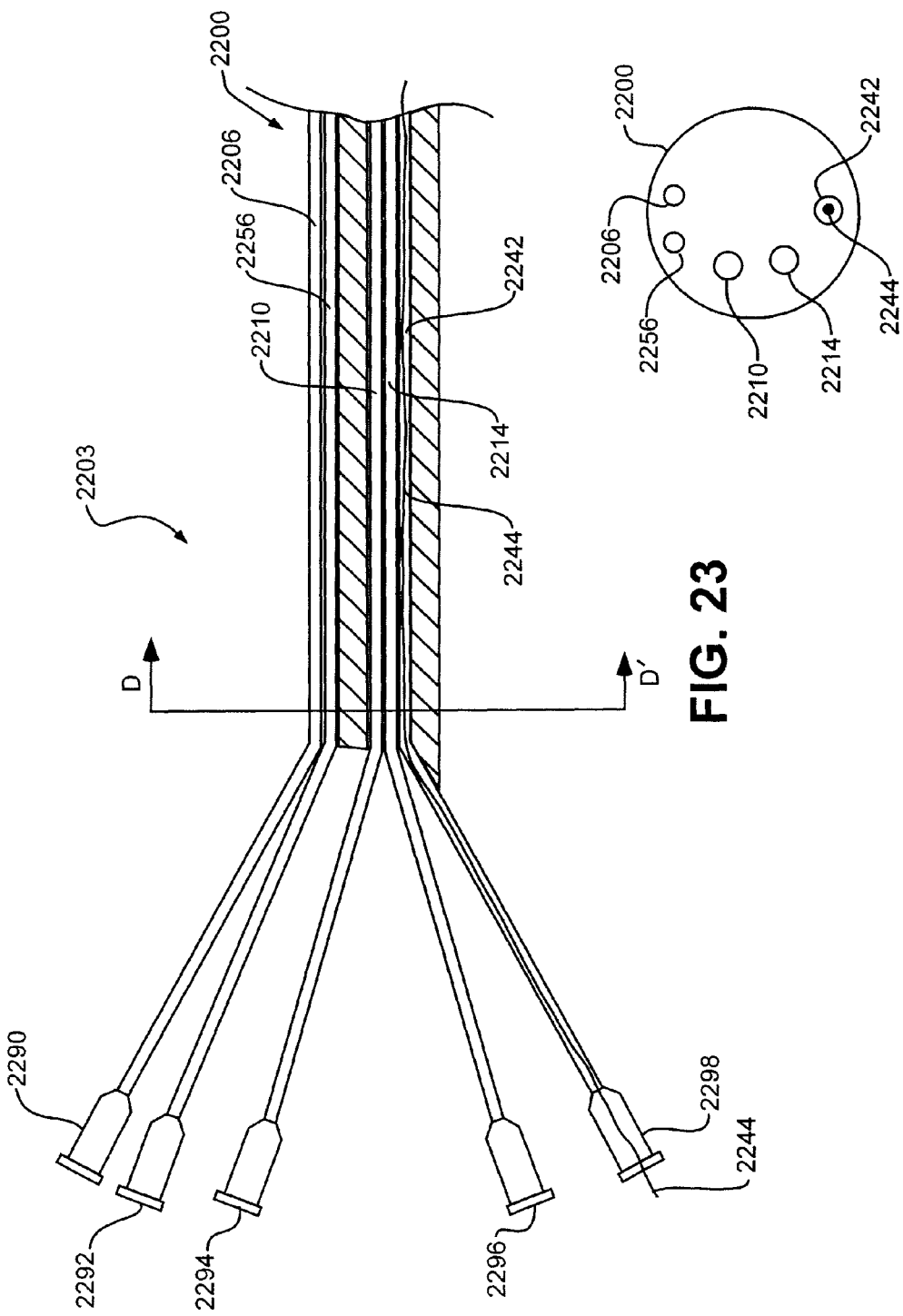

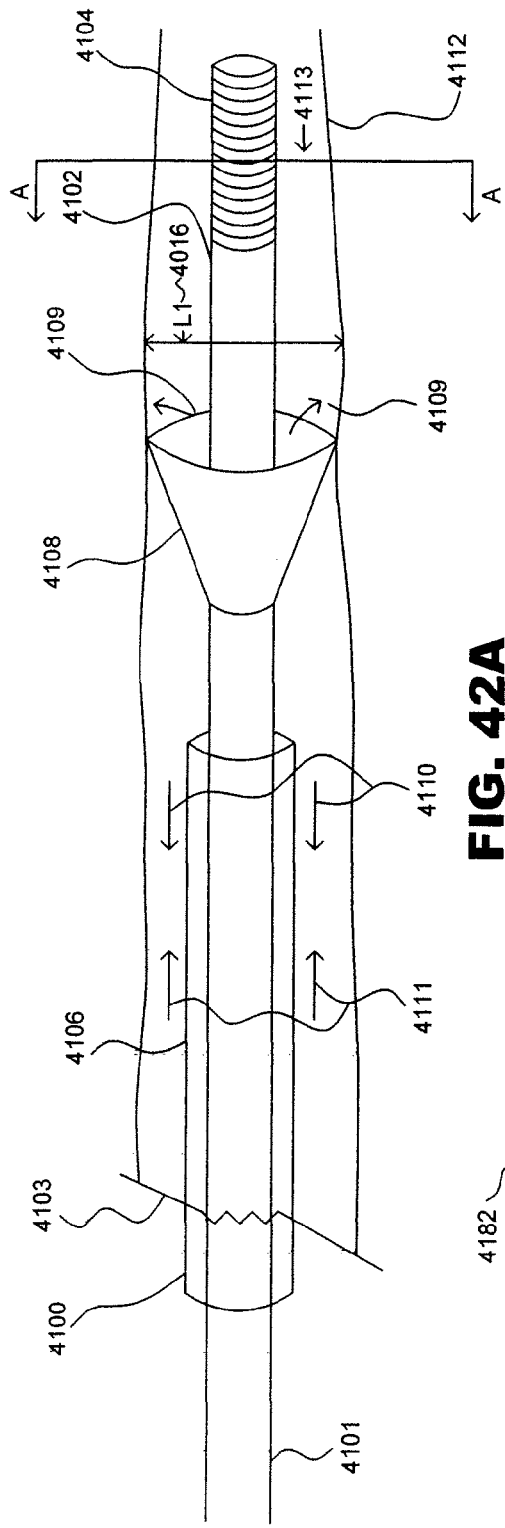
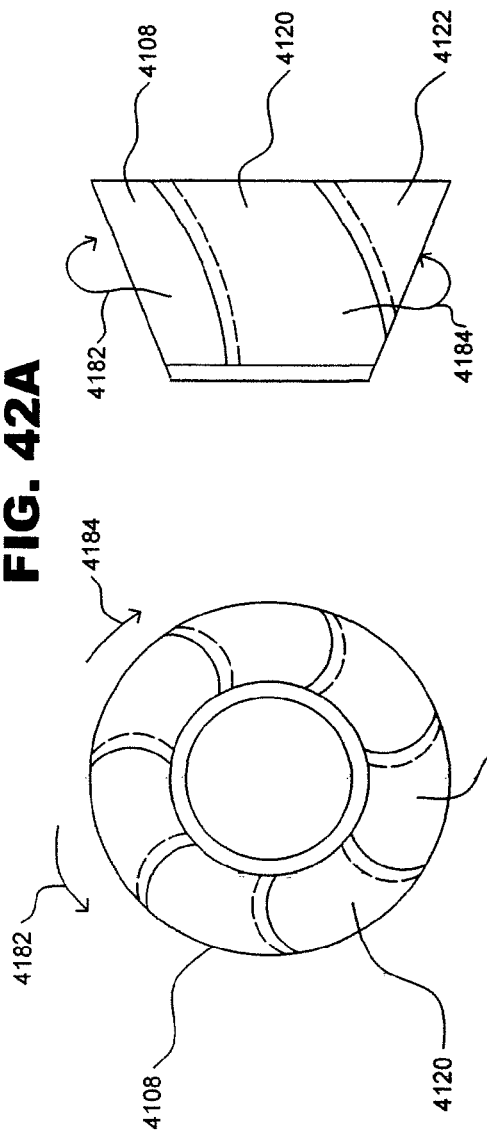
FIG. 42A
FIG. 42C
FIG. 42B

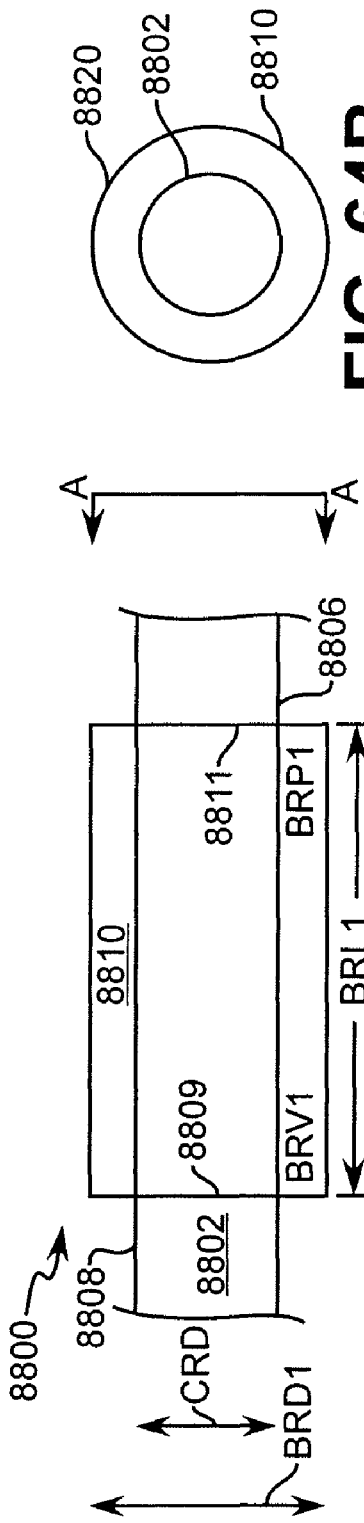
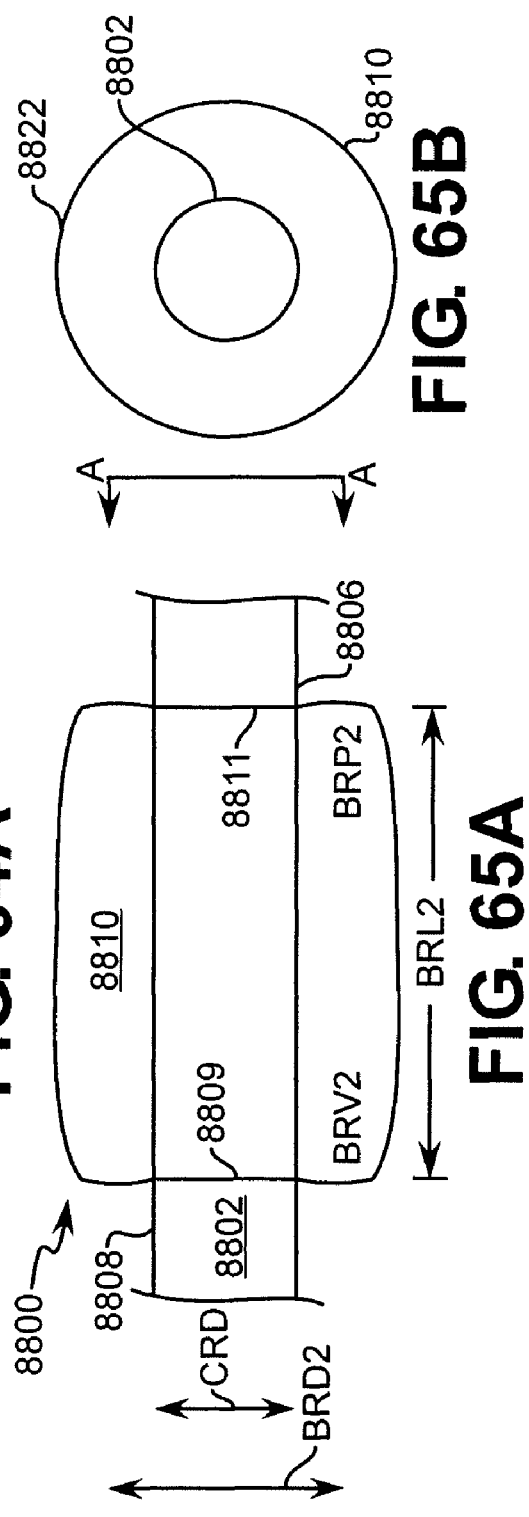

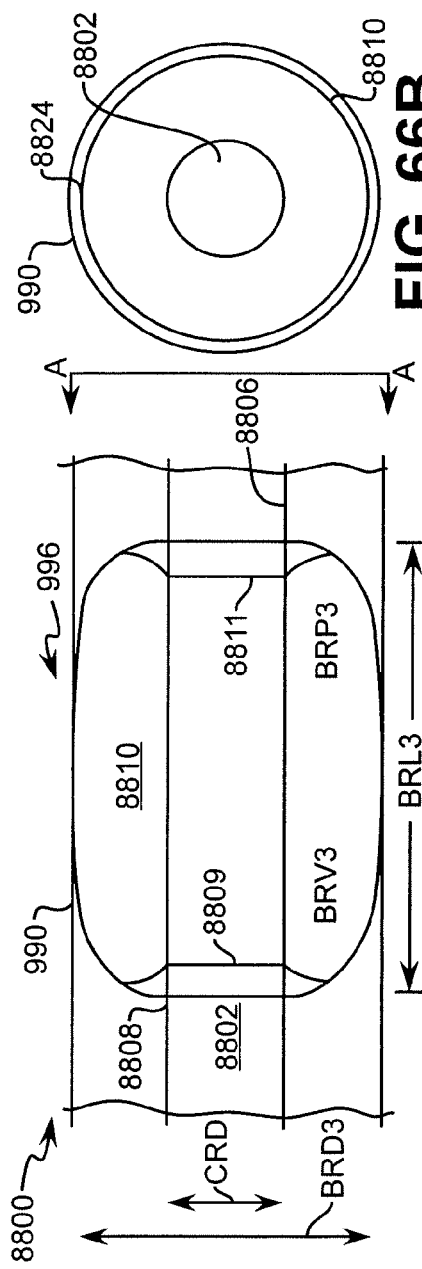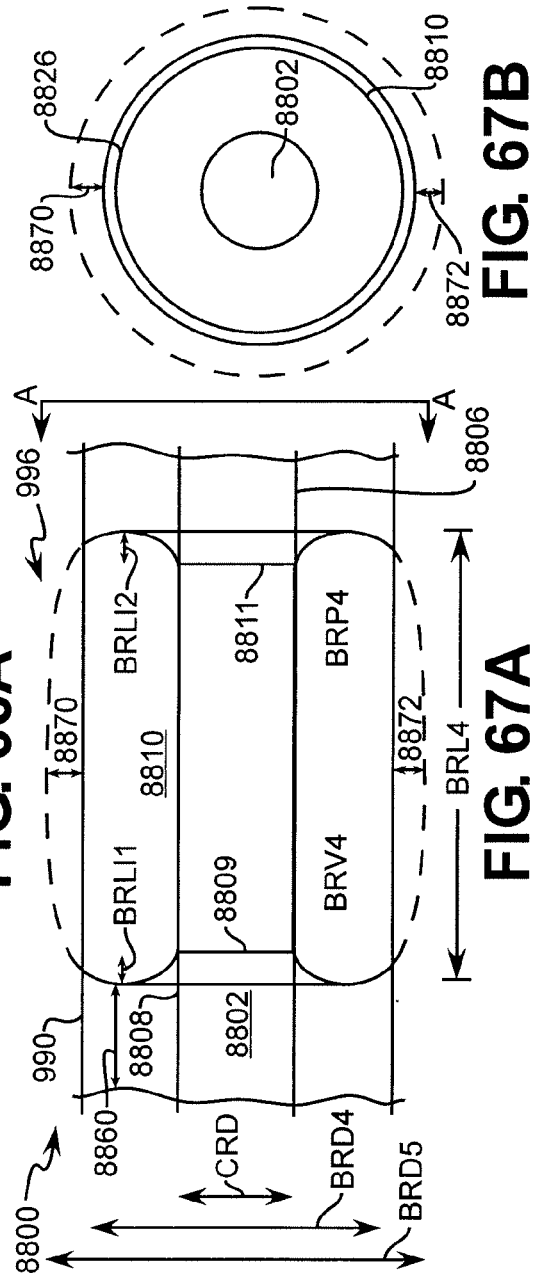

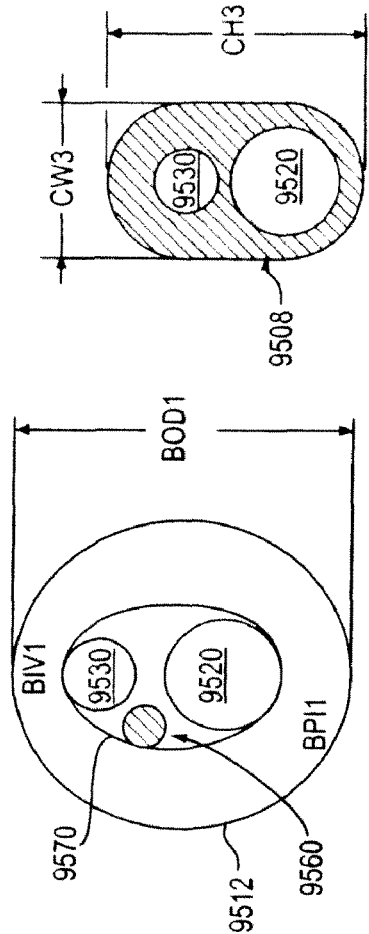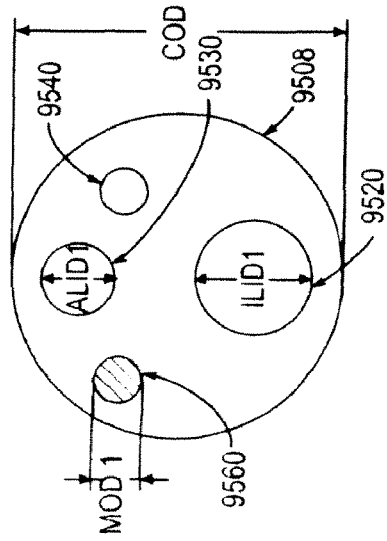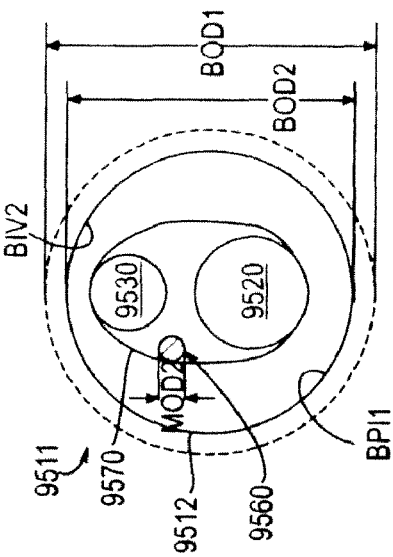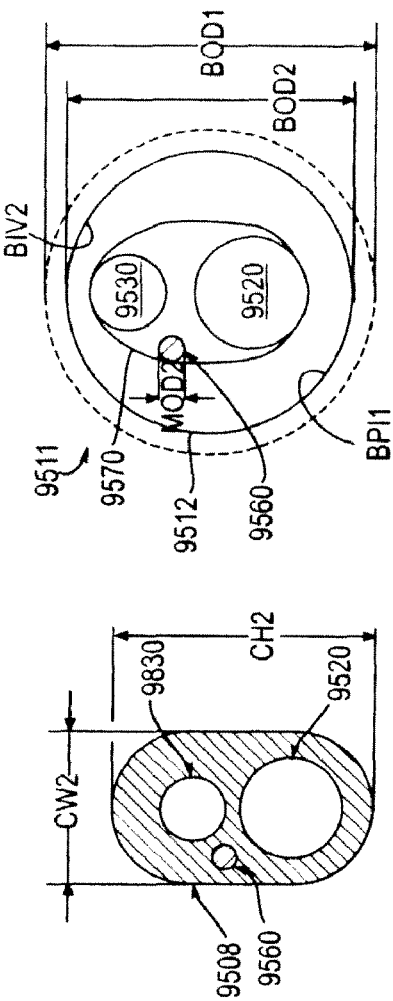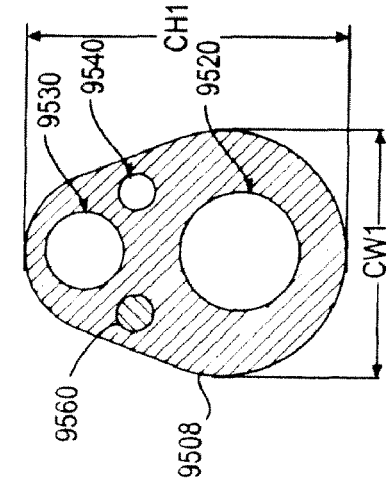

CROSS-SECTION VIEW B-B

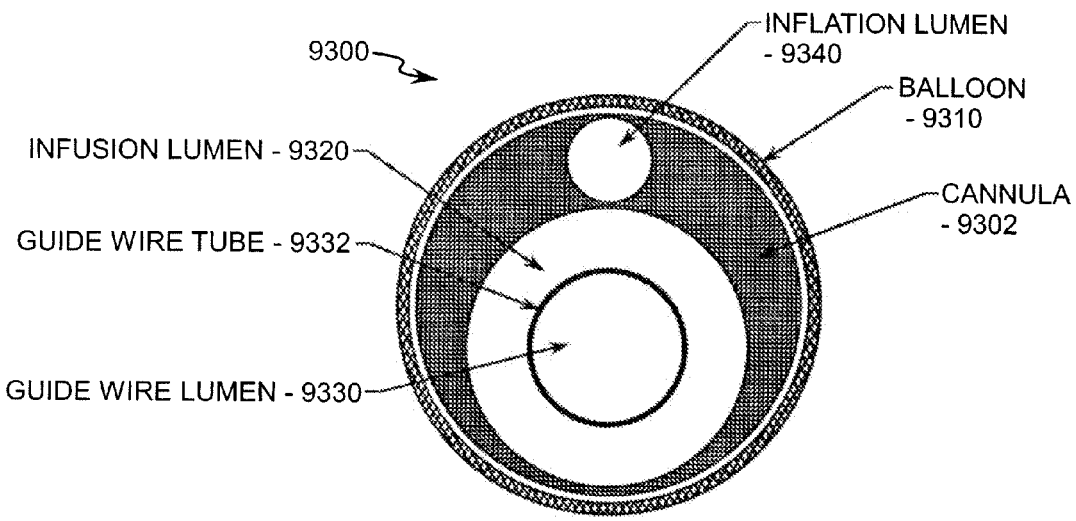
FIG. 73
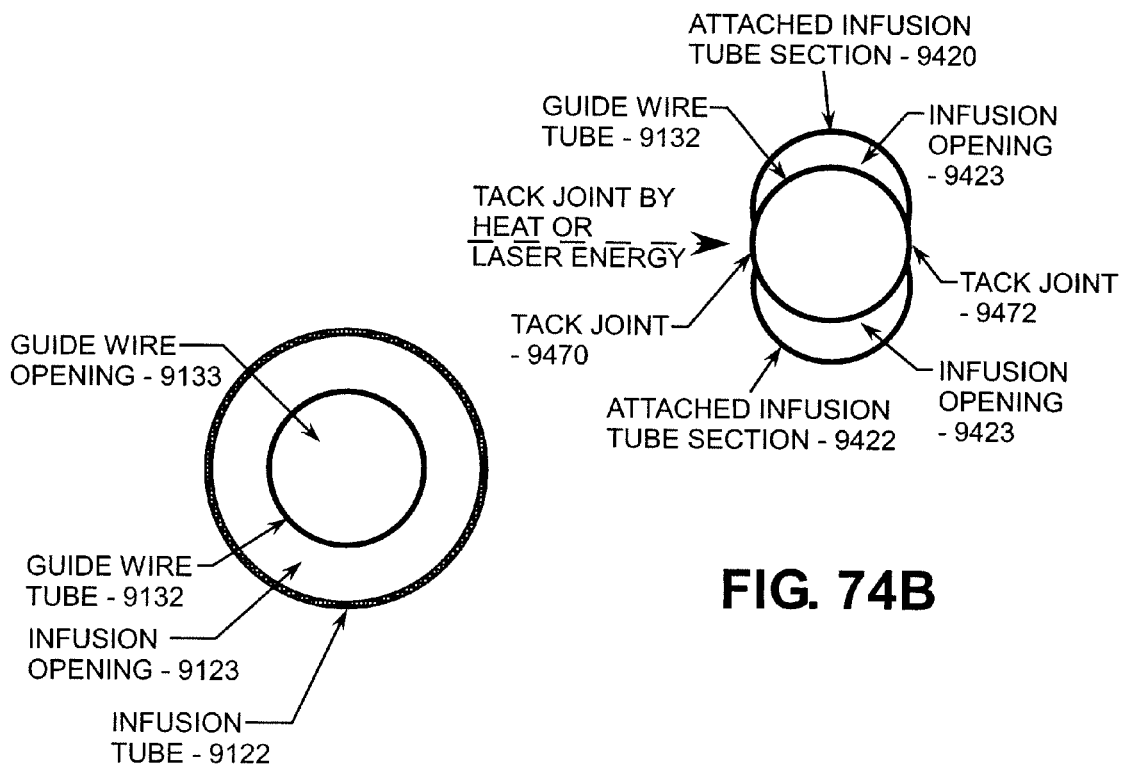
FIG. 74A
FIG. 74B

UNLATCHED TO ALLOW IT TO
BE FILLED/REMOVE BUBBLES

BUBBLES/AIR REMOVED, LATCHED

KNOB TURNED TO DRAW IN
MAX AMOUNT OF FLUID.

KNOB TURNED TO INFLATE
BALLOON TO OCCLUSION OD

UNLATCHED TO DEFLATE THE
BALLOON (RE-LATCH TO
RE-INFLATE BALLOON)

INFUSION TREATMENT AGENTS, CATHETERS, FILTER DEVICES, AND OCCLUSION DEVICES, AND USE THEREOF

This application is a Divisional application of application Ser. No. 10/800,323, filed Mar. 11, 2004, now abandoned which claims the benefit of provisional application Ser. No. 60/467,402, filed May 1, 2003, entitled "Multiple Occlusion Device", and is a Continuation-in-Part of application Ser. No. 10/387,048, filed Mar. 12, 2003, now U.S. Pat. No. 7,250,041, entitled "Retrograde Pressure Regulated Infusion", and claims the priority benefit thereof.

BACKGROUND

Local treatment with a substance such as a drug at a particular internal site of a patient, as opposed to systemic treatment, has become increasingly important.

Such local access is useful not only for substance delivery but for other treatments, such as myocardial revascularization, as well. Myocardial revascularization forms "holes" in ischemic ventricular tissue to increase blood flow to the treated area.

For example, to achieve local treatment of tissue, physicians can use catheters and occlusion devices. Specifically, cardiovascular guide catheters are generally percutaneous devices that the physician advances through a vasculature of a patient to a treatment region and are uses to guide other catheters or devices to the region. Delivery catheters generally deliver a treatment agent to a treatment region in a patient's vasculature and typically are inserted through another catheter (e.g., a guide catheter). Additionally, occlusion devices, such as balloons, may connect to a delivery catheter to occlude a treatment region in the vasculature. Guidewires are generally devices that guide through the vasculature to a treatment region and typically can be inserted through another catheter (e.g., an introducer).

SUMMARY

In various embodiments, there is disclosed an infusion-occlusion system for infusing a treatment agent to a treatment region of an artery or vein (including a blood vessel of the human heart) that includes a delivery catheter, a guide catheter adapted to receive the delivery catheter, a pressure increasing device adapted to be connected to the delivery catheter, a pressure-sensing device adapted to be connected to the delivery catheter, an inflation device adapted to be connected to the delivery catheter, and a guidewire with an occlusion device adapted to be received within the guide catheter. In another embodiment, the guide catheter of the catheter kit is provided with an occlusion device at the distal end of the guide catheter. In another embodiment, the delivery catheter of the catheter kit is provided with an occlusion device at the distal end of the delivery catheter.

Examples of occlusion devices include balloons of a material and dimension to have an outer diameter that inflated to selected diameters when the balloon is inflated with a selected inflation pressure or volume of gas or fluid. The balloon may be inflated by an inflation device having a high volume, low pressure syringe for initially inflating the balloon to a controlled low pressure initial diameter and having a low volume syringe for further inflating the balloon with a controlled volume increment(s) to produce controlled diameter increase(s) up the an occlusion diameter. Moreover, an occlusion device may be a composite balloon having an inner liner and an outer layer of different materials, a high compliance low pressure balloon, or a filter device that restricts particles from passing through but does not restrict fluid, such as blood. Also, according to some embodiments, occlusion devices may include various types of balloons, such as a high compliance low pressure balloons having a thermoplastic blend copolymer material with a polyether block amide resin moiety or a polyetheramide moiety. Likewise, according to some embodiments, occlusion devices may include various types of high-compliance low-tension balloons, such as a composite or multi-layer expanded PolyTetraFlouroEthylene (ePTFE) balloon having an inner liner.

For instance, according to some embodiments, a catheter, such as a guide catheter, may include a coronary sinus access guide with a collection cage or filter device, to filter unwanted particles or material from blood. Also, a delivery catheter may be a catheter that has a support mandrel extending therethrough or may have lumen or tubes in a coaxial or co-linear orientation with the longitudinal axis of the catheter.

In another embodiment, there is disclosed a method of providing treatment in a vessel of a patient that includes placing a guide catheter in the vessel of the patient, feeding a delivery catheter through the guide catheter, where the delivery catheter is provided with an occlusion device at its distal end, feeding at least one guidewire with an occlusion device through the guide catheter or the delivery catheter, deploying the occlusion device(s) of the guidewire(s), deploying the occlusion device at the delivery end of the delivery catheter, administering a treatment agent through the delivery catheter, disengaging all the occlusion devices, and removing the guidewire(s), the delivery catheter, and the guide catheter from the vessel of the patient. In another embodiment, the method further provides for aspirating the vessel of the patient before disengaging all of the occlusion devices. Also described is are methods including occluding a blood vessel, infusing treatment agent, such as progenitor cells (such as progenitor cells derived from bone marrow), to treat a treatment region of the blood vessel for a first time period, then allowing blood or treatment agent perfusion or flow to the treatment region for a second period of time, and repeating infusing and perfusion as necessary to accomplish sufficient treatment.

Specific examples of apparatus to allow for blood or treatment agent perfusion or flow to the treatment region include occlusion balloons that can be deflated and inflated to selected outer diameter, catheters having perfusion lumen that bypass and exit holes in the catheter on either end of the occlusion device, and catheters having guidewire lumen with exit holes through the catheter proximal to the occlusion device and an exit port at the distal end of the catheter. Additional features, embodiments, and benefits will be evident in view of the figures and detailed description presented herein.

BRIEF DESCRIPTION OF THE DRAWINGS

FIG. 5 schematically illustrates a guide catheter.

FIG. 6 shows a sectional view of FIG. 5 through line C-C' of FIG. 5.

FIG. 23 illustrates a balloon catheter tip proximal end.

FIG. 24 shows a section view of FIG. 23 through Line D-D'.

FIG. 42A illustrates the guidewire of FIG. 41 with the occlusion device open.

FIG. 42B, is a front view of FIG. 42A from perspective "A".

FIG. 42C, is a side of the occlusion device of FIG. 42A showing the occlusion device overlapping leaflets.

FIG. 64A is a cross sectional view of a cannula and a balloon.

FIG. 64B is a cross-sectional view the apparatus of FIG. 64A from perspective "A".

FIG. 65A shows the balloon and cannula of FIG. 64A, with the balloon inflated to a second inflation volume.

FIG. 65B is a cross-sectional view the apparatus of FIG. 65A from perspective "A".

FIG. 66A shows the cannula and balloon of FIG. 65A, with the balloon inflated to a third inflation volume.

FIG. 66B is a cross-sectional view the apparatus of FIG. 66A from perspective "A".

FIG. 67A shows the cannula and balloon of FIG. 66A, with the balloon inflated to a selected fourth inflation volume.

FIG. 67B is a cross-sectional view the apparatus of FIG. 67A from perspective "A".

FIG. 69B is a cross section view of the first section of FIG. 69A from perspective "A".

FIG. 69C is a cross sectional view of the second section of FIG. 69A from perspective "B".

FIG. 69D is a cross sectional view of the balloon section of FIG. 69A from perspective "C".

FIG. 69E is a cross sectional view of the third section of FIG. 69A from perspective "D".

FIG. 69F is a cross section view of the fourth section of FIG. 69A from perspective "E".

FIG. 70 is a cross sectional view of the balloon section of FIG. 69A from perspective "C", with the balloon inflated to a second volume that is less than that shown in FIG. 69D.

FIG. 73 is a cross-sectional view of a cannula and a balloon, where the cannula has coaxially and co-linearly aligned lumens.

FIG. 74A is a cross-sectional view of the apparatus of FIG. 71A from perspective "C" before forming tack joints between the guidewire tube and the infusion tube.

FIG. 74B is the structure of FIG. 74A after forming tack joints between the guidewire tube and the infusion tube.

DETAILED DESCRIPTION

Figure 1:
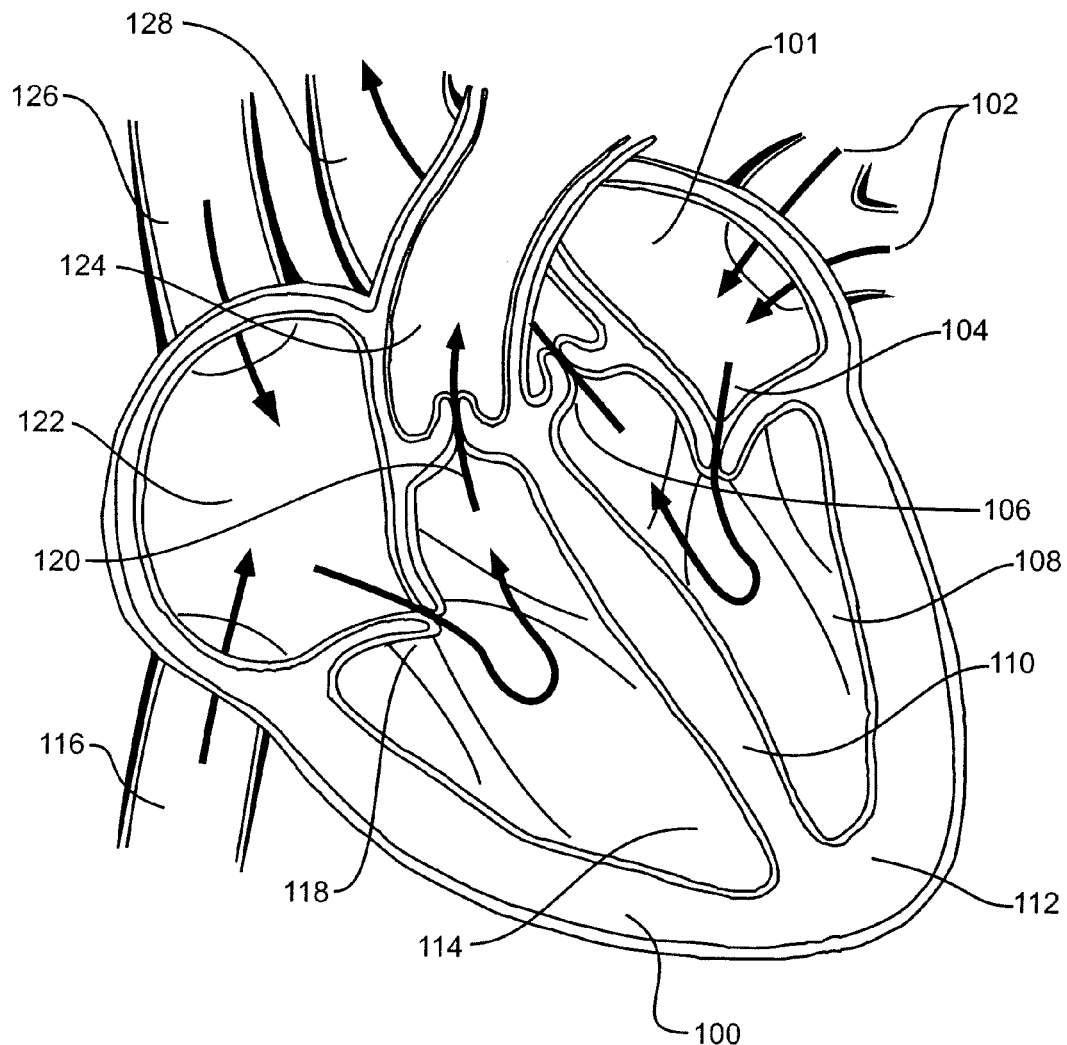
FIG. 1 schematically illustrates a cross-section of the heart showing blood flow throughout the heart.

Referring first to FIG. 1, a cross-sectional view of a heart is shown to illustrate blood flow throughout the heart. Deoxygenated blood returning from the body comes into heart 100 from either superior vena cava 126 or inferior vena cava 116 and collects in right atrium 122. Right atrium 122 contracts to pump the blood through tricuspid valve 118 where it flows into right ventricle 114. Right ventricle 114 contracts to send the blood through pulmonary valve 120 into pulmonary artery 124 where it goes into the lungs (not shown). The oxygenated blood returning from the lungs flows through pulmonary veins 102 where it flows into left atrium 101. Left atrium 101 contracts sending the blood through bicuspid or mitral valve 104 and into left ventricle 108. When left ventricle 108 contracts, the blood is sent through aortic valve 106 and into aorta 128. Left ventricle 108 and right ventricle 114 are separated by ventricular septum 110.

Figure 2:
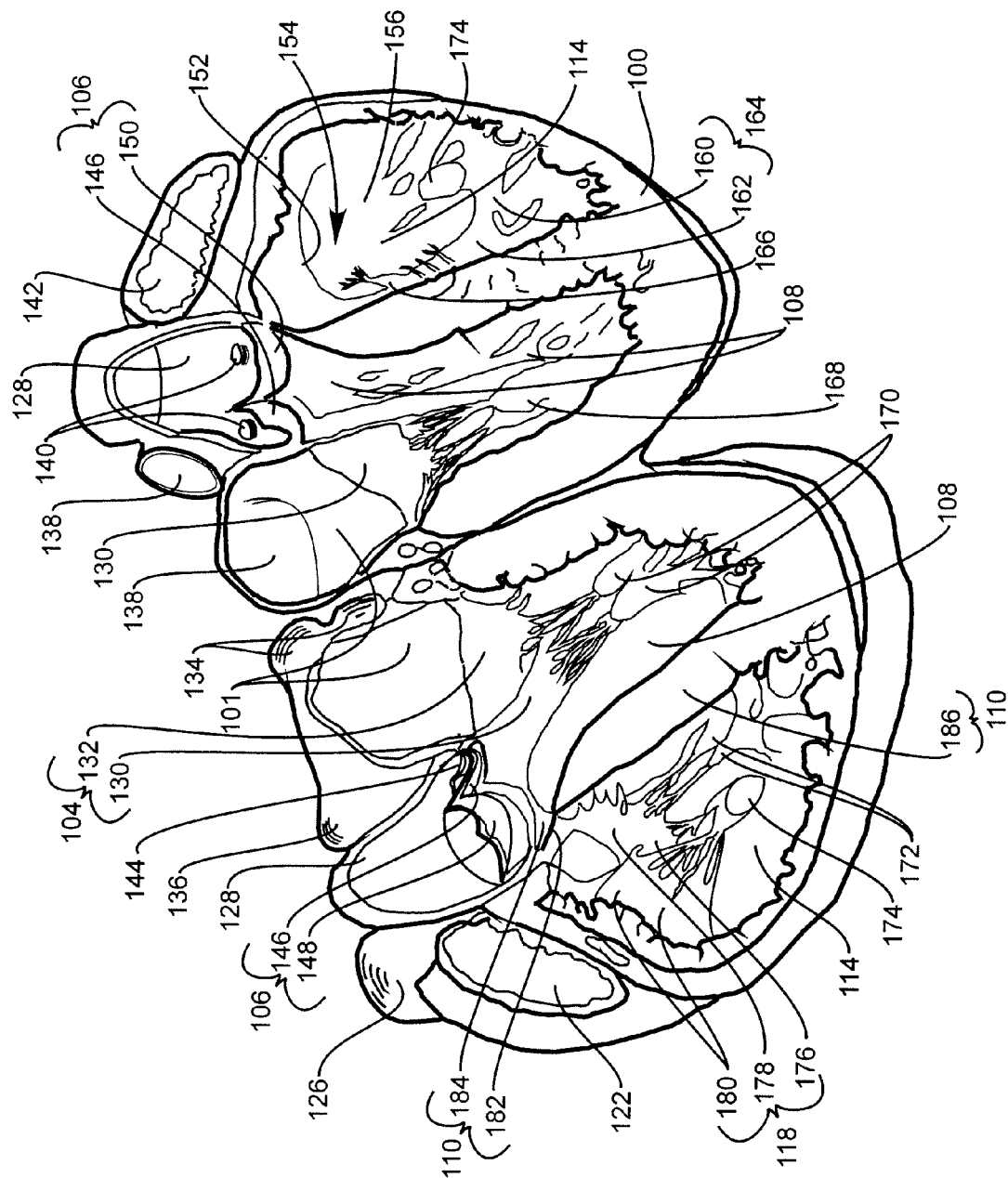
FIG. 2 schematically illustrates a vertical cross-section of the heart.

Referring to FIG. 2, a more detailed vertical cross-section of heart 100 is shown. Blood first collects in right atrium 122 from superior vena cava 126 or other veins. Right atrium 122 also includes right auricle 142. When right atrium 122 contracts, blood is sent through tricuspid valve 118 and into right ventricle 114. Tricuspid valve 118 is made up of three cusps: posterior cusp 176, septal cusp 178, and anterior cusp 180 (shown retracted). Right ventricle 114 has a number of muscles that contract to send blood out of right ventricle 114. Some of the muscles in right ventricle 114 include right anterior papillary muscle 174 (shown cut), and right posterior papillary muscle 172. Other parts of the anatomy of right ventricle 114 includes conus arteriosis 156, supra ventricular crest 152, and moderator band 160 and septal band 162 of septal marginal trabacula 164. The blood outflow to the pulmonary trunk is marked by arrow 154. Pulmonary trunk is shown as 138. The blood returning from the lungs returns by left pulmonary veins 134 and right pulmonary veins 136 where it collects in left atrium 101. Left atrium 101 also includes left auricle 138. When left atrium 101 contracts, blood is sent through mitral valve 104 which is made up of posterior cusp 132 and anterior cusp 130. Blood flows through mitral valve 104 and into left ventricle 108. Muscles in the left ventricle include left posterior papillary muscle 170, left anterior papillary muscle 168. Septum 110 separates left ventricle 108 from right ventricle 114. Septum 110 includes the muscular part of intraventricular septum 186, interventricular part of the membranous septum 182, and the atrial ventricular part of membranous septum 184. When left ventricle 108 contracts, blood is sent through aortic valve 106 which includes left semi-lunar cusp 146, posterior semi-lunar (non-coronary) cusp 148, and right semi-lunar cusp 150.

Most of the blood flows through aortic valve 106 and into ascending aorta 128, although some of the blood is diverted into the openings of coronary arteries 140.

Figure 3A:
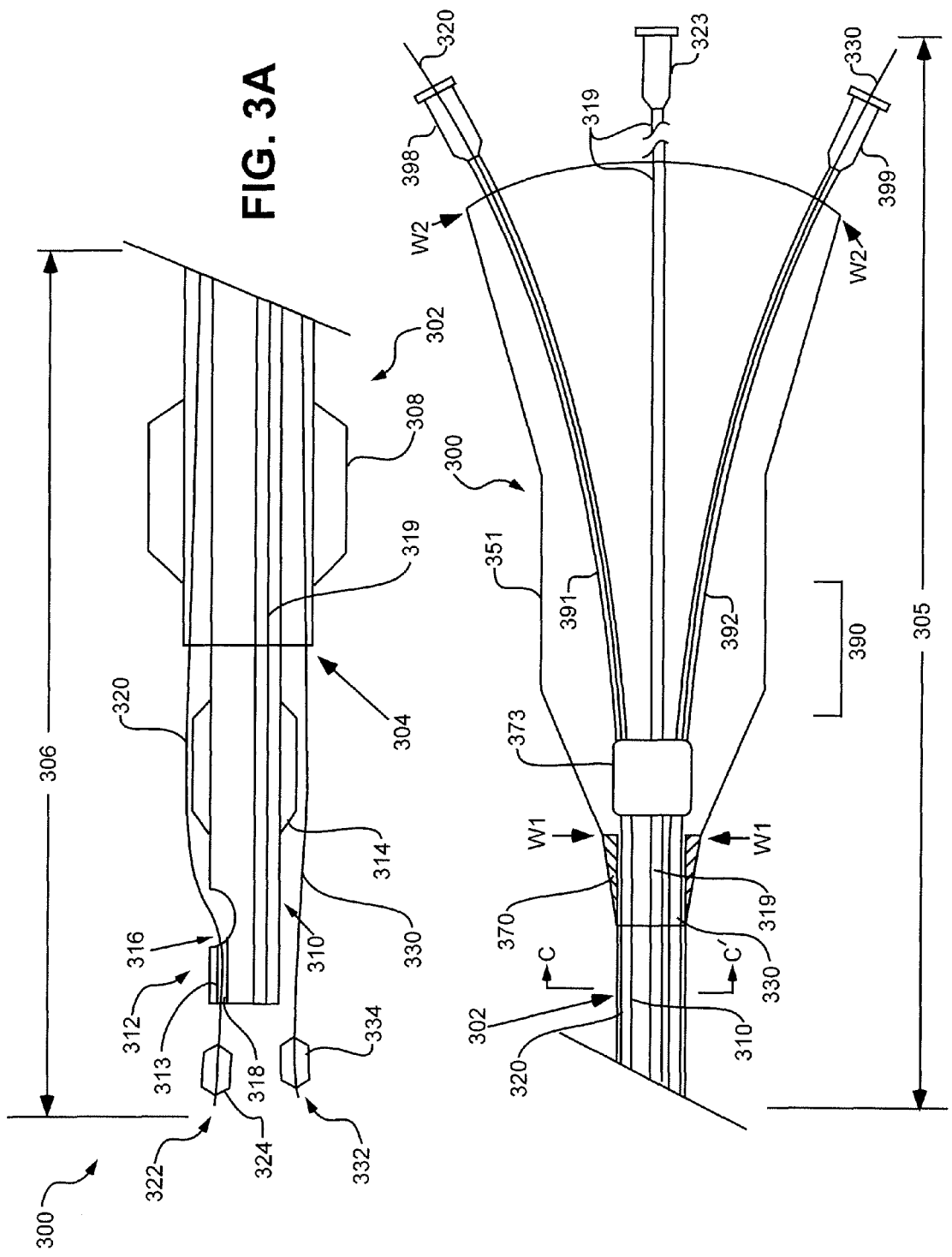
FIG. 3A illustrates a catheter system having a guide catheter, delivery catheter, guide wires, and multiple occlusion devices.

Referring now to FIG. 3A, a catheter system having a guide catheter, a delivery catheter, guidewires and multiple occlusion system is illustrated. In various embodiments, system 300 includes guide catheter 302 having proximal portion 305 and distal portion 306. System 300 includes guide catheter 302 having lumen 304, for allowing system 300 to be fed and maneuvered over a guidewire, such as guidewire 320 or guidewire 330. In various embodiments, lumen 304 extends the length of guide catheter 302 from proximal portion 305 to distal portion 306. Representatively, in a procedure, a guidewire 320 or 330 may be initially placed through a treatment region in a physiological lumen (e.g., a blood vessel) After placement, guide catheter 302 is advanced on and over the guidewire to or through a treatment region in an over the wire (OTW) fashion. In another embodiment, system 300 may be a rapid transfer type catheter assembly and only a portion of system 300 (e.g., a distal portion) is advanced over the guidewire (also see FIG. 37). Guidewire 320 or guidewire 330 may be retracted or removed once system 300 is placed at a treatment region.

System 300 includes guide catheter 302 having a lumen 304. Guide catheter 302 includes distal portion 306 having occlusion balloon 308 about distal portion 306. Delivery catheter 310 is shown disposed through lumen 304 of guide catheter 302. Delivery catheter 310 has distal end 312. Balloon 314 attaches at distal end 312. Notch 316 is located at distal end 312 and guidewire opening 318 opens into lumen 313 of delivery catheter 310 and is provided distally adjacent notch 316. Guidewire 320 is disposed through notch 316 and lumen 313 within delivery catheter 310 and out guidewire opening 318 of delivery catheter 310. Guidewire 320 includes distal end 322 and occlusion device 324. Occlusion device 324 may be an occlusion balloon attached to the exterior surface of guidewire 320 at or adjacent distal end 322 by adhesive, heat bonding, laser bonding, or shrink wrap bonding. Also shown disposed through guide catheter lumen 304 is guidewire 330. Guidewire 330 includes distal end 332 and occlusion device 334. Also note that occlusion device 334 may be an occlusion balloon attached to the exterior surface of guidewire 330 at or adjacent distal end 332 by adhesive, heat bonding, laser bonding, or shrink-wrap bonding. In this embodiment, guidewire 330 is shown disposed through guide catheter 302 (e.g., from a proximal end to a distal end of the guide catheter) but is not engaged by delivery catheter 310.

Proximal portion 305 of system 300 may reside outside the body of a patient while the remainder of system 300 is percutaneously introduced into patient's vasculature through a blood vessel. As shown in FIG. 3A, proximal portion 305 of system 300 includes hub 351. Hub 351 includes guidewire 320, guidewire 330, and treatment agent delivery lumen 319. In various embodiments, relative to the materials for the various cannulas described herein, a housing of hub 351 is a hard or rigid polymer material, e.g., a polycarbonate or acrylonitrile bubadiene styrene (ABS). A distal end of hub 351 has an opening to accommodate a proximal end of guide catheter 302. Hub 351 also has guidewire track 391, guidewire track 392, and a number of cavities at least partially through hub 351 (extending in a distal to proximal direction) to accommodate guidewire 320, guidewire 330, and treatment agent delivery lumen 319. Treatment agent delivery lumen 319 may be used to infuse a treatment agent including liquids, drugs, infusion pellets, suspended cells, stem cells, microspheres, peptides, growth factors, or various other appropriate liquids, materials, and therapeutic agents (mixed with blood or not) to be delivered locally or to a treatment region in a blood vessel. Also, delivering a treatment agent may include performing an infusate-uptake-enhancing procedure such as of electroporation, ultrasonic excitation, or photodynamic therapy. A proximal portion of hub 351 flares to create a spacing between guidewire 320 and guidewire 330, and treatment agent delivery lumen 319 (i.e., a distal end of hub 351 has width W1 sufficient to accommodate a proximal end of guide catheter 302 and a proximal end of hub 351 has width W2 that is greater than width W1). Hub 351 also includes medial section 390 which may have various appropriate lengths such as between a fraction of an inch and 10 inches to allow hub 351 to function appropriately. Moreover, guide catheter 302, delivery catheter 310, or hub 351 may include additional lumen, tubes, or cannula to inflate or expand occlusion devices, balloons, or to provide pressure measurements or pressure relief.

For example, in various embodiments, hub 351 may have at least the following functions: guidewire movement and control, guide catheter movement and control, delivery catheter movement and control, occlusion device expansion and retraction, balloon inflation and deflation, treatment agent delivery, and aspiration of fluid or particles from a treatment region of a blood vessel. With reference to FIG. 3A, in this embodiment, hub 351 also includes strain relief 370 catheter holder 373 (e.g., such as for holding a delivery catheter disposed through lumen 304), treatment agent delivery port 323, guidewire port 398, and guidewire port 399. A proximal end of guide catheter 302 terminates inside hub 351 near a distal end of hub 351. Guidewire 320, guidewire 330, and treatment agent delivery lumen 319 extend proximally beyond a proximal end of guide catheter 302 and may be secured in respective cavities through hub 351.

FIG. 3A also shows a distal portion of hub 351 including strained relief 370. Strained relief 370 may be an elastic tubular component that may act to reduce stress and inhibit shaft (e.g., of guide catheter 302) kinking for/or during the transition, movement, or control of a guidewire, such as guidewire 320 or guidewire 330, a catheter, such as guide catheter 302 or delivery catheter 320, or other functions identified above for hub 351.

Figure 3B:
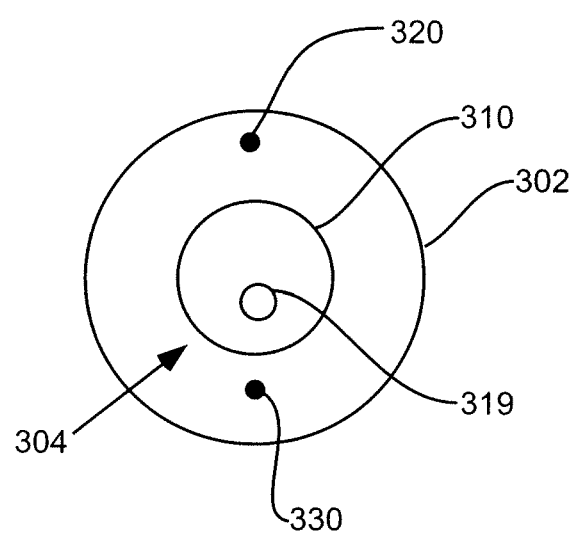
FIG. 3B shows a sectional side view of FIG. 3A through line C-C' of FIG. 3A.

FIG. 3B shows a sectional side view of FIG. 3A through line C-C' of FIG. 3A. FIG. 3B shows guidewire 320 and guidewire 330 disposed within lumen 304 of guide catheter 302. FIG. 3B also shows delivery catheter 310 disposed through guide catheter 302, wherein treatment agent delivery lumen 319 is disposed within delivery catheter 310.

According to various embodiments, the components of system 300, such as guide catheter 302, delivery catheter 310, balloon 308, balloon 314, occlusion devices 324 and 334, hub 351, strained relief 370, catheter holder 373, medial section 390, and other cannula or tubes surrounding lumens may be made of a material including materials described herein for such components, as well as materials described herein for balloons. For example, the components of system 300 may include a polycarbonate or acrylonitrile bubadiene styrene (ABS); a biocompatible polymer such as a polyether block amide resin; a biocompatible polymer blend of polyurethane and silicone a polymer having a structure of a regular linear chain of rigid polyamide segments interspaced with flexible polyether segments, a styrenic block copolymer (SBC), or a blend of SBC's; a thermoplastic blend copolymer material having one of a polyether block amide resin moiety and a polyetheramide moiety; a styrene isoprene styrene (SIS), a styrene butadiene styrene (SBS), a styrene ethylene butylene styrene (SEBS), a polyetherurethane, an ethyl propylene, a ethylene vinyl acetate (EVA), an ethylene methacrylic acid, an ethylene methyl acrylate, and an ethylene methyl acrylate acrylic acid; a material from a material family of one of styrenic block copolymers and polyurethanes; a nylon material; a melt processible polymer; or a low durometer material. It is also contemplated that other components of system, apparatus, or devices described herein, such as other catheters, cannulas, balloons, filter devices, occlusion devices, tubes (e.g., such as lumen 989, lumen surrounding material, lumen sleeves, lumen cannula or lumen tubes, such as described below with respect to infusion lumen 9520 or accessory lumen 9530 of FIGS. 69A-F), syringes, pressure increasing devices, pressure transfer devices, pressure maintaining devices, or pumps described below made of a material including materials described above.

In use, system 300 may be referred to as a "rapid transfer type system" designed to have the distal end of guide catheter 302 advanced percutaneously to a desired first location in a blood vessel where balloon 308 may be inflated to occlude the blood vessel or to fix the distal end of guide catheter 302 at the first location. Note that balloon 308 may be inflated later on in the use of system 300, such as after delivery catheter 310 is advanced as described below. Next, guidewire 320 may be advanced percutaneously to a desired second location in the same or a different blood vessel so that the distal end 312 of delivery catheter 310 can be advanced or tracked over guidewire 320 by feeding lumen 131 over guidewire 320. Then, balloon 314 may be inflated to occlude the blood vessel or to fix the distal end of delivery catheter 310 at or adjacent to the second location. It is also contemplated that guidewire 330 may be advanced through a blood vessel and to a third location. Occlusion devices 324 or 334 may be expanded to occlude blood vessels, such as at those locations, to define a distal end of a treatment region or treatment area. The treatment agent infuses into the blood vessel from treatment agent delivery lumen 319 of delivery lumen 310 (e.g., where the region of interest, treatment agent, and infusion of treatment agent from the delivery catheter are in accordance with corresponding descriptions herein).

Figure 4:
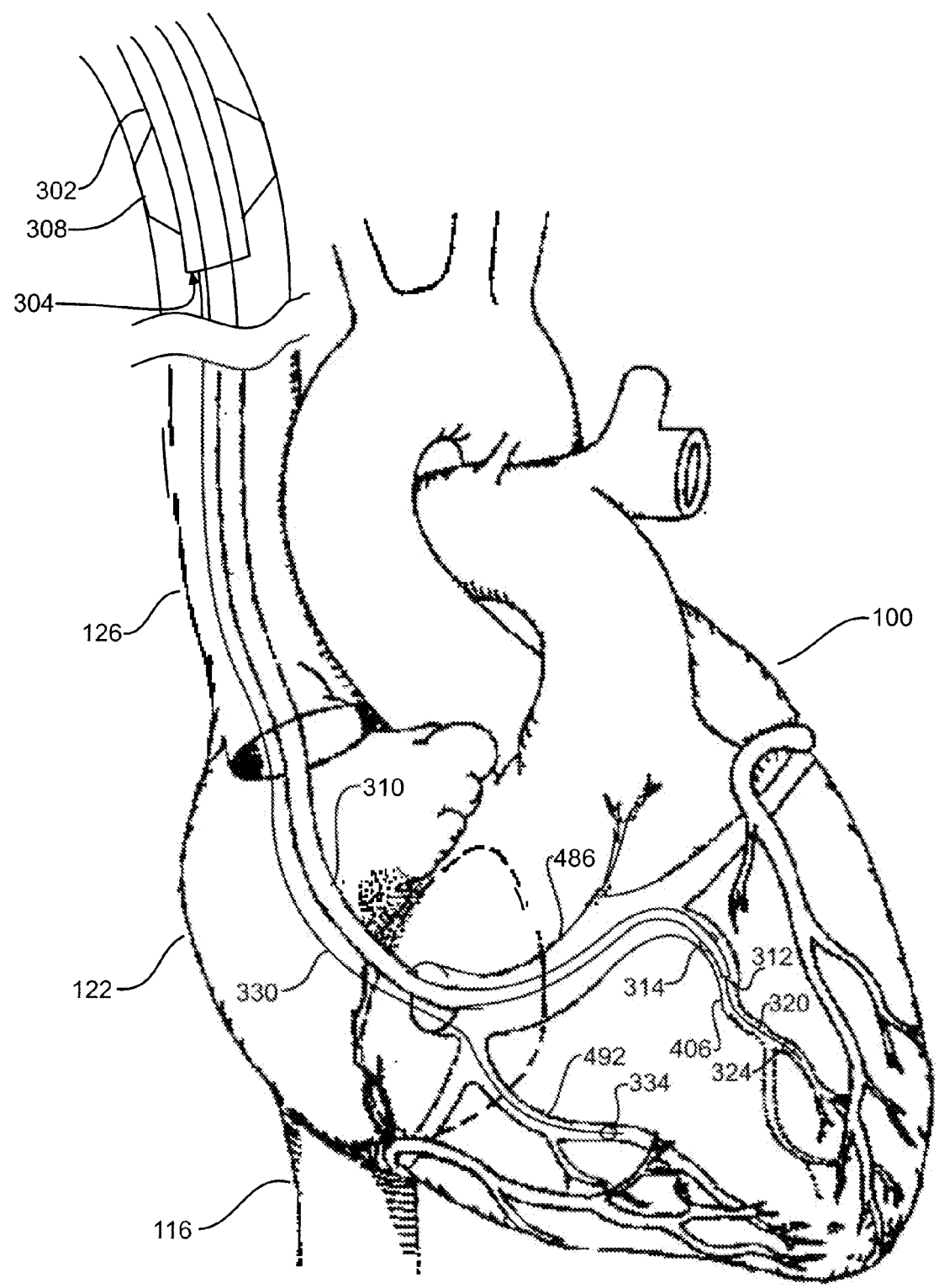
FIG. 4 schematically illustrates the placement of the catheters of FIGS. 3A and 3B in the coronary sinus.

For instance, in one example, guide catheter 302 may be fed and maneuvered as described above into blood vessels of a person's heart. More particularly, FIG. 4 schematically illustrates the placement of the catheters of FIGS. 3A and 3B in the coronary sinus, such as coronary sinus 3286 of FIGS. 32-33. As shown in FIG. 4, delivery catheter 310 may be fed through lumen 304 of guide catheter 302 and into middle cardiac vein 406, such as by being fed through lumen 304 before or after guide catheter 302 is placed through a treatment region in an OTW fashion, or is placed through a treatment region in a rapid transfer type fashion. Guidewire 320 may also be fed through guide catheter 302 through guidewire opening 318 of delivery catheter 310 and into middle cardiac vein 406 distal to distal end 312 of delivery catheter 310. Guidewire 330 may be fed through lumen 304 and into small cardiac vein 492. Next, occlusion device 324, occlusion device 334, and balloon 314 may be engaged to occlude small cardiac vein 492, and respectively occlude a portion of middle cardiac vein 406 between balloon 314 and occlusion device 334. Next, balloon 308 may be engaged. A treatment agent may be fed through treatment agent delivery cannula 319 distal to balloon 314 and proximal to occlusion device 324. Occlusion device 334 is engaged, and balloon 308 is engaged to prevent the treatment agent from reaching the right atrium through shunts or anastimoses. Following the conclusion of the administration of the treatment agent, occlusion device 324, occlusion device 334, and balloon 314 may be disengaged, and guidewire 320, delivery catheter 310, and guidewire 330 are removed from lumen 304 of guide catheter 302. Then, coronary sinus 486 may be aspirated (e.g., see hole 988 of FIG. 9 and accompanying text) and then balloon 308 disengaged and guide catheter 302 removed from the coronary sinus.

Embodiments also include system 300 having a filter device instead of balloon 308. For instance, the system and process described above for FIGS. 3A, 3B and 4 may also apply to a system and process having filter device 720, instead of and at the location of balloon 308, to restrain and aspirate particles shown and described below for FIGS. 7-19.

Referring now to FIG. 5, a guide catheter is illustrated. FIG. 5 shows guide catheter 502 which may or may not be or be part of system 300, such as if guide catheter 502 is part of guide catheter 302, as shown and described with respect to FIG. 3. In particular, guide catheter 502 has proximal end 504 and distal end 506, which may be or be part of proximal end 305 or distal end 306, as shown and described with respect to FIG. 3. Lumen 508 is shown in FIG. 5 extending through guide catheter 502 from guide catheter opening 514 at proximal end 504 to distal end 506. Guide catheter 502 also has balloon 510 attached around the exterior surface of catheter 502 at or adjacent distal end 506. Lumen 508 or balloon 510 may correspond to lumen 304 or balloon 308, as shown and described with respect to FIG. 3. FIG. 5 also includes balloon inflation cannula 512 within guide catheter 502 from proximal end 504 to opening 513 within balloon 510.

FIG. 6 shows a sectional view of FIG. 5 through line C-C' of FIG. 6. As shown in FIG. 6, balloon inflation cannula 512 is disposed within guide catheter 502 such as by being disposed through guide catheter opening 514 and extended into a portion of balloon 510, such as to provide opening 513 to inflate balloon 510.

In various embodiments, proximal end 504 includes guide catheter opening 514 and balloon inflation cannula 512. Also valve device 516, with selector mechanism 518. Guide catheter 502 may have an opening extending from lumen 508 at distal end 506 to guide catheter opening 514 at proximal end 504. Thus, in embodiments implementing valve device 516, selector mechanism 518 may be disengaged to allow the opening extending from lumen 508 to guide catheter opening 514 to remain open. Alternatively selector mechanism 518 may be engaged, such as by turning, to cause valve device 516 to close the opening between lumen 508 and guide catheter opening 514 at valve device 516 and instead direct any fluid flowing through the opening and toward guide catheter opening 514 through nozzle 520 and out of valve device 516. In some embodiments, the fluid flows such as into collecting reservoir 524, which in some embodiments connected to nozzle 520 such as by a hose connected to nozzle 520. Thus, selector mechanism 518 is engaged, for example, to aspirate fluid such as blood or particles such (e.g., see hole 988 of FIG. 9 and accompanying text), form a treatment region of a blood vessel through lumen 508, and out of nozzle 520. This could be used, for example, to aspirate a vessel distal to balloon 510, before deflating balloon 510 so that fluid will be removed from the vessel.

According to various embodiments, guide catheter 502 may be an appropriate length for reaching a treatment region of a subject during a medical procedure, such as by having a length of between three inches and five feet. Also, guide catheter 502, balloon 510, and balloon inflation cannula 512 may be formed of materials similar to those for forming components of system 300. Moreover, balloon inflation cannula 512 may include one or more of a synthetic or natural latex or rubber, such as a polymer material; a polyetheramide; a plasticiser free thermoplastic elastomer; a thermoplastic blend; a block copolymer of polyether and polyester (e.g., such as a polyester sold under the trademark Hytrel® of DUPONT COMPANY); a biocompatible polymer such as a polyether block amide resin (e.g., for instance, PEBAX® of ATOCHEM CORPORATION); a polycarbonate or acrylonitrile bubadiene styrene (ABS); a biocompatible polymer such as a polyether block amide resin; a styrene isoprene styrene (SIS), a styrene butadiene styrene (SBS), a styrene ethylene butylene styrene (SEBS), a polyetherurethane, an ethyl propylene, an ethylene vinyl acetate (EVA), an ethylene methacrylic acid, an ethylene methyl acrylate, an ethylene methyl acrylate acrylic acid, a material from a material family of one of styrenic block co-polymers and polyurethanes, a melt processible polymer, a low durometer material, and nylon. Likewise, balloon 510 may be attached to guide catheter 502 by processes described herein for attaching a balloon to a catheter, including by laser, adhesive, shrink tube bonding, and heat bonding.

In other embodiments, proximal end 504 of guide catheter 502 is provided with flap 519 instead of valve device 516. Flap 519 is, for example, a material similar to a material for inflation cannula 512 (e.g., such as materials described above with respect to components of system 300, or a synthetic or natural latex or rubber, or other materials that can block fluid flow). Flap 519 has a suitable dimensions to block off and occlude lumen 508, such as to prohibit blood or treatment agent from flowing past flap 519. Thus, flap 519 serves to close guide catheter opening 514 when there are no devices disposed in or through guide catheter 502 such as a device or cannula holding flap 519 open. For instance, flap 519 may be attached to the inside of catheter 502 along lumen 508, at one or more locations, by one or more of a hinge, a pin, an anchor, laser bonding, adhesive bonding, and heat bonding. Thus, when the device, catheter, or cannula (not shown) is inserted into guide catheter opening 514, the device or cannula pushes flap 519 opens with some degree of force, such as by forcing flap 519 from close position CL to open position OP, as shown in FIGS. 5 and 6. For instance, a device, catheter, or cannula inserted into guide catheter opening 514 in direction 583 can push flap 519 from close position CL to open position OP, as shown in FIGS. 5 and 6, and allow lumen 508 to define an opening extending from guide catheter opening 514 to distal opening 594. After the device or cannula is removed from guide catheter opening 514 or pushing flap 519 open, flap 519 has a property that causes it to resist or occlude a flow of any liquid or particles flowing from lumen 508 towards guide catheter opening 514. Hence, after the device or cannula is removed from pushing flap 519 open, flap 519 has a property or is mounted to close, such as by causing flap 519 to move from open position OP to close position CL, and to be biased in closed position CL with sufficient force to stop or occlude a flow of any liquid or particles flowing from lumen 508 towards guide catheter opening 514 Thus, when closed, flap 519 prevents fluid originating from opening 594 from flowing through lumen 508 within guide catheter 502 and flowing out guide catheter opening 514.

In other embodiments, proximal end 504 of guide catheter 502 includes sealing cap 530 adapted to seal guide catheter opening 514 instead of valve device 516 or flap 519. Sealing cap 530 serves to seal guide catheter opening 514 such as by having threads that engage other threads at the proximal end of guide catheter 502, or by having a recess for engaging a lip at the proximal end of guide catheter 502. Thus sealing cap 530 may be used to seal off proximal end of guide catheter 502 when attached thereto, and may be removed from proximal end of guide catheter 502 such as to aspirate a treatment region of a vessel as described above with respect to valve device 516. More particularly, cap 530 may be attached to guide catheter 502 until such time as it is desired to aspirate a vessel distal to balloon 510 (e.g., such as after the balloon is inflated and before deflating the balloon). At that time, cap 530 can be removed, and liquid from the vessel can flow from lumen 508 through guide catheter 502 out guide catheter opening 514 and into collection receptacle 532.

Figure 7:
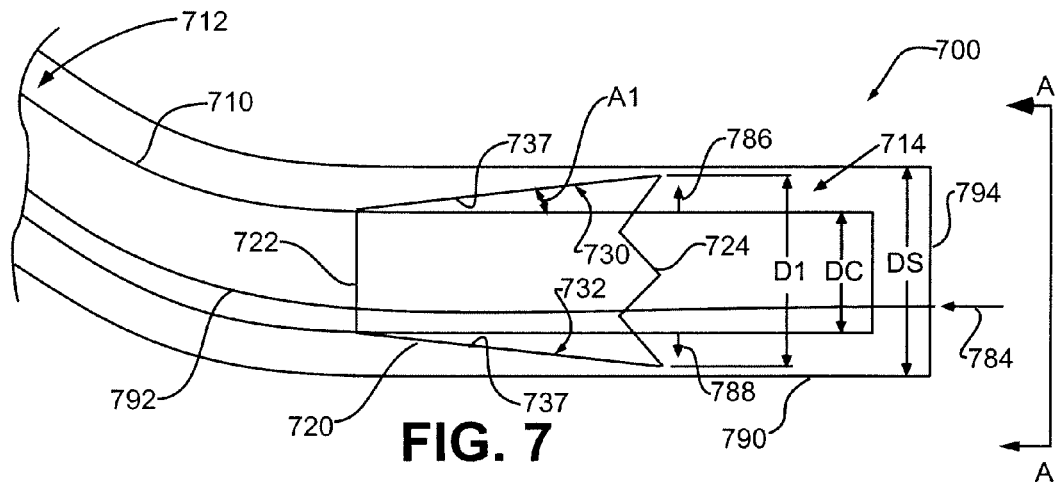
FIG. 7 is a side view of a cannula and a filter device in a sheath.

Furthermore, according to some embodiments, catheters, such as a guide catheter, include a filter device capable of filtering certain particles from passing through the catheter but not restricting fluid flow. For instance, a coronary sinus access guide or catheter may have a collection cage or filter device to filter unwanted particles or material from blood. For example, FIG. 7 is a side view of a cannula and a filter device in a sheath. As shown in FIG. 7, apparatus 700 includes cannula 710, such as a cannula having a dimension suitable for percutaneous advancement through a blood vessel, includes proximal section 712 and distal end 714. FIG. 7 also shows filter device 720 having proximal portion 722 axially coupled or connected to an exterior surface of cannula 710 at or adjacent distal end 714. For instance, an inner diameter of proximal portion 722 may be attached to an exterior surface of cannula 710 by laser bonding, adhesive bonding, heat bonding, or other bonding techniques at an appropriate location adjacent to distal end 714 to filter unwanted particles or material from blood flowing in direction 784 in a treatment region, such as treatment region 996.

Filter device 720 also has distal portion 724 having a first diameter D1 under a first set of conditions. For example, a first set of conditions may include filter device 720 being restrained (e.g., to less than an inner diameter of a blood vessel into which it will be placed) by sheath 790, or restricted by a retraction or contraction pressure, such as a pressure resulting from a deflated balloon, tendon, or self-contracting filter device.

Thus, as shown in FIG. 7, diameter D1 is smaller than and restrained by diameter of the sheath DS, and is larger than diameter of the cannula DC, forming first angle A1 between generally conical-shaped inner surface 737 and the surface of cannula 710. For example, according to some embodiments, first angle A1 shown in FIG. 7 may be an angle between 0° and 20°, such as an angle of 2°, 3°, 4°, 5°, 6°, or 10°. As a result distal portion 724 may have a first diameter between 1 mm and 14 mm, such as by having an outer diameter corresponding to French size 5F, 6F, 7F, 8F, 9F, 10F, 12F, 15F, 18F, 24F, and 30F.

Figure 8:
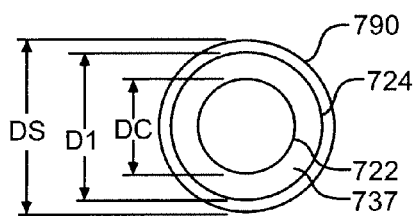
FIG. 8 is a view of FIG. 7 from perspective "A".

FIG. 8 is a view of FIG. 7 from perspective "A". FIG. 8 shows conical shape inner surface 737 at filter device 720 including proximal portion 722 having a diameter approximately equal to diameter of cannula DC and distal portion 724 having first diameter D1. FIG. 8 also shows sheath 790 having diameter of sheath DS, such as a diameter of sheath sufficient to restrict or contain the diameter of distal portion 724 to first diameter D1. Note that although in FIGS. 7 and 8, cannula 710, proximal portion 722, distal portion 724, and sheath 790 are shown having side sections through line A-A' that are approximately circular, various other closed shapes are contemplated such as an oval, a square, a triangle, a trapezoid, an ellipse, or a combination thereof.

Moreover, sheath 790 may be retracted in a proximal direction (e.g., direction 784) so that sheath end 794 is pulled back beyond distal portion 724 allowing first diameter D1 to expand beyond a diameter of the sheath DS. Similarly, according to some embodiments, pull wire 792 (e.g., such as a wire disposed within sheath 790 extending from distal end 714 to a proximate end of sheath 790 external to the body of a subject) may be pulled or removed, such as by being pulled in direction 784, to form a seam in sheath 790 (e.g., such as where pull wire 792 was before removal) so that sheath 790 may be entirely or partially removed from encasing cannula 710 or filter device 720. More particularly, filter device 720 may have a property such that first diameter D1 of distal portion 724 can be transformed, enlarged, or expanded to a second diameter under a second set of conditions. Consequently, first diameter D1 can be transformed to become a second diameter, such as in response to expansion pressures 730 and 732 applied to generally conical-shaped inner surface 737.

Figure 9:
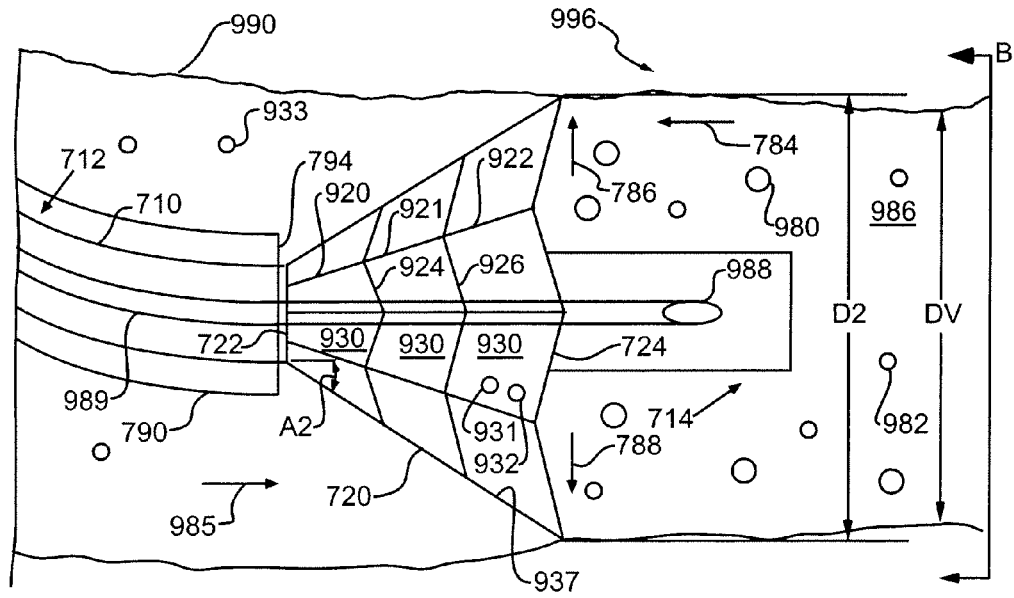
FIG. 9 is a side view of a distal end of a cannula including a filter device having a distal portion with a second diameter that is approximately the inner diameter of a blood vessel at a treatment region.

In various embodiments, distal portion 724 has a different second diameter under a second set of conditions, where the second diameter approximates an inner diameter of a blood vessel. For example, FIG. 9 is a side view of a distal end of a cannula including a filter device having a distal portion with a second diameter that is approximately the inner diameter of a blood vessel at a treatment region. Specifically, FIG. 9 shows cannula 710 percutaneously advanced through blood vessel 990, and sheath 790 retracted so that sheath end 794 is retracted beyond proximal portion 722 allowing filter device 720 to expand in directions 786 and 788 so that distal portion 724 has different second diameter D2 under the second set of conditions (e.g., retraction of sheath 790) that is at least equivalent to inner diameter of blood vessel DV at treatment region 996.

Note that treatment region 996 may be a treatment region proximate to where distal portion 724 contacts blood vessel 990, and optionally included the region contained in blood vessel 990 distal to filter device 720 and containing distal end 714. For example, second diameter D2 may be a diameter approximately equal to the diameter of a blood vessel at a region or point of interest, a diameter slightly less than that of a blood vessel at a point or treatment region, or a diameter slightly greater than that of a diameter of a blood vessel at a point or treatment region. More particularly, second diameter D2 may be greater than the diameter of blood vessel 990 at a point or treatment region, such as by being in a range of between 0% and 25% larger, such as by being 3% larger, 5% larger, 10% larger, or 15% larger in diameter.

Specifically, filter device 720 may have a property such that first diameter D1 can be transformed to become second diameter D2 in response to expansion pressures having a total of between approximately two atmospheres in pressure and six atmospheres in pressure applied to generally conical-shaped inner surface 737 (e.g., such as caused by pressures 730 and 732) to cause surface 737 to expand to second generally conical-shaped inner surface 937. According to some embodiments, expansion pressures 730 and 732 may be the result of, applied by, or caused by, a fluid flow in direction 784. For example, expansion pressures 730 and 732 may be applied by a flow of blood 986 in direction 784 having a pressure greater than 2.0 millimeters of Mercury (mmHg) in pressure to cause distal portion 724 to expand in directions 786 and 788.

Also, according to some embodiments, filter device 720 includes self-expanding materials (e.g., such as shape memory alloys, including for example, Nickel-Titanium) or other materials that have shape memory where the memorized shape is the expanded shape. To modify the shape (e.g., to restrict the shape) a sheath may be placed over filter device 720. Removing the restriction will allow the shape memory material to return to its memorized shape (e.g., an expanded shape). Specifically, for example, filter device 720 may include a self-expanding frame portion to provide the second set of conditions under which distal portion 724 has second diameter D2.

Furthermore, according to some embodiments, filter device 720 may have a property, such as including a material, such that under the second condition (e.g., the condition described above wherein second diameter D2 approximates an inner diameter of a blood vessel) filter device 720 will restrain from flowing through filter device 720 plurality of particles 980 having a particle size greater than an average particle size of blood cells 982. More specifically, for example, as shown in FIG. 9, filter device 720 may restrain particles 980 (e.g., such as infusion pellets, suspended cells, stem cells, or microspheres) in fluid 986 flowing in direction 784, from flowing through filter device 720. Thus, particles having a particle size approximately that of an average particle size of blood cells, such as blood cells 982, contained in fluid 986 flowing in direction 784, may travel through filter device 720 without being restrained (e.g., such as if unrestrained blood cell 983 originated in treatment region 996). For example, a typical red blood cell has a size of approximately 7 micrometers in diameter, and a typical white blood cell has a size of between approximately 7 and 15 micrometers in diameter.

Consequently, according to some embodiments, filter device 720 may include a material, such as material 930 having or pierced by a plurality of openings, such as openings 931 and 932, having a dimension suitable to allow a fluid, such as blood, to pass therethrough. More particularly, openings 931 and 932 may have a dimension suitable to allow a fluid including blood cells 982 to flow through the openings and having a dimension suitable to restrain particles 980 having a particle size greater than an average particle size of blood cells. For example, openings 931 and 932 may have a diameter of between 10 micrometers and 100 micrometers in diameter. Thus, openings 931 and 932 may act like a trap, a sieve, or a strainer of particles to restrain particles 980. Moreover, according to some embodiments, particles, materials, and matter restrained by filter device 720 may be restrained such as by causing the particles, material, or matter to bond to or be coupled to filter device 720, to rest against filter device 720, or to be restrained within the area of blood vessel 990 distal to filter device 720, such as the area including distal end 714. It is contemplated that material 930 may include various suitable materials such as natural or synthetic material, plastic, stainless steel, PEBAX 91 (a biocompatible polymer such as a polyether block amide resin, sold under the trademark PEBAX® of ATOCHEM CORPORATION, PUTEAUX, FRANCE), embolic protection material, or various other appropriate filtration materials.

Material 930 may be connected or attached to a frame portion, such as by laser bonding, adhesive bonding, thermal bonding, mechanical restriction (e.g., such as if material 930 is woven or sewn through structure or portions of the frame, such as a structure having space between pieces of the structure or holes in the frame), or various other appropriate attachment methods.

For example, filter device 720 may include a frame portion defined by proximal portion 722 and distal portion 724. According to some embodiments, an inner diameter of the frame portion may be attached to an outer surface of cannula 710, at proximal portion 722 such as by laser bonding, adhesive bonding, thermal bonding, mechanical bonding (e.g., such as is described above for attaching material 930 to the frame portion), or various other techniques of bonding sufficient to preclude all or a portion of the inner diameter of filter device 720 from becoming separated from the outer surface of cannula 710. For example, a sufficient attachment would preclude a portion or all of an inner diameter of filter device 720 from becoming detached from the outer surface of cannula 710 during expansion or retraction of distal portion 724, a first set of conditions, a second set of conditions, during restriction of a fluid flowing through filter device 720, or during aspiration of particles from treatment region 996, such as is described herein (e.g., see hole 988 of FIG. 9 and accompanying text).

It is contemplated that the frame portion may include one or more of a leaflet-shaped support, a helical-shaped support, a cone-shaped support, a spar-shaped support, a basket-shaped support, a ring-shaped support (e.g., to allow material 930 to form a "parachute" shape), or a combination thereof. More specifically, a frame portion may have a plurality of extending supports extending from proximal portion 722 to distal portion 724, such as a spar, a rod, a shaft, a dowel, a pull, a spine; and a plurality of cross supports disposed between the plurality of extending supports, such as a rib, a cross-link, and a cross-wrap wrapped around, over, or under the extending support. In addition, it is contemplated that filter device 720 or the frame portion of filter device 720 may include one or more of tubing, wires, ribs, ribbons, forged materials, extruded materials, cast materials, and deposited materials. For example, FIG. 9 shows filter device 720 having longitudinally disposed, circumferentially spaced elements, including elements 920, 921, and 922. Moreover, filter device 720 may include ribs or cross supports, such as ribs 924 and 926.

Figure 10:
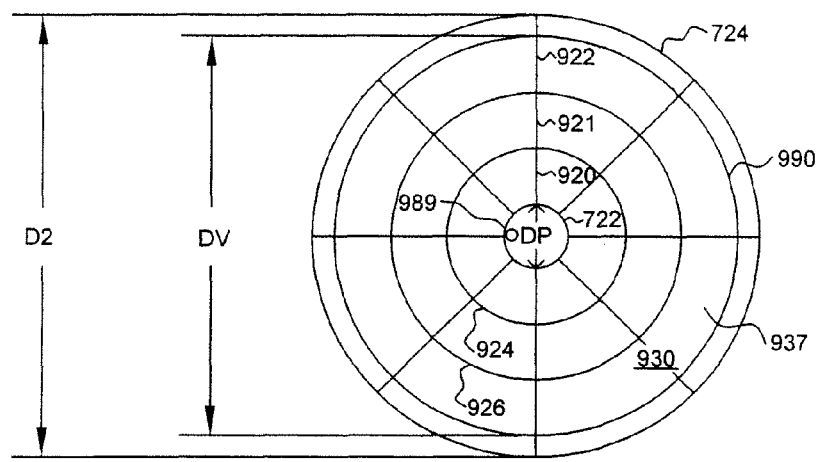
FIG. 10 is a view of FIG. 9 from perspective "B".

Likewise, filter device 720 may include a material stretched on a frame portion to form a generally conical-shaped inner surface. For example, FIG. 10 is a view of FIG. 9 from perspective B. FIG. 10 shows proximal portion 722 having diameter of proximal portion DP and material 930 stretched to form generally conical-shaped inner surface 937 between proximal portion 722 and distal portion 724 having second diameter D2. Thus, frame portion 720 may have material 930 on, over or under longitudinally disposed elements or spars spaced and defining a conical shape extending from proximal portion 722 to distal portion 724, such as is shown by conical shape 937 of FIGS. 9 and 10 or conical shape 737 shown in FIGS. 7 and 8. FIG. 10 also shows blood vessel 990 having diameter of vessel DV which is slightly less than second diameter D2. Thus, in various embodiments, it is contemplated that second diameter D2 approximates an inner diameter of a coronary sinus of a subject at a treatment region, such as by having a diameter of between 6.5 millimeters and 11 millimeters. Also, material 930 may be stretched on a frame portion, such as a frame including elements 920, 921, and 922 or ribs 924 and 926 to form generally conical-shaped inner surface 737 under a first set of conditions and generally conical-shaped inner surface 937 under a different second set of conditions.

In addition, FIG. 9 shows generally conical-shaped inner surface 937 forming second angle A2 between generally conical-shaped inner surface 937 and the surface of cannula 710. According to some embodiments, second angle A2 may be an angle between 5° and 85°, such as an angle of 10°, 20°, 25°, 30°, 35°, 40°, 45°, 50°, 55°, 60°, and 65°. Consequently, distal portion 724 may have second diameter D2 in a range between three mm and 15 mm, such as, an outer diameter corresponding to French size 9F, 12F, 15F, 18F, 24F, 28F, 30F, 32F, and 34F.

Furthermore, according to some embodiments, distal portion 724 may have various cross sectional aspects or shape. Specifically, although distal portion 724 is shown in FIGS. 7 and 9 having a w-shaped profile, distal portion 724 may have various appropriate shaped profiles, such as an m-shape, a flat shape, a c-shape, an s-shape, or a shape including one or more of the previously mentioned shapes. Likewise, elements 920, 921, and 922, as well as ribs 924 and 926 may also have various appropriate shapes, such as those described above with respect to distal portion 724. Also, it is contemplated that a self-expanding or self-contracting frame may include frame structure, portions, elements, or ribs having a metallurgy with a memory, an elastic material, nitinol (NiTi), a shaped memory alloy (e.g., such as a memory alloy that when formed to a shape remembers or returns to that shape if not restrained or damaged). For example, a self-expanding or self-extracting frame may be a metal frame with a helical-spring shape, or a shape including ribs with a memory, that flexes when constrained.

Once particles are restrained, such as with the filter devices restraining particles, material, and matter, according to various embodiments, filter device 720 may include a property to allow aspiration of the particles, material, and matter being restrained. Specifically, cannula 710 may include one or more holes, such as hole 988 through the exterior surface of cannula 710, as shown in FIG. 9, to allow aspiration of restrained particles, such as particle 980. Thus, hole 988 may be used to aspirate or draw unwanted material, such as infusion pellets, suspended cells, stem cells, or microspheres out of the treatment zone or treatment region, such as via evacuation or suction to pull the unwanted material through hole 988 and into cannula 710. For example, aspiration of restrained particles is contemplated to include aspiration of fluid 986, and blood cells 982, such as via a suction or vacuum provided at hole 988 provided via a cannula including lumen 989 extending from hole 988 through cannula 710 to proximal section 712. According to some embodiments lumen 989 may include a surrounding material, sleeve, cannula or lumen, such as described below with respect to infusion lumen 9520 or accessory lumen 9530 of FIGS. 69A-F. Hole 988 may be located between 0.2 mm and 10 cm from the end of distal end 714.

Figure 11:
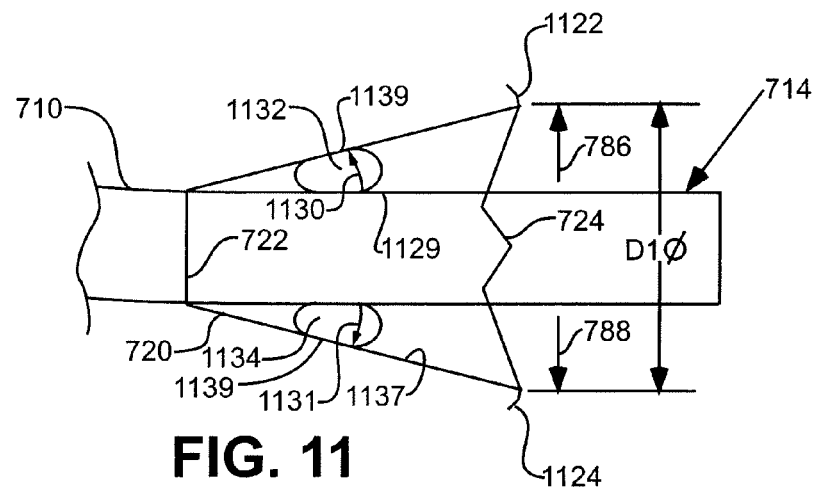
FIG. 11 is a side section view of a filter device with a distal portion having a first diameter and balloons coupled to the filter device or the cannula.

Distal portion 724 may be expanded from first diameter D1 (FIGS. 7 & 8) to second diameter D2 (FIGS. 9 & 10) as a result of filter device 720 being self-expanding, expansion pressure from fluid flow in direction 784, or various other appropriate systems or devices, such as for applying pressures 730 and 732. For example, FIG. 11 is a side section view of a filter device with a distal portion having a first diameter and balloons attached to the filter device or the cannula. FIG. 11 shows balloons 1132 and 1134 attached to filter device 720 at attachment locations 1139, and attached to cannula 710, such as at attachment locations 1129, such that inflation of balloons 1132 and 1134 (e.g., such as inflation via cannulas as described below in FIGS. 17 and 18) transforms distal portion 724 of filter device 720 from first diameter D1 to a second diameter. According to some embodiments, the balloons may be attached to the filter device or cannula at attachments locations 1129 or 1139, such as by an adhesive, heat bonding, laser bonding, welding, or stitching.

Thus, for example, balloons 1132 and 1134 may be inflated with sufficient pressure to cause an expansion pressure as described with respect to FIGS. 7 and 9 (e.g., such as pressure similar to those described above for pressure 730 and 732) applied to generally conical-shaped inner surface 1137 (e.g., such as similar to conical shape 737 described above).

Figure 12:
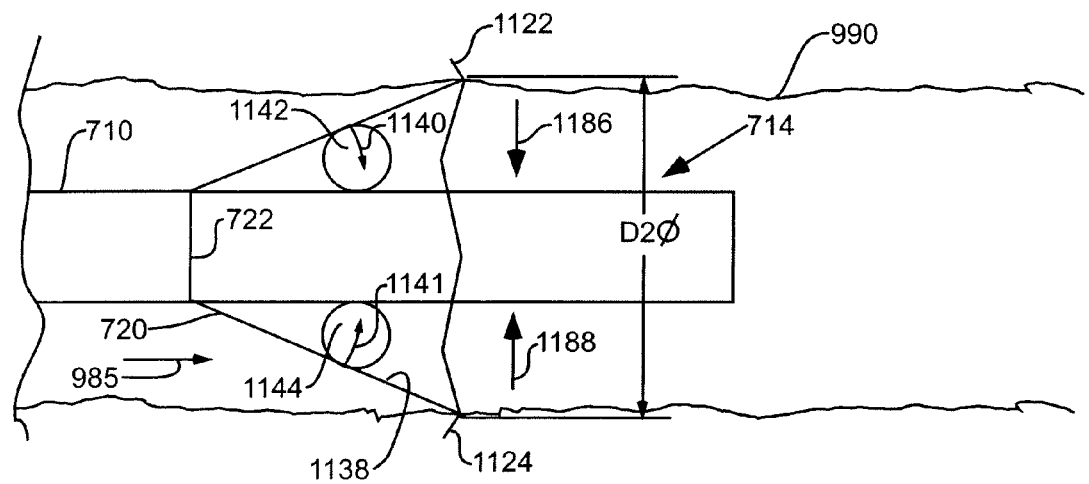
FIG. 12 is a side-section view of a filter device with a distal portion having a second diameter, wherein the filter device is attached to inflated balloons which are attached to a cannula.

Consequently, balloons 1132 and 1134 may be inflated to have a volume greater than that shown in FIG. 11 to transform distal portion 724 from first diameter D10 to a larger second diameter. For example, FIG. 12 is a side-section view of a filter device with a distal portion having a second diameter, wherein the filter device is attached to inflated balloons, which are attached to a cannula. FIG. 12 shows inflated balloons 1142 and 1144 attached to filter device 720 and cannula 710 (e.g., such as described above with respect to balloons 1130 and 1131) for transforming distal portion 724 of filter device 720 from first diameter D10 to second diameter D20. For instance, in various embodiments, inflated balloons 1142 and 1144 may be balloons 1132 and 1134 respectively, after inflation to become balloons 1142 and 1144. Note that according to some embodiments, diameter D10 may be a diameter similar to those described above with respect to first diameter D1, and second diameter D20 may be a diameter similar to those described above with respect to second diameter D2.

Also, according to some embodiments, filter device 720 may include anchors proximate to distal portion 724 for engaging tissue, to anchor filter device 720, or cannula 710 to an inner diameter of a blood vessel. For instance, FIG. 11 shows a filter device with a distal portion having anchors capable of engaging tissue of a blood vessel. As shown in FIG. 11, anchors 1122 and 1124 proximate to distal portion 724, where anchors 1122 and 1124 include a protruding barb capable of engaging tissue of a blood vessel, such as by piercing the inner diameter tissue to a sufficient depth to engage a sufficient amount of the tissue of blood vessel 990 to prohibit and anchor from being removed from its engagement of blood vessel 990, such as by the flow of liquid or blood in direction 784 toward filter device 720. Moreover, anchors 1122 and 1124 may be attached to elements or ribs of a frame of filter device 720 such as element 922 and rib 926 of FIG. 9. Thus, anchors 1122 and 1124 may be extended in directions 786 and 788 as shown in FIG. 11, to engage tissue of blood vessel as shown in FIG. 12. Consequently, anchors 1122 and 1124 may be disengaged from tissue of blood vessel 990 such as by retraction of distal end 724 or by moving filter device 720 in direction 985. Hence, anchors 1122 and 1124 may be disengaged from tissue, such as by retracting or contracting distal portion 724 to move anchors 1122 and 1124 in directions 1186 and 1188 as shown in FIG. 12.

Figure 13:
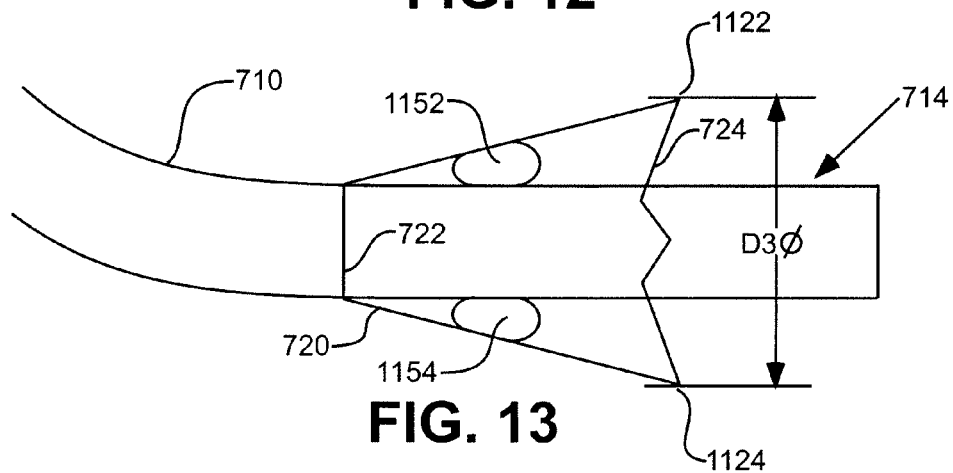
FIG. 13 is a side section view of a filter device with a distal portion having a third diameter, where the filter device is attached to deflated balloons which are attached to a cannula.

For instance, filter device 720 may have a property such that second diameter 1120 can be transformed to become or constrict to approximately first diameter D10 in response to a retraction or contraction pressure such as shown by pressures 1140 and 1141 of FIG. 12. According to some embodiments, sufficient retraction pressure may be in the range of between approximately two atmospheres in pressure and 35 atmospheres in pressure applied to generally conical-shaped inner surface 1138. More particularly, as shown in FIG. 12, balloons 1142 and 1144 attached to filter device 720 and cannula 710 may be deflated (e.g., such as via lumens as described below with respect to FIGS. 17 and 18) to transform distal portion 724 of filter device 720 from second diameter D20 approximately to first diameter D10. For example, FIG. 13 is a side section view of a filter device with a distal portion having a third diameter, where the filter device is attached to deflated balloons which are attached to a cannula. FIG. 13 shows deflated balloons 1152 and 1154 attached to filter device 720 (e.g., as described above with respect to attachment at attachment locations 1139) and attached to cannula 710 (e.g., such as described above with respect to attachment at attachment locations 1129) such that distal portion 724 is transformed to third diameter D30. For instance, in various embodiments, deflated balloons 1152 and 1154 may be balloons 1132 and 1134 respectively, after inflation and deflation (e.g., such as after inflation of balloons 1132 and 1134 to become balloons 1142 and 1144, and deflation of balloons 1142 and 1144 to become balloons 1152 and 1154).

Therefore, for example, inflated balloons 1142 and 1144 may be deflated to cause pressures 1140 and 1141 sufficient to create a retraction pressure as described above, applied to generally conical-shaped inner surface 1138, thereby retracting distal portion 724 to directions 1186 and 1188 from second diameter 1120 to third diameter D30 as shown in FIG. 13, which may be a diameter in a range of between 100 percent and 130 percent of D10.

Figure 14:
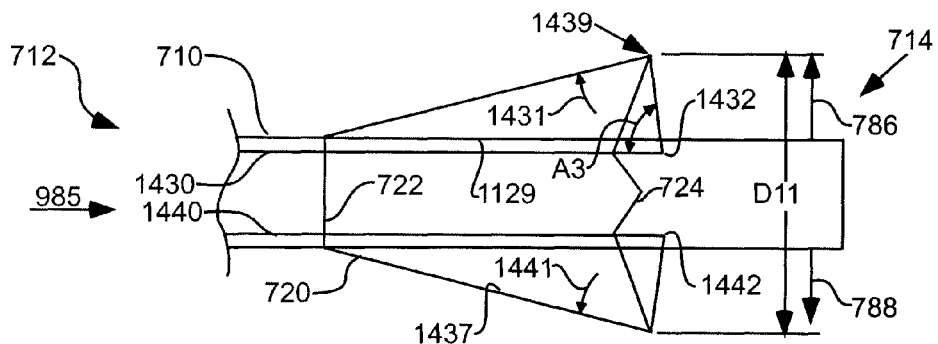
FIG. 14 is a side sectional view of a filter device having a distal portion attached to tendons which pivot at pivot point and extend through a cannula.

FIG. 14 is a side view of a distal portion of a cannula including a filter device having a distal portion attached to tendons which pivot at a pivot point and extend through a cannula. As shown in FIG. 14, filter device 720 includes tendons 1430 and 1440 which extend from proximal section 712 of cannula 710 to pivot points 1432 and 1442 and then are attached to distal portion 724, such as via attachment at attachment locations 1439. Note that attachment attachment locations 1439 may be an attachment achieved such as is described with respect to attachment at attachment locations 1139 and 1129. Tendons 1430 and 1440 may extend from proximal section 712 of cannula 710 to pivot points 1432 and 1442, such as via lumens as described below in FIGS. 17 and 18. Thus, tendons 1430 and 440 may be actuated such as by releasing tension or extending the tendons in direction 985 to transform distal portion 724 from first diameter D11 to a second diameter (e.g., such as a result of an expansion pressure similar to those described above with respect to FIGS. 7-13 and pressures 730 and 732 applied to generally conical inner surface 1437). It is contemplated that generally conical inner surface 1437 may be similar to conical shape 737 as described above. It is also to be appreciated that tendons 1430 and 1440 may extend through proximal section 712 such as to exit a proximal portion of cannula 710 exterior to the body of a subject so that tendons 1430 and 1440 may be locked in a locking position. More particularly, tendons 1430 and 1440 may extend through a tendon port similar to port 398 above (see FIG. 3 and accompanying text) and be locked in a locking position, such as by a locking mechanism disposed within a proximal portion of cannula 710, a tendon port, or external to the tendon port. Hence, tendons 1430 and 1440 may be retained in their locking position until it is desired to actuate them as described above. Moreover, after actuation of tendons 1430 and 1440 as described above, the tendons may be manipulated, or retracted as described below and returned to a locking position, such as their original locking position before actuation.

Moreover, tendons 1430 and 1440 may be of various suitable materials such as natural or synthetic fiber, plastic, stainless steel or various other appropriate metals. Likewise, pivot points 1432 and 1442 may be hard points such as a point where the tendon exits cannula 710 or a lumen as described below with respect to FIGS. 17 and 18. Moreover pivot point 1432 and 1442 may contain various appropriate pivot structures such as a curved surface, a hard point, an exit hole of an inflation lumen, an exit of a lumen such as lumens described below in FIGS. 17 and 18, or an aspiration hole such as hole 988 (see FIG. 9 and accompanying text), or a small wheel.

Figure 15:
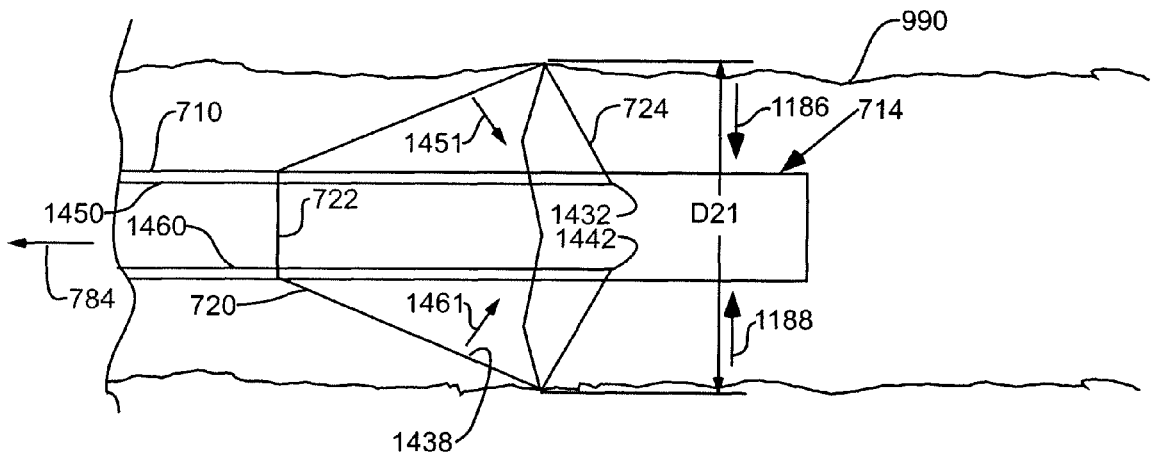
FIG. 15 is a side section view of a filter device with a distal portion having a second diameter, wherein the filter device is attached to tendons which extend through a cannula.

For example, FIG. 15 is a side section view of a filter device with a distal portion having a second diameter, wherein the filter device is attached to tendons which extend through a cannula. FIG. 15 shows actuated or released tendons 1450 and 1460 attached or coupled to distal portion 724 and cannula 710 (e.g., such as described below in FIGS. 17 and 18) for transforming distal portion 724 from first diameter D11 to second diameter D21. Note that according to some embodiments, diameter D11 may be a diameter similar to those described above with respect to first diameter D1 (see FIG. 7 and accompanying text), and second diameter D21 may be a diameter similar to those described above with respect to second diameter D2.

Figure 16:
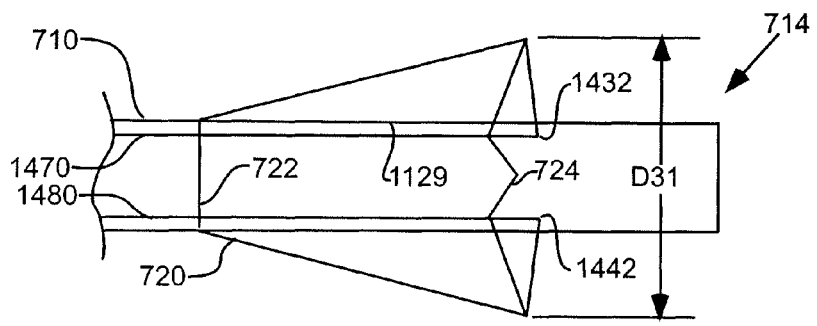
FIG. 16 is a side section view of a filter device with a distal portion having a third diameter and tendons attached to the distal portion and extending through a cannula.

Actuated or released tendons 1450 and 1460 may be manipulated, such as by retracting or pulling tendons 1450 and 1460 in direction 784 to move distal portion 724 in directions 1186 and 1188 to transform second diameter D21 into a third diameter, such as a diameter approximately equal to first diameter D11. For example, FIG. 16 is a side section view of a filter device with a distal portion having a third diameter and tendons attached to the distal portion and extending through a cannula. As shown in FIG. 16, reactuated or pulled tendons 1470 and 1480 are attached to distal portion 724, pivot at pivot points 1432 and 1442, and extend through cannula 710, such that distal portion 724 is transformed to third diameter D31. It is contemplated that third diameter D31 may be a diameter similar to those described above with respect to third diameter D30.

Suitable actuation or manipulation tension for tendons 1430 and 1440 includes a range of tension between for example, zero pounds and five pounds such as a suitable tension for causing or countering an expansion pressure (e.g., such as caused by pressures 730 and 732) and or retraction pressure (e.g., such as described by pressures 1140 and 1141) as described above.

According to some embodiments, distal portion 724 may also be retracted from the second diameter to approximately the first diameter by various other appropriate designs or systems including a self contracting filter device, such as using materials similar to the self expanding filter device described above, but having an opposite transformation principle. Likewise, distal portion 724 may be retracted by a sheath such as sheath 790. Specifically, as shown in FIG. 9, sheath 790 may be moved in direction 985, to retract and cover over filter device 720 such as where the force of sheath moving in a distal direction causes retraction of distal portion 724. Specifically, sheath 790 may be moved in direction 985 of FIG. 9 until the configuration of FIG. 7 is accomplished (e.g., with sheath 790 over distal portion 724 of filter device 720).

Besides the above descriptions of retracting the second diameter of distal portion 724, it is contemplated that filter device 720 can be removed from blood vessel 990 without retraction of the second diameter. For example, distal portion 724 may have a property such that it can be retracted in direction 784 along blood vessel 990 without damaging or breaching blood vessel 990. Specifically, distal portion 724 may have atraumatic tips (e.g., such as by having properties at second diameter D2 as shown in FIG. 9, or atraumatic tips instead of anchors 1122 and 1124 at positions shown in FIG. 12) such that filter device 720 can be retracted in direction 784 while having second diameter D2 or second diameter D20 under a second set of conditions. The tension on distal portion 724 is such that second diameter D20 may fluctuate (constrain or expand) as filter device 720 moves through one or more blood vessels.

Note that FIG. 14 also shows third angle A3 formed between tendon 1430 extending through lumen 710 and a point at which tendon 1430 is attached or coupled to distal portion 724. For example, according to some embodiments, third angle A3 shown in FIG. 14 may be an angle between 10° and 210°, such as an angle of 45°, 60°, 70°, 80°, 90°, 100°, 120°, and 125°.

According to some embodiments it is possible to mix technologies described above with respect to restraining distal portion 724 by a retraction or contraction pressure, expanding distal portion 724 by an expansion pressure, or retracting distal portion 724 by a retraction or contraction pressure. For example, it is possible for filter device 720 and cannula 710 to include a self expanding filter device, or balloon expanded filter device, restrained by tendons, wherein the distal portion of filter device 720 may be expanded to a second diameter by self expansion or inflation of the balloons as described above, and then retracted to a third diameter by deflation of the balloons or manipulation of the tendons as described above. Likewise, it is possible for filter device 720 and cannula 710 to include a self expanding filter device, or balloon expanded filter device, restrained by a sheath, wherein the distal portion of filter device 720 may be expanded to a second diameter by self expansion or inflation of the balloons as described above, and then retracted to a third diameter by deflation of the balloons or manipulation of tendons attached to the distal portion, as described above.

Figure 17:
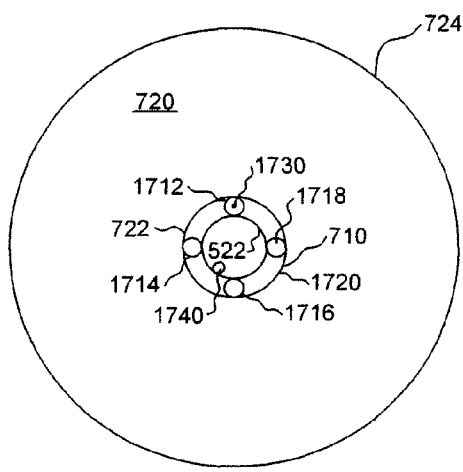
FIG. 17 is a front cross sectional view of the filter device of FIG. 9 showing a proximal portion of the filter device axially attached to an exterior surface of a cannula and lumens extending through the cannula.

FIG. 17 is a front cross sectional view of the filter device of FIG. 9 showing a proximal portion of the filter device axially attached to an exterior surface of a cannula and lumens extending through the cannula. As shown in FIG. 17, filter device 720 has distal portion 724 and proximal portion 722 attached to an exterior surface of cannula 710. For example, in embodiments, FIG. 17 may be a front cross sectional view of a filter device and cannula from perspective "A" of FIG. 12 or 15. FIG. 17 also shows lumens 1712, 1714, 1716, and 1718 extending within cannula 710, such as to extend from proximal section 712 of cannula 710 to a point distal to proximal portion 722 of filter 720 (See FIGS. 7, 9, and 11-16, and accompanying text). In addition, lumen 1740 is shown extending along inner surface of cannula 1722 from proximal section 712 of cannula 710 to a point distal to proximal portion 722 of filter 720. It is to be appreciated that lumens 1712, 1714, 1716, 1718, or 1740 may exit cannula 710 through exit holes or openings in the proximal end, distal end, or exterior of cannula 710, similar to how inflation lumen 9540 extends from proximal end 9504 to balloon 9510 and exits an inflation opening within balloon 9510, as described below with respect to balloon inflation lumen 9540 of FIGS. 69A-F. For example, lumens 1712, 1714, 1716, 1718, or 1740 may be lumens sufficient for passing inflation gas or fluid through, such as for inflating and deflating balloons 1132, 1134, 1142, or 1144 as described above (see FIGS. 11-13 and accompanying text). Also, lumens 1712, 1714, 1716, 1718, or 1740 may have a pivot point as any hole or opening where a lumen exits cannula 710, such as by having pivot point 1432 or 1442 at an opening where the lumen exits the exterior surface of cannula 710. Likewise, lumens 1712, 1714, 1716, 1718, or 1740 may be lumens sufficient for extending, acuating, releasing, extending, manipulating, or pulling tendons 1430, 1440, 1450, or 1460 therethrough (see FIGS. 14-16 and accompanying text). Specifically, lumen 1712 is shown in FIG. 17 with tendon 1730 extended therethrough (e.g., tendon 1730 may be a tendon such as tendon 1430, 1450, or 1470).

Furthermore, lumens described herein, such as lumen 1712 and lumen 1714 may provide for aspiration of particles, material, and matter as described above with respect to hole 988 (e.g., see FIG. 9 and accompanying text). Moreover, lumens 1712, 1714, 1716, 1718, or 1740 may be include a surrounding material, sleeve, cannula or lumen, such as described below with respect to infusion lumen 9520 or accessory lumen 9530 of FIGS. 69A-F In addition, according to some embodiments, any or all of lumens 1712, 1714, 1716, 1718, or 1740 may be used to inflate or deflate a balloon (e.g., such as balloons 1132, 1134, 1142, or 1144 as described above with respect to FIGS. 11-13 and accompanying text) as well as have a tendon extending therethrough (e.g., such as for acuating, releasing, extending, manipulating, or pulling tendons 1430, 1440, 1450, or 1460 therethrough as described above with respect to FIGS. 14-16 and accompanying text). Specifically, for example, lumen 1712 may be used for inflating and deflating balloons as described herein, as well as for having a tendon for actuation or manipulation as described herein, extending therethrough.

Note that it is contemplated that balloons described herein will be inflated and deflated using fluids, including fluids described herein as a treatment agent. Likewise, it is also contemplated that lumens described herein, such as lumen 1712 and 1714, may provide the capability to inflate or deflate occlusion devices and balloons, to contain tendons, to contain guide wires, to provide for delivery of treatment agent, to provide for aspiration of treatment agent or particles, or to provide for pressure release, such as by providing those capabilities for filter 720, devices other than filter 720, or at various regions of interest other than treatment region 996. Thus, balloons 1132, 1134, 1140, 1141, 1152, and 1154 (See FIGS. 11-13, and accompanying text), as well as lumens 1712, 1714, 1716, 1718, and 1740 may contain and provide sufficient pressure of a fluid, including a treatment agent, to inflate and deflate balloons as described herein.

Figure 18:
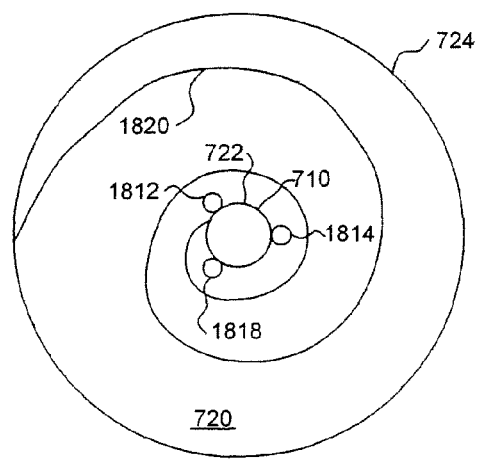
FIG. 18 is a front cross sectional view of a filter device having a proximal portion axially attached to an exterior surface of a cannula, wherein the filter device has a helical spring shape.

Although FIG. 17 shows four lumens extending through cannula 710, according to some embodiments, any number of lumens may be associated with cannula 710, filter device 720 other devices, or regions of interest as described herein. Constraints on the number of lumens that may be associated with cannula 710, include the number lumen or cannula necessary for a particular purpose and the overall size (e.g., inner or outer diameter) of a system for delivery of a treatment agent to a treatment region. For example, in an embodiment where filter device 720 has a helical spring shape, three lumen may be associated with cannula 710 to restrain, actuate, manipulate, or extend distal portion 724 of the filter device. More particularly, FIG. 18 is a front cross sectional view of a filter device having a proximal portion axially attached to an exterior surface of a cannula, wherein the filter device has a helical spring shape. FIG. 18 shows filter device 720 having proximal portion 722 axially attached to an exterior surface of cannula 710, wherein filter device 720 includes helical spring shape 1820. Helical spring shape 1820 may provide filter device 720 with a self-expanding frame, a self-contracting frame, or a frame portion (e.g., such as for having material stretched on the frame) as described herein. FIG. 18 also shows lumens 1812, 1814, and 1818 extending along the outer surface of cannula 710 from proximal section 712 of cannula 710 to a point distal to proximal portion 722 of filter 720. Lumens 1812, 1814, or 1818 may be a lumen such as is described above with respect to lumen 1712.

Figure 19:
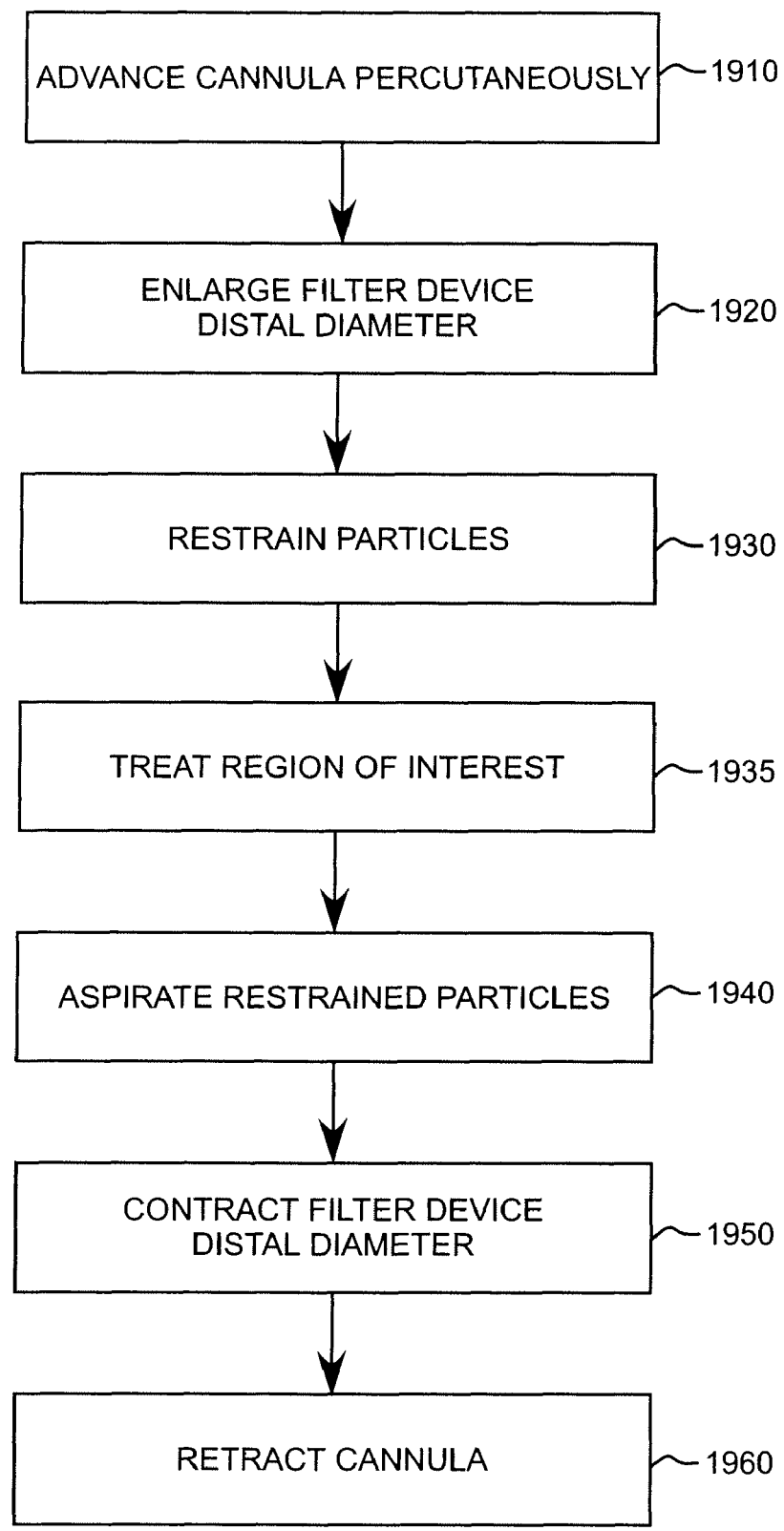
FIG. 19 is a flow diagram of a process for using a filter device to restrain and aspirate particles.

The various configurations of filter device 720 and lumen 710 described herein can be used to restrain and aspirate particles, material, and matter as described above for a variety of catheters, including guide catheters, delivery catheters, guide wires, and other cannula. For example, FIG. 19 is a flow diagram of a process for using a filter device to restrain and aspirate particles. At block 1910 a cannula, such as cannula 710, is advanced percutaneously through a blood vessel, such as blood vessel 990, wherein the cannula includes an exterior surface at or adjacent a distal end of the cannula axially coupled or connected to a proximal portion of a filter device, such as filter device 720. It is contemplated that the cannula may be advanced via a retrograde advancement, such as by being pushed up or down a blood vessel (e.g., such as a blood vein or artery) against or with a flow of blood. Specifically, the cannula may be advanced, such as from one blood vessel into a smaller blood vessel to provide retrograde infusion treatment, to a treatment region such as a region in a coronary sinus of a subject.

At block 1920, the distal diameter of a filter device, such as first diameter D1, is transformed or enlarged to a different second diameter, such as second diameter D2, that is approximately equivalent to an inner diameter of a blood vessel at a treatment region, such as diameter of vessel DV of blood vessel 990 at treatment region 996. For example, first diameter D1 may be expanded in directions 786 and 788 to second diameter D2 until second diameter D2 approximates an inner diameter of a coronary sinus of a subject at a treatment region. Moreover, it is contemplated that second diameter D2 may be expanded sufficiently to make a pressure wave form in the blood vessel or coronary sinus become ventricularized.

At block 1930 particles, material, or matter may be restrained from flowing through the filter device, such as by restraining a plurality of particles having a particle science greater than an average particle size of blood cells contained in blood flowing through the filter device. Thus, after block 1920, it is contemplated that a liquid including a drug, treatment agent, infusion pellets, suspended cells, stem cells, microspheres, or other drugs or treatment agent mentioned herein may be delivered or infused through a lumen extending from proximal section 712 of cannula 710 to treatment region 996 (e.g., to treat vessel 990 at treatment region 996). During or after delivery of the liquid, particles, material, or matter, such as described above, as well as stem cells, microspheres, metal, particles from devices, pieces of tissue, or other drugs or treatment agents mentioned herein may be restrained by the filter device, such as is described above with respect to filter device 720.

For instance, in various embodiments, at block 1935 a treatment agent mentioned herein is infused to a treatment region of a blood vessel, such with respect to FIGS. 3, 63, 69A-70, and 82. Specifically, a treatment tagent may be infused to a treatment region via a delivery catheter disposed through a lumen extending from proximal section 712 to distal end 714 of cannula 710, and extending to a region of a blood vessel.

At block 1940 the restrained particles are aspirated. For example, a plurality of particles being restrained, such as particles 980, can be aspirated proximate to the exterior surface of cannula 710, such as is described above with respect to hole 988 proximate to distal end 714 or lumen 1712 (e.g., see FIG. 9 and accompanying text). It is contemplated that aspirating may occur during delivery of liquid or after delivery of liquid as described above at block 1930.

At block 1950 the distal diameter of the filter device is contracted. For example, second diameter D2 may be contracted or retracted to a diameter that is approximately that of first diameter D1 (e.g., such as third diameter D30, or D31 as described above) in response to a retraction pressure (e.g., such as pressure 1140 and 1141, or 1451 and 1461).

At block 1960 the cannula and attached filter device are retracted, such as by retracting or withdrawing the cannula back out of vessel 990 and out of the subject. For example, as noted above, it is contemplated that cannula 710 and filter device 720 may be retracted without modifying distal portion 724 of filter device 720 (e.g., to leave distal portion 724 at second diameter D2), or may be retracted or removed from the subject after transforming or contracting second diameter D2 to become approximately the first diameter (e.g., block 1950).

Note that according to some embodiments, the process for using filter device 720 to restrain and aspirate particles shown and described above for FIG. 19 may also apply for an apparatus similar to apparatus 700 as shown in FIGS. 7-18, but having an occlusion device or balloon attached to cannula 710 instead of and at the location of filter device 720. Specifically, the process for using filter device 720 of FIG. 19 may have an occlusion device or balloon, instead of filter device 720, enlarged at block 1920 and restraining particles and fluid at block 1930, by occluding the blood vessel, such as is shown and described with respect to balloon 308 of FIGS. 3A, 3B, and 4. It can be appreciated that the other blocks of FIG. 19 also apply to a process having an occlusion device or balloon in place of filter device 720.

Figure 20:
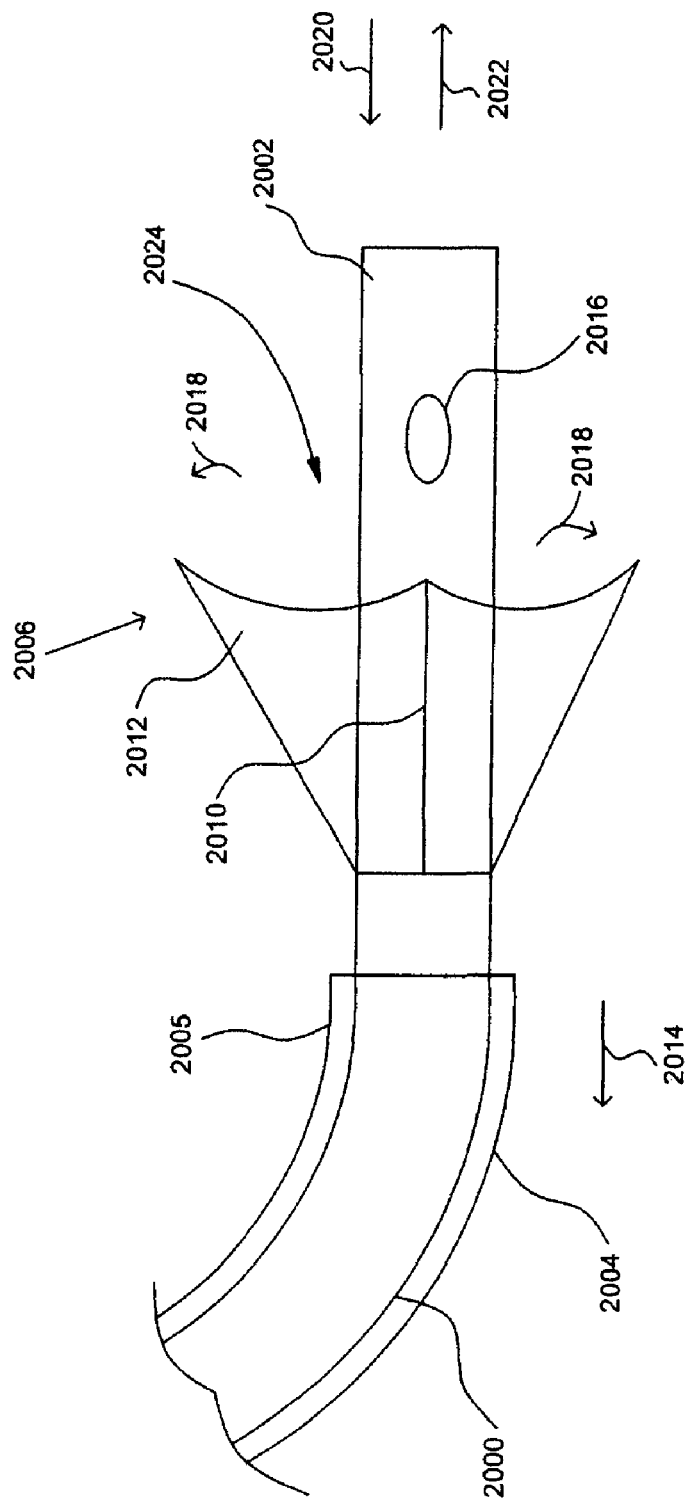
FIG. 20 illustrates a guide catheter with an occlusion device.

Referring now to FIG. 20, there is illustrated a guide catheter. Guide catheter 2000 has distal end 2002 and proximal end (not shown). Adjacent distal end 2002 is occlusion device 2006. Occlusion device 2006 may be provided with self-expanding frame 2010, and material 2012 stretched between frame structure or portions. Frame 2010 may be made of an elastic material or a superelastic material, for example, nitinol or NiTi, wherein NiTi or a material described above with respect to forming the frame portion of filter device 720. For example, guide catheter 2000 may be a guide catheter as described herein, such as cannula 710 described for FIG. 7 above, and frame 2010 may be a framed portion such as described above with respect to filter 720 described for FIG. 7. Moreover, in various embodiments, material 2012 may act as an occlusion device, such as by having no holes through it, or having a property such that fluid does not flow through it. For example, material 2012 may include one or more of a synthetic or natural latex or rubber, such as a polymer material; a polyetheramide; a plasticiser free thermoplastic elastomer; a thermoplastic blend; a block copolymer of polyether and polyester (e.g., such as a polyester sold under the trademark Hytrel® of DUPONT COMPANY); a biocompatible polymer such as a polyether block amide resin (e.g., for instance, PEBAX® of ATOCHEM CORPORATION); a polycarbonate or acrylonitrile bubadiene styrene (ABS); a biocompatible polymer such as a polyether block amide resin; a styrene isoprene styrene (SIS), a styrene butadiene styrene (SBS), a styrene ethylene butylene styrene (SEBS), a polyetherurethane, an ethyl propylene, an ethylene vinyl acetate (EVA), an ethylene methacrylic acid, an ethylene methyl acrylate, an ethylene methyl acrylate acrylic acid, a material from a material family of one of styrenic block copolymers and polyurethanes, a melt processible polymer, a low durometer material, nylon, and other materials that can block fluid flow.

Sheath 2004, for example, a retractable or a tear-away sheath, such as sheath 790, is shown pulled away from occlusion device 2006 in direction of arrow 2014. When guide catheter 2000 is deployed into a vessel (e.g., such as is described above with respect to deployment of cannula 710 for FIG. 7, and including a blood vessel of a subject or fluid flow 2020 occurs in direction of arrow 2014.

Distal end 2005 of sheath may be covering occlusion device 2006. After distal end 2002 of catheter is located in a preferred location, sheath 2004 may be moved in a proximal direction (e.g., a direction of arrow 2014) to uncover occlusion device 2006. Thereafter, self-expanding frame 2010 forces open device 2006 in direction of arrows 2018 so that occlusion device 2006 occupies substantially the entire vessel. Any fluid flowing through vessel in direction of arrows 2020 must then pass through material 2012, or be trapped by material 2012.

In another embodiment, if guide catheter is placed in a vessel with fluid flow in the direction of arrow 2022, then occlusion device 2006 may be turned around so that opening 2024 of occlusion device 2006 faces into the direction of fluid flow (e.g., see arrow 2022). Therefore, frame 2010 and fluid flow 2020 or 2022 serve to force occlusion device 2006 against the interior walls of a vessel (not shown). Aspiration side-hole 2016 may be provided adjacent distal end 2002 in guide catheter 2000 such as at a location and to function as is described above with respect to hole 988 for FIG. 9 (e.g., distal to a proximal end of occlusion device 2006). Thus, aspiration side-hole 2016 may be used to aspirate fluid or particles from a vessel distal to device 2006.

Figure 21:
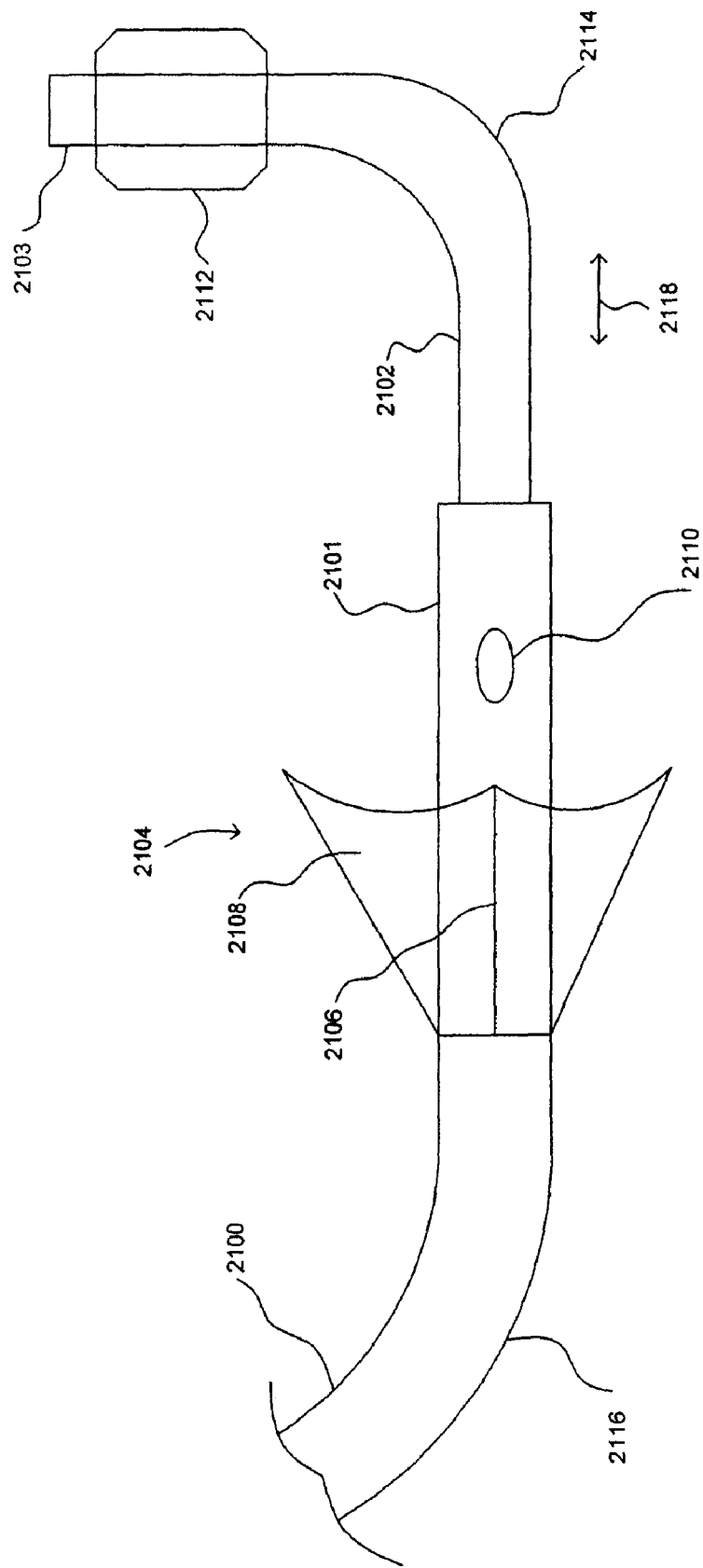
FIG. 21 illustrates a telescoping guide catheter system.

Referring now to FIG. 21, there is illustrated a telescoping guide catheter system. Telescoping guide catheter system includes outer guide catheter 2100 having proximal end (not shown) and distal end 2101. Outer guide catheter 2100 has an inner diameter adapted to contain inner guide catheter 2102, for example, the outside diameter of inner guide catheter 2102 is smaller than the inside diameter of outer guide catheter 2100, so that outer guide catheter 2100 and inner guide catheter 2102 may be slidingly engaged. Inner guide catheter 2102 has proximal end (not shown) and distal end 2103. Outer guide catheter 2100 is provided with occlusion device 2104 at distal end 2101, and inner guide catheter 2102 is provided with occlusion device 2112 at distal end 2103.

As illustrated, occlusion device 2104 includes frame 2106, for example, an elastic frame, and material 2108 stretched between structure or portions of frame 2106. For example, frame 2106 may have a similar structure, functionality, and material as that described above for frame 2010 of FIG. 20. Likewise, material 2108 may have a similar structure, functionality, and material as that described above for material 2012 of FIG. 20. There may also be provided a sheath (not shown) to cover occlusion device 2104 until such time as it is to be deployed, and the same or a different sheath may be used for device recovery. Catheter 2102 may also include aspiration side-hole 2110 at distal end 2101, which may be used to aspirate fluid or particles distal to occlusion device 2104, such as at a location and to function as is described above with respect to hole 988 for FIG. 9. In FIG. 21, occlusion device 2112 is shown as balloon 2112, which may be any type of balloon or occlusion device such as occlusion device 2006, or may be filter device such as filter device 720.

Inner guide catheter 2102 has first curve 2114, and outer guide catheter 2100 has second curve 2116. For example, according to some embodiments, first curve 2114 may be an angle between 10° and 125°, such as an angle of 10°, 20°, 30°, 45°, 60°, 80°, 90°, 100°, 120°, and 125°. Also, according to some embodiments, second curve 2116 may be an angle between 10° and 90°, such as an angle of 10°, 15°, 20°, 25°, 35°, 45°, 60°, 70°, 80°, and 90°. By sliding inner guide catheter 2102 back and forth in direction of arrows 2118 within outer guide catheter 2100, and rotating outer guide catheter 2100 or inner guide catheter 2102, distal end 2103 may be steered and tracked through a vessel network.

Note that according to some embodiments proximate end 712 of FIG. 7, a proximate end of guide catheter 2000, or a proximate end of guide catheter 2100 may be attached to or extend to a guide catheter proximate portion, such as a proximate portion similar to proximate portion 305 of FIG. 3, and having the necessary holders, tracks, cannulas, lumens, and ports to provide for the functionality of cannula 710 of FIG. 7, guide catheter 2000, or guide catheter 2100, or any other guide catheter as described herein.

Figure 22:
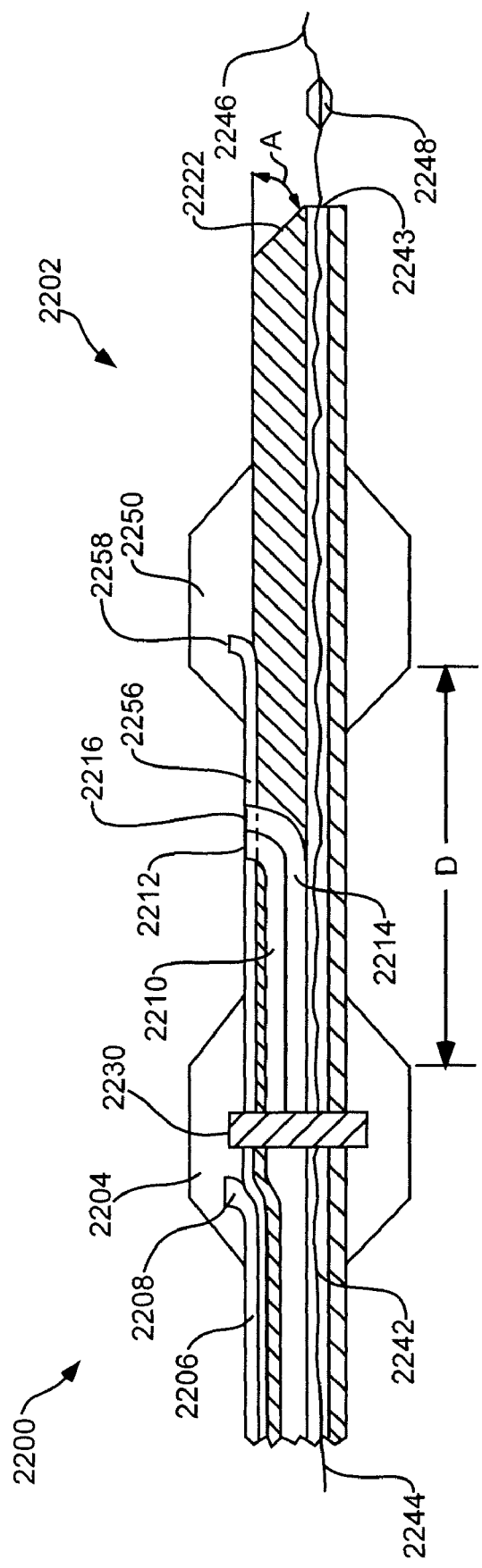
FIG. 22 illustrates a balloon catheter tip with a guidewire.

Referring now to FIGS. 22 and 23, there is illustrated the distal end and proximal end of a balloon catheter. Balloon catheter 2200 may be a delivery or infusion catheter having distal end 2202 and proximal end 2203. Adjacent distal end 2202 of catheter is first balloon 2204. First balloon inflation cannula 2206 has a lumen there through and distal end including first opening 2208 within first balloon 2204 to inflate or deflate first balloon 2204. There is also provided second balloon 2250, with second balloon 2250 distal to first balloon 2204. First balloon 2204 or second balloon 2250 may be made of various appropriate natural rubber, polymer, lined ePTFE, thermoplastic blend, copolymer materials, having various appropriate dimensions, and being attached to balloon catheter 220 by various procedures (e.g., such as laser bonding, adhesive bonding, or heat bonding) as described herein.

First balloon 2204 may be a distance from second balloon 2250 sufficient to block a proximal and a distal end of a treatment region, such as a region for delivering a treatment agent. For example, distance D defining a region for delivering a treatment agent between first balloon 2204 and second balloon 2250 may be a distance in the range between one centimeter and 20 centimeters, such as a distance of 10 centimeters.

Moreover, according to some embodiments, first balloon 2204 or second balloon 2250 may have a maximum inflated outer diameter of between two millimeters and 15 millimeters, such as by having an outer diameter during inflation of 10 millimeters. Furthermore, according to some embodiments, first balloon 2204 or second balloon 2250 may employ a wedge or conical tapered shape, such as a shape having a tapered outer diameter towards distance D of four millimeters and an increasing diameter to a maximum diameter away from distance D of 10 millimeters. Thus it is possible to select balloons having a tapered profile to promote better sealing of a treatment region in a vessel as well as better centering of the balloons upon inflation. Likewise, the size and shape of first balloon 2204 and second balloon 2250 may be selected to provide a treatment region that may be pressurized, such as by a pressurized infusion of treatment agent as described herein, while preventing the flow of infused treatment agents out of the treatment region. For example, second balloon 2250 can be selected to prevent the flow of treatment agents out of a treatment region, such as defined within a blood vessel along distance D, while first balloon 2204 can be selected to prevent the backflow of infused treatment agents out of the treatment region and towards proximal end 2203. Next, the size, shape, and material of first balloon 2204 and second balloon 2250 may be selected to establish a desired pressure gradient within a vessel at the location of proximate to or between first balloon 2204 and second balloon 2250. More particularly, size, shape, material, and inflation pressure of first balloon 2204 and second balloon 2250 may be selected such that a treatment region as defined by distance D within a vessel may be pressurized, such as with a treatment agent, to a pressure between one and 30 atmospheres (e.g., such as to a pressure of between six and eight atmospheres).

First balloon 2204 and second balloon 2250 may be the same shape, size, or material, or first balloon 2204 may have a different shape, size, or material than second balloon 2250. Second balloon inflation cannula 2256 has a lumen there through and includes distal end and second opening 2258 within second balloon 2250 to inflate or deflate second balloon 2250. In another embodiment, first balloon inflation lumen 2206 and second balloon inflation cannula 2256 are the same lumen, with two openings 2208 and 2258, while in another embodiment (as illustrated), first balloon inflation lumen 2206 is different than and not connected to second balloon inflation cannula 2256.

Pressure-sensing cannula 2210 has distal end and pressure sensing opening 2212, which enables pressure-sensing, such as via a pressure sensing device with respect to fitting 2548, or other measurements or parameters to be taken in a region of a vessel between first balloon 2204 and second balloon 2250, or where ever distal end 2202 is placed. Delivery cannula 2214 has distal end and delivery opening 2216 which enables a fluid or treatment agent path from proximal end 2203 of balloon catheter 2200 to opening 2216 between first balloon 2204 and second balloon 2250.

In various embodiments, balloon catheter 2200 has a tapered tip. Tapered tip of catheter 2200 may enable easier tracking of distal end 2202 of catheter through a blood vessel. In various embodiments, distal end 2202 may have tapered cut 2222, which may be curved to have the profile shown in FIG. 22. Other configurations of distal ends 2202 are envisioned which would ease tracking through a blood vessel. For example, tapered cut 2222 may be at angle "A" with respect to the longitudinal axis of catheter 2200, where angel "A" may be an angle between 10° and 90°, such as an angle of 10°, 15°, 20°, 25°, 35°, 45°, 60°, 70°, 80°, and 90°. Also, tapered cut 2222 may have or form a tapered shape with respect to the longitudinal axis of catheter 2200, where the tapered shaped may include one or more of a convex, a concave, and a three dimensionally shaped cut. Thus, tapered cut 2222 can have angle "A" and a tapered shape sufficient to allow balloon catheter 2200 to be fed through a vessel such as is described above with respect to feeding guide catheter 302 through a vessel; or to be fed through another catheter such as guide catheter 302 or 502, such as is described above with respect to delivery catheter 310 being fed through guide catheter 302. Balloon catheter 2200 may have an outer diameter or outer dimension to fit within a guide catheter such as guide catheter 302 or guide catheter 502. For example, balloon catheter 2200 may have an outer diameter of between 5 French and 6 French and be capable of fitting within a guide catheter having an outer diameter of between 8 French and 9 French.

Balloon catheter 2200 may have one or more radio-opaque markers applied to its outer diameter, such as by adhesive, laser bonding, or heat bonding, or may include a filler such as barium sulfate added to the polymeric material used to form balloon catheter 2200 near distal end 2202 to track the position of distal end 2202. According to some embodiments, such markers or filler may have various widths such as a width between one millimeter and two centimeters, and may extend around a portion of or completely around the circumference of balloon catheter 2200.

For example, catheter 2200 may also include marker 2230, for example, a radio-opaque marker, which may serve to ease visualization of distal end 2202 of catheter 2200 with a diagnostic visualization system. There may also be provided a second marker (not shown) adjacent second balloon 2250, so that first marker 2230 and second marker (not shown) may be used to locate first balloon 2204 and second balloon 2250, respectively.

Catheter 2200 may also include guidewire cannula 2242 to extend from proximal end 2203 through catheter 2200 to guidewire opening 2243. Guidewire cannula 2242 has distal end and guidewire opening 2243, adjacent distal end 2202 of catheter 2200. Guidewire cannula 2242 has dimensions to receive guidewire 2244. Guidewire 2244 is illustrated, where guidewire 2244 has distal end 2246 and occlusion device 2248 attached to guidewire 2244 adjacent guidewire distal end 2246. Occlusion device 2248 may be attached to guidewire 2244 by various appropriate methods including laser bonding, adhesive bonding, thermal bonding and other bonding processes for attaching an occlusion device, such as a balloon, to a guidewire or catheter. In addition, balloon catheter 2200 and guide catheter 1002 may have a length such as is described above with respect to the length of guide catheter 302.

FIG. 23 also shows first balloon inflation cannula 2206 attached to first balloon inflation port 2290, such as via adhesive bonding, heat bonding, threaded bonding or various other appropriate bonding processes for attaching first balloon inflation port 2290 sufficiently so that an appropriate volume and pressure of liquid may pass therethrough to inflate first balloon 2204. Likewise, second balloon inflation cannula 2256 is attached to second balloon inflation port, such as is described above with respect to first balloon inflation port 2290. Pressure sensing cannula 2210 is attached to pressure sensing port 2294 similar to methods described above for attaching port 2290 to cannula 2206, and sufficiently to allow a volume in pressure of fluid to float through pressure sensing port 2294, such as to a pressure sensing device attached to pressure sensing port 2294, such as is described herein with respect to a pressure sensing device with respect to fitting 2548. Next, delivery cannula 2214 is attached to delivery port 2296, such as is described above with respect to attachment of port 2290 to cannula 2206, and sufficiently for delivery of a volume and pressure of a liquid or treatment agent and to a treatment region, to provide a treatment or treatment region as described herein. Finally, guidewire cannula 2242 is attached to guidewire port 2298, similarly to the attachment described above for attaching port 2290 to cannula 2206, and sufficiently so that guidewire 2244 can extend through guidewire port 2298 and can be manipulated, controlled, and used to place guidewire distal end 2246 or occlusion device 2248 at a desired region within a vessel as described herein.

Figure 37:
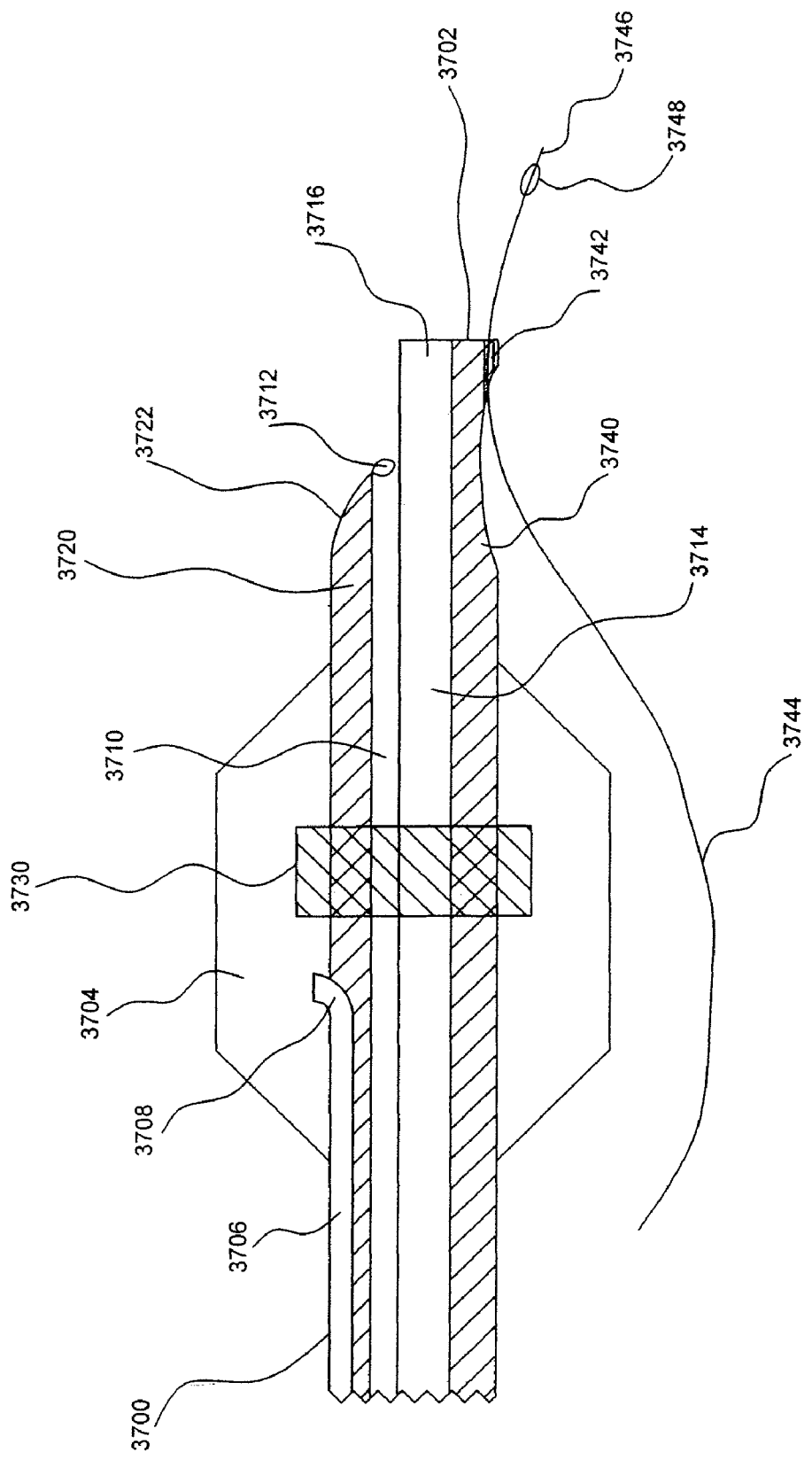
FIG. 37 illustrates a balloon catheter tip with a guidewire.

FIG. 24 shows a section view of FIG. 23 through line D-D'. As shown in FIG. 24, first balloon inflation cannula 2206, second balloon inflation cannula 2256, pressure sensing cannula 2210, delivery cannula 2214, and guidewire cannula 2242 are shown disposed through balloon catheter 2200 such as from proximal end 2203 to distal end 2202. Furthermore, guidewire 2244 is shown fed through or disposed through guidewire cannula 2242, such as is described above. In another embodiment, guidewire and guidewire lumen (not shown) are in a monorail or OTW configuration. It is also contemplated that the guidewire and guidewire lumen (not shown) can te in a rapid-transfuser type configuration, such as illustrated in FIGS. 3 and 37, and described in accompanying text.

Figure 25:
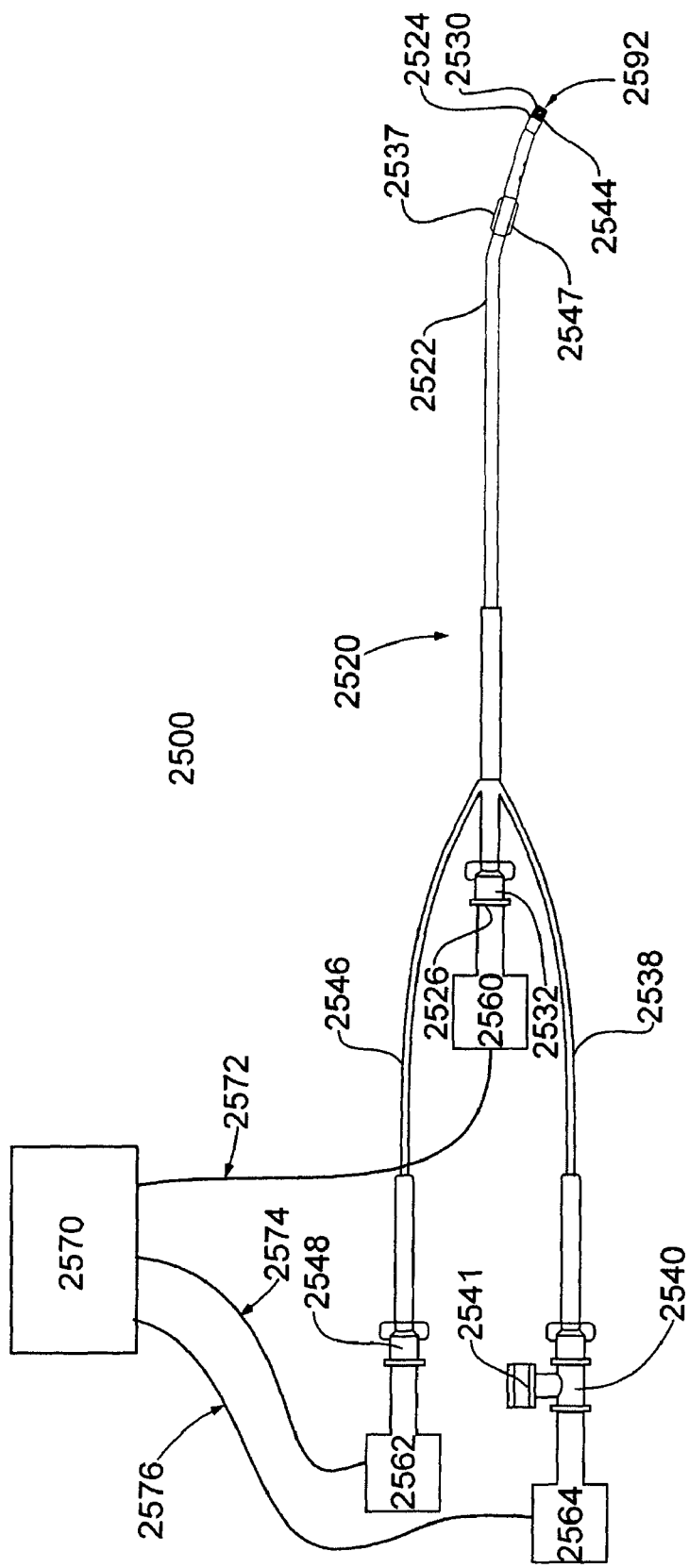
FIG. 25 schematically illustrates a delivery catheter system.
Figure 26:
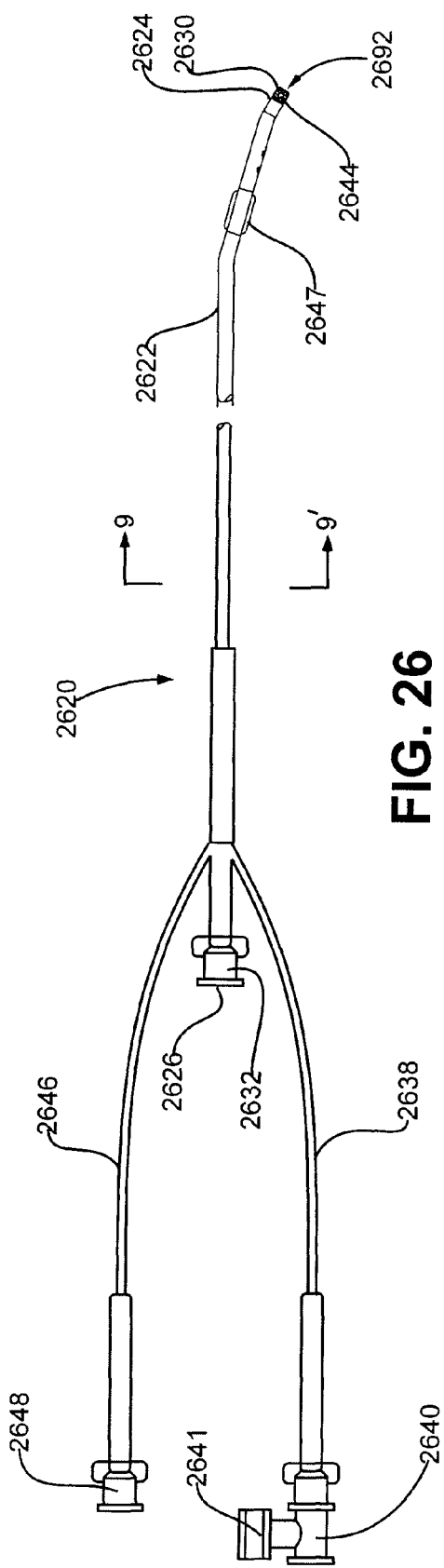
FIG. 26 schematically illustrates a side elevational view of a delivery catheter.
Figure 28:
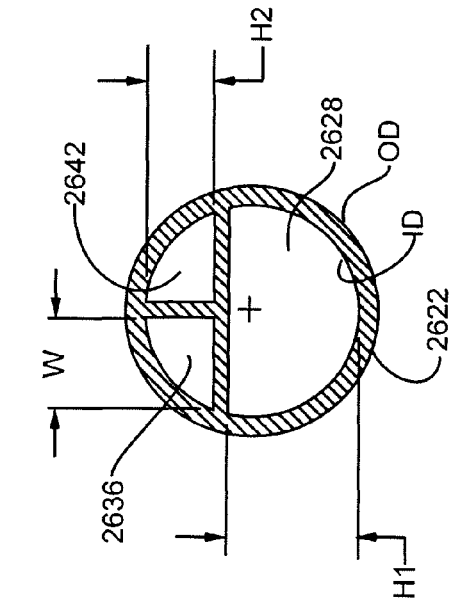
FIG. 28 schematically illustrates transverse cross-sections of the delivery catheter of FIG. 26 taken along the line 9-9.

FIG. 25 illustrates a catheter system. Catheter system 2500 includes delivery catheter 2520 having flexible shaft 2522, distal end 2524, proximal end 2526, with a delivery lumen extending therebetween. For instance, delivery catheter 2520 or any delivery catheter may have a distal end has an outer diameter less than about 10 mm, seven mm, five mm or three mm. In addition, according to some embodiments, delivery catheter 2520 or any delivery catheter may have a flexible shaft made of a bio-compatible polymer, a bio-compatible polymer having a durometer hardness of about 30 to about 100 shore D, a bio-compatible polymer having a durometer hardness of about 50 to about 70 shore D, a polyether block amide resin, or a flexible shaft that is radiopaque. Soft tip 2530 is bonded to distal end 2524 of shaft 2522. The delivery lumen extends from fitting 2532 at proximal end 2526 through shaft 2522 and through soft tip 2530 to outlet port 2592 in soft tip 2530. Note that a delivery lumen may have cross-sectional area suitable for advancing into a cardiovascular system of a patient and to deliver a treatment agent to a treatment region in a blood vessel of the patient. Suitable cross-sectional areas include at least about 0.95 mm$^2$, 2 mm$^2$, 3 mm$^2$, 5 mm$^2$, or 10 mm$^2$. One or more side holes in communication with the delivery lumen may also be provided near distal end 2524 of shaft 2522. Pressure increasing device 2560 is shown attached to fitting 2532.

Catheter 2520 is provided with balloon 2547 on distal end 2524 of catheter 2520, which balloon 2547 is adapted to occlude the coronary sinus or another vessel when inflated. An inflation lumen extends through shaft 2522 and is in communication with the interior of balloon 2547 through opening 2537. Specifically, the inflation lumen, or any other inflation lumen may be a balloon inflation lumen within a flexible tube or cannula shaft (e.g., such as a lumen having a surrounding material, sleeve, cannula or lumen, such as described below with respect to infusion lumen 9520 or accessory lumen 9530 of FIGS. 69A-F). Near proximal end 2526, the inflation lumen is connected to inflation extension tube 2538 attached to shaft 2522 having fitting 2540 at its proximal end shown attached to inflation device 2564. Optionally, pressure release valve 2541 may be connected to inflation extension tube 2538 to prevent over inflation of balloon 2547. Extension tube 2538 may have a surrounding material, sleeve, cannula or lumen, such as described below with respect to infusion lumen 9520 or accessory lumen 9530 of FIGS. 69A-F.

A pressure lumen is also provided in shaft 2522 which opens at pressure port 2544 on side-wall of shaft 2522 near distal end 2524, or in soft tip 2530 as illustrated. The pressure lumen is connected to extension tube 2546 attached to shaft 2522 near proximal end 2526. Extension tube 2546 has fitting 2548 at its proximal end shown connected to pressure measuring device 2562. Extension tube 2546 may have a surrounding material, sleeve, cannula or lumen, such as described below with respect to infusion lumen 9520 or accessory lumen 9530 of FIGS. 69A-F.

Pressure increasing device 2560 is shown connected by connection 2572 to controller 2570. Pressure measuring device 2562 is shown connected to controller 2570 by connection 2574. Inflation device 2564 is shown connected to controller 2570 by connection 2576.

In various embodiments, distal end 2524 of catheter 2520 is inserted into a vessel, for example, the coronary sinus. Once distal end 2524 of catheter 2520 is in place, balloon 2547 may be inflated by inflation device 2564. Pressure measuring device 2562 measures pressure distal to balloon 2547 through pressure port 2544 on side-wall of shaft 2522. Once the pressure waveform in the vessel has become ventricularized, for example, blood beating against balloon 2547 in a similar rhythm to a heartbeat, inflation of balloon 2547 is stopped by controller 2570. At this point, pressure increasing device 2560 begins to force a liquid through catheter 2520 to soft tip 2530 to outlet port 2592. Liquid is forced into the vessel distal to balloon 2547. Pressure measuring device 2562 measures pressure distal of balloon while liquid is being forced by pressure increasing device 2560. Controller 2570 controls pressure increasing device 2560 to regulate fluid flow and pressure, by the information provided by pressure measuring device 2562. After a sufficient period of time, controller 2570 stops the delivery of liquid by pressure increasing device 2560, then deflates balloon 2547 with inflation device 2564, and catheter 2520 may then be removed from the vessel. It is worth explaining that although references are made herein to a pressure lumen and a pressure-sensing device (e.g., such as is describe above with respect to FIG. 25), it is considered that a pressure lumen, can be used for measuring other parameters including flow, oxygen saturation, pH, or temperature. Similarly, a pressure-sensing device, can be exchanged with another device to measure one of the parameters above. Moreover, although system 2500 describes a catheter with three lumens, it is envisioned that a cannula or catheter (e.g., such as is describe above with respect to FIG. 25), may have four or more lumens. Specifically, a cannula or catheter as described herein, may include a balloon inflation lumen, a delivery lumen, and two parameter measurement lumens (e.g., such as one lumen to measure pressure and another lumen to measure temperature).

Figures 33, 34:
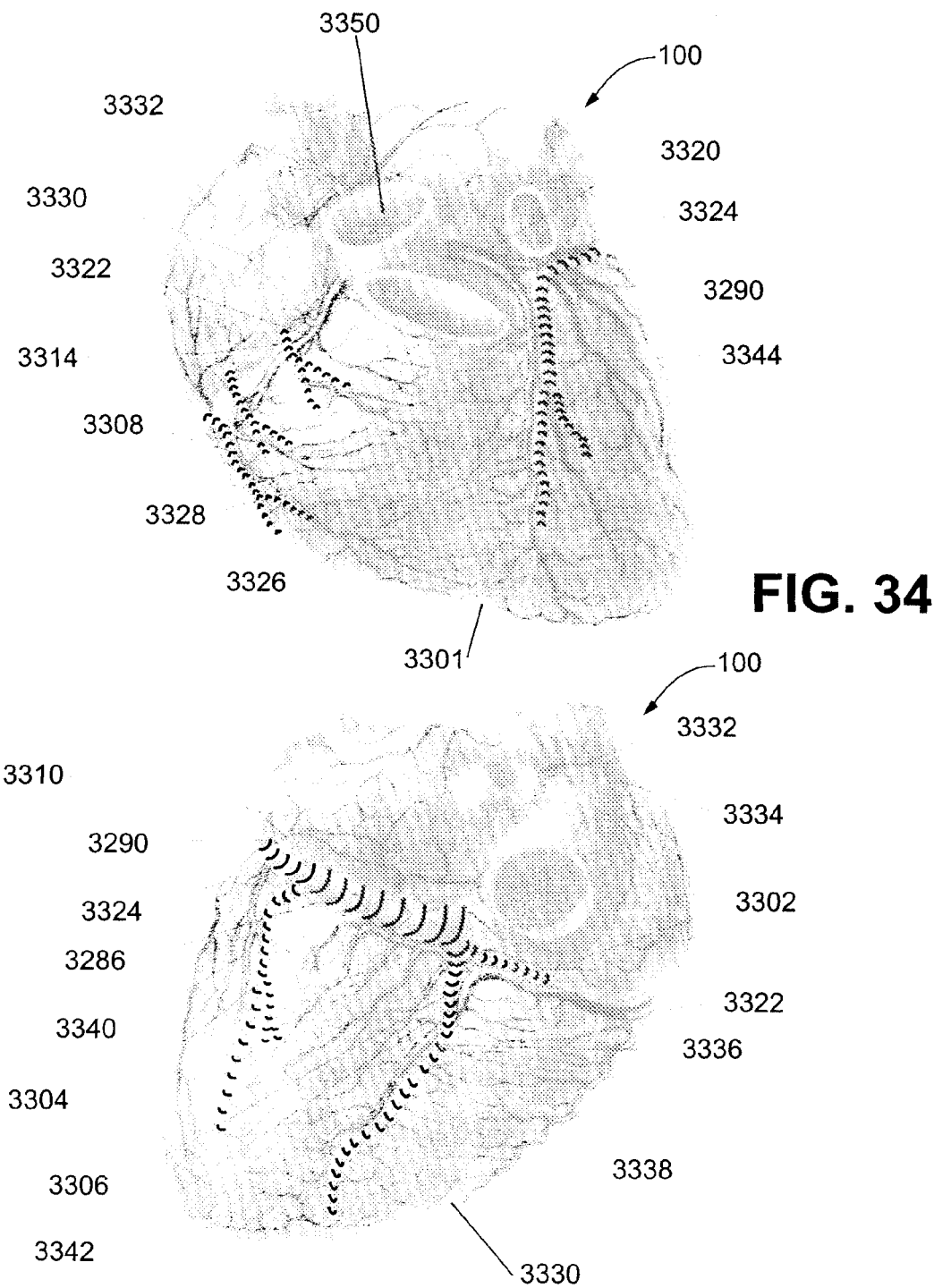
FIG. 33 schematically illustrates the diaphragmatic surface of the heart.
FIG. 34 schematically illustrates the sternocostal surface of the heart.

Delivery catheter 2620 is shown in FIGS. 26, 27, 28 and 29. Delivery catheter 2620 includes flexible shaft 2622 having distal end 2624, proximal end 2626 and delivery lumen 2628 extending therebetween. In various embodiments, shaft 2622 is at least about 50 cm long, and in another embodiment, at least about 60 cm long, between proximal end 2626 and distal end 2624, so that distal end 2624 may be positioned in the coronary sinus or another vessel (as seen in FIGS. 33 and 34) with proximal end 2626 extending out of the patient through a puncture in a peripheral vein, such as a femoral vein. Shaft 2622 is made of a material such that it is sufficiently flexible to navigate this path without difficulty. In various embodiments, shaft 2622 is made of a biocompatible polymer such as a polyether block amide resin, for example, PEBAX®, a registered trademark of Atochem, with a durometer in a range of about 50 to about 72 Shore D. In another embodiment, a portion, including the entire portion, of shaft 2622 is radiopaque to permit fluoroscopic observation thereof to facilitate positioning. Radiopaque markers may be applied to the shaft near distal end 2624, or a filler such as barium sulfate may be added to the polymeric material used to form shaft 2622.

To allow percutaneous introduction of delivery catheter 2620 in a peripheral vein, in various embodiments, shaft 2622 will have an outer diameter ("OD") of no more than about 5.0 mm from distal end 2624 to at least about 30 cm proximal thereto, and in another embodiment, to at least about 50 cm proximal thereto.

In some embodiments, delivery catheters described herein (e.g., such as balloon catheter 2200, delivery catheter 2520, or delivery catheter 2620) may be adapted for introduction through a commercially-available 9 French or 10 French introducer sheath or a suitably sized guide catheter, or by feeding over a guidewire, or for introduction by surgical cut-down into a comparably-sized blood vessel (e.g., such as an artery of vein, including a peripheral vein). Additionally, the delivery catheters described herein may be adapted to be introduced through guide catheters (e.g., such as catheter 302, 502, 2000, or 2100) to be delivered to a location of a blood vessel from which the distal end of the delivery catheter (e.g., such as distal end 2524 or 2624) may be advanced to a treatment region of a blood vessel to be treated by infusing a treatment agent (e.g., such as by infusion through system 2500, as described above).

In various embodiments, a guide catheter (e.g., such as a guide catheter to be used with a delivery catheters described herein) is adapted to be fed into a femoral vein, then to an external iliac vein, then to a common iliac vein, to inferior vena cava 116), then into right atrium 122, and into coronary sinus 3286 (see FIG. 32), and can then be fed further into venus system on exterior of heart (see FIGS. 33 and 34). In another embodiment, guide catheter is adapted to be fed into an external jugular vein or an internal jugular vein, into superior vena cava 126, and then into right atrium 122 and into coronary sinus 3286, where guide catheter may stay in coronary sinus 3286 (see FIG. 32), or be fed further into the venus system on exterior of the heart (see FIGS. 33 and 34).

In various embodiments, a suitable guide catheter is described in a co-pending patent application Ser. No. 10/293,535, filed on Nov. 12, 2002. Co-pending patent application Ser. No. 10/293,535, filed on Nov. 12, 2002 is herein incorporated by reference in its entirety. The guide catheter disclosed in the co-pending patent application may be inserted into a blood vessel, such as a femoral vein. Note that that guide catheter has a first convex curved portion, a concave curved portion distal to the first convex curved portion, and a second convex curved portion distal to the concave curve portion. Suitable guide catheters may also include an occlusion balloon at a distal end (e.g., such as catheter 302, 502, and 2100 having balloons 308, 510, and 2112, respectively). Other suitable guide catheters include the Viking Opima Line™ (a trademark of Guidant Corporation), the ACS Viking™ line of guide catheters (a trademark of Guidant Corporation), and the ACS RAD Curve™ line of guide catheters (a trademark of Guidant Corporation). Appropriate guide catheters also include EasyTrak® guiding catheters, Rapido® guiding catheters, and telescoping guide catheters, for example, CS-MP REF 7300 and CS-IC 90 REF 666776-101.

Figure 27:
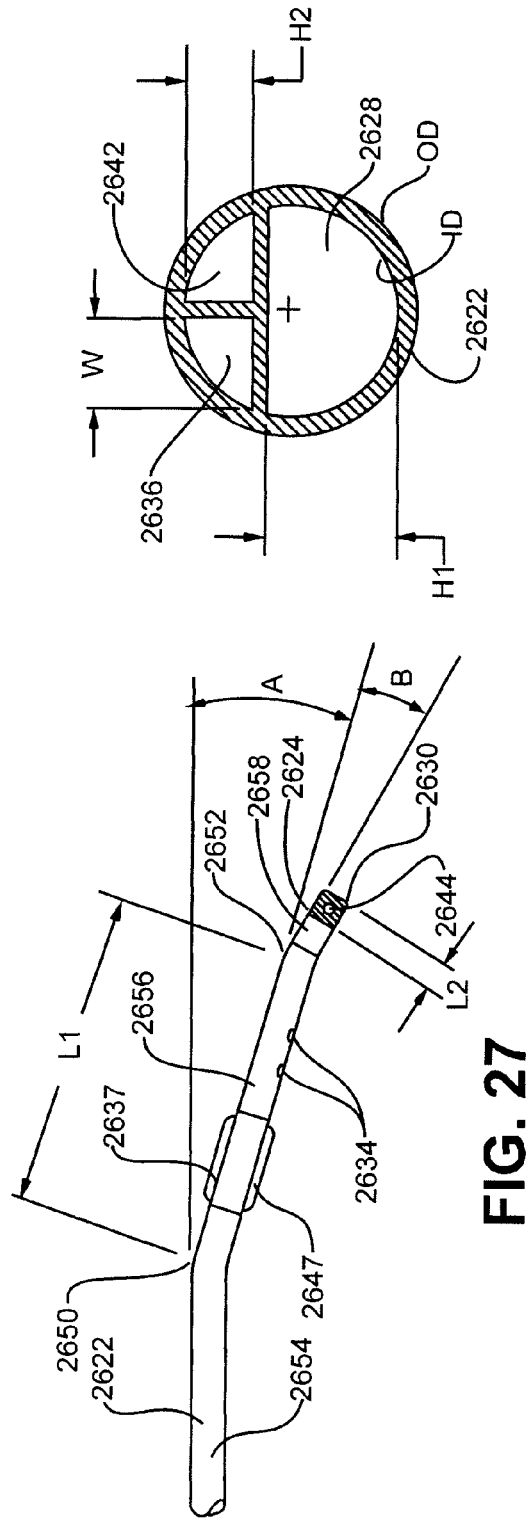
FIG. 27 schematically illustrates a side view of the distal portion of the delivery catheter of FIG. 26.

Referring again to FIGS. 26-29, soft tip 2630 (of for example, PEBAX® with a durometer of 20 to 30 Shore D) is bonded to distal end 2624 of shaft 2622 to reduce the risk of trauma to the coronary sinus or other vessels. Delivery lumen 2628 extends from fitting 2632 at proximal end 2626 through shaft 2622 and through soft tip 2630 to outlet port 2692 in the distal end of soft tip 2630. Side holes 2634 in communication with delivery lumen 2628 may also be provided near distal end 2624 of shaft 2622 as shown in FIG. 27. In various embodiments, delivery lumen 2628 preferably has a cross-sectional area no less than about 4 mm$^2$ at any point between proximal end 2626 and outlet port 2692 to facilitate delivery of treatment agent at sufficient flow rates while keeping the pressure at which the treatment agent is delivered low enough to avoid excessive hemolysis if there is a blood component of the treatment agent, as described more fully below. In various embodiments, the inner diameter (ID) of delivery lumen 2628 is at least about 2.8 mm, and height H1 is at least about 1.8 mm.

Catheter 2620 is provided with balloon 2647 on distal end 2624 of catheter 2620 which is adapted to occlude the coronary sinus or another vessel (see FIGS. 33 and 34) when inflated. In various embodiments, balloon 2647 includes a biocompatible polymer such as a polyether block amide resin, for example, PEBAX® (a registered trademark of ATOCHEM CORPORATION, PUTEAUX, FRANCE). In another embodiment, balloon 2647 is a biocompatible polymer blend of polyurethane and silicone, for example PurSil™ (a trademark of THE POLYMER TECHNOLOGY GROUP, BERKELEY, CALIFORNIA). In various embodiments, balloon 2647 has an inflated diameter range of about four mm to about nine mm, an uninflated diameter of about three mm, and a working length of about six mm. For instance, a balloon as described above with respect to balloons 308, 510, and 2112, may be inflated as described below with respect to balloons 8810 and 9510, or by an inflation device such as apparatus 9700 or 9800 of FIG. 75A-81.

In various embodiments, balloon 2647 may be located at least about 15 mm from distal end 2624 of shaft 2622 so that, during positioning, if balloon 2647 is pulled out of the coronary sinus, there is sufficient length of shaft 2622 distal to the balloon that will remain in the coronary sinus to eliminate the need to relocate distal end 2624 in the coronary sinus.

In various embodiments, balloon 2647 is formed by dipping a mandrel in liquefied polymer and curing as needed. Balloon 2647 may be attached to shaft 2622 by, for example, heat welding or an adhesive.

Inflation lumen 2636 extends through shaft 2622 and is in communication with the interior of balloon 2647 through opening 2637. Near proximal end 2626, inflation lumen 2636 is connected to inflation extension tube 2638 attached to shaft 2622 having fitting 2640 at its proximal end for attachment to an inflation fluid delivery device. In various embodiments, inflation lumen 2636 is configured to allow delivery of inflation fluid or gas at a sufficient rate to fully inflate balloon 2647 in about two seconds. In another embodiment, inflation lumen 2636 has a height H2 of about 0.5-0.9 mm and a width W of about 0.9-1.3 mm. Inflation lumen 2636 may alternatively be a coaxial lumen around shaft 2622, enclosed by a separate tubular member (not shown). Extension tube 2638 may have a surrounding material, sleeve, cannula or lumen, such as described below with respect to infusion lumen 9520 or accessory lumen 9530 of FIGS. 69A-F.

Optionally, pressure relief valve 2641 may be connected to inflation extension tube 2638 to prevent overinflation of balloon 2647, which might damage the tissue of the coronary sinus or another vessel. Pressure relief valve 2641 is configured to open and relieve fluid pressure from inflation lumen 2636 when balloon 2647 exceeds the maximum desired inflated pressure or diameter, e.g., about 9 mm. This may be accomplished by pre-inflating balloon 2647 to the maximum inflated diameter without pressure relief valve 2641 mounted to the delivery catheter, thereby plastically deforming balloon 2647 to its fully inflated size. Balloon 2647 is then collapsed onto the shaft by applying a vacuum to inflation lumen 2636, and pressure relief valve 2641 is mounted to inflation extension tube 2638. In use, when delivery catheter 2620 is positioned in the coronary sinus, inflation of balloon 2647 to the desired inflated size will require relatively low pressure, e.g. less than about 0.5-2.0 psi. However, once the maximum inflated size is reached, the pressure will increase significantly, causing pressure relief valve 2641 to open, thus preventing overinflation of balloon 2647. A suitable pressure relief valve 2641 is available from, for example, Smart Products, Inc. of San Jose, Calif., under the name "Luer Check Valve."

In another embodiment, balloon 2647 may be self-inflating, wherein the treatment agent itself acts as the inflation fluid for balloon 2647, eliminating the need for a separate inflation lumen 2636 in shaft 2622. In this embodiment, delivery lumen 2628 communicates with the interior of balloon 2647 in such a way that balloon 2647 will inflate fully to occlude the coronary sinus only during delivery of treatment agent. For example, a fluid path between delivery lumen 2628 and balloon 2647 may be provided such that all or a major portion of the treatment agent delivered through delivery lumen 2628 first enters the balloon to cause balloon 2647 to inflate, before treatment agent flows into the coronary sinus through outlet holes in shaft 2622 distal to balloon 2647, or through outlet holes in the balloon itself. One way to accomplish this is by a reduction in the diameter of the lumen distal to balloon 2647 such that a sufficient head pressure is established to inflate balloon 2647 and administer a treatment agent from shaft 2622.

Pressure lumen 2642 may also be provided in shaft 2622 which opens at pressure port 2644 on side-wall of shaft 2622 near distal end 2624, or in soft tip 2630 as illustrated. Pressure lumen 2642 is connected to extension tube 2646 attached (e.g., via adhesive) to shaft 2622 near proximal end 2626 and includes fitting 2648 at its proximal end suitable for connection to pressure monitoring equipment. In this way, pressure in the coronary sinus distal to balloon 2647 may be monitored during treatment agent delivery to ensure that pressure within the coronary sinus is maintained at a safe level. Extension tube 2646 may have a surrounding material, sleeve, cannula or lumen, such as described below with respect to infusion lumen 9520 or accessory lumen 9530 of FIGS. 69A-F.

Pressure relief valve (e.g., not shown, but such as relief valve 2641) connected to inflation extension tube 2638, may also be connected to delivery lumen 2628 to ensure that treatment agent pressure does not exceed a predetermined level, avoiding hemolysis in the blood component of the fluid or protecting the coronary sinus from excessive infusion pressure. In various embodiments, pressure in the range of about zero to about five mmHg could be measure at port 2644.

Figure 29:
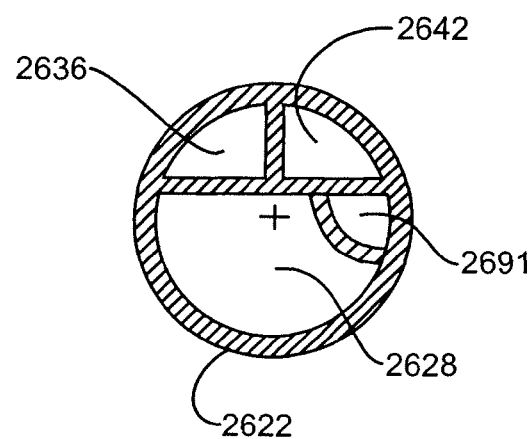
FIG. 29 schematically illustrates transverse cross-sections of the delivery catheter of FIG. 26 taken along the line 9-9.

As shown in FIG. 29, distal portion of shaft 2622 may include delivery lumen 2628, inflation lumen 2636, pressure lumen 2642, and guidewire lumen 2691. Guidewire lumen 2691 is adapted to receive a guidewire, where the guidewire may be used for navigating through the vasculature or the guidewire may be provided with a balloon on a distal end of the guidewire.

As shown in FIG. 27, distal portion of shaft 2622 may include first bend 2650 and second bend 2652, which facilitate the placement of distal end 2624 in the coronary sinus. In various embodiments, second bend 2652 may be distance L2 of between about three mm and 10 mm in distance from distal end of soft tip 2630, and first bend 2650 may be a distance $L_1$ of between 20 mm and 40 mm in distance proximal to second bend 2652. First and second bends 2650, 2652 may subtend various angles depending upon patient anatomy and surgeon preference. In various embodiments configuration, first bend 2650 subtends an angle A of between about 20° and about 70° relative to the longitudinal axis of proximal portion 2654 of shaft 2622. In another embodiment, second bend 2652 may subtend an angle B of about 30° to about 40° relative to mid-portion 2656 of shaft 2622.

A liquid containing a treatment agent or drug, e.g., a caroporide solution, may be introduced into proximal end 2626 of catheter 2620, which extends outside of the patient, under sufficient pressure so that the fluid containing the treatment agent can be forced to pass through the coronary sinus, through the capillary beds (not shown) in the patient's myocardium, and optionally through coronary arteries (not shown) and ostia associated with the respective coronary arteries (not shown) into the ascending aorta (not shown).

In various embodiments, balloon 2647 on the distal extremity of catheter 2620 is inflated to occlude the coronary sinus or another vessel to prevent fluid loss into the right atrium. A liquid containing a treatment agent such as adenosine is directed through catheter 2620 into the coronary sinus or another vessel and the pressure and volumetric flow rate of the treatment agent within the coronary sinus or another vessel are maintained sufficiently high (e.g. at least 100 ml/min at about 40 mm Hg) so that the treatment agent will pass through the coronary veins, and reaching the capillary beds, and optionally on to the coronary arteries (not shown) and out the ostia (not shown).

Treatment agent is delivered through delivery catheter 2620 at a flow rate sufficient to maintain desired treatment by periodic or continual infusions. However, treatment solution pressure within the coronary sinus or another vessel should be less than about 50 mm Hg to avoid tissue damage. In various embodiments, the treatment agent is a mixture of blood and a treatment agent such as an antioxidant, in various embodiments at a ratio or four parts blood to one part antioxidant solution (by volume). This antioxidant solution may be mixed into oxygenated blood.

The treatment agent may be directed to fitting 2632 on proximal end of delivery catheter 2620, and delivered to the coronary sinus, or another vessel, in various embodiments at a flow rate of at least about 100 ml/min. and in another embodiment, at about 200 ml/min. If treatment agent includes a blood component, the pressure required to pump the treatment agent through the lumen of the delivery catheter ("pump pressure") should not exceed 300 mmHg to avoid excessive hemolysis of the blood component. Treatment agent flow through delivery catheter 2620 is maintained on a periodic basis, e.g., about every 15-30 seconds for 2-4 minutes, so long as the heart is to remain under treatment.

Figure 30:
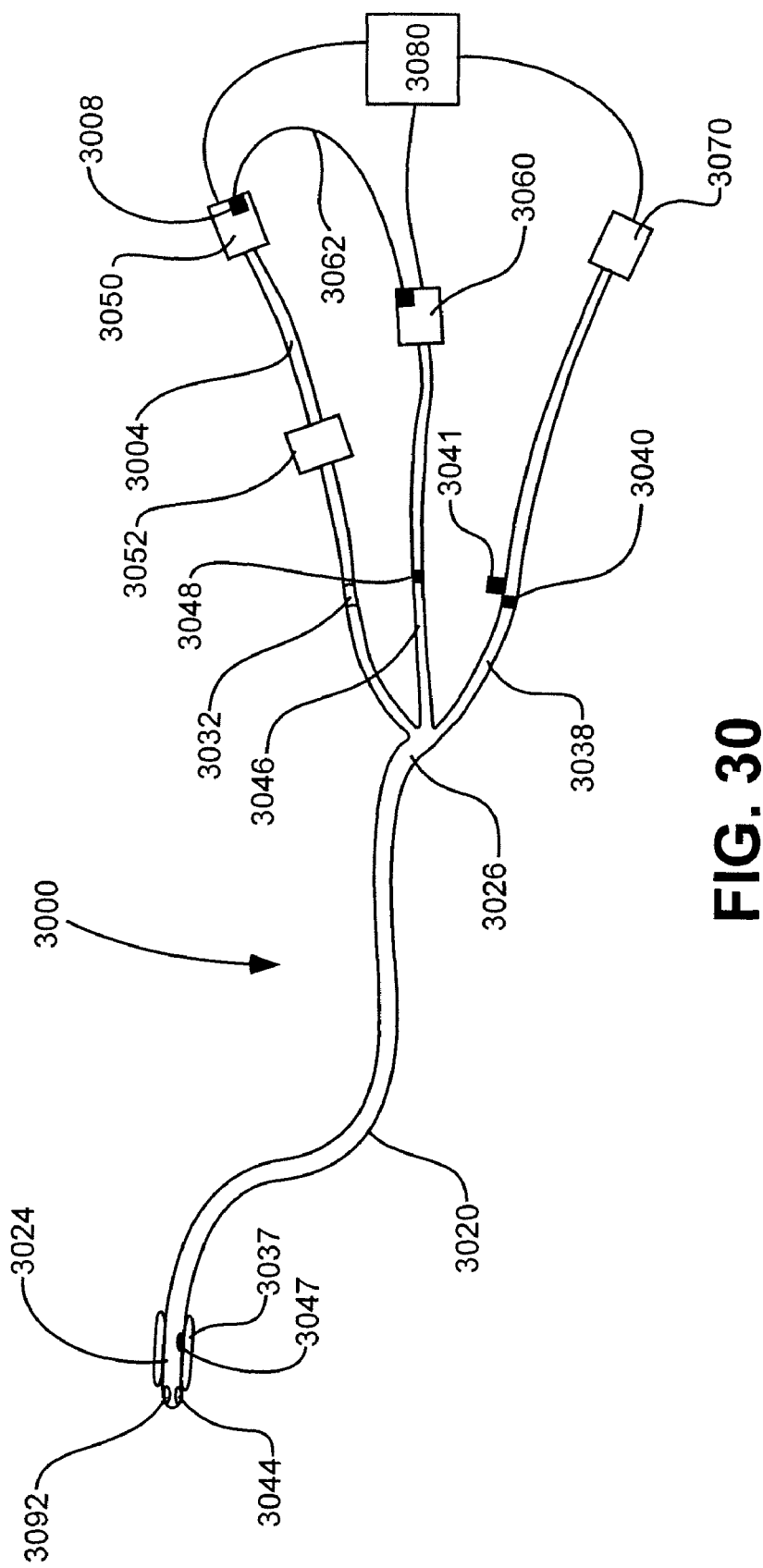
FIG. 30 schematically illustrates a catheter system.

Referring now to FIG. 30, another embodiment of a catheter system is illustrated. Catheter system 3000 includes delivery catheter 3020 (for example, delivery catheter 2620, 3122, 3201, 3510, 3920, or any other catheter or cannula.). Delivery catheter 3020 includes proximal ends 3026 (for example, 2626) and distal end 3024 (for example, 2624, 3112, 3260). Delivery catheter 3020 includes a delivery lumen (not shown) (for example, 2628, or any other delivery lumen, tube or cannula as described herein). Delivery lumen connects outlet port 3092 (for example, 2692, 3162, 3154, 2628, 3228, 3992, or any other treatment agent delivery or infusion opening, exit, or port) on distal end 3024 of catheter and has fitting 3032 (for example, 2632) on proximal end 3026 of catheter. Fitting 3032 may be connected to a pressure increasing device 3050 (for example, 5600, 5700, or 5800) by device outlet 3004 (for example, 5604, 5718, or 5818). Intermediate to device outlet 3004 and fitting 3032 there may be located one or more (in series) of pressure-transferring device, pressure-maintaining, or pressure-dampening device 3052 (for example, 5900, 6000, 6100).

On distal end 3024 of catheter is located balloon 3047 (for example balloon 8810, 9510, filter device 710, or any other balloon, occlusion device, or filter device as described herein) with inflation lumen (not shown) (for example, 2636, 3936, or any other inflation lumen, tube or cannula), where inflation lumen has opening 3037 (for example, 2637, 3172), which serves to inflate or deflate balloon 3047. Inflation lumen is through catheter 3020 from opening 3037 (for example, 2637, 3172) to inflation extension tube 3038 (for example, 2638), which has fitting 3040 (for example, 2640) at the proximal end of inflation extension tube 3038. There is also optionally provided pressure relief valve 3041 (for example, 2641) adjacent to fitting 3040. Inflation device 3070 (for example, apparatus 9700, 9800 of FIGS. 75A-81 or any other balloon or occlusion device inflation device) may be connected to fitting 3040. Extension tube 3038 may have a surrounding material, sleeve, cannula or lumen, such as described below with respect to infusion lumen 9520 or accessory lumen 9530 of FIGS. 69A-F.

Delivery catheter 3020 may also have a pressure lumen (not shown) (for example, 2642, 3142, 3220, accessory lumen 9530, or any other lumen, tube, or cannula capable of measuring pressure or inserting a pressure sensing device through), where pressure lumen has pressure port 3044 (for example, 2644, 3136, 3228, 3944) at distal end of pressure lumen. Pressure lumen extends from pressure port 3044 to extension tube 3046 (for example, 2646). Extension tube 3046 has fitting 3048 (for example, 2648) at proximal end of extension tube 3046. Pressure-sensing device 3060 may be connected to fitting 3048. Extension tube 3046 may have a surrounding material, sleeve, cannula or lumen, such as described below with respect to infusion lumen 9520 or accessory lumen 9530 of FIGS. 69A-F.

In various embodiments, system 3000 has controller 3080, such as a controller (e.g., including an automatic, computer, or machine controller) adapted to control a pressure increasing device, a pressure-sensing device, or an inflation device as described herein. More particularly, pressure-sensing device 3060 may be connected to pressure measurement connection 3008 (for example, 5708 or 5808 of FIGS. 57 and 58) of pressure increasing device 3050 by pressure measurement connection 3062. Optionally, there may be provided system controller 3080, for example, a computer or mini-computer, which is connected to pressure increasing device 3050, pressure-sensing device 3060, or inflation device 3070. For example, system controller 3080 may access a memory including instructions (e.g., such as machine readable instructions) to control a pressure increasing device, a pressure-sensing device, an inflation device, in infusion device, or any device or apparatus. Specifically, controller 3080 may be used to control inflation or deflation of a balloon to various outer diameters (e.g., see FIGS. 55 and 68 herein, which illustrates a balloon outside diameter growth rate) by inflating a balloon with a selected inflation pressure or volume.

Moreover, system controller 3080 may be used to control an amount of treatment agent infused, a period of time during which treatment agent is infused, a period of time during which an occlusion device occludes a blood vessel (e.g., such as first period of time 9670, or a period of time that filter device 720 (e.g., see FIGS. 7-19 and accompanying text) is expanded within the blood vessel), or a period of time during which blood or treatment agent is allowed to perfuse or flow through a treatment region in a blood vessel (e.g., such as second period of time 9680). Similarly, system controller 3080 may be used to control a treatment process for infusion of a treatment agent into an artery or vein of a patient using devices, apparatus, methods, or processes described herein (e.g., such as according to the process described with respect to FIG. 3, 19, 54, 55, 63, or 82).

Figure 31:
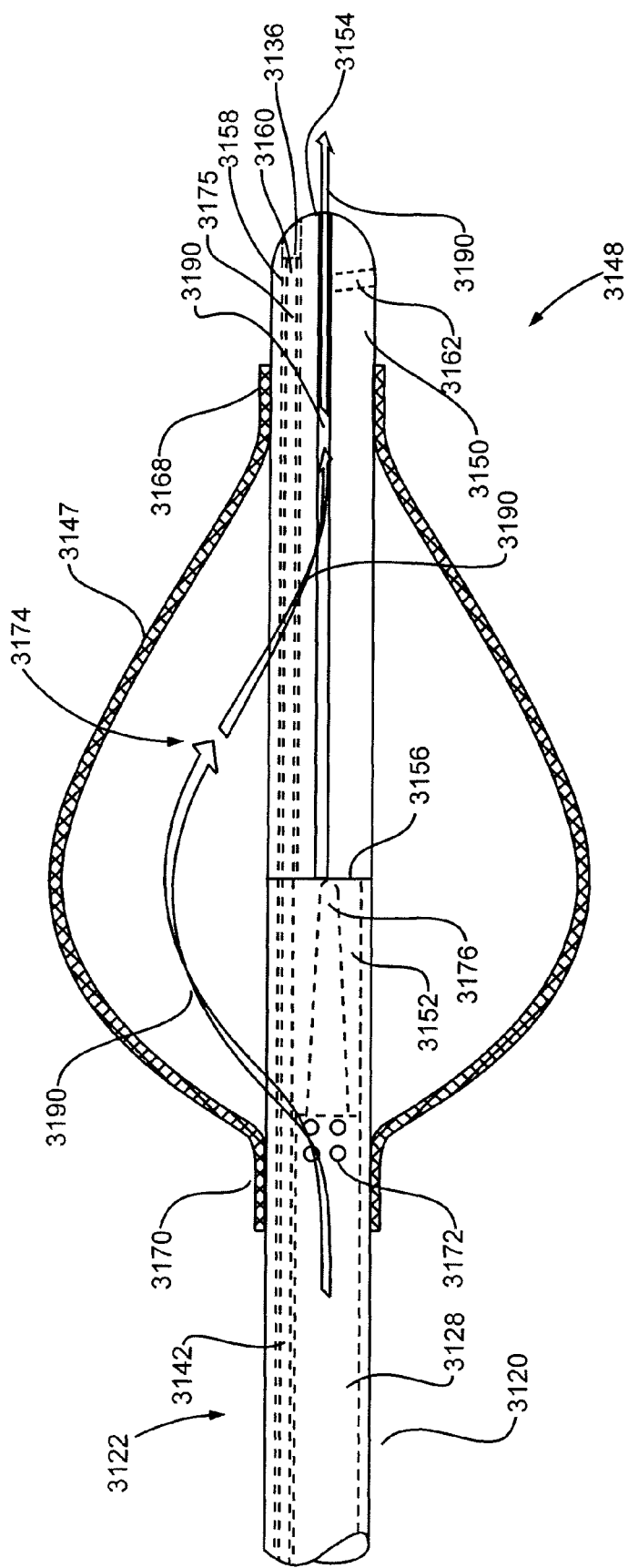
FIG. 31 schematically illustrates a sectional view of a catheter with a self inflating balloon.

A suitable self-inflating balloon configuration is illustrated in FIG. 31. FIG. 31 illustrates the structure and operation of self inflating balloon 3147 and flow tip 3148 of catheter 3120. Pear shaped balloon 3147 tapers gradually from its widest diameter to form distal circular cuff 3168, and tapers more quickly from its widest diameter to form proximal circular cuff 3170. Proximal cuff 3170 coaxially receives catheter body 3122 and is attached thereto to form a fluid tight seal between cuff 3170 and catheter body 3122. Distal cuff 3168 coaxially receives and attaches to flow tip 3148.

Plurality of radial holes 3172 extend through body of catheter 3122 from within infusion lumen 3128, proximal of flow tip base plug 3152, into interior space 3174 enclosed by balloon 3147. Thus the flow of treatment agent through catheter 3120 shown by arrows 3190 exits infusion lumen 3128 through holes 3172, enters balloon interior 3174, flows into flow channels 3158 and exits each flow channel 3158 through its side exits 3162, or distal exits 3154. The aggregate cross sectional area of holes 3172 filling balloon interior 3174 exceeds the aggregate cross sectional area of flow channels 3158 draining balloon interior 3174, providing a positive pressure within balloon interior 3174 to keep balloon 3147 inflated while the treatment agent flows through catheter 3120.

Pressure monitoring lumen 3142 extends through one of open channels 3158 via extension tube 3175. Extension tube 3175 may have a surrounding material, sleeve, cannula or lumen, such as described below with respect to infusion lumen 9520 or accessory lumen 9530 of FIGS. 69A-F. Extension tube 3175 extends from flow tip body 3150, where pressure monitoring lumen 3142 exits flow tip body 3150, through one of flow channels 3158, and terminates proximally adjacent flow channel distal exit (not shown), to form pressure lumen distal opening 3136. The pressure monitoring equipment (not shown) is thus in pressure communication with the inside of the coronary sinus or another vessel in which pressure lumen distal opening 3136 is located. Because the pressure lumen distal opening 3136 is recessed into the flow channel 3158, there is less chance of it becoming occluded by the wall of the coronary sinus, or another vessel.

Also note that stylet well 3176 can coaxially sink into base plug 3152 of flow tip 3148 for receiving a stylet (not shown), and providing additional reinforcement at distal end 3156 of catheter body 3122 where the stylet (not shown) impacts base plug 3152 of flow tip 3148.

Figure 32:
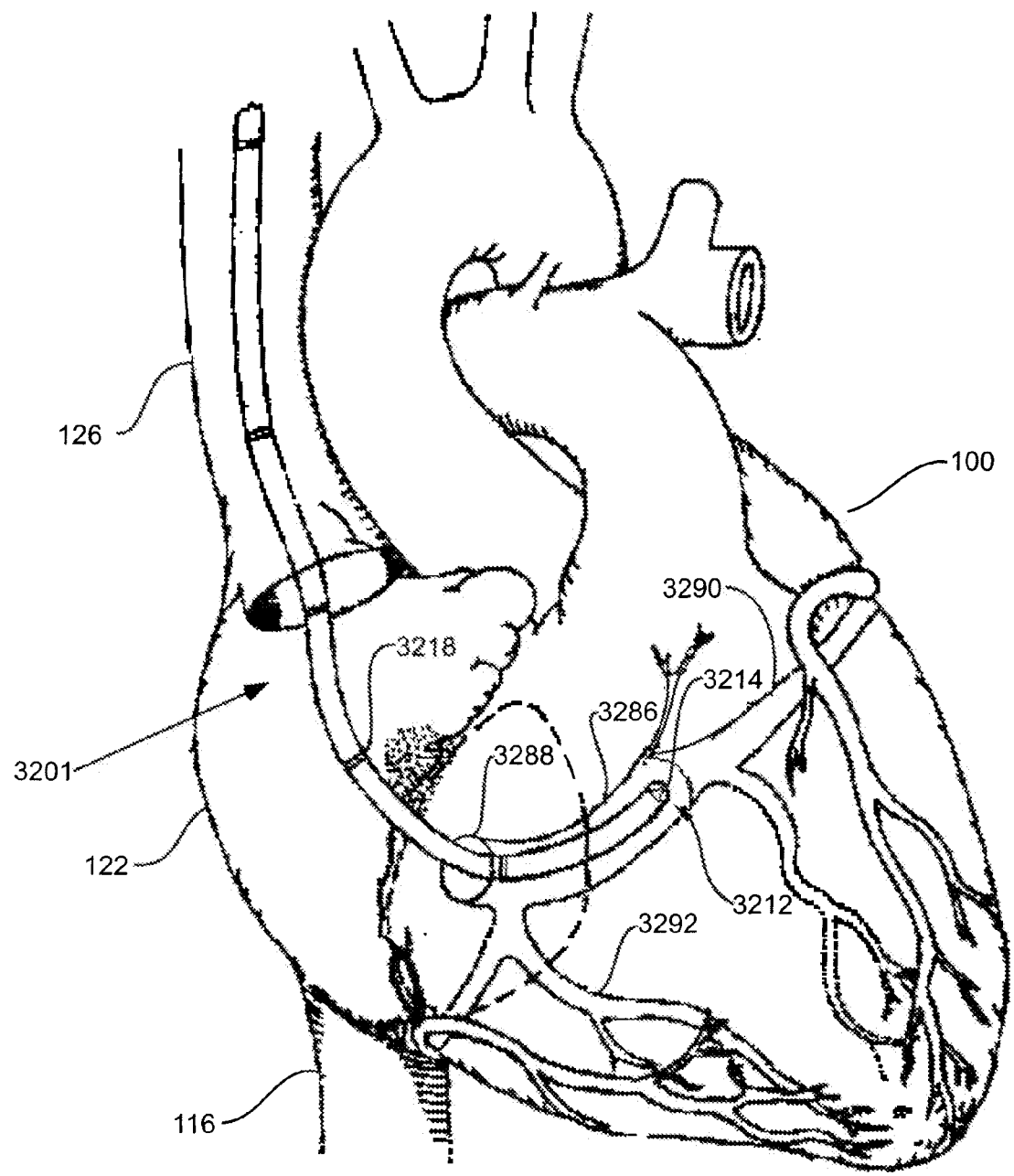
FIG. 32 schematically illustrates the placement of a catheter in the coronary sinus.

FIG. 32 depicts catheter 3201 positioned within heart 100. Catheter 3201 may be inserted percutaneously through a blood vessel, such as an artery or vein. Specifically, catheter 3201 can be advanced through a percutaneous venus entry, such as through a femoral vein, and tip 3212 is guided through right atrium 122 into coronary sinus 3286. Blood drains into right atrium 122 via superior vena cava 126 and interior vena cava 116, and from coronary sinus 3286 via coronary sinus ostium 3288. Moreover, blood drains from the myocardium to coronary sinus 3286 via great cardiac vein 3290 and small cardiac vein 3292.

Tip 3212 having port 3214 is inserted into coronary sinus 3286 to a depth from about zero to about four inches (zero to about 10.2 cm) from coronary sinus ostium 3288. Optionally, markers 3218 may be provided on catheter 3201 and optionally spaced about two inches apart along catheter 3201; in various embodiments, markers 3218 are radiopaque.

Referring now to FIG. 33, which illustrates diaphragmatic surface of heart 3300. Coronary sinus 3286 is shown feeding into right atrium. Great cardiac (anterior interventricular) vein 3290, oblique vein of left atrium 3310, and posterior vein of left ventricle 3304 feed into coronary sinus 3286. Also, middle cardiac (posterior interventricular) vein 3306, and small cardiac vein 3308 feed into coronary sinus 3286. All the veins are provided with arrows to show direction of ordinary blood flow into coronary sinus 3286 and into right atrium.

Referring now to FIG. 34, sternocostal surface of heart 3301 is shown. Great cardiac (anterior interventricular) vein 3290 is shown, as are anterior cardiac veins of right ventricle 3314, and small cardiac vein 3308.

Left coronary artery 3320 and right coronary artery 3322 feed out of aorta 3350. Branching off of left coronary artery 3320 are circumflex branch of left coronary artery 3324, and anterior interventricular branch (left anterior descending) of left coronary artery 3344, and interventricular septal branches 3326. Feeding off of right coronary artery 3322 are atrial branch of right coronary artery 3330, and right marginal branch of right coronary artery 3328.

Referring again to FIG. 33, right coronary artery 3322 is shown. Feeding off of right coronary artery 3322 are right marginal branch 3338, and interventricular septal branches 3342. Other branches from left coronary artery (3320 in FIG. 34) are circumflex branch of left coronary artery 3324, and posterior left ventricular branch 3340. Also shown in FIG. 33 are sinuatrial nodal branch 3332, and sinuatrial node 3334.

Figure 35:
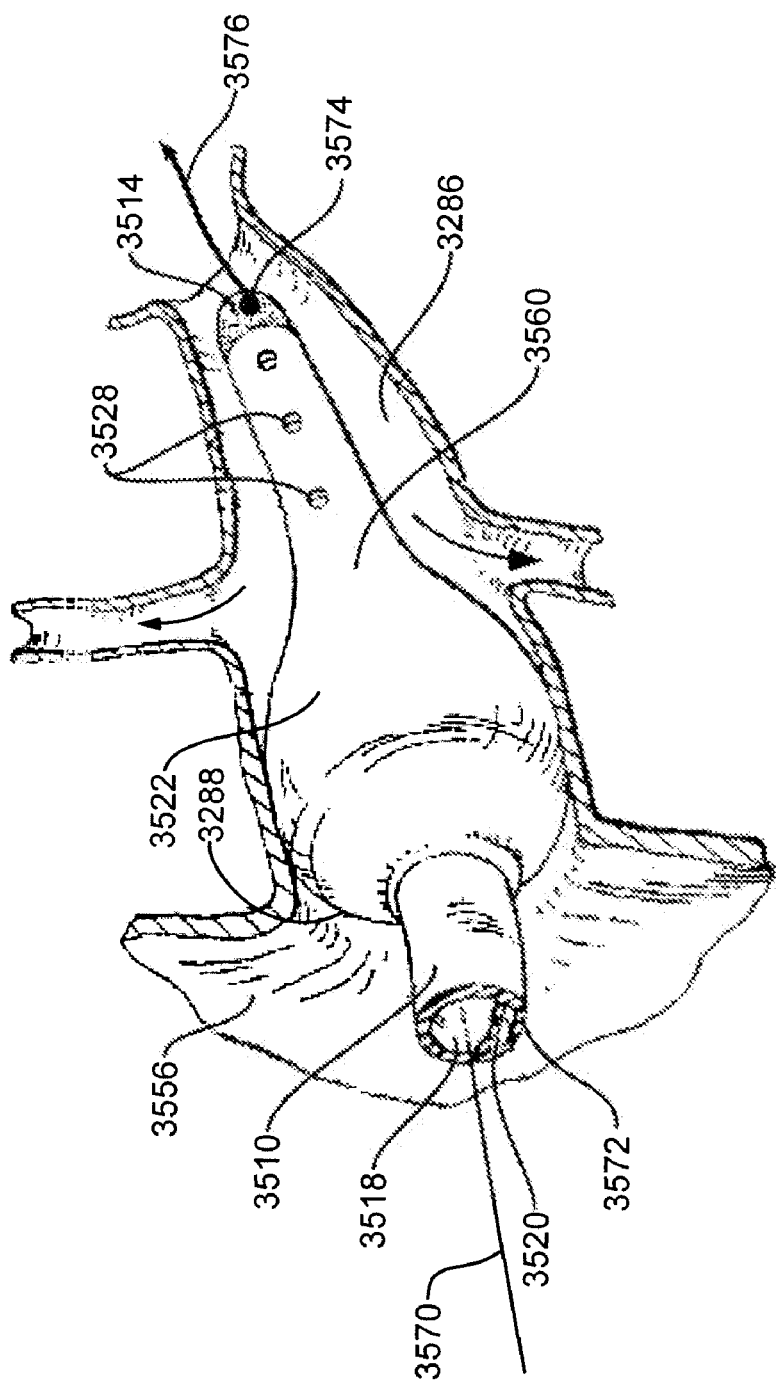
FIG. 35 schematically illustrates a partial cross-sectional perspective view of a catheter within the coronary sinus.

FIG. 35 illustrates distal end 3560 of catheter 3510 within coronary sinus 3286. Catheter 3510 has tip 3514 at distal end 3560, and plurality of lumen outlets 3528 proximal to tip 3514. Balloon 3522 is shown occluding coronary sinus 3286 and coronary sinus ostium 3288 adjacent to right atrium wall 3556. Balloon 3522 on catheter 3510 may also be used to occlude other veins distal to coronary sinus 3286, for example, great cardiac vein 3290, anterior cardiac vein of right ventricle 3314, and small cardiac vein 3308 (shown in FIGS. 33 and 34). In this embodiment, a self-inflating balloon is shown with infusion lumen 3518 through which a treatment agent flows and inflates balloon 3522 then flows out of lumen outlets 3528. Pressure-sensing lumen 3520 is also provided. In another embodiment, a third lumen was provided (not shown) to inflate balloon 3522 when balloon 3522 is not self-inflating. There is also provided guidewire 3570, having distal end 3576. Guidewire 3570 is fed through guidewire lumen 3572, which guidewire lumen 3572 has distal opening 3574 at tip 3514.

Figure 36:
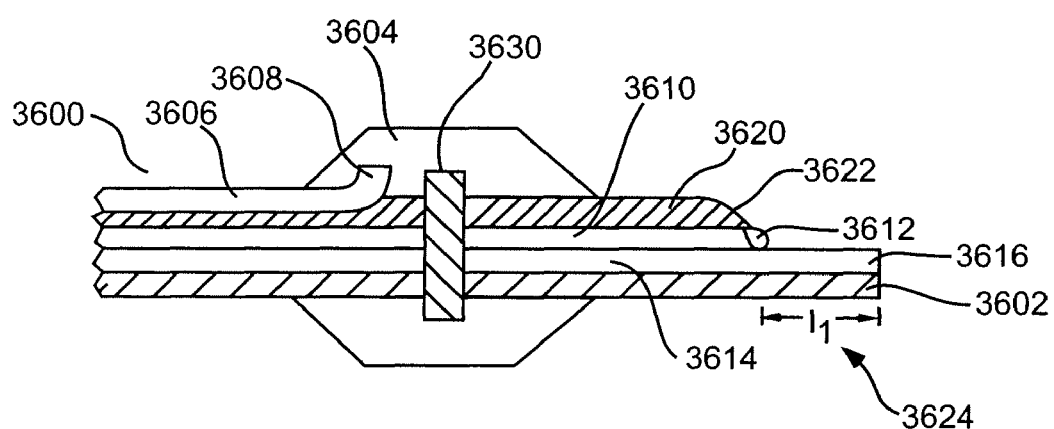
FIG. 36 illustrates a tapered balloon catheter tip.

Referring now to FIG. 36 is a staggered tip of a balloon catheter. Balloon catheter 3600 has distal end 3602 and proximal end (not shown). Adjacent distal end 3602 of catheter is balloon 3604. Balloon inflation lumen 3606 has distal end and opening 3608 within balloon 3604 to inflate or deflate balloon 3604. Pressure-sensing lumen 3610 has distal end and opening 3612 which enables pressure-sensing lumen 3610 to sense pressure or other measurements or parameters wherever distal end 3602 of catheter is placed. Delivery lumen 3614 has distal end and opening 3616 which enables a fluid path from proximal end (not shown) of catheter to distal end 3602 of catheter.

Staggered tip of catheter 3600 may enable easier tracking of distal end 3602 of catheter through a blood vessel. In various embodiments, pressure-sensing lumen 3610 or catheter body 3620 adjacent pressure-sensing lumen 3610 have tapered cut 3622 which may be curved. According to some embodiments, tapered cut 3622, may have an angle and a tapered shape, such as is described above with respect to tapered cut 2222 of FIG. 22. In various embodiments, distance $L_1$ marked with reference numeral 3624 is the distance between distal end 3612 of pressure-sensing lumen 3610 and distal end 3616 of delivery lumen 3614. In various embodiments, $L_1$ 3624 may be between about 0.5 millimeters and five millimeters.

In another embodiment, catheter 3600 is illustrated. Catheter has balloon inflation lumen 3606, balloon 3604, delivery lumen 3610 having opening 3612, and pressure-sensing lumen 3614 having opening 3616. Catheter 3600 has a staggered tip where opening 3612 of delivery lumen 3610 is distance $L_1$ 3624 from opening 3616 of pressure-sensing lumen 3614. In addition, catheter body 3620 adjacent opening 3612 of delivery lumen 3610 may have a tapered or curved shape 3622.

In another embodiment, catheter 3600 may include marker 3630, for example a radio-opaque marker, which may serve to ease visualization of distal end 3602 of catheter 3600 with a diagnostic or visualization system.

Referring now to FIG. 37, is a staggered tip of a balloon catheter. Balloon catheter 3700 has distal end 3702 and proximal end (not shown). Adjacent distal end 3702 of catheter is balloon 3704. Balloon inflation lumen 3706 has distal end and opening 3708 within balloon 3704 to inflate or deflate balloon 3704. Pressure-sensing lumen 3710 has distal end and opening 3712 which enables pressure-sensing lumen 3710 to sense pressure or other measurements or parameters wherever distal end 3702 of catheter is placed. Delivery lumen 3714 has distal end and opening 3716 which enables a fluid path from proximal end (not shown) of catheter to distal end 3702 of catheter. Staggered tip of catheter 3700 may enable easier tracking of distal end 3702 of catheter through a blood vessel. In various embodiments, pressure-sensing lumen 3710 or catheter body 3720 adjacent pressure-sensing lumen 3710 have tapered cut 3722 which may be curved. According to some embodiments, tapered cut 3722, may have an angle and a tapered shape, such as is described above with respect to tapered cut 2222 of FIG. 22. There is also provided an indentation 3740 proximal to distal end 3702, with guidewire lumen 3742 distal to indentation 3740. Indentation 3740 and guidewire lumen 3742 are adapted to receive guidewire 3744. Guidewire 3744 has proximal end (not shown) and distal end 3746. Guidewire 3744 may be provided with balloon 3748 adjacent distal end 3746. In use, catheter 3700 may be tracked over the guidewire through by feeding distal end 3702 of catheter over guidewire 3744 by way of lumen 3742. This "over the wire" (OTW) is also known as monorail.

Figure 38:
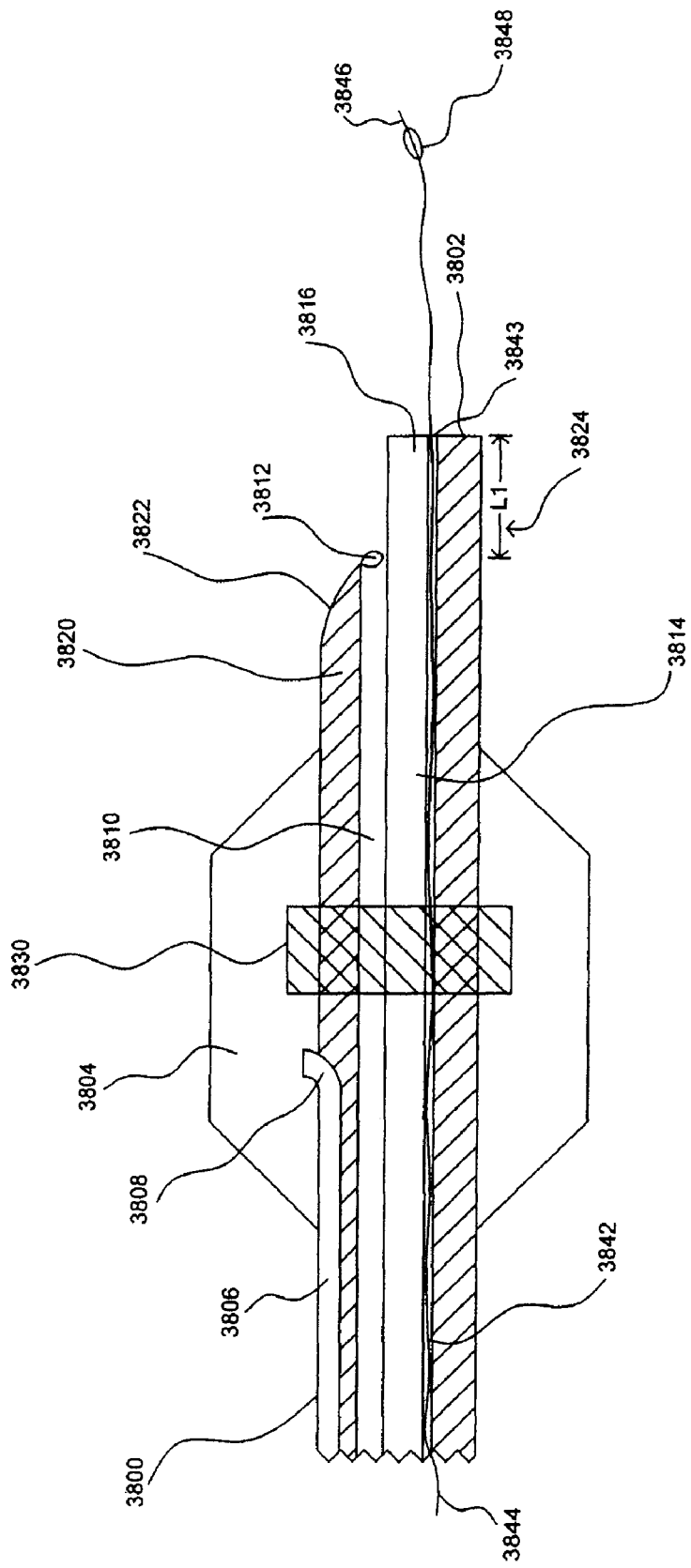
FIG. 38 illustrates a balloon catheter tip with a guidewire.

Referring now to FIG. 38, the staggered tip of a balloon catheter. Balloon catheter 3800 has distal end 3802 and proximal end (not shown). Adjacent distal end 3802 of catheter is balloon 3804. Balloon inflation lumen 3806 has distal end and opening 3808 within balloon 3804 to inflate or deflate balloon 3804. Pressure-sensing lumen 3810 has distal end and opening 3812 which enables pressure-sensing lumen 3810 to sense pressure or other measurements or parameters wherever distal end 3802 of catheter is placed. Delivery lumen 3814 has distal end and opening 3816 which enables a fluid path from proximal end (not shown) of catheter to distal end 3802 of catheter.

Staggered tip of catheter 3800 may enable easier tracking of distal end 3802 of catheter through a blood vessel. In various embodiments, pressure-sensing lumen 3810 or catheter body 3820 adjacent pressure-sensing lumen have tapered cut 3822 which may be curved. According to some embodiments, tapered cut 3822, may have an angle and a tapered shape, such as is described above with respect to tapered cut 2222 of FIG. 22. In various embodiments, distance $L_1$ marked with reference numeral 3824 is the distance between distal end 3812 of pressure-sensing lumen 3810 and distal end 3816 of delivery lumen 3814. In various embodiments, $L_1$ 3824 may be between about 0.5 mm and about five mm.

Catheter 3800 may also include marker 3830, for example, a radio-opaque marker, which may serve to ease visualization of distal end 3802 of catheter 3800 with a diagnostic visualization system.

Catheter 3800 may also include guidewire lumen 3842 through catheter 3800. Guidewire lumen 3842 has distal end and opening 3843 adjacent distal end 3802 of catheter. Guidewire lumen 3842 is adapted to receive a guidewire. Guidewire 3844 is illustrated, where guidewire 3844 has distal end 3846 and balloon 3848 adjacent distal end 3846.

Figure 39:
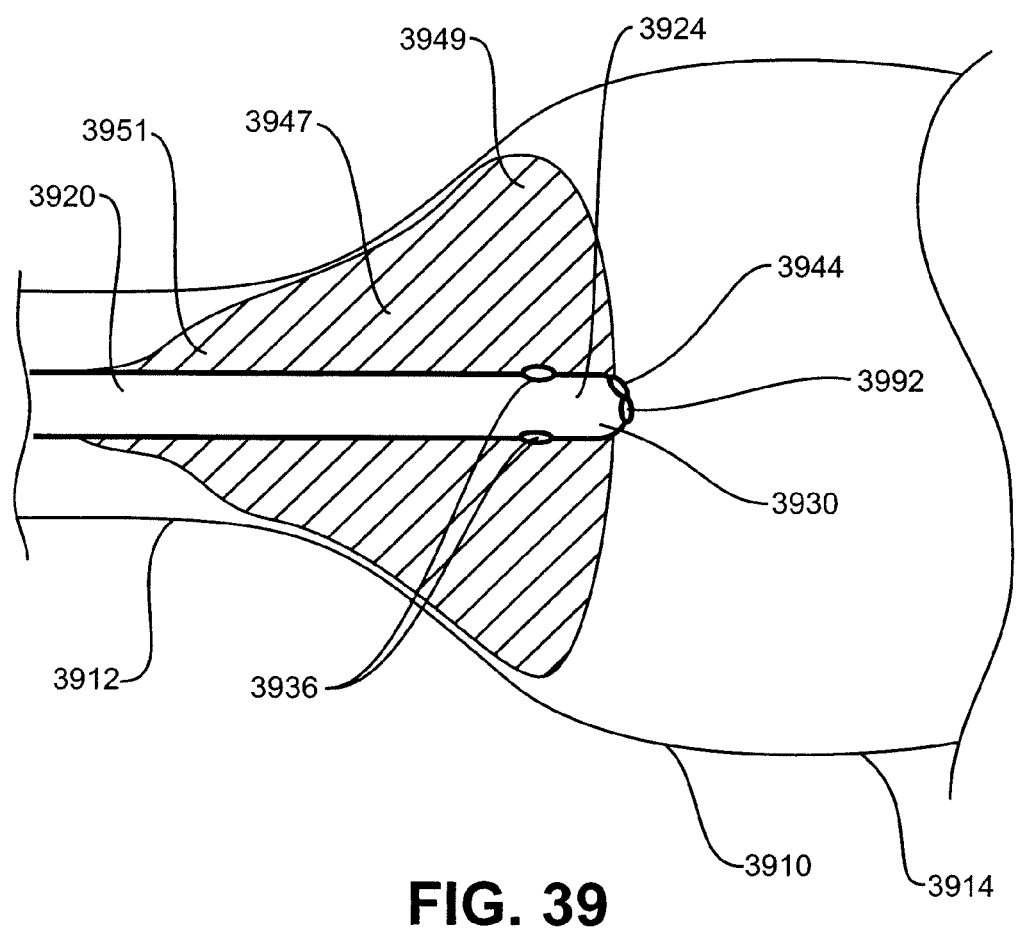
FIG. 39 schematically illustrates a catheter within a vein.

Referring now to FIG. 39, which shows catheter 3920 within blood vessel 3910 (e.g., such as a vein or artery). Catheter 3920 includes balloon 3947 on distal end 3924 of catheter 3920. Also, on distal end 3924 is outlet port 3992 to deliver a treatment agent into blood vessel 3910. Pressure port 3944 is on distal end 3924 to measure a pressure in blood vessel 3910. Balloon 3947 is inflated by outlet ports of inflation lumen 3936. Blood vessel 3910 is divided into two portions, first portion 3914 is distal to balloon 3947, and second portion 3912 is proximal to balloon 3947. Balloon 3947 serves to seal against inner wall of blood vessel 3910, and provide a pressure separation between first portion 3914 and second portion 3912. In various embodiments, treatment agent flowing through outlet port 3992 serves to increase the size of first portion 3914 due to the high pressure exerted by treatment agent on blood vessel walls in first portion 3914. This causes first portion 3914 to have a larger diameter than second portion 3912, and a frusto-conical shape taper is created between first portion 3914 and second portion 3912. In this embodiment, balloon 3947 is tapered to accommodate the frusto-conical shape of the taper between first portion 3914 and second portion 3912.

In various embodiments, balloon 3947 may be tapered by having distal end 3949 of balloon have a thinner wall thickness than proximal end 3951 of balloon 3947, so that fluid or gas inserted into balloon 3947 through outlet port of inflation lumen 3936 serves to make the distal end 3949 of balloon larger than proximal end 3951 of balloon 3947. In another embodiment, balloon 3947 may have uniform wall thickness of proximal end 3951 and distal end 3949, but the balloon is molded or formed in a tapered shape, or otherwise formed so that balloon 3947 will assume a tapered shape when inflated.

In various embodiments, a pressure-sensing device may be connected to pressure port 3944 via an attachment to fitting 3648 at proximal end of extension tube 2646 of catheter 2620 (shown in FIGS. 26-29). In various embodiments, pressure-sensing device may be attached to proximal end of pressure lumen 2642 (shown in FIG. 28-29). In another embodiment, a pressure-sensing device may be fed through pressure lumen 2642 adjacent to pressure port 2644 on side-wall of shaft 2622 near distal end 2624 of catheter 2620 (shown in FIGS. 26-29). In various embodiments, pressure-sensing device is disposable. In another embodiment, pressure-sensing device is a disposable piezo-electric pressure sensor, for example, a piezo-electric pressure sensor manufactured by Utah Medical Products, Inc., which is attached to fitting 2648 (shown in FIG. 26).

In various embodiments, an inflation device may be connected to inflation lumen 3936 via attachment to fitting 2640 at proximal end of inflation extension tube 2638 attached to shaft 2622 and inflation lumen 2636 extending through catheter 2620. In various embodiments, the inflation device is a syringe. In another embodiment, the inflation device is a pump, for example, a centrifugal pump, a gear pump, or a reciprocating pump. In another embodiment, balloon 2647 is inflated with carbon dioxide, saline, or contrast medium by the inflation device.

Figure 40:
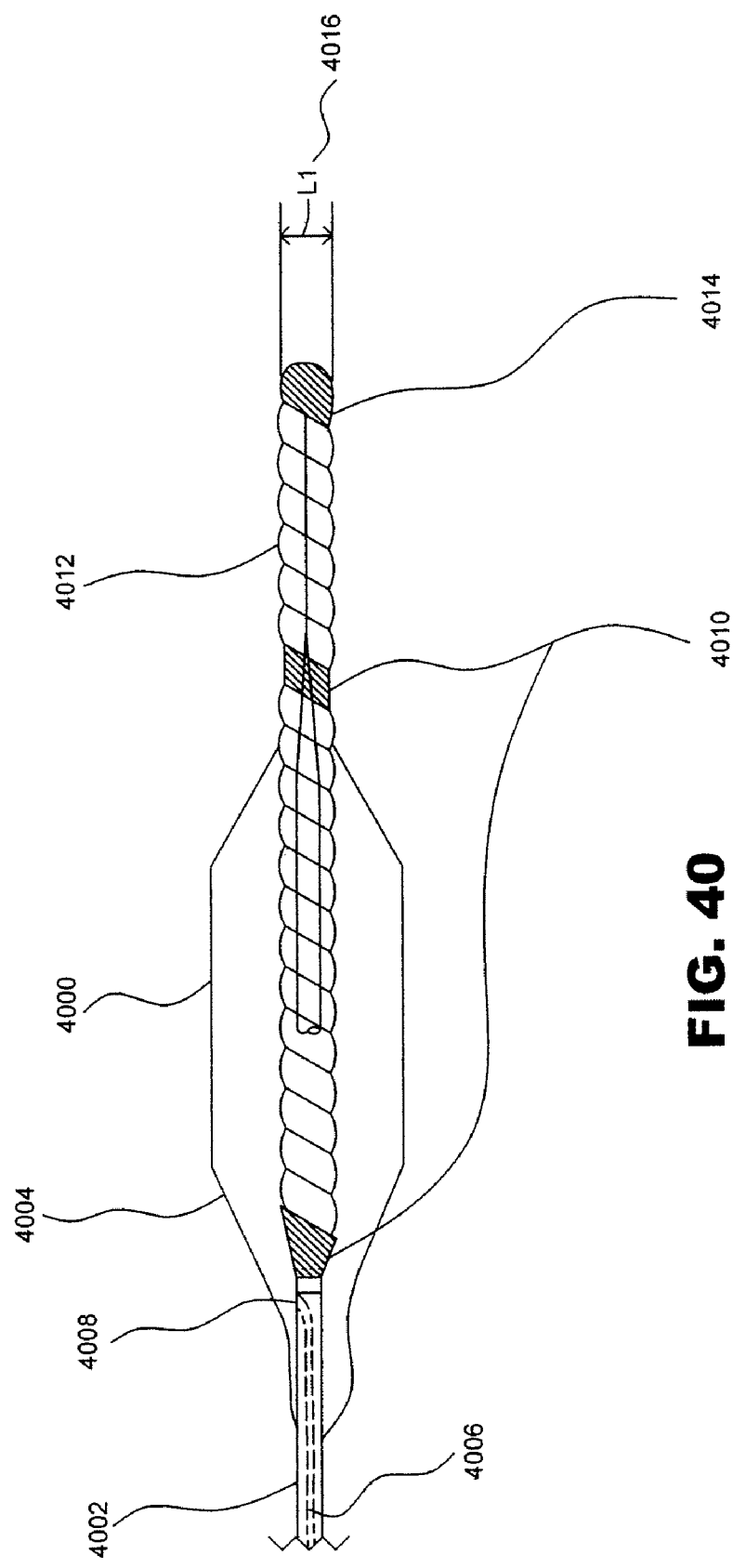
FIG. 40 illustrates a guidewire tip with an occlusion device.

Referring now to FIG. 40, is illustrated guidewire 4000. Guidewire 4000 has distal end 4002. At distal end 4002 is balloon 4004. Balloon 4004 may be inflated or deflated by balloon inflation lumen 4006 though guidewire 4000. Balloon inflation lumen 4006 has distal end and opening 4008 within balloon 4004. There may be provided one or more markers 4010 to aid visualization, for example under fluoroscopy, at distal end 4002 of guidewire. Spring 4012 is provided about guidewire at distal end 4002 to improve tracking of distal end 4002 through curves. In various embodiments, spring 4012 imparts a natural curve to distal end 4002. Tip 4014 is provided to minimize damage to vessels as tip 4014 travels through vessels. Tip 4014 has diameter $L_1$ 4016. In various embodiments, $L_1$ is between about 0.005 inches and 0.025 inches.

Figure 41:
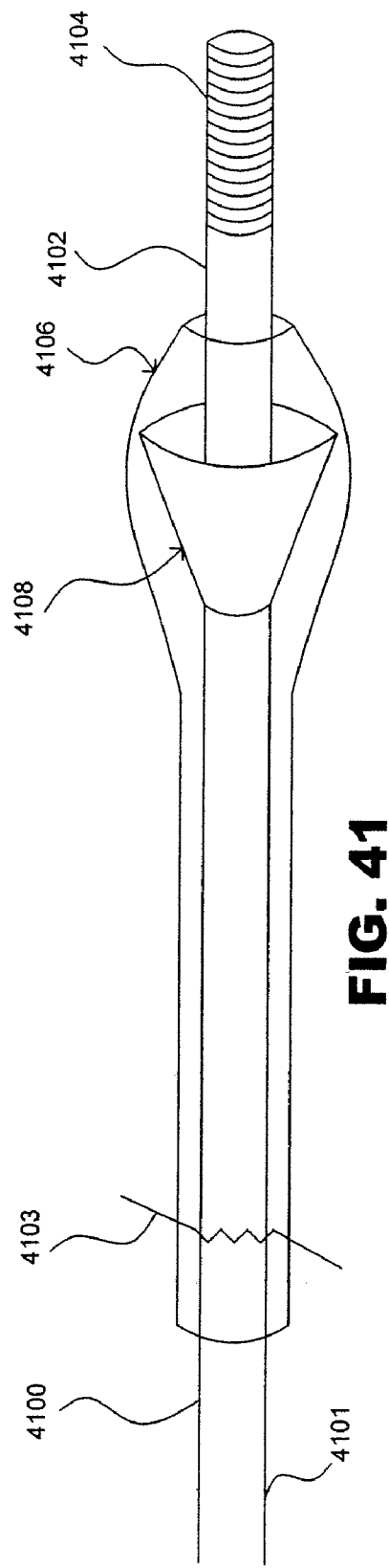
FIG. 41 illustrates a guidewire with an occlusion device.

Referring now to FIG. 41, guidewire 4100 has proximal end 4101 and distal end 4102. For ease of illustration, break 4103 is provided. Guidewire has sheath 4106 (e.g., such as sheath 790 as shown and described with respect to FIGS. 7-9) about guidewire from proximal end 4101 to distal end 4102. FIG. 41 shows sheath 4106 enclosing occlusion device 4108. Distal end 4102 also includes floppy tip 4104. FIG. 42A illustrates the guidewire of FIG. 41 with the occlusion device open. As shown in FIG. 42A, sheath 4106 has been laterally moved in the direction of arrows 4110 to uncover occlusion device 4108. Distal end 4102 of guidewire is within vessel 4112. Vessel 4112 has fluid flow in the direction of arrow 4113. When sheath 4106 is moved, to uncover occlusion device 4108, fluid flow within vessel 4112 forces open occlusion device 4108 in the direction of arrows 4109. Occlusion device 4108 then occludes vessel 4112 (e.g., such as by since occlusion device being forced against vessel wall by fluid flow within vessel 4112). Suitable materials for occlusion device 4108 may include one or more of a synthetic or natural latex or rubber, such as a polymer material; a polyetheramide; a plasticiser free thermoplastic elastomer; a thermoplastic blend; a block copolymer of polyether and polyester (e.g., such as a polyester sold under the trademark Hytrel® of DUPONT COMPANY); a bio-compatible polymer such as a polyether block amide resin (e.g., for instance, PEBAX® of ATOCHEM CORPORATION); a polycarbonate or acrylonitrile bubadiene styrene (ABS); a biocompatible polymer such as a polyether block amide resin; a styrene isoprene styrene (SIS), a styrene butadiene styrene (SBS), a styrene ethylene butylene styrene (SEBS), a polyetherurethane, an ethyl propylene, an ethylene vinyl acetate (EVA), an ethylene methacrylic acid, an ethylene methyl acrylate, an ethylene methyl acrylate acrylic acid, a material from a material family of one of styrenic block copolymers and polyurethanes, a melt processible polymer, urethane, polyurethane, polyethylene, polypropylene, polybutylene, copolymers of ethylene, propylene, butylene, a low durometer material, nylon, and other materials that can block fluid flow.

FIG. 42B, is a front view of FIG. 42A from perspective "A". FIG. 42B shows an embodiment of occlusion device 4108 having overlapping leaflets. First leaflet 4120 is shown overlapping second leaflet 4122 from the front. FIG. 42C, is a side of the occlusion device of FIG. 42A showing the occlusion device overlapping leaflets. FIG. 42C shows occlusion device 4108 with second leaflet 4120 overlapping first leaflet 4122 from the back. In another embodiment, occlusion device 4208 is a single member, without leaflets. For instance, occlusion device 4108 may be a single member with fold lines to prevent crimping of occlusion device 4108 when retracted by sheath 4106 (e.g., such as if filter device 720 were a solid member or material).

In use, distal end 4102 of guidewire 4100 is fed into vessel 4112. Once distal end 4102 of guidewire has been located in the correct position, sheath 4106 may be pulled back in the direction of arrows 4110 to expose occlusion device 4108. Fluid flow in the direction of arrow 4113, within vessel 4112, forces open occlusion device 4108 in the direction of arrows 4109 to occlude vessel 4112. At the end of the procedure, sheath 4106 may be advanced in the direction of arrows 4111 to recover or disengage occlusion device 4108 and force it closed. At that point, distal end 4102 may be removed from vessel 4112. In another embodiment, before removing distal end 4102, sheath 4106 may be removed, and a second sheath (not shown) may be fed over proximal end 4101 of guidewire to recover occlusion device 4108. Second sheath may have a larger diameter to trap fluid, particles, or foreign objects which were caught in occlusion device 4108. In this embodiment, second sheath (not shown) is fed in direction of arrows 4111 until occlusion device 4108 has been closed and then distal end 4102 may be removed from vessel 4112.

In various embodiments, occlusion device 4108 may be provided with leaflets or fold lines to ease deployment and recapture of occlusion device. For instance, in various embodiments, occlusion device 4108 may be opened (such as after sheath 4106 has been pulled back) by rotation of guidewire 4100 to cause occlusion device 4108 to rotate in direction 4182 to open occlude vessel 4112 (see FIGS. 42A-42C). Specifically, rotation of occlusion device 4108 in direction 4182 causes leaflets of the device (e.g., including first and second leaflets 4120 and 4122) to open. Similarly, occlusion device 4108 may be closed, such as for removal, by rotation of guidewire 4100 to cause occlusion device 4108 to rotate in direction 4184 to recover or disengage occlusion device 4108 by forcing it closed (see FIGS. 42B-42C). Thus, rotation of occlusion device 4108 in direction 4184 causes leaflets of the device (e.g., including first and second leaflets 4120 and 4122) to close or form a smaller outer diameter than shown in FIG. 42A.

Figure 43:
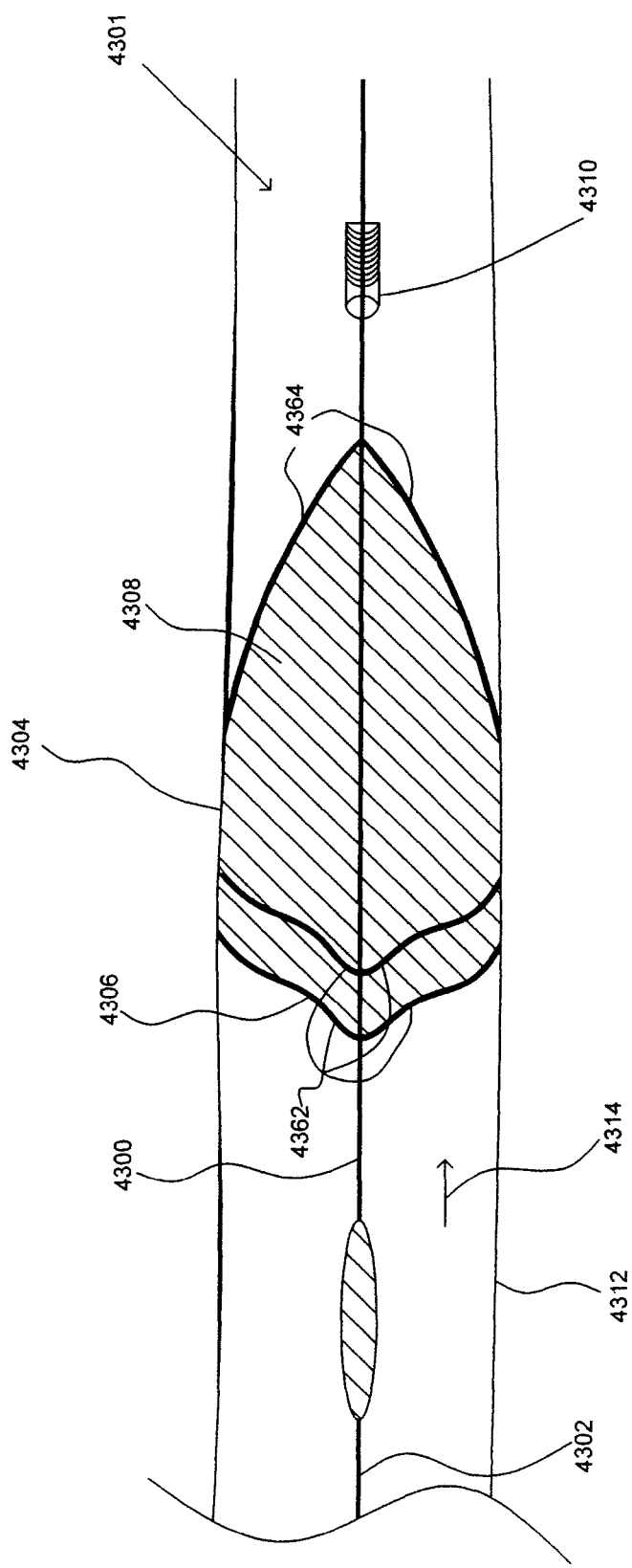
FIG. 43 illustrates a guidewire with an occlusion device.

Referring now to FIG. 43, guidewire 4300 is illustrated having a proximal section 4301 and distal end 4302. Occlusion device 4304 is provided adjacent distal end 4302. Occlusion device 4304 has a frame 4306, and basket 4308 stretched between the structure of frame 4306. For instance, frame 4306 is shown having distal frame 4362 and proximal frame 4364 to support basket 4308, such as where basket 4308 forms a scoup, cone, "parachute", or net shape between distal frame 4362 and proximal frame 4364 by being on, over, between, or attached to distal frame 4362 and proximal frame 4364. Suitable materials for basket 4308 include urethane, polyurethane, polyethylene, polypropylene, polybutylene, copolymers of ethylene, propylene, or butylene, latex, elastomers, PEBAX®, nylon and other materials that can block fluid flow. Also, suitable materials for frame 4306 include an elastic material, nitinol (NiTi), or self-expanding materials (e.g., such as shape memory alloys, including for example, Nickel-Titanium) or other materials that have shape memory where the memorized shape is the expanded shape. To modify the shape (e.g., to restrict the shape) a sheath may be placed over occlusion device 4304. Removing the restriction will allow the shape memory material to return to its memorized shape (e.g., an expanded shape) without being damaged. In the case shown by FIG. 43, sheath 4310 is provided over guidewire 4300 to be place over or restrain occlusion device 4304 (e.g., sheath 4310 may be a material or function as described above for sheath 790 or 4106 as described above with respect to FIGS. 7-9, and 41 respectively).

According to some embodiments, basket 4308 may be connected or attached to a frame 4306, such as by laser bonding, adhesive bonding, thermal bonding, mechanical restriction (e.g., such as if material basket 4308 is woven or sewn through structure of the frame, such as structure including gaps between the structure or holes in the frame), and or various other appropriate attachment methods as described herein. Likewise, an inner diameter of the frame 4306, such as in inner diameter of proximal frame 4364, may be attached to an outer surface of guidewire 4300, such as by laser bonding, adhesive bonding, thermal bonding, mechanical bonding.

In use, distal end 4302 is placed within vessel 4312, with sheath 4310 covering occlusion device 4304. When distal end 4302 is located in an appropriate location, sheath 4310 is pulled back, and frame 4306, which includes an elastic or expanding material to apply an expanding force to occlusion device 4304, forces open occlusion device 4304 stretching basket 4308 across vessel 4312 to occlude fluid flow. In addition, fluid flow in the direction of arrow 4314 forces open occlusion device 4304 and acts to press basket 4308 against the walls of vessel 4312, by also applying a force on the inside surfaces of basket 4308 which creates an expanding force to occlusion device 4304.

According to some embodiments, occlusion devices may include various types of balloons made of various materials and according to various manufacturing techniques. For example, in various embodiments, devices 720, 2006, 2104, 4108, 4304 as described herein; balloons 308, 314, 510, 2112, 2204, 2250, 2547, 2647, 3047, 3147, 3522, 3604, 3704, 3804, 3947, 4004, 4420, 4520, 4820, 8810, 9510 as described herein; or any other catheter, cannula, tube, sheath, balloon or occlusion device, may be made from or include a polymer material, such as a synthetic or natural latex or rubber. Moreover, the polymer material may be a polyether block amide resin, a polyetheramide, or a plasticiser free thermoplastic elastomer, for example, PEBAX®, a registered trademark of Atochem. Similarly, balloons or occlusion devices described herein may be made from or include a blend of different types of PEBAX®. In various embodiments, balloons or occlusion devices described herein may be made from or include a styrenic block copolymer (SBC), or a blend of SBC's. Suitable SBC's include SBC's sold under the tradename Kraton Polymers® a registered trademark of Shell Oil Company, SBC's sold under the tradename Vector® a registered trademark of Dexco Polymers, and SBC's sold under the tradename Europrene® a registered trademark of Polymeri Europa.

Figure 44:
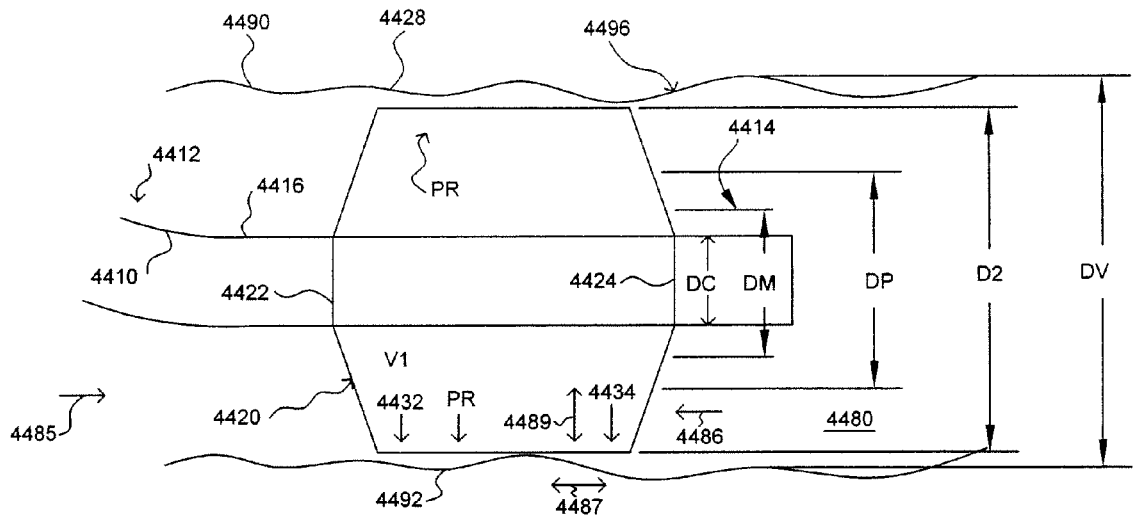
FIG. 44 is a cross-sectional view of a cannula and a balloon.

In fact, in some embodiments, balloons mentioned above, or other balloons or occlusion device, may include various types of a high-compliance or low-tension balloons, such as a composite or multi-layer expanded PolyTetraFlouroEthylene (ePTFE) balloon having an inner liner. For example, FIG. 44 is a cross-sectional view of a cannula and a balloon. As shown in FIG. 44, cannula 4410 (e.g., such as a cannula having a dimension suitable for percutaneous advancement through a blood vessel, such as advancement in direction 4586 through blood vessel 4490) includes proximal end 4412, distal end 4414, and exterior surface 4416. FIG. 44 also shows balloon 4420 (e.g., such as balloon mentioned above, or another balloon or occlusion device) axially connected to exterior surface 4416 of cannula 4410, at or adjacent distal end 4414. Also shown are diameter of cannula DC, pre-inflation diameter of balloon DM, inflated diameter of balloon D2, post-inflation deflated diameter of balloon DP, and diameter of vessel DV.

According to some embodiments, balloon 4420 may have a property such that when inflated balloon 4420 will expand in size to an outer diameter sufficient for occlusion of a blood vessel at an inflation pressure (or at an inflation volume with respect to balloon 8810 or apparatus 9700 or 9800 of FIGS. 75A-81) and less than sufficient to cause an axial force on an inner diameter of the blood vessel. For instance, FIG. 44 shows balloon 4420 inflated to outer diameter D2 sufficient for occlusion of blood vessel 4490 at inflation pressure PR, which is a pressure less than sufficient to cause an axial force, such as a force in directions 4487, on inner diameter 4492 of blood vessel 4490.

More particularly, balloon 4420 may include a property such that when inflated to volume V1, balloon 4420 will expand in size to outer diameter D2 that is approximately inner diameter DV of blood vessel 4490 at inflation pressure PR, which is a pressure less than sufficient to exert an axial strain on blood vessel 4490 in directions 4487. Thus, balloon 4420 may be a high-compliance balloon that expands radially and longitudinally upon inflation and forms a plurality of radial outer diameters during inflation to an outer diameter sufficient to occlude the blood vessel at an inflation pressure that does not appreciably expand the blood vessel radially (e.g., such as by occluding the blood vessel at a location while the inner diameter of the blood vessel at the location stays within five percent its pre-occlusion inner diameter). Furthermore, balloon 4420 may be a low-tension balloon, such as a balloon that expands radially and longitudinally upon inflation and forms a plurality of radial outer diameters during inflation and deflation, but does not form wings. For example, balloon 4420 may have a balloon pre-inflated outer diameter DM between three mm and five mm at an inflation pressure of between zero atmospheres and one atmosphere in pressure, and a balloon inflated outer diameter D2 between five mm and nine mm at an inflation pressure between six atmospheres and eight atmospheres in pressure. In addition, according to some embodiments, pressure PR may be a pressure sufficient to cause balloon 4520 to occlude the blood vessel without radially expanding the blood vessel.

In addition, balloon may have a property to cause post-inflation deflated outer diameter DP of balloon 4420 to retract to within 20% of pre-inflated outer diameter DM of balloon 4420. It is also contemplated that balloon 4420 may include one or more of the following characteristics: effective modulus of less than 1.5 MPa (e.g., such as during insertion into a blood vessel, use as an occlusion device, and removal from the blood vessel), and elongation of less than 500% at breaking, a tension set of less than 30%, a tension strength of at least 200 MPa, and an inflation range of pressure between zero and six atmospheres in pressure. In various embodiments, balloon 4420 may have a tension set of less than 30% in residual strength after elongation to 300%, such as by having a tension set of 20%, 15%, 10%, or 5%. Specifically, according to various embodiments, balloon 4420 may have a property to withstand an inflation pressure of between six and eight atmospheres of pressure and retract to within 20% of balloon 4420's initial pre-inflation dimension, upon removal of inflation pressure.

It is also contemplated that balloon 4420 may have a wall thickness that varies with respect to the axis of cannula 4410, so that when balloon 4420 is inflated, it has a tapered profile. For instance, according to various embodiments, balloon 4420 has a first wall thickness at first axial distance 4432 from distal end 4414 of the cannula and a different second wall thickness at different second axial distance 4434 from distal end 4414 of cannula 4410. Thus, when balloon 4420 is inflated, it will expand to a first outer diameter at distance 4432 and a different second outer diameter at distance 4434.

Similarly, it is contemplated that balloon 4420 may have a pre-inflated outer diameter that varies along the axis of cannula 4410 so that when balloon 4420 is inflated, it has a tapered profile. In various embodiments, when deflated, balloon 4420 has a first pre-inflated outer diameter at distance 4432 and a second pre-inflated outer diameter at distance 4434. Thus, when inflated, balloon 4420 will expand in size to a first outer diameter at distance 4432 and a different second outer diameter at distance 4434. An illustration of a balloon having a tapered profile is shown in FIG. 39.

In accordance with embodiments, balloon 4420 may be formed by various appropriate processes. For example, balloon 4420 may be formed by injection molding a material, extruding a material, solvent casting a material, or dip coating a material to form a balloon. Moreover, it is contemplating that extruding may include extruding a material such that balloon 4420 has a deflated outer diameter in a range of between 0.5 mm and five mm in diameter. For instance, material may be extruded such that balloon 4420 has a deflated outer diameter of 1.5 mm, and a thickness sufficient to reach an inflated outer diameter of nine mm at less than six atmospheres of inflation pressure.

Furthermore, in embodiments, balloon 4420 may include one or more of a silicone rubber; a polyurethane such as Pursil™, or another biocompatible silicone polyether urethane; Pebax™ such as polyether-block co-polyamide polymer, polyether-block anide; diene polymers and their copolymers; isoprenes; neoprenes; diene; styrene; butadienes; styrene-isoprene-styrene block co-polymers; styrene-butadiene-styrene co-polymers; partially or fully crosslinked versions of these same polymers, such as a Kraton™ (e.g., such as Kraton™ 1161K, which is a styrene-isoprene-styrene tri-block co-polymer with 85% isoprene and 15% styrene), any styrene-isoprene-styrene tri-block co-polymer with up to 100% isoprene and up to 50% styrene; unsaturated dienes, their co-polymers and partially or fully crosslinked versions of these same; and an aliphatic polymethane with polydimethyl siloxane backbone. Note that for bondability of such polymers, one or more functional groups may be chemically added to the polymer structure. In particular, balloon 4420 may include one or more of a silicone rubber, a Kraton™, and a styrene-isoprene-styrene tri-block co-polymer treated with one or more of the following additives: thiuram disulfide derivatives (R'R" N—(C=5)-S—S—(C=5)-NR'R"), mercaptobenzothiazoles, aminomercaptobenzothrazole (e.g, such as to vulcanized a silicone rubber), sulfides, and azides. Therefore, for example, balloon 4420 may include any of the materials listed above, and may be treated with an additive such as by treating balloon outer diameter 4428 with one or more of the additives mentioned above.

Figure 45:
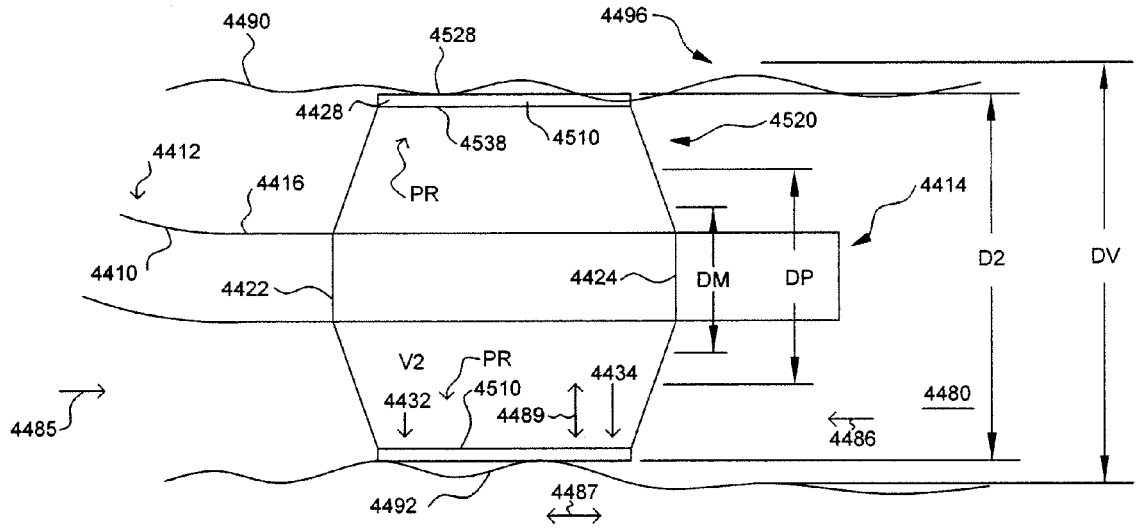
FIG. 45 is a cross-section view of a cannula and a lined ePTFE balloon.

Finally, in accordance with embodiments, outer diameter 4428 of balloon 4420 may be bonded to an inner diameter of a plurality of fused layers of ePTFE. For example, FIG. 45 is a cross-section view of a cannula and a lined ePTFE balloon. FIG. 45 shows balloon 4520 having a plurality of fused layers of ePTFE 4510 with inner diameter 4538 of the ePTFE layers bonded to outer diameter 4428 of balloon liner 4420. According to some embodiments, balloon liner 4420 described below as a liner for balloon 4520 may be balloon 4420 described above for FIG. 44, or any of balloons 308, 314, 510, 2112, 2204, 2250, 2547, 2647, 3047, 3147, 3522, 3604, 3704, 3804, 3947, 4004, 4520, 4820, 8810, 9510, 9110, 9210, 9310, 9910, 9920.

According to some embodiments, balloon 4520 may have a property such that when inflated balloon 4520 will expand in size to an outer diameter sufficient for occlusion of a blood vessel at an inflation pressure (or at an inflation volume with respect to balloon 8810 or apparatus 9700 or 9800 of FIGS. 75A-81) and less than sufficient to cause an axial force on an inner diameter of the blood vessel. For instance, FIG. 45 shows balloon 4520 inflated to outer diameter D2 sufficient for occlusion of blood vessel 4490 at inflation pressure PR, which is a pressure less than sufficient to cause an axial force, such as a force in directions 4487, on inner diameter 4492 of blood vessel 4490. Note that according to some embodiments, a pressure less than sufficient to cause an axial force, includes a pressure less than sufficient to cause an axial force of more than 25 percent of the radial pressure caused by a balloon on the inner diameter of a blood vessel.

More particularly, balloon 4520 may include a property such that when inflated to volume V2, balloon 4520 will expand in size to outer diameter D2 that is approximately inner diameter DV of blood vessel 4490 at inflation pressure PR, which is a pressure less than sufficient to exert an axial strain on blood vessel 4490 in directions 4487. Thus, balloon 4520 may be a high-compliance or low-tension balloon, such as a balloon that expands radially and longitudinally upon inflation or forms a plurality of radial outer diameters during inflation and deflation, but does not form wings. In addition, according to some embodiments, pressure PR may be a pressure sufficient to cause balloon 4520 to occlude the blood vessel without radially expanding the blood vessel.

In addition, in accordance with embodiments, fused layers of ePTFE 4510 may include one or more layers of ePTFE windings. For example, fused layers of ePTFE 4510 may include one or more layers of ePTFE windings wound over each other in concentric, overlaying, intersecting, or criss-cross patterns, wound according to a process, such as is described below with respect to FIG. 46. Specifically, an ePTFE winding may be one or more strips or ribbons of ePTFE material greater in length than in width, where the width of the material is less than or equal to the distance between proximal coupling 4422 and distal coupling 4424 as shown in FIG. 45. Thus, windings of ePTFE material may be supplied from spools, such as spools for storing or supplying ribbon, cloth material, or tape. Also, it is contemplated that fused layers of ePTFE 4510, or windings of ePTFE material may be porous or may include a property such that the layers or windings of ePTFE do not stretch or have a limited ability to stretch axially, or with respect to the width of the fused layers of ePTFE or ePTFE windings. Thus, during inflation or deflation, balloon 4520 may include a property such that fused layers of ePTFE 4510 expand and contract radially but have no substantial expansion or contraction axially. Note that according to some embodiments, no substantial expansion or contraction axially, includes not expanding or contracting axially in length by a distance of more than 5 percent of the outer diameter distance of the layers. For example, fused layers of ePTFE 4510 may expand and retract in directions 4489 but have no substantial expansion axially in directions 4487 as shown in FIG. 45. Moreover, for the embodiment shown in FIG. 45, it is contemplated that balloon liner 4420 may expand and contract axially in directions 4487 as well as radially in directions 4489.

Thus, according to some embodiments, balloon 4520 may have a property to cause balloon 4520 to have a post-inflation deflated outer diameter that retracts to within 20% of a pre-inflated outer diameter of balloon 4520. Specifically, balloon liner 4420 may cause balloon 4520 to retract when deflated to a post-inflated deflated outer diameter DP that is approximately 440% greater than the pre-inflated outer diameter DM of balloon 4520. Moreover, balloon 4520 may include a property such that during inflation outer radial surface 4528 of balloon 4520 is parallel to the axis of cannula 4410, and surface 4528 expands radially in directions 4489 but has no substantial expansion axially in directions 4487, or along a direction parallel to the axis of cannula 4410.

Similarly to balloon 4420 of FIG. 44, fused layers of ePTFE 4510 may include a property such that during inflation and deflation, fused layers of ePTFE 4510 form a plurality of radial outer diameters, such as diameters DM, D2, and DP, but do not form wings. Also, balloon 4420 or balloon 4520 may include a property such that inflated outer diameter D2 approximates an inner diameter of a coronary sinus of a subject at a treatment region and may be sufficient in diameter to make a pressure waveform of fluid in a coronary sinus or blood vessel become ventricularized. Specifically, balloon 4420 or balloon 4520 may have an outer diameter D2 sufficient to make pressure waveform 4486 of fluid 4480 in blood vessel 4490 become ventricularized. It is also contemplated that diameter D2 may be a diameter sufficient to expand an inner diameter of a blood vessel without damaging or bursting the blood vessel. In other embodiments, inflated outer diameter D2 of balloon 4420 or balloon 4520 may expand inner diameter DV of blood vessel 4490 sufficient to increase the permeability of a wall of blood vessel 4490 to a treatment or biological agent infused into the blood vessel proximate or super-adjacent to the balloon (e.g., such as a treatment agent described herein, infused at treatment region 4496).

In embodiments, balloon 4520 may have a pre-inflated outer diameter between three mm and five mm at a pressure of between zero and one atmosphere (e.g., such as approximately zero atmospheres), and a balloon inflated outer diameter D2 between seven mm and eleven mm inflation pressure PR, of between six and eight atmospheres. Embodiments of balloon 4520 also include a balloon having inflated outer diameter D2 in a range of between five mm and nine mm in diameter at a pressure of less than six atmospheres.

Figure 55:
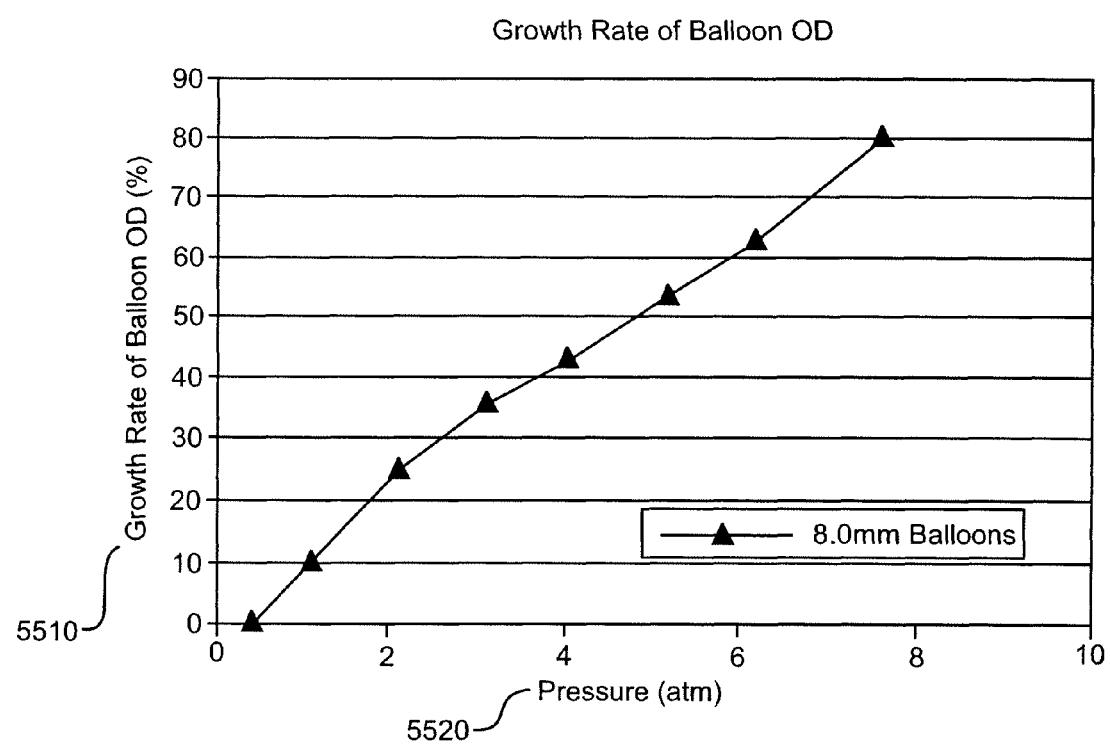
FIG. 55 illustrates a balloon outside diameter growth rate.

Likewise, according to some embodiments, balloon 4420, or balloon 4520 may have an outside diameter growth rate such as that shown in FIG. 55. Specifically, for an inflation pressure between two and six atmospheres, balloon 4420 or balloon 4520 may include a property such that the balloon will inflate to increase in outer diameter by at least 15% in diameter as compared to a prior outer diameter, for each one atmosphere increase in inflation pressure. Notably, the semi-linear relationship between outer diameter and inflation pressure as shown in FIG. 55 for balloon 4420 or balloon 4520 allows a balloon to be calibrated to determine an amount or volume of liquid, such as volumes V1 or V2, for providing a desired inflation pressure, such as pressure PR. Thus, once a calibration curve of inflation volume versus inflation pressure for a balloon for various inflation volumes of liquid is created, it is possible to select a desired inflation pressure and determine the amount or volume of liquid required to provide that desired pressure. Then, the balloon may be inserted into a subject, such as via percutaneous insertion as described herein, and filled with the predetermined volume of fluid to provide the desired inflation pressure. Therefore, the various configurations of balloon 4420 or balloon 4520 described herein can be used to occlude a blood vessel, such as an artery or vein in the human heart as is described herein. Furthermore, according to some embodiments, cannula 4410 of FIGS. 44 and 45 may be a guide catheter, a delivery catheter, or a guidewire, such as described herein.

Figure 46:
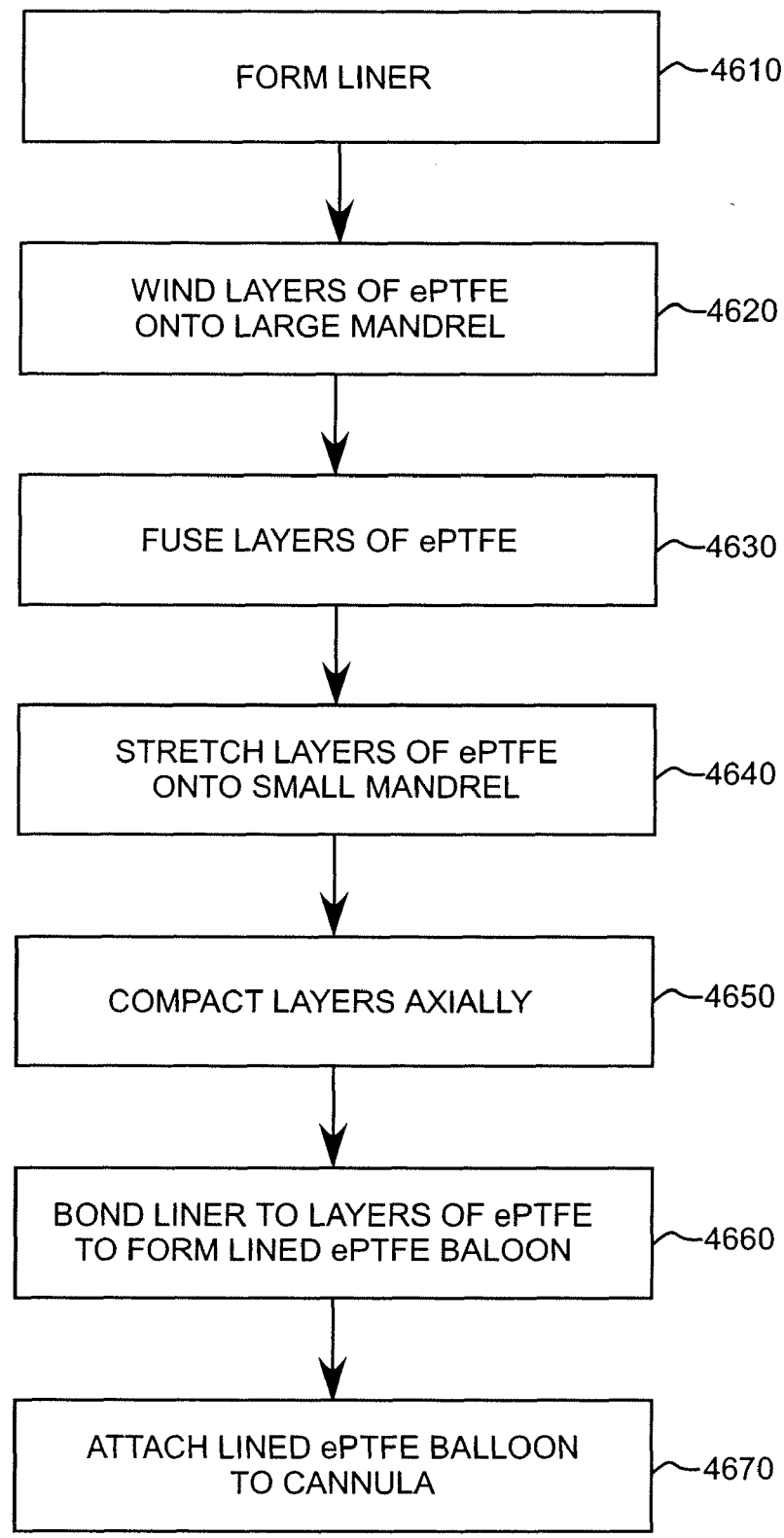
FIG. 46 is a flow diagram of a process for forming a lined ePTFE balloon.

In addition, according to some embodiments, various appropriate processes may be used to form a lined ePTFE balloon or an ePTFE composite balloon, such as balloon 4520. For example, FIG. 46 is a flow diagram of a process for forming a lined ePTFE balloon. At block 4610, a balloon liner is formed, such as by forming balloon 4420 as described above.

At block 4620, layers of ePTFE are wound onto a large mandrel, such as by wrapping ePTFE windings, as described above, around a mandrel having a diameter in a range of between 10 mm and 12 mm in diameter. According to some embodiments, the diameter of the large mandrel may be selected to be a diameter that is in a range between one mm and two mm larger than the desired diameter of the lined ePTFE balloon when inflated. Specifically, for example, a 10 mm diameter large mandrel may be used when forming a lined ePTFE balloon, such as balloon 4520, to have an inflated diameter D2 of 9 mm. Likewise, a mandrel of 11 mm may be used to produce a lined ePTFE balloon having an inflated diameter of 12 mm.

Figure 47:
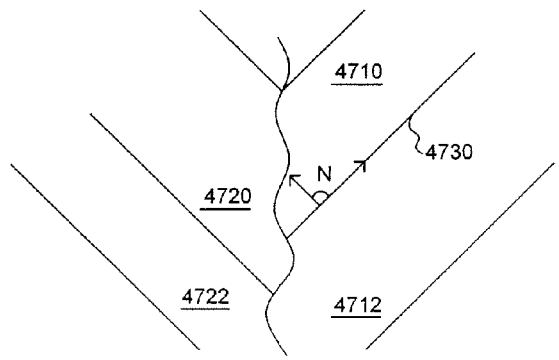
FIG. 47 is an elevated cut-away view of layers of ePTFE windings.

In addition, according to some embodiments, the layers of ePTFE may be formed by ePTFE windings, strips, or ribbons, such as those described above for fused layers of ePTFE 4510. For instance, windings of ePTFE material may be wound onto a large mandrel to form multiple layers of ePTFE that overlay, intersect, are concentric with, or criss-cross other windings or layers of ePTFE in various patterns and at various angles. Thus, fused layers of ePTFE 4510 may include one layer of ePTFE windings wound over another layer of ePTFE windings such that the one layer of windings forms an "X" pattern, a "W" pattern, a "S" pattern, or a criss-cross pattern. For example, FIG. 47 is an elevated cutaway view of layers of ePTFE windings. As shown in FIG. 47, first ePTFE windings 4710 and 4712 are wound over second ePTFE windings 4720 and 4722, such that first ePTFE windings 4710 and 4712 are at an angle, as shown by angle N of between 30° and 120° with respect to second ePTFE windings 4720 and 4722. Specifically, in FIG. 47, angle N is 90°. However, it is contemplated that angle N may be various other angles between 30° and 120° such as, an angle of 35°, an angle of 45°, an angle of 60°, an angle of 90°, or an angle of 115°.

Besides winding ePTFE windings in various patterns to form ePTFE layers, various numbers of ePTFE layers may be wound or formed as necessary to ensure that there are enough layers to ensure that the ePTFE layers or windings do not come apart or separate (e.g., such as during inflation and deflation), but not so many ePTFE windings or layers that expansion is inhibited beyond a desired inflation diameter of expansion. For instance, when forming plurality of fused ePTFE layers 4510, a sufficient number of ePTFE layers may be wound or formed such that when balloon 4520 is completed, fused ePTFE layers 4510 do not separate when ePTFE balloon 4520 is inflated to inflation pressure PR of between 6 and 8 atmospheres in pressure. More particularly, as shown in FIG. 47, a first ePTFE layer having first ePTFE windings 4710 and 4712 may be formed over a second ePTFE layer having second ePTFE windings 4720 and 4722 to form balloon 4520 such that when balloon 4520 is inflated first ePTFE windings 4710 and 4712 do not separate from second ePTFE windings 4720 and 4722. Moreover, according to some embodiments, sufficient ePTFE layers and windings may be provided so that ePTFE layers or windings do not separate along seams, such as seam 4730 between first ePTFE windings 4710 and 4712. Although FIG. 47 shows only two ePTFE layers, it is contemplated that fused ePTFE layers 4510 may include more than two layers, such as by including three layers, four layers, five layers, six layers, seven layers, or 10 layers. Thus, for instance, block 4620 may include windings between two and six ePTFE layers in a single direction in a "bandage" wrapped style so that seams between ePTFE windings in a single layer are bonded or super-adjacent to each other.

At block 4630, layers or windings of ePTFE, such as from block 4620, are fused together, such as by heating the layers or windings wound onto the large mandrel. For instance, layers of ePTFE wound onto a large mandrel may be heated at a temperature between 350° C. and 400° C. for a duration of greater than 10 minutes and less than 60 minutes, as necessary to sinter the plurality of ePTFE layers or windings. Thus, plurality of fused ePTFE windings 4510 may include windings such as first windings 4710 and 4712 wound over second windings 4720 and 4722 onto a large mandrel and heated to a temperature of approximately 380° C. for a duration of between 20 and 30 minutes so as to fuse first windings 4710 and 4712 to each other and to second windings 4720 and 4722. After fusing, fused ePTFE layers may be removed from the large mandrel.

At block 4640, the fused layers of ePTFE are stretched onto a small mandrel. For instance, a small mandrel may be placed within an inner diameter of the fused ePTFE layers and the fused ePTFE layers may then be stretch apart along the axis of the small mandrel sufficiently so that the ePTFE layers are stretched onto, touch, or conform to the small mandrel. Thus, a distal end and a proximate end of the fused ePTFE layers may be gripped or connected to and stretched apart in opposite directions until the fused layers of ePTFE are stretched sufficiently as described above. After the fused layers are sufficiently stretched, they may be stabilized by heating. For example, the layers may be stabilized over a set temperature and time, such as by heating to a temperature of 380° C. for a duration of between 30 seconds and two minutes in duration (e.g., such as for approximately one minute). Moreover, according to some embodiments, the outer diameter of the small mandrel may be selected to be a diameter in a range of between two mm and three mm larger than the desired deflated diameter of a lined ePTFE balloon before inflation. For example, the small mandrel may have an outer diameter between two and three mm larger than deflated diameter DM of balloon 4520.

At block 4650, the stretched fused layers of ePTFE are compacted axially, such as by being compacted in directions opposite of directions 4487. For instance, fused layers of ePTFE stretched onto a small mandrel may then have their outer diameter wrapped with a TEFLON™ tape, a "plumbers" tape, or maybe constrained with a steel tube. Then the wrapped or constrained layers of ePTFE may be compacted axially so that the wrapping or constraining of their outer diameter controls expansion of the outer diameter during compacting. For instance, according to some embodiments, compacting includes sufficiently compacting axially inwards (e.g., such as in directions opposite of directions 4487) a distal end and a proximate end of the stretched fused layers of ePTFE, such that during inflation of the lined ePTFE balloon (e.g., such as during inflation of balloon 4520 to inflation pressure PR), the compacted stretched fused layers of ePTFE (e.g., such as fused ePTFE layers 4510) may not expand axially (e.g., such as by being incapable of expanding in directions 4487). Moreover, according to some embodiments compacting may include sufficiently compacting axially inwards a distal end and a proximate end of the compacted stretched fuses of ePTFE such that during inflation of the lined ePTFE balloon (e.g., such as described above) the compacted stretched fused layers of ePTFE (e.g., such as fused ePTFE layers 4510) may expand axially (e.g., such as in directions 4487) by a selected percentage of an axial size of the compacted stretched fused layers of ePTFE, during inflation of the lined ePTFE balloon. Hence, more particularly, the stretched fused layers of ePTFE may be compacted sufficiently at block 4650 so that during inflation of balloon 4520, fused ePTFE layers 4510 may expand axially in directions 4487 by a selected percentage of the length of the compacted stretched fused layers of ePTFE along the longitudinal axis of the small mandrel.

Furthermore, according to some embodiments, compacting may include compacting sufficiently to reduce the porosity of the windings or layers of ePTFE. After compacting, it is contemplated that the compacted stretched fused layers of ePTFE be stabilized over a set temperature and time, such as is described above for stabilizing the fused stretched layers of ePTFE with respect to block 4640. After stabilizing the TEFLON™ tape, "plumbers" tape, or tube may be removed from the ePTFE layers and the ePTFE layers may be removed from the small mandrel.

Moreover, it is contemplated that the large mandrel or small mandrel associated with blocks 4620 and 4640 may be tapered so that the lined ePTFE balloon formed has a tapered profile, such that when inflated, the balloon with expand in size to a first outer diameter at a first position and a different second outer diameter at a different second position. Thus, the large mandrel and the small mandrel may be selected to have a tapered profile so that ePTFE layers have a tapered profile and form lined ePTFE balloon 4520 that when inflated will expand in size to a first outer diameter at first axial distance 4432 from distal end 4414 of the cannula and will expand in size to a different second outer diameter at different second axial distance 4434 from distal end 4414 of the cannula, such as to provide a tapered profile similar to that shown in FIG. 39.

At block 4660, the layers of ePTFE may be bonded to a balloon liner to form a lined ePTFE balloon, such as balloon 4520. It can be appreciated that an inner diameter of the compacted stretched fused layers of ePTFE may be chemically modified before bonding to a balloon liner. Specifically, inner diameter 4538 of ePTFE layers 4510 may be modified with a plasma polymerization of acrylic acid or a chemical etch of sodium naphthalene before being bonded to balloon 4420. Moreover, it is considered that bonding may include vulcanizing an inner diameter of the compacted stretched fused layers of ePTFE to a liner having an outer diameter of silicone rubber material. Also, according to some embodiments, bonding may include hydrogen bonding an inner diameter of the compacted stretched fused layers of ePTFE with a balloon liner having an outer diameter of polyurethane material.

Likewise, in embodiments, bonding may include bonding an inner diameter of the compacted stretched fused layers of ePTFE with a balloon liner having an outer diameter of material such as materials described above for forming balloon 4420 or treated of modified with additives, such as additives described above with respect to balloon 4420. Specifically, chemical modifications to an outer diameter of a balloon liner, such as balloon 4420, are considered before bonding the balloon liner to the compacted stretched fused layers of ePTFE.

According to various embodiments, the bonding at block 4660 may include inserting a balloon liner, such as balloon 4420, into the inner diameter of the compacted stretched fused layers of ePTFE, such as into inner diameter 4538 of fused layers of ePTFE 4510. Then, the outer diameter of the compacted stretched fused layers of ePTFE, such as outer diameter 4528 may be constrained with, for example, a TEFLON™ tape, a "plumbers" tape, or a steel tube. Next, the balloon liner, such as balloon 4420, may be inflated to cause an outer diameter of the balloon liner, such as outer diameter 4428, to contact or bond to the inner diameter of the constrained compacted stretched fused layers of ePTFE, such as inner diameter 4538. For example, the balloon liner may be inflated to an inflation pressure of between 10 and 50 psi, such as to approximately 30 psi. Next, it is contemplated that the constrained compacted stretched fused layers of ePTFE, such as layers of ePTFE 4510, may be heated sufficiently to bond the outer diameter of the balloon liner, such as outer diameter 4428, to the inner diameter of the compacted stretched fused layers of ePTFE, such as inner diameter 4538. For example, the layers of ePTFE may be heated such as described with respect to stabilizing the layers of ePTFE with respect to block 4640.

After bonding the liner to the layers of ePTFE, the constraining tape or steel tube can be removed and the resulting lined ePTFE balloon can be attached to a cannula. For example, at block 4670, lined ePTFE balloon 4520 may be attached to cannula 4410 such as by methods for attaching occlusion devices to a cannula as described herein. Specifically, proximal end 4422 or distal end 4424 of balloon 4420 or balloon 4520 may be attached to cannula 4410 using one of an adhesive, a crimping bond, a laser bond, and a heat bond, such as to bond proximal end 4422 or distal end 4422 to surface 4416 of cannula 4410. Moreover, it is contemplated that such bonding may include ultraviolet (UV) light adhesive or UV thermal bonding. Finally, it is considered, that cannula 4410 may be a cannula described herein, such as including a guide catheter, delivery catheter, or guidewire.

Also, in embodiments, occlusion or filter devices 720, 2006, 2104, 4108, 4304 as described herein; balloons 308, 314, 510, 2112, 2204, 2250, 2547, 2647, 3047, 3147, 3522, 3604, 3704, 3804, 3947, 4004, 4420, 4520, 4820, 8810, 9510, 9110, 9210, 9310, 9910, 9920 as described herein; and any other catheter, cannula, tube, sheath, balloon or occlusion device, may be formed of material including a polymer material, such as a polyurethane-silicone blend (e.g., for example, PurSil™), a homopolymer of an olefin, or a co-polymer of an olefin and one or more other material(s). In various embodiments, a filter device, catheter, cannula, tube, sheath, or balloon or occlusion device, may have a coating applied to its inside or outside surface, such as, for example, a hydrophilic coating.

Additionally, in various embodiments, a filter device, catheter, cannula, tube, sheath, balloon or occlusion device, may be made of or include a material that minimizes allergic reactions or provides improved control of expansion outer diameter during inflation and deflation. For instance, such a balloon can be used in a vessel having a diameter range of about four mm to about nine mm diameter. Moreover, such a filter device, balloon, or occlusion device may be designed or formed to have a larger distal outer diameter and a smaller proximal outer diameter when inflated (e.g., be thicker distally in outer diameter when inflated and thinner proximally).

Specifically, such a filter device, balloon, or occlusion device may have a conical shape.

In various embodiments, a balloon as mentioned herein may be placed in a blood vessel, such as the coronary sinus or a cardiac vein. For example, a balloon can be advanced to a location in the great cardiac vein, a branch of the great cardiac vein, the middle cardiac vein, the small cardiac vein, or a coronary artery. Thus, the coronary sinus or the cardiac vein may be elastic in nature, so the balloon may prevent vessel hematomas or occlusion of adjacent coronary artery by functioning as a sealer, and not a dilator. In various embodiments, the balloon is very compliant, achieving occlusion at low pressure for a range of vessel sizes. For example, a diameter of the coronary sinus may range from about 6.5 mm to about 11 mm, a diameter of the great cardiac vein may range from about 4.0 mm to about 7.5 mm, and the diameter of a branch of the great cardiac vein may range from about 2.5 mm to about 5.0 mm.

It is also considered that a balloon may be placed in a blood vessel, such as the coronary sinus or a cardiac vein. For example, a balloon described herein may be advanced to a location in the great cardiac vein, a branch of the great cardiac vein, the middle cardiac vein, or the small cardiac vein, or a coronary artery to occlude the vessel before the infusion or retro-infusion of a fluid or treatment agent. In this embodiment, the balloon is able to extend if the vessel is enlarged during the infusion or retro-infusion and maintain occlusion of the vessel.

In some embodiments, a balloon may be made from or include material such as a polyether block amide, a polyetheramide, and mixtures thereof. Similarly, a balloon may be made from or include a polymer having a structure of a regular linear chain of rigid polyamide segments interspaced with flexible polyether segments. In an embodiment, a balloon may be made from or include a polymer or a mixture of two or more of the polymers having the tradename PEBAX® (a registered trademark of ATOCHEM), for example Pebax 63D and 55D, or for example one or more PEBAX® polymers having a Shore D hardness less than 70D. In an embodiment, a balloon as described herein, such as for occluding a blood vessel may be made from or include a polymer or a mixture of two or more of the polymers represented by the formula:

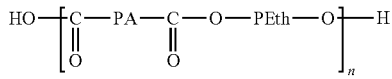

(Where PA represents a polyamide segment, and PEth represents a polyether segment, and "n" represents an integer of at least one.)

In an embodiment, a balloon to be inflated to a selected inflation pressure or volume may occlude a blood vessel at a pressure of about 0.5 to about five atmospheres. In another embodiment, a balloon may achieve a growth rate greater than about 40% while maintaining a pressure below four atmospheres or even below one atmosphere. Here, the balloon pressure is kept low despite an increase in diameter because of the elasticity of the balloon material. In an embodiment, the balloon may have an expanded outer diameter between about 1.5 millimeters (mm) and about 18 mm when inflated. Moreover, the balloon may have a double wall thickness between about 0.0003 and about 0.0038 inches or a minimum hoop strength of at least about 23,000 pounds per square inch (psi). In another embodiment, the balloon may be either heat bonded, laser bonded, shrink tube or wrap bonded, or attached with an adhesive to a catheter, cannula, port, lumen, or tube as described herein.

Figure 48:
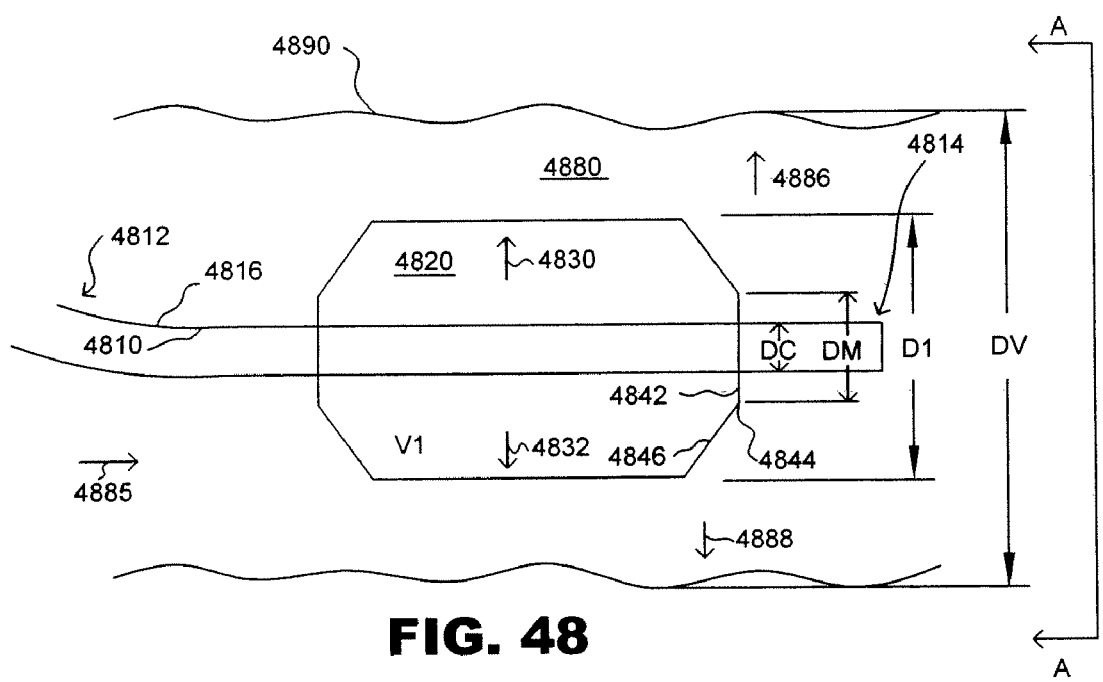
FIG. 48 is a cross section view of a cannula and a balloon.

In some embodiments, a balloon or occlusion device, may be a high compliance low pressure balloon. For example, FIG. 48 is a cross section view of a cannula and a high compliance low pressure balloon. As shown in FIG. 48, cannula 4810 (e.g., such as a cannula having a dimension suitable for percutaneous advancement through a blood vessel, such as advancement in direction 4885 through blood vessel 4890), includes proximal end 4812, distal end 4814, and exterior surface 4816. FIG. 48 also shows balloon 4820 axially connected to exterior surface 4816 of cannula 4810, at or adjacent distal end 4814. FIG. 48 shows cannula 4810 having diameter of cannula DC, and balloon 4820 having minimal wing diameter DM, and balloon outer first diameter D1. Blood vessel 4890 is shown having diameter of vessel DV and fluid 4880 (e.g., such as blood or treatment agent). Balloon 4820 may be a balloon, occlusion device, or filter device such as described herein.

Furthermore, according to some embodiments, balloon 4820 may include material or matter having a polymer moiety represented by the formula

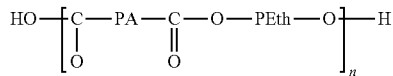

wherein PA represents a polyamide moiety, and PEth represents a polyether moiety, and "n" represents an integer of at least one. In addition, according to some embodiments, balloon 4820 may include a thermoplastic blend copolymer material having one of a polyether block amide resin moiety and a polyetheramide moiety. In addition, according to some embodiments, balloon 4820 may be restricted or restrained from expansion or inflation, such as by a sheath (e.g., such as sheath 790 described above for FIGS. 7-10), to have first diameter D1.

Figure 49B:
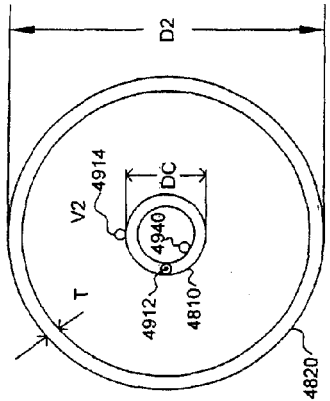
FIG. 49B may be a cross sectional view of FIG. 49A from perspective "A", according to an embodiment.
Figure 49A:
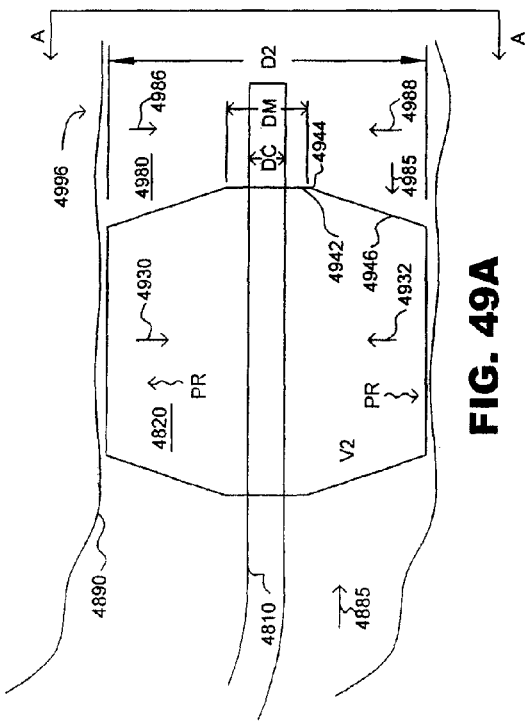
FIG. 49A is a cross sectional view of a cannula and a balloon inflated to occlude a blood vessel.

According to some embodiments, balloon 4820 may have a property such that balloon 4820 will inflate, such as in directions 4886 and 4888 as a result of pressures 4830 and 4832 increasing balloon first volume V1, to an inflated balloon outer second diameter that will occlude a blood vessel. For example, FIG. 49A is a cross sectional view of a cannula and a balloon inflated to occlude a blood vessel. As shown in FIG. 49A, balloon 4820 is inflated to second diameter D2 that will occlude blood vessel 4990, such as by substantially preventing fluid 4980 from flowing in blood vessel 4890 past balloon 4820 in direction 4985. Likewise, FIG. 49A shows balloon 4820 inflated to have volume V2, and exert pressure PR on an inner diameter of blood vessel 4890.

Consequently, according to some embodiments, balloon 4820 may include a property such that balloon 4820 can achieve a volumetric expansion (e.g., such as by expanding from first volume V1 to second volume V2) of greater than about 40% during inflation. Specifically, balloon 4820 may have a property such that it may inflate according to the growth rate chart of FIG. 55. Moreover, balloon 4820 may be able to expand or inflate to an inflated outer diameter, such as second diameter D2, between 1.5 millimeters and 18 millimeters in diameter. Likewise, according to some embodiments, balloon 4820 may be inflated to second diameter D2 to occlude blood vessel 4890 at a predetermined pressure, such as pressure PR, of between 0.5 atmospheres and 5.0 atmospheres of pressure. More particularly, balloon 4820 may include a property such that it will inflate to a predetermined pressure, such as pressure PR, sufficient to make a pressure waveform in a blood vessel become ventricularized. For example, balloon 4820 may inflate to a predetermined pressure to make a pressure waveform of blood or fluid, such as fluid 4980, traveling in direction 4985 become ventricularized. Thus, balloon 4820 may be inflated to a predetermined volume, such as second volume V2, or a predetermined inflated outer diameter, such as second diameter D2.

Furthermore, balloon 4820 may have deflated a double wall thickness between 0.0003 and 0.0038 inches in thickness. For example, FIG. 49B may be a cross sectional view of FIG. 49A from perspective "A", according to an embodiment. FIG. 49B shows single wall thickness T of balloon 4820, wherein T is ½ of the double wall thickness. Moreover, according to some embodiments, balloon 4820 may have a minimum hoop strength of at least about 23,000 psi strength. Also, balloon 4820 may include a property such that the balloon will have a durometer hardness of between 50 Shore D and 70 Shore D. Next, balloon 4820 may be axially connected to an exterior surface of a cannula, such as cannula 4810, wherein the cannula may be a guide cannula, a delivery cannula, or a guide wire as described herein.

FIG. 49B also shows cannula 4810 having lumens 4912, 4914, and 4940. Lumen 4912 may be a lumen such as lumen 1712 described above for FIG. 17. Lumen 4914 may be a lumen such as lumen 1812 described above for FIG. 18. Lumen 4940 may be a lumen such as lumen 1740 described above for FIG. 17. It is also considered any of that lumens 4912, 4914, and 4940 may be similar to a guidewire lumen, accessory lumen or pressure lumen as described herein.

Figure 50:
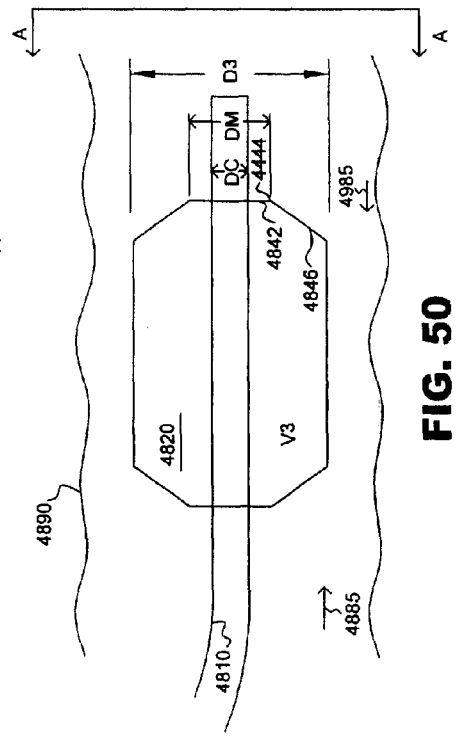
FIG. 50 is a cross sectional view of a cannula and a postinflated deflated balloon.

According to some embodiments, balloon 4820 may include a property such that the balloon will deflate, such as in directions 4986 and 4988 as a result of pressures 4930 and 4932 to reduce second volume V2, to a post-inflated deflated balloon outer third diameter. For example, FIG. 50 is a cross sectional view of a cannula and a postinflated deflated balloon. As shown in FIG. 50, balloon 4820 is postinflated deflated to third volume V3 and third diameter D3. Specifically, balloon 4820 may be deflated to third diameter D3 that will allow balloon 4820 to be withdrawn from a blood vessel, such as withdrawn in direction 4985 from blood vessel 4890. Consequently, postinflated deflated volume of balloon 4820, such as third volume V3 may be approximately equal to preinflated volume of balloon 4820, such as volume V1.

Figure 51:
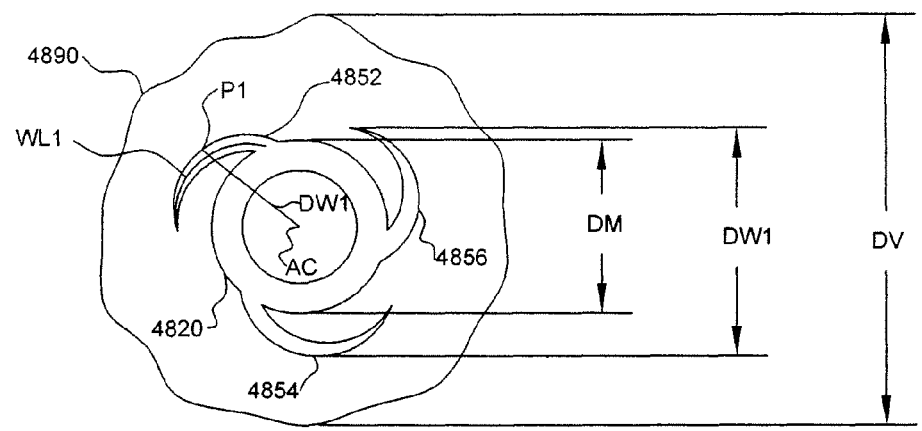
FIG. 51 is a cross sectional view of FIG. 48 from perspective "A".

Furthermore, according to some embodiments, balloon 4820 may include a property such that it has at least three wings before being inflated and after being deflated. For example, FIG. 51 may be a cross sectional view of FIG. 48 from perspective "A", according to an embodiment. FIG. 51 shows balloon 4820 having wings 4852, 4854, and 4856 before balloon 4820 being inflated. Moreover, each wing has a wing length defined by the length of a line extending within the wing along a medial axis of a cross-section of the wing. For example, FIG. 51 shows wing 4852 having wing length one WL1 defined by the length of a line extending within wing 4852 along a median access of a cross section of wing 4852, such as shown by wing length one WL1 in FIG. 51.

Figure 52:
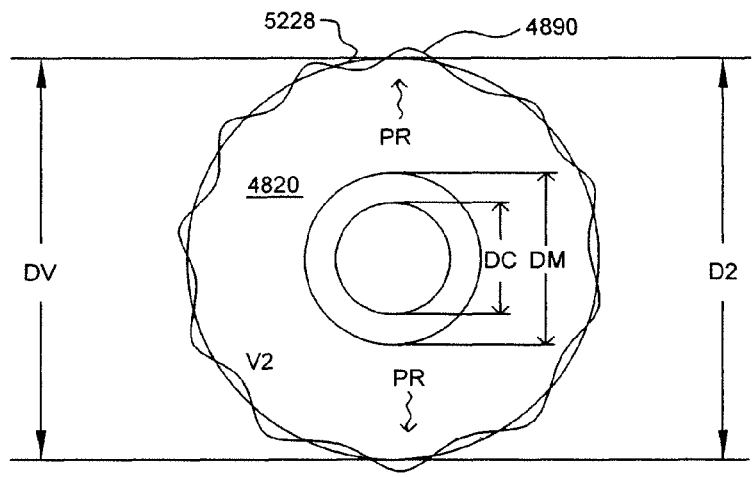
FIG. 52 is a cross sectional view of FIG. 49A from perspective "A".

In addition, balloon 4820 includes a property such that the wings of balloon 4820 are subsumed into the outer diameter of balloon 4820 when inflated. For example, FIG. 52 may be a cross sectional view of FIG. 49A from perspective "A", according to an embodiment. FIG. 52 shows balloon 4820 having outer balloon diameter 5228 when inflated, and second diameter D2 which is approximately equivalent to that of or at least equivalent to that of an inner diameter of a blood vessel at a treatment region. Thus, second diameter D2 may be approximately equivalent to or at least equivalent to diameter of vessel DV of blood vessel 4890. Moreover, according to some embodiments, second diameter D2 may be a diameter sufficient to occlude a blood vessel, such as blood vessel 4890.

Figure 53:
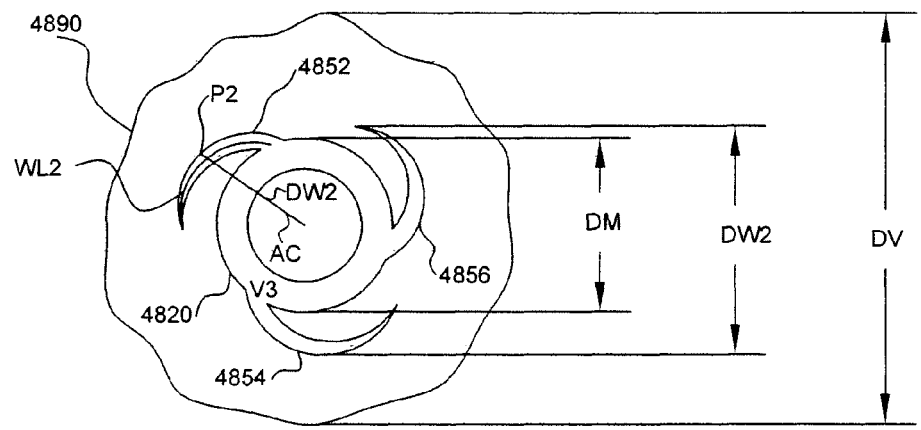
FIG. 53 is a cross sectional view of FIG. 50 from perspective "A".

Further, balloon 4820 may include a property such that the balloon will have at least three wings before being inflated and after being deflated, wherein a pre-inflated wing length for each wing is approximately equal to a post-inflated deflated wing length for each wing. For example, FIG. 53 may be a cross sectional view of FIG. 50 from perspective "A", according to an embodiment. FIG. 53 shows postinflated deflated wing length two WL2 of wing length 4852 being a wing length that is approximately equal to preinflated wing length one WL1. Thus, although balloon 4820 is shown before inflation in FIG. 49A and after being inflated and deflated in FIG. 53, the wing length of wing 4852 before inflation is approximately equal to that for wing 4852 after being inflated and deflated.

However, according to some embodiments, balloon 4820 may include a property such that an outer diameter point farthest away from the access of cannula 4810 for each wing is approximately 30% greater for the postinflated deflated wing than it is for the preinflated wing. For example, FIG. 51 shows wing 4852 having outer diameter point one P1 defined by a point of wing 4852 radially farthest away from axis of the cannula AC, and wing diameter one DW1 defined by a length of a straight line extending from axis of cannula AC, radially out to the outer diameter point one P1. Similarly, FIG. 53 shows wing 4852 after being inflated and deflated having outer diameter point two P2 defined by a point of the wing radially farthest away from axis of the cannula AC, and a wing diameter two DW2 defined by a length of a straight line extending from axis of the cannula AC, radially out to outer diameter point two P2. Thus, according to some embodiments, preinflated wing diameter DW1 for wing 4852 is approximately 30% less than postinflated deflated wing diameter DW2 of wing 4852. Hence, although the wing length for a postinflated deflated wing is approximately equal to that of a preinflated wing, the wing diameter for a postinflated deflated wing may be greater than that for a preinflated wing, such as in a range between 10% and 50% greater in wing diameter.

Figure 54:
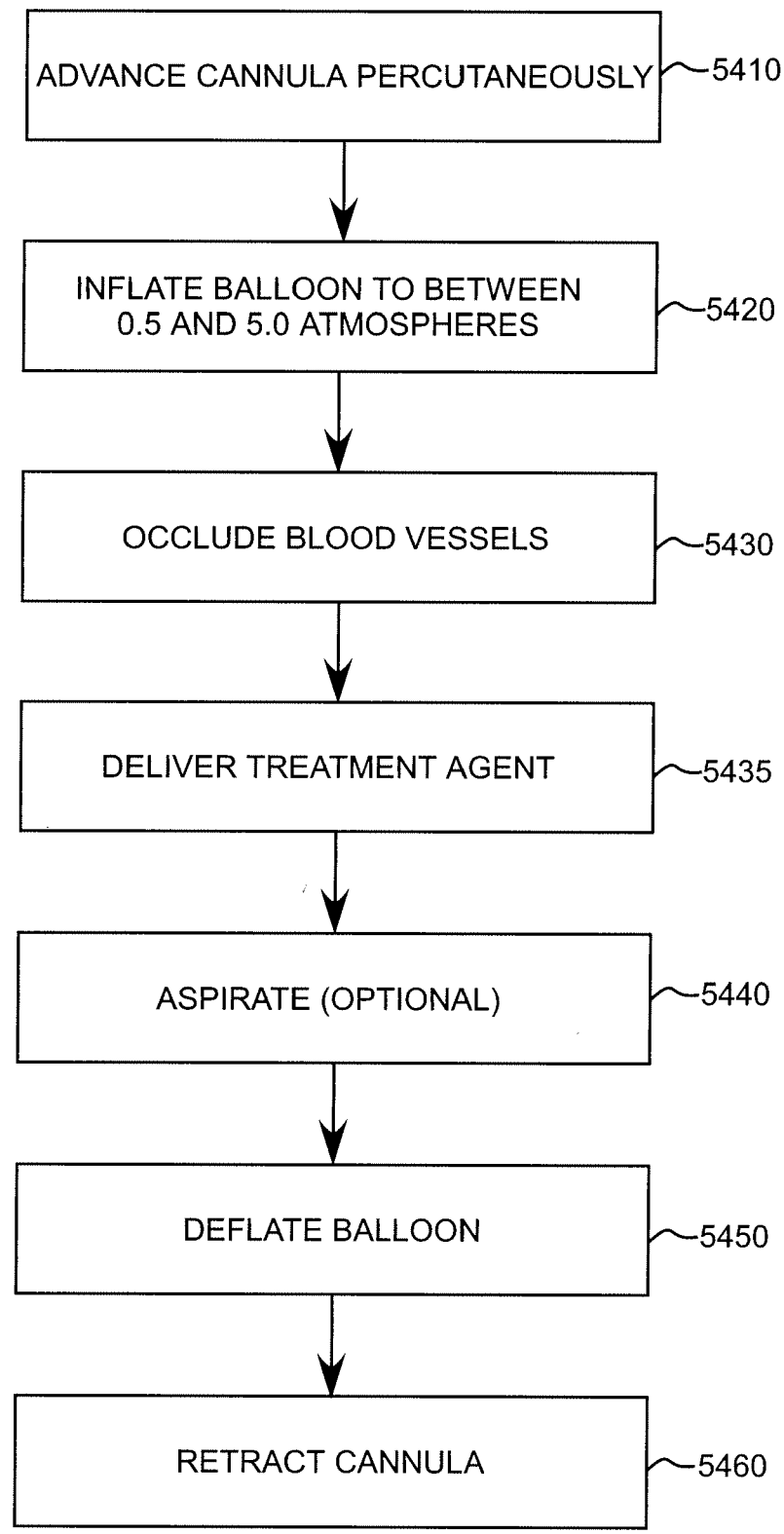
FIG. 54 is a flow diagram of a process for using a balloon to occlude a blood vessel or vein.

Therefore, the various configurations of balloon 4820 and lumen 4810 described herein can be used to occlude a blood vessel, such as by using a high compliance low pressure balloon for balloon 4820, as described above. For example, FIG. 54 is a flow diagram of a process for using a balloon (e.g., such as any balloon or occlusion device described herein, including embodiments of balloon 4820 described with respect to FIGS. 48-53 and views thereof) to occlude a blood vessel (e.g., such as a process that may be used with system controller 3080, or a treatment process for infusion of a treatment agent into an artery or vein of a patient using devices, apparatus, methods, or processes described herein (e.g., such as according to the process described with respect to FIG. 3, 19, 54, 55, 63, or 82). At block 5410 a cannula, such as cannula 4810, is advanced percutaneously through a blood vessel, such as blood vessel 4890, wherein a balloon, such as balloon 4820, is axially connected to an exterior surface of the cannula at or adjacent the distal end of the cannula. It is contemplated that the cannula may be advanced via a retrograde advancement, such as by being pushed up a blood vessel with or against a flow of blood, such as from one vessel into a smaller vessel to provide retrograde infusion treatment.

Specifically, the cannula may be advanced to a treatment region such as a region in a coronary sinus or vein of a subject (e.g., such as treatment region 4996).

At block 5420, the balloon is inflated to between 0.5 atmospheres and 5.0 atmospheres of pressure. For example, balloon 4820 may be inflated so that first diameter D1 is increased to second diameter D2, as described above. Also, according to some embodiments, balloon 4820 may be inflated by inflating to an expansion pressure of between two atmospheres in pressure and six atmospheres in pressure applied to an inner diameter of a blood vessel, such as diameter of vessel DV, at a treatment region such as region 4996. Moreover, according to some embodiments, balloon 4820 may be inflated to a predetermined volume (e.g., such as volume V2), a predetermined second diameter in a range between four millimeters and 17 millimeters in diameter (e.g., such as second diameter D2), or a predetermined pressure of between 0.5 atmospheres and six atmospheres in pressure (e.g., such as pressure PR).

At block 5430 the blood vessel is occluded. Specifically, balloon 4820 may be inflated to expand first diameter D1 to second diameter D2 until second diameter D2 approximates an inner diameter of a coronary sinus or a coronary blood vessel of a subject at a treatment region or until second diameter D2 is sufficient to make a pressure waveform of fluid in the coronary sinus or coronary vein become ventricularized, such as is described herein.

At block 5435 a treatment agent is delivered, such as to a treatment region. For example, a treatment agent may include infusion pellets, suspended cells, stem cells, microspheres, blood cells, drugs, or various other appropriate liquids and materials as described herein. Likewise, it is contemplated that such treatment agents may be delivered to treatment region 4996, such as by being delivered as part of or as all of liquid 4980. Note that it is contemplated that balloon 4820 may be inflated or deflated using fluids, including fluids described herein as a treatment agent.

At block 5440 the option of aspirating a treatment region is provided. For example, treatment region 4996 may be aspirated such as by a hole in distal end 4814 of cannula 4810 or via a hole through exterior surface 4816 of cannula 4810 at distal end 4814. Specifically, for instance, liquid 4980 may be aspirated as described above with respect to hole 988 for FIG. 9. Thus, as shown in FIG. 49, liquid 4980 in treatment region 4996 may optionally be aspirated. It is contemplated that liquid 4980 may include a drug, treatment agent, infusion pellets, suspended cells, stem cells, microspheres, or various other appropriate liquids or materials as mentioned herein.

At block 5450 balloon 4820 is deflated, such as described herein. For example, balloon 4820 may be deflated to a post inflation deflation volume, such as third volume V3, approximately equal to a preinflated volume, such as first volume V1, of balloon 4820.

At block 5460 cannula 4810 may be retracted, such as to withdraw balloon 4820 back out of vessel 4890 and out of the subject.

FIG. 55, illustrates a balloon outside diameter growth rate, such as for an occlusion or filter device (e.g., including devices 720, 2006, 2104, 4108, 4304 as described herein), a balloon (e.g., such as balloons 308, 314, 510, 2112, 2204, 2250, 2547, 2647, 3047, 3147, 3522, 3604, 3704, 3804, 3947, 4004, 4420, 4520, 4820, 8810, 9510, 9110, 9210, 9310, 9910, 9920 as described herein), or other balloons or occlusion devices.). For instance, FIG. 55 may show the outside diameter growth rate 5510 for an eight mm balloon starting with the uninflated outside diameter, and growing to the balloon's inflated outer diameter, where the growth rate is plotted as a function of inflation pressure 5520. FIG. 55 shows a balloon with a growth rate or elasticity of about 25% at a pressure of about two atmospheres. In another embodiment, a balloon may have a growth rate or elasticity of about 40% at a pressure of about 3.5 atmospheres.

In various embodiments, balloon outer diameter sizing (e.g., such as to occlude a blood vessel with a balloon) is controlled by monitoring factors including venous pressure waveform changes distal to the balloon. For instance, inflation of the balloon may be continued until a waveform becomes ventricularized.

Figure 56:
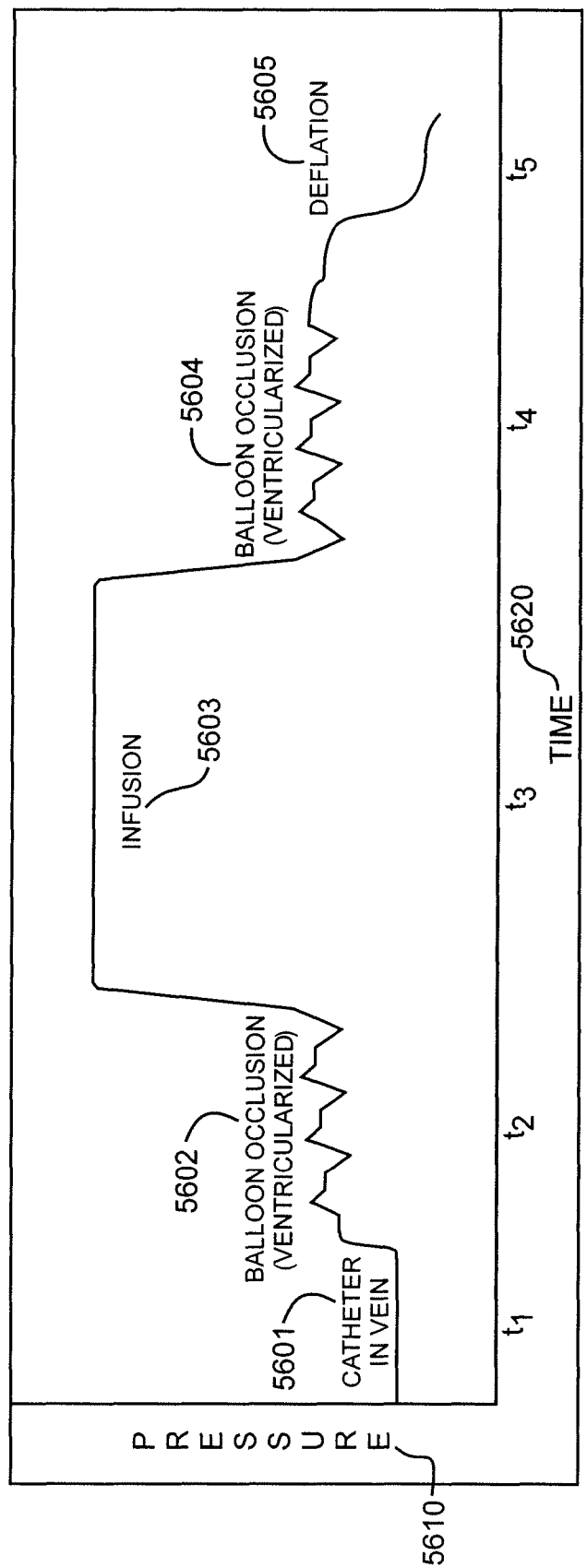
FIG. 56 illustrates a graph of blood vessel pressure over time.

FIG. 56 illustrates a graph showing pressure distal to a balloon 6510 in a blood vessel as a function of time 6520 (e.g., such as the pressure at treatment region 996 to be infused with a treatment agent, where the treatment region may be distal to, or proximal to a balloon occluding a blood vessel.). It is to be appreciated that the process related to FIG. 56 may be a process that may be used with a system controller (e.g., such as a system controller that may access a memory including machine readable instructions, such as system controller 3080), or a treatment process for infusion of a treatment agent into an artery or vein of a patient using devices, apparatus, methods, or processes described herein (e.g., such as according to the process described with respect to FIG. 3, 19, 54, 55, 63, or 82). Reference numeral 6501 illustrates time t1 during which a catheters or cannula is advance percutaneously so that a distal end of the catheter or cannula can be located in the coronary sinus or another vessel.

Reference numeral 5602 corresponds to time t2 during which a balloon, such is inflated to occlude the coronary sinus or another blood vessel. The coronary sinus or other blood vessel may be occluded, for example by inflating an occluding balloon or device until the coronary sinus or other blood vessel has a pressure waveform that becomes ventricularized.

Reference numeral 5603, corresponding to time t3 during which a treatment agent, such as described herein, is infused or introduced into the blood vessel and increases the pressure in the vessel to a relatively higher pressure distal to the balloons (or at treatment region 996).

At the conclusion of the infusion period, t3, time t4 referred to by reference numeral 5604, is a period of time where the pressure distal to the balloon is a lower pressure following infusion, even though the coronary sinus or other vessel is still occluded by a balloons or occlusion device.

Figure 82:
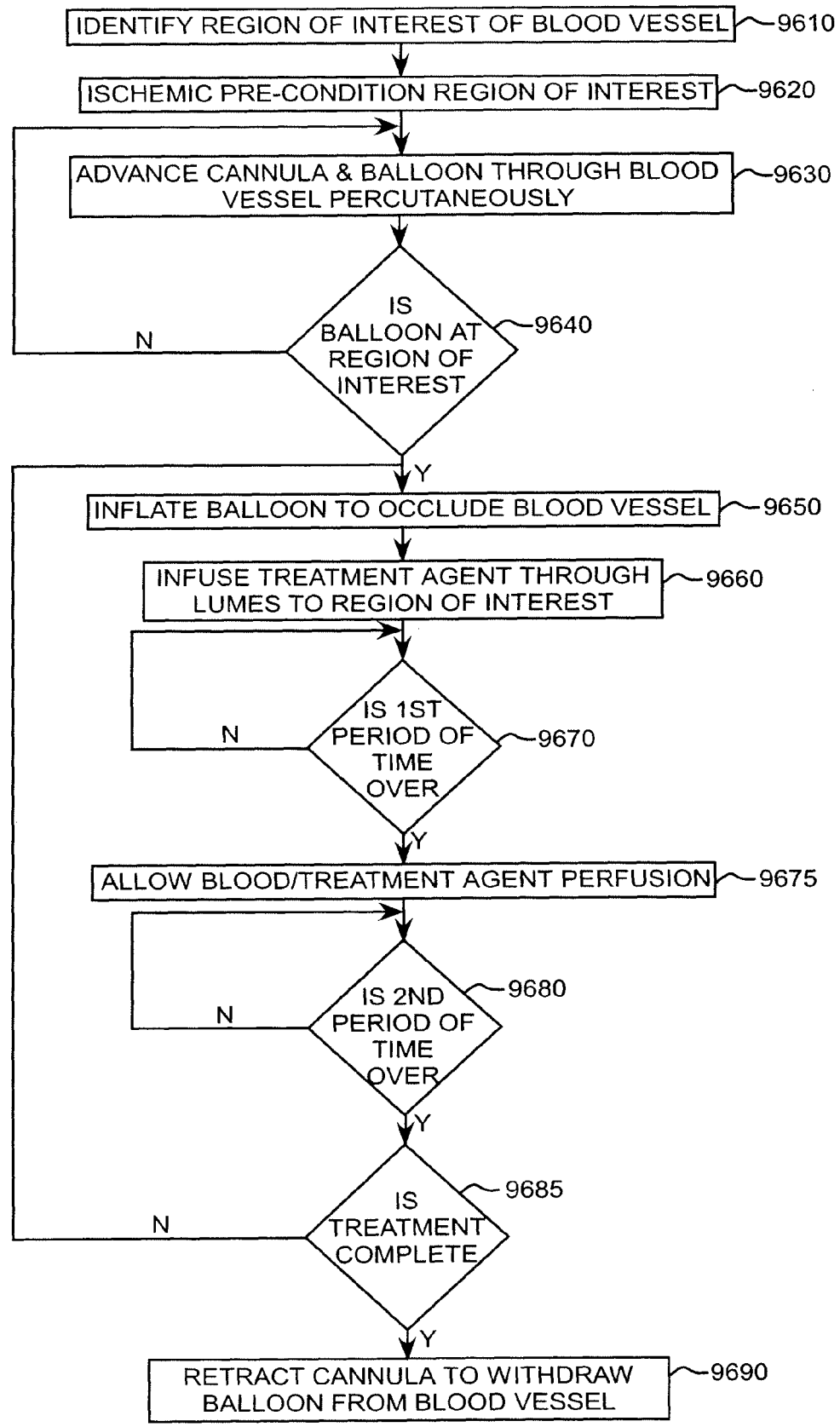
FIG. 82 is a flow diagram of a process for treating a treatment region of a blood vessel with one or more treatment agents or progenitor cells.

Reference numeral 5605, refers to time t5, during which the occluding balloon or device is deflated, and the catheter or cannula may be removed so that the perfusion (e.g., such as according to the process described with respect to FIG. 82) or flow of blood or treatment agent can resume in the coronary sinus or another vessel.

In various embodiments, the plot illustrated in FIG. 56 allows for an efficient treatment agent or drug infusion from a vein or artery to tissue to be treated with the possibility of "hands-off" operation. In various embodiments, when the pressure waveform changes to a "ventricularized" waveform of venous pressure, a balloon-sizing indicator notifies the operator or control system to stop balloon inflation. After balloon inflation has been stopped, a pressure sensor can measure the infusion pressure needed for an effective therapeutic dosage of a liquid containing a treatment agent. Infusion of a treatment agent can be accomplished with auto-infusion with a controller (e.g., such as controller 3080), or by an operator manually (e.g., such as by apparatus 9700 or 9800 of FIGS. 75A-81).

Suitable treatment agents to be used with catheters or cannula include a liquid carrying one or more treatment agents.

In another embodiment, a treatment agent or liquid includes one or more drugs or treatment agents, such as is used to prevent reperfusion injury. For instance, according to some embodiments, a treatment agent may be or include a liquid having one or more antibodies, for example, the antibodies against CD 11/18, P-selectin, L-selectin, ICAM, or VCAM. In another embodiment, the liquid includes IGF-I, estrogen, or GIK solution. In another embodiment, the liquid includes drugs like adenosine or its isoforms, Na/H exchangers, or Na/K exchangers. In another embodiment, the liquid can include cells, for example, cardiomyocites or multi-potent or ologo-potent cells like stem cells or progenitor cells. Also, the liquid may include angiogenic cells, or other types of structural cells like skeletal or smooth muscle cells. In another embodiment the liquid includes biological agents or genes, for example, VEGF, FGF, or HGF. In another embodiment, liquid includes one or more of the following: Calpain I, insulin, adenosine, antioxidants, glutathione peroxidase, vitamin E (alpha tocopherol), Na+—H+ exchange inhibitors, caroporide (HOE 642), agents that open $K_{ATP}$ channels, nitric oxide (NO), endothelin receptor antagonists, tetrahydrobiopterin, statins, sevoflurane, propofol, pinacidil, morphine, verapamil, and blends or mixtures thereof.

Figure 57:
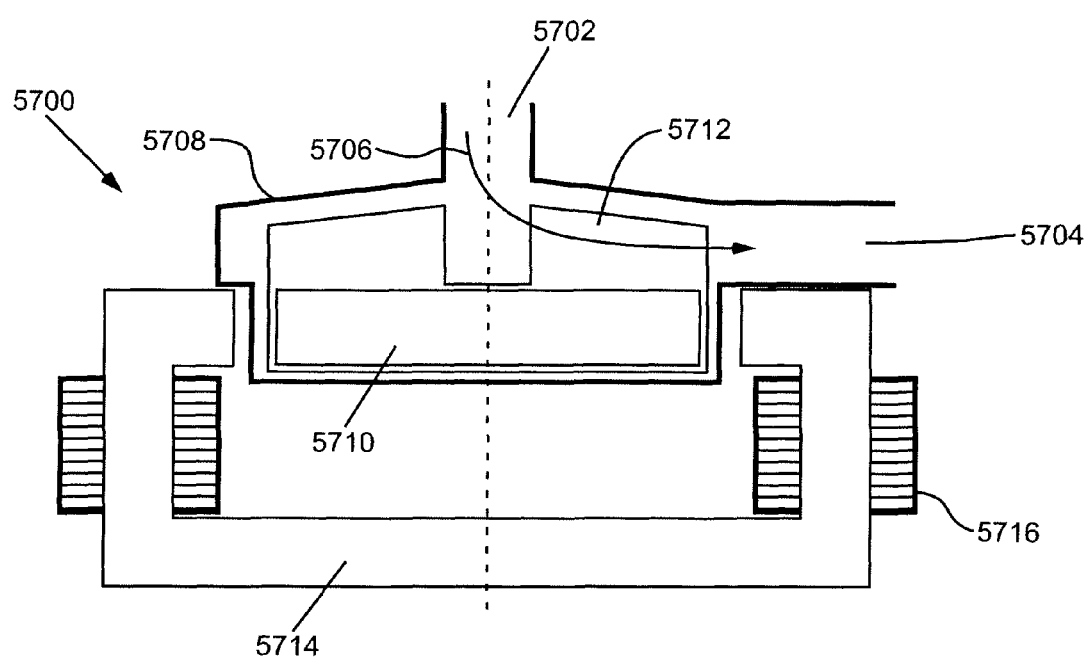
FIG. 57 illustrates a cross-sectional view of a centrifugal pump.

In an embodiment, a pressure increasing device may be attached to fitting 2632 at proximal end 2626 of catheter 2620 (e.g., see FIGS. 26-29, and fitting 3032 at proximal end 3026 of catheter 3020 of FIG. 30) to deliver a liquid that is or includes a treatment agent, through delivery lumen and to a blood vessel, such as at treatment region 996 (e.g., such as via a catheter, cannula, or deliver lumen as described herein). In various embodiments, the pressure increasing device is a syringe. In embodiments, the pressure increasing device may be a pump (which may or may not include one or more syringes). For example, the pressure increasing device can be a centrifugal pump, a reciprocating pump, or a gear pump. In various embodiments, the pump is able to achieve a low flow rate at a high pressure. One suitable pump is illustrated in FIG. 57. Centrifugal pump 5700 includes inlet 5702 and outlet 5704 so that the fluid flows as marked by arrow 5706. Pump 5700 has pumphousing 5708 to contain fluid and rotor 5710 which has impeller 5712 attached. In various embodiments, impeller 5712 rotates to create a centrifugal force to force fluid from inlet 5702 to outlet 5704 as shown by arrow 5706. Pump 5700 also includes stator 5714 which has winding 5716 attached. In various embodiments, rotor 5710 is removably connected to stator 5714, and there is no direct mechanical connection between stator 5714 and rotor 5710. In various embodiments, rotor 5710 and impeller 5712 are driven by a magnetic force generated by winding 5716. In various embodiments, rotor 5710 and pump housing 5708 are disposable, while stator 5714 and winding 5716 are not disposable. In another embodiment, the fluid flows through inlet 5702 to outlet 5704, which fluid path is sterilized, while stator 5714 and winding 5716 are not sterilized. It is considered that a suitable pump can be a disposable infusion pump or a magnetically-levitated centrifugal pump with a disposable rotor chamber.

Figure 58:
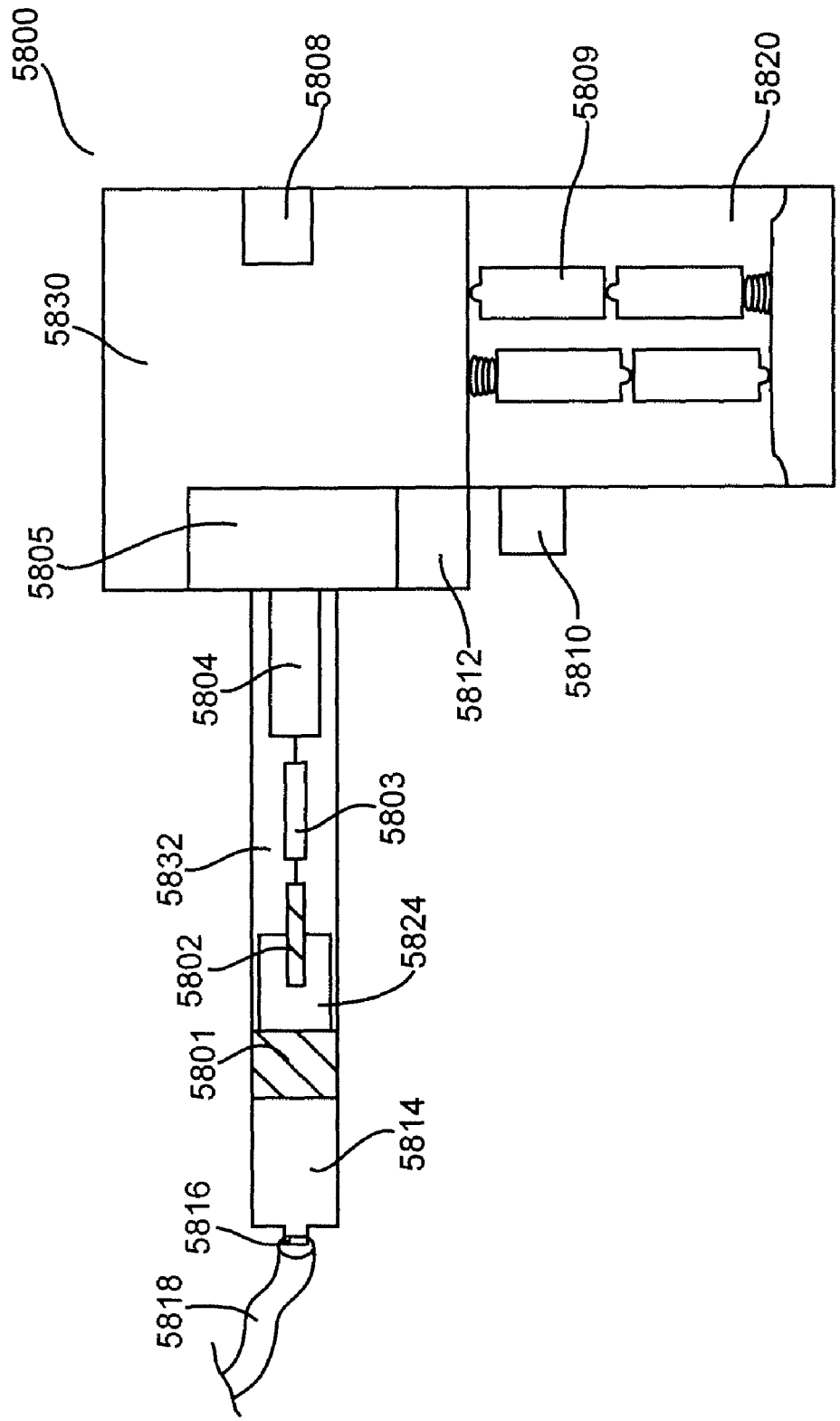
FIG. 58 schematically illustrates a pressure increasing device.

In another embodiment, a suitable pressure increasing device is illustrated in FIG. 58. Pump 5800 includes handle 5820 with batteries 5809, and activator button 5810. Connected to handle 5820 is body 5830 of pump 5800. Body 5830 includes pressure measurement connection 5808, micro-controller 5805, and motor driver chip 5812. Pump 5800 also includes attachment 5832 with motor 5804, motor coupler 5803, where coupler 5803 is connected to lead screw 5802. Lead screw 5802 is fed into non-rotating threaded coupling 5824, so that when motor 5804 is activated, rotational force and motion from motor 5804 is transferred through coupler 5803 to lead screw 5802 to advance or retract non-rotating threaded coupling 5824, depending on the direction of rotation. Non-rotating threaded coupling 5824 is attached to plunger 5801, so that when non-rotating threaded coupling 5824 moves, plunger 5801 also moves. Plunger 5801 can move distally to make reservoir 5814 smaller, or proximally to make reservoir 5814 larger. At the distal end of reservoir 5814 is nozzle 5816 attached to outlet 5818.

In operation, user (not shown) may activate pump 5800 by pressing button 5810. Pressing button 5810 causes microcontroller 5805 to activate, which in turn activates motor driver chip 5812 which sends a current from batteries 5809 to motor 5804. This causes motor 5804 to rotate, sending a rotational motion and force through coupler 5803 to lead screw 5802. Rotating lead screw 5802 causes non-rotating threaded coupling and plunger 5801 to advance or retract, depending on the rotation of motor 5804 and lead screw 5802. Advancing plunger 5801 causes an increase in pressure and a decrease in volume in reservoir 5814 causing fluid or gas stored in reservoir 5814 to be forced through nozzle 5816 and into outlet 5818. In various embodiments, to maintain a suitable pressure, pressure feedback from the patient may be received into pump 5800 through pressure measurement connection 5808, which pressure information is fed to micro-controller 5805, which activates motor driver chip 5812, to activate motor 5804 to increase pressure, or to deactivate motor 5804 to allow pressure to drop, or to reverse the direction of motor 5804 to decrease pressure.

Figure 59:
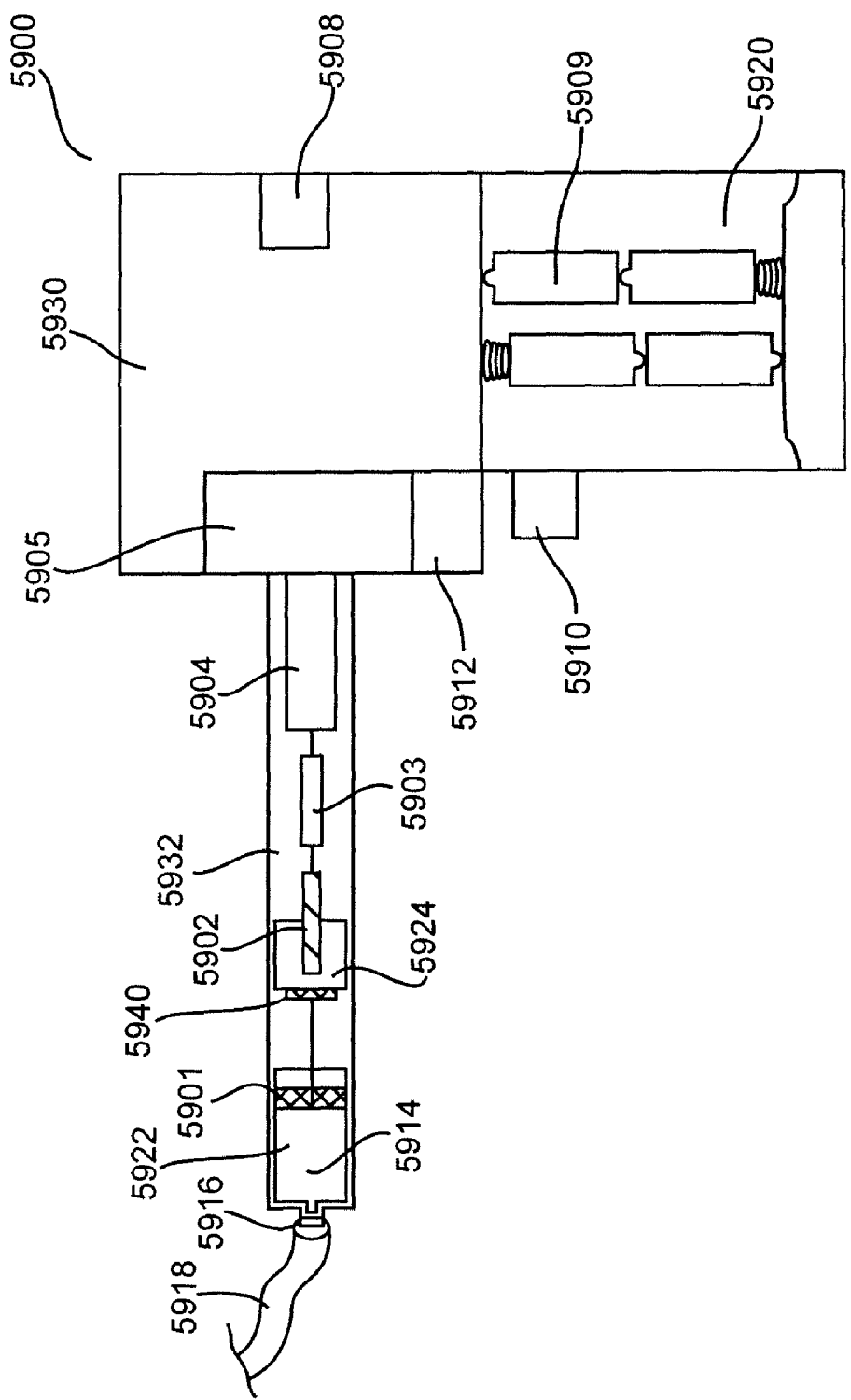
FIG. 59 schematically illustrates a pressure increasing device.

Another suitable pressure increasing device is illustrated in FIG. 59. Pump 5900 includes handle 5920 having batteries 5909, and activation button 5910. Handle 5920 is connected to body 5930, which includes pressure measurement connection 5908, motor driver chip 5912, and micro-controller 5905. Connected to body 5930 is attachment 5932 with motor 5904, coupler 5903, and lead screw 5902. Lead screw 5902 feeds into non-rotating threaded coupling 5924, which is attached to syringe or abutted against head 5940. Syringe 5922 is located in a suitably shaped opening, the distal end of handle 5932, and includes syringe head 5940, plunger 5901, reservoir 5914, and nozzle 5916. Nozzle 5916 feeds into outlet 5918. In another embodiment, syringe 5922 may be disposable and thrown away after each treatment. In another embodiment, syringe 5922 may be removed and cleaned or sterilized before the next treatment. In some embodiments, the pump, such as pump 5900 may have multiple syringes with different treatment agents.

In operation, pump 5900 may be activated by a user (not shown) by button 5910, which activates micro-controller 5905, which activates motor driver chip 5912, which in turn activates motor 5904, by sending a current from batteries 5909 to motor 5904. Motor 5904 rotates coupler 5903, which rotates lead screw 5902 to advance or retract non-rotating threaded coupling 5924, which serves to advance or retract syringe head 5940, respectively. If syringe head 5940 is advanced, plunger 5901 is also advanced towards the distal end of handle 5932 which serves to increase the pressure and decrease the volume of reservoir 5914, which forces fluid or gas stored in reservoir 5914 through nozzle 5916 and into outlet 5918. If syringe head 5940 is pulled towards proximal end of handle 5932, then the pressure in reservoir 5914 is lowered, and the volume in reservoir 5914 is increased, and fluid may be pulled from outlet 5918 through nozzle 5916 and into reservoir 5914. In various embodiments, a pressure measurement from the patient may be delivered into pump 5900 through pressure measurement connection 5908, which information is fed to micro-controller 5905 then into motor driver chip 5912 which is used to control motor 5904 to advance or retract syringe head 5940 to raise or lower pressure in reservoir 5914, respectively.

Figure 60:
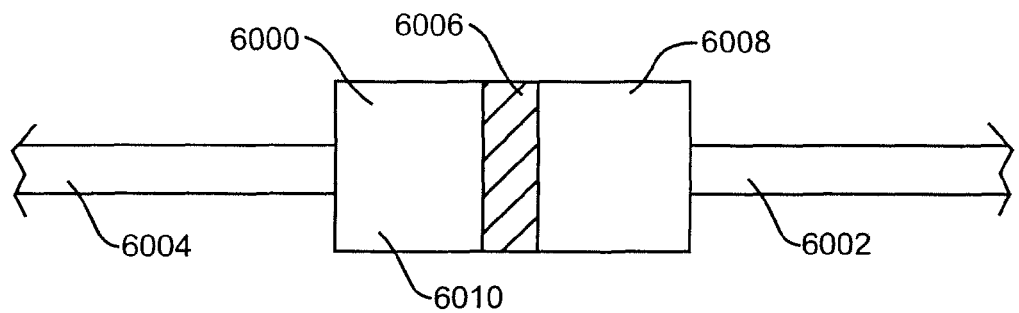
FIG. 60 schematically illustrates a pressure transferring device.

Referring now to FIG. 60, there is illustrated a suitable pressure transferring device. Pressure transferring device 6000 includes fluid inlet 6002, and fluid outlet 6004. Plunger 6006 is located in device 6000, which plunger 6006 serves to separate inlet reservoir 6008 from outlet reservoir 6010. As a fluid is pumped into inlet 6002, fluid enters inlet reservoir 6008 and exerts a force upon plunger 6006. This forces plunger 6006 distally, which increases the pressure and lowers the volume of outlet reservoir 6010, which forces the fluid in outlet reservoir 6010 into outlet 6004. Conversely, when a fluid is forced into outlet 6004 and into outlet reservoir 6010, it exerts a force on plunger 6006, and forces plunger 6006 proximally, which increases the pressure and lowers the volume of inlet reservoir 6008 and forces the fluid in inlet reservoir 6008 into inlet 6002. Device 6000 serves to equalize the pressures in inlet 6002 and inlet reservoir 6008, with the pressures in outlet 6004 and outlet reservoir 6010. Device 6000 may be used immediately before a catheter, so that a relatively expensive treatment agent can be placed in outlet reservoir 6010 and outlet 6004, while a relatively inexpensive liquid, for example a saline solution or water, can be placed in inlet reservoir 6008 and inlet 6002, with a pump (not shown) or other pressure increasing device connected to inlet 6002.

Figure 61:
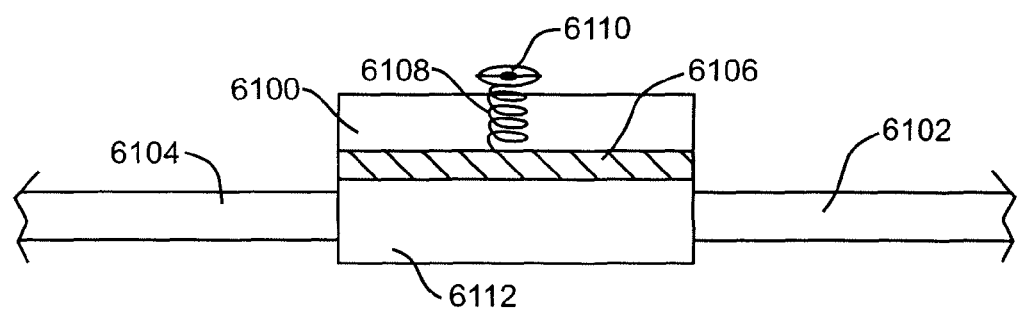
FIG. 61 schematically illustrates a pressure-maintaining or dampening device.

Referring now to FIG. 61, is a pressure-maintaining or dampening device 6100. Device 6100 has inlet 6102 and outlet 6104. Inside device 6100 is plunger 6106 which serves to seal fluid into pressure reservoir 6112. As fluid flows from inlet 6102 into pressure reservoir 6112, the fluid exerts a force on plunger 6106 which compresses spring 6108, until the force exerted by spring 6108 equals the force exerted by the fluid in pressure reservoir 6112 on plunger 6106. When the fluid stops flowing from inlet 6102 into pressure reservoir 6112, there will be a fluid flow provided to outlet 6104 as plunger 6106 is forced down by compressed spring 6108, decreasing the size of fluid reservoir 6112. This downward movement of plunger 6106 continues until pressure in pressure reservoir 6112 equals downward pressure exerted by spring 6108. In another embodiment, spring adjusting device 6110 may be provided to adjust the tension of spring 6108, so that more or less force is required to compress spring 6108.

Figure 62:
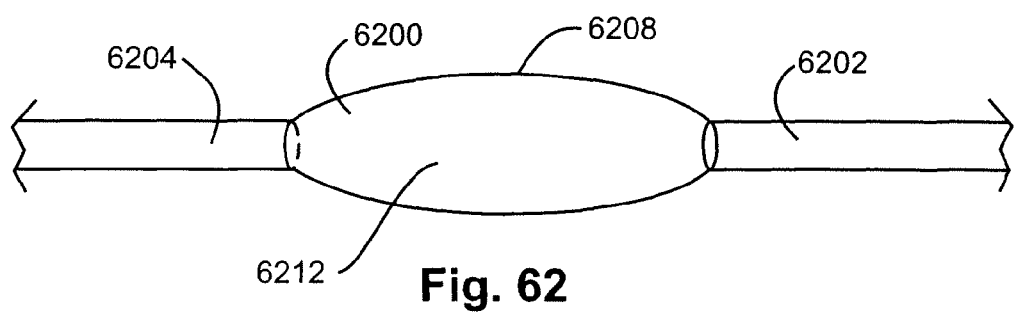
FIG. 62 schematically illustrates a pressure-maintaining or dampening device with inlet and outlet.

Referring now to FIG. 62, is a pressure-maintaining or dampening device 6200, with inlet 6202 and outlet 6204. As fluid flows through inlet 6202 and into pressure reservoir 6212, the fluid causes reservoir 6212 to force walls 6208 of device 6200 outwards until the inward force exerted by walls 6208 equals the outward force exerted by fluid in pressure reservoir 6212. When the fluid flow through inlet 6202 stops, fluid flow to outlet 6204 continues until force exerted by walls 6208 equals force exerted by fluid in pressure reservoir 6212. Walls 6208 may be made of a flexible material, for example rubber. Materials and thickness of walls 6208 may be adjusted so that an appropriate pressure may be maintained within fluid reservoir 6212.

Figure 63:
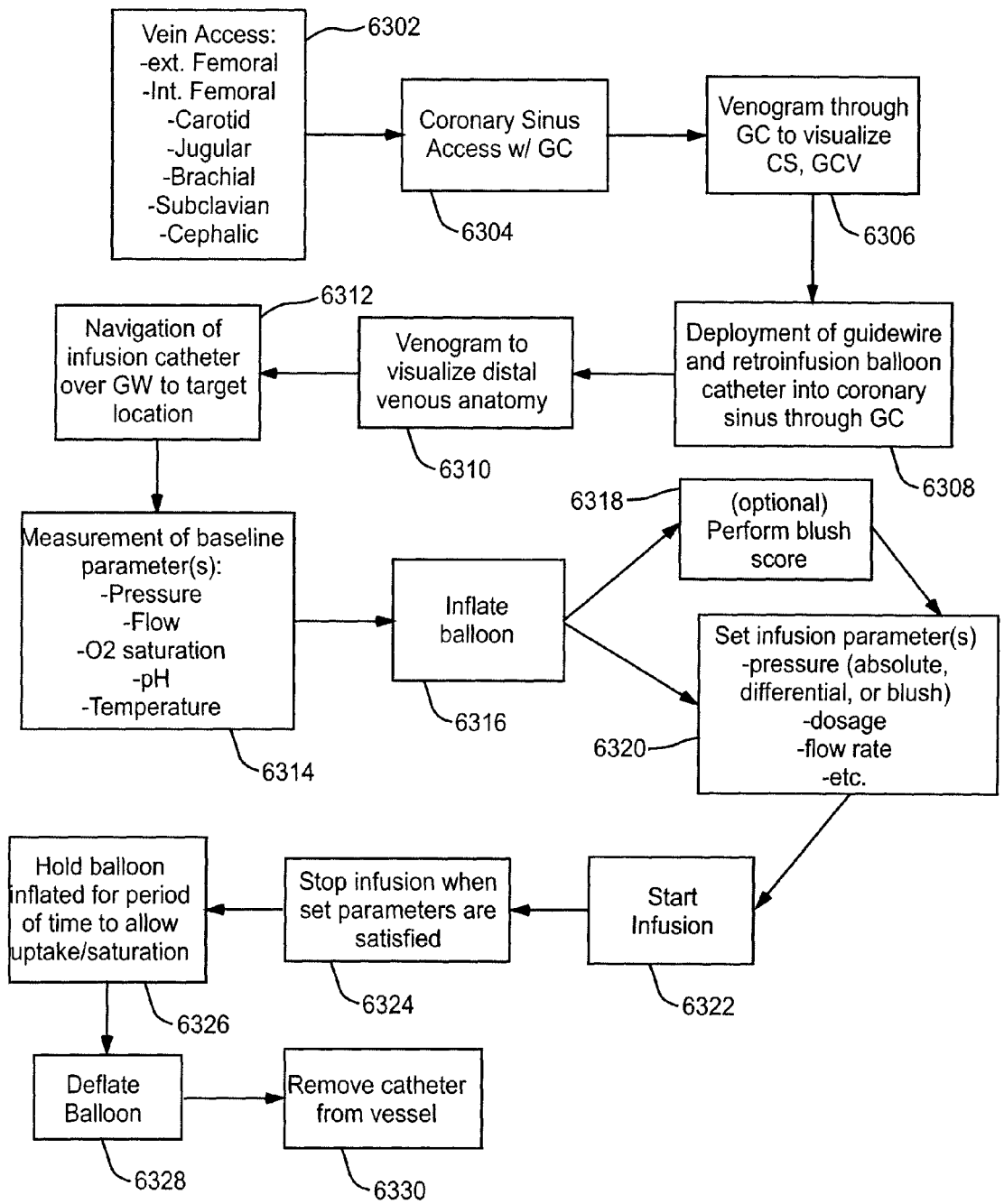
FIG. 63 is a flow diagram of a method of treating a patient, in accordance with an embodiment.

Referring now to FIG. 63, is a flow diagram of a process or method of treating a patient, in accordance with an embodiment. First, a vein is accessed 6302 by a catheter, for example, the exterior femoral vein, the interior femoral vein, carotid, jugular, brachial, subclavian, or saphalic vein is accessed by distal end of a guide catheter. Coronary sinus 6304 is accessed with a guide catheter through either the inferior vena cava or superior vena cava. Venogram 6306 is performed through the guide catheter to visualize coronary sinus or great cardiac vein. Deployment of guidewire and retroinfusion balloon catheter 6308 into the coronary sinus through the guide catheter. Venogram 6310 to visualize distal venus anatomy. Navigation of infusion catheter over guidewire 6312 to a target location. Measurement of baseline parameters 6314, for example, pressure, flow, oxygen saturation, pH, or temperature at the target location. Inflate balloon 6316 to occlude coronary sinus or other vessel where balloon catheter has been placed, for example the target location. Perform blush score 6318, an optional step to determine blush pressure. Set infusion parameters 6320, for example, absolute pressure, differential pressure, blush pressure, dosage, or flow rate. Start infusion 6322. Optional measuring of infusion parameters and feedback to a controller. Stop infusion 6324 when set parameters are satisfied. Hold balloon inflated 6326 for a period of time to allow uptake or saturation. Deflate balloon 6328. Remove catheter, guide catheter or guidewire, from vessel 6330.

Note that it is contemplated that the process described above with respect to FIG. 63, any or all of the pressure increasing devices, pumps, pressure transfer devices, or pressure maintaining devices described herein may be controlled manually, automatically, or by a machine, such as by system controller 3080, or according to a treatment process for infusion of a treatment agent into an artery or vein of a patient using devices, apparatus, methods, or processes described herein (e.g., such as according to the process described with respect to FIG. 3, 19, 54, 55, or 82).

In another embodiment, a catheter may be used to locally administer a treatment or therapeutic agent. Copending U.S. application Ser. No. 10/246,249 filed on Sep. 18, 2002 discloses suitable treatment agents and suitable methods of administering the treatment agents. Copending U.S. application Ser. No. 10/246,249 filed on Sep. 18, 2002 is herein incorporated by reference in its entirety. U.S. Pat. No. 6,346,098, issued to Yock et al., discloses a suitable method of locally administering a treatment agent. U.S. Pat. No. 6,346,098, issued to Yock et al., is herein incorporated by reference in its entirety.

Note that all embodiments of devices, apparatus, methods, or processes described herein are contemplated to include treatment including by one or more balloons, occlusion devices, or filter devices (e.g., such as balloon 2647, 3147, 3522, 3947, 2547, 3047, 3604, 3704, 3804, 4004, 308, 2204, 2250, 2112, 314, 510, 4420, 4520, 4620, 4820, 8810, 9510, 9110, 9210, 9310, 9910, 9920, or other balloons or occlusion devices) that may have an outer diameter that is volume controlled (e.g., see balloon 8810) or pressure controlled (e.g., see balloons 4520, 4620, and 4820) to expand to, occlude, or filter fluid in a blood vessel (e.g., such as an artery or vein of a human being). For example, an outer diameter may be volume controlled by controlling the amount of inflation volume of a gas (e.g., such as air, carbon dioxide, or a gas having a fluoroscopy contrast agent) or a liquid (e.g., such as water, saline solution, or a fluid having a fluoroscopy contrast agent) used to inflate the occlusion device. Specifically, an inflation volume may be incrementally increased by a selected volume amount over a range of total inflation volume to cause the outer diameter of an occlusion balloon to incrementally increase by a predictable amount for each incremental increase in volume. Thus, equal or unequal incremental increases in inflation volume can be used to cause equal or unequal increases in occlusion device outer diameter, over a desired total diameter range.

For instance, according to some embodiments, additional inflation fluid volume does not increase pressure because the high compliance balloon grows in outer diameter. Furthermore, according to some embodiments, when the outer diameter reaches a constraint, such as the inner diameter of a blood vessel as described herein, the balloon has a property, dimension, or is configured such that additional inflation fluid volume does not increase pressure or force in a direction perpendicular to the outer diameter (e.g., such as in a direction towards the inner diameter of the blood vessel), because the high compliance balloon grows in an axial direction within the blood vessel. It is also contemplated that when the outer diameter of the balloon reaches a constraint, additional inflation fluid volume will increase pressure or force in a direction perpendicular to the outer diameter of the balloon, but not appreciably. Specifically, in accordance with an embodiment, additional inflation fluid volume will increase pressure or force in a direction perpendicular to the outer diameter of the balloon by a non appreciable amount, such as by between zero and 10 percent increase in pressure (e.g., where the pressure in a direction perpendicular to the outer diameter of the balloon may be equal to the inflation pressure within the balloon).

For example, FIG. 64A is a cross sectional view of a cannula and a balloon. FIG. 64A shows apparatus 8800 having cannula 8802 with a dimension suitable for percutaneous advancement through a blood vessel (e.g., such as blood vessel 990 mentioned herein) and having a cannula proximal end (not shown, but such as proximal end 9504 shown and described with respect to FIGS. 69A-F) and distal end 8806. FIG. 64B is a cross-sectional view of apparatus 8800 of FIG. 64A from perspective "A". Cannula 8802 may be a cannula similar to cannula 710 or any other catheter or cannula. FIGS. 64A and B also show cannula 8802 having diameter CRD such as a diameter for a guide catheter, delivery catheter, or guidewire catheter as described herein. Balloon 8810 is axially attached to exterior surface 8808 at or adjacent distal end 8806 of cannula 8802 at proximal attachment 8809 and distal attachment 8811. Balloon 8810 may be a balloon such as a balloon or occlusion device as described herein.

According to some embodiments, balloon 8810 may have a property such that when inflated to a plurality of selected increasing inflation volumes, balloon 8810 forms a plurality of predictably increasing radial outer diameters, and has an inflation pressure that increases by less than five percent in pressure while being inflated to the plurality of selected increasing inflation volumes.

Moreover, balloon 8810 may be is adapted to inflate to an outer diameter in a range of about 2 mm to about 20 mm, such as to occlude a blood vessel having an inner diameter in a range of between 1.5 mm and 19.5 mm. Specifically, balloon 8810 may selected or inflated by a sufficient inflation volume or pressure to inflate to an outer diameter approximately 0.5 mm greater than the inner diameter of the blood vessel it is to occlude. Thus, balloon 8810 may inflate to an outer diameter of about 2 mm to occlude a blood vessel having an inner diameter of about 1.5 mm, and may inflate to an outer diameter of about 20 mm to occlude a blood vessel having an inner diameter of about 19.5 mm.

Also shown in FIGS. 64A and B, balloon 8810 has first diameter BRD1, first length BRL1, first inflation volume BRV1 and first inflation pressure BRP1. According to some embodiments first length BRL1 may be a selected preinflated length greater than two millimeters in length, such as a length of between two millimeters and 30 millimeters, (e.g., including first length BRL1 equal to three millimeters, between five and six millimeters, between eight and 10 millimeters, between five and 10 millimeters, or greater than 30 millimeters in length). In addition, first diameter BRD1 may be a preinflated outer diameter of between 0.25 inches and 0.65 inches in diameter (e.g., such as first diameter BRD1 of 0.44 inches) that inflates to expand to an outer diameter of 18 millimeter when inflated without bursting or permanently deforming. Next, balloon 8810 may have a preinflated single wall thickness of between 0.001 inches and 0.02 inches in thickness (e.g., such as a wall thickness of 0.003 inches) at a preinflation pressure below one atmosphere in pressure, such as a preinflation pressure of zero atmosphere.

FIG. 65A shows the balloon and cannula of FIG. 64A, with the balloon inflated to a second inflation volume. FIG. 65B is a cross-sectional view of apparatus 8800 of FIG. 65A from perspective "A". FIGS. 65A and B show balloon 8810 inflated to second inflation volume BRV2, second inflation pressure BRP2, second length BRL2, and second diameter BRD2. For example, second inflation volume BRV2 may be one of a plurality of selected increasing inflation volumes to cause balloon 8810 to form a second predictably increasing radial outer diameter, second diameter BRD2, and to have a second inflation pressure, BRP2 that may or may not be less than five percent greater than first inflation pressure BRP1.

FIG. 66A shows the cannula and balloon of FIG. 65A, with the balloon inflated to a third inflation volume. FIG. 66B is a cross-sectional view of apparatus 8800 of FIG. 66A from perspective "A". Balloon 8810 is inflated to third inflation volume BRV3, third inflation pressure BRP3, third length BRL3, and third diameter BRD3. For example, FIGS. 66A and B show balloon 8810 inflated to a selected increasing third inflation volume BRV3 to form predictably increasing radial outer diameter third diameter BRD3 and having third inflation pressure BRP3 that may increase by less than five percent in pressure as compared to second inflation pressure BRP2.

Thus, according to some embodiments, balloon 8810 may be inflated with a plurality of selected increasing inflation volumes increasing from zero to 2.0 cubic centimeters. In some cases, balloon 8810 may be inflated with a plurality of selected increasing inflation volumes that including increasing inflation volume from 0.05 cubic centimeters to 0.2 cubic centimeters by steps of additional controlled volumes in increments of between 0.005 cubic centimeters in volume and 0.05 cubic centimeters in volume (e.g., such as 0.01 cubic centimeters in volume), to form a plurality of predictably increasing outer diameters that increase to an outer diameter between 1.25 millimeters and 18 millimeters in diameter, by steps of between 0.2 millimeters and 0.4 millimeters increase in diameter. For instance, balloon 8810 may be inflated by selected increasing inflation volumes to cause the outer diameter to increase to a plurality of predictably increasing outer diameters that are equally spaced increments in diameter between 0.2 millimeters and 0.4 millimeters, such as to increase outer diameter by 0.25 millimeters for each selected increasing inflation volume until balloon 8810 is inflated to an outer diameter sufficient to occlude a blood vessel. It is also considered that balloon 8810 may be inflated with an inflation pressure of between 0.5 atmospheres and six atmospheres in pressure, such as to reach a sufficient outer diameter to occlude a blood vessel. Additionally, FIGS. 66A and B show balloon 8810 having third diameter BRD3 which may or may not be sufficient to occlude blood vessel 990 at treatment region 996.

FIG. 67A shows the cannula and balloon of FIG. 66A, with the balloon inflated to a selected fourth inflation volume. FIG. 67B is a cross-sectional view of apparatus 8800 of FIG. 67A from perspective "A". Here, balloon 8810 is inflated to fourth inflation volume BRV4, fourth inflation pressure BRP4, fourth length BRL4, and fourth diameter BRD4. For example, FIGS. 67A and B show balloon 8810 inflated to a selected increasing fourth inflation volume BRV4 to form a predictably increasing fourth outer diameter BRD4 and to have a fourth inflation pressure BRP4 that may be greater than first inflation pressure BRP1, second inflation pressure BRP2, or third inflation pressure BRP3 by less than five percent in pressure. Thus, balloon 8810 may be inflated to fourth inflation volume BRV4 sufficient to cause fourth inflation pressure BRP4 to allow balloon 8810 to occlude blood vessel 990 at treatment region 996, such as to occlude a flow or volume of fluid such as blood or treatment agent from passing through blood vessel 990 past balloon 8810 in directions 8860. According to some embodiments, fourth inflation volume BRV4 may be a total inflation volume of gas or fluid up to 2.0 cubic centimeters, such as a volume of between 0.03 cubic centimeters and 0.4 cubic centimeters (e.g., where inflation volume, such as fourth inflation volume BRV4 may be a total inflation volume of gas or fluid within balloon 8810, and does not include any gas or fluid within cannula 8802, or within a lumen, a tube, an inflation lumen, a catheter, a shaft, or other structure related to inflating balloon 8810 extending within cannula 8802 or within balloon 8810).

In addition, fourth inflation pressure BRP4 may be an inflation pressure of between one atmosphere and six atmosphere in pressure, such as a pressure between three atmosphere and four atmosphere, or between four atmosphere and five atmosphere in pressure. Note, fourth inflation pressure BRP4 may be within five percent of any of inflation pressures BRP1 through BRP3, thus any of inflation pressures BRP1 through BRP3 may also be between one atmosphere and six atmosphere in pressure, or may in fact be equal to fourth inflation pressure BRP4. Further, according to some embodiments, BRP3 or BRP4 may be a pressure sufficient to occlude the blood vessel without radially expanding the blood vessel appreciable, such as by expanding the blood vessel by less than five or ten percent in outer diameter.

Also, according to some embodiments, balloon 8810 may include a property such that when inflated to a first inflation volume (e.g., such as third inflation volume BRV3) balloon 8810 has a first inflated axial length (e.g., such as third length BRL3) and an outer diameter (e.g., such as third diameter BRD3) of the balloon exerts a first inflation pressure (e.g., such as third inflation pressure BRP3) on an inner diameter of a blood vessel (e.g., such as blood vessel 990) sufficient to occlude the blood vessel at a treatment region (e.g., such as treatment region 996). Moreover, when inflated to a second greater inflation volume (e.g., such as fourth inflation volume BRV4) balloon 8810 has a second inflated axial length (e.g., such as fourth length BRL4) that is sufficiently greater than the first inflated axial length (e.g., such as third length BRL3) to allow the outer diameter of the balloon (e.g., fourth diameter BRD4) of the balloon to exert a second inflation pressure (e.g., such as fourth inflation pressure BRP4) on the inner diameter of the blood vessel (e.g., such as blood vessel 990) that is less than appreciable, such as by being less than five percent greater than the first inflated pressure (e.g., such as third inflation pressure BRP3). Specifically, as shown in FIGS. 67A and B, when balloon 8810 is inflated to fourth inflation volume BRV4, instead of growing to fifth inflation diameter BRD5, balloon 8810 is constrained by the inner diameter of blood vessel 990 and only grows to fourth diameter BRD4 (e.g., where fourth diameter BRD4 is a diameter that may be within five or 10 percent of third diameter BRD3). Hence, for balloon 8810 to retain fourth inflation pressure BRP4 equal to or within five percent of third inflation pressure BRP3, instead of balloon 8810 growing in diameter to fifth diameter BRD5, the balloon grows axially in length to fourth length BRL4, which is greater than third length BRL3, and which is greater than first length BRL1 by BRLI1 plus BRLI2.

To design a balloon that limits fourth inflation pressure BRP4 as described above consideration or selection of the following may be made: a deflated length of the balloon, a target inflated outer diameter of the balloon, the diameter and characteristics of the cannula, deflated balloon diameter, balloon wall thickness, type of inflation gas or liquid, type of balloon material, diameters of the plurality of predictably increasing radial balloon outer diameters, volumes of the plurality of selected increasing balloon inflation volumes, inner diameter of the blood vessel at the treatment region, blood or fluid flow pressure in the blood vessel proximate to the balloon, inflation pressure of the balloon during occlusion, actual outer diameter of the balloon in the blood vessel during occlusion, and other appropriate considerations such as those described herein.

For instance, first length BRL1 may be selected between eight and 10 millimeters in length for a balloon to have a final radial outer diameter of 3.25 millimeters (e.g., such as if fourth diameter BRD4 were equal to 3.25 millimeters). Similarly, a first length BRL1 of between five and six millimeters may be selected for a balloon to have a final radial outer diameter of 4.25 millimeters (e.g., such as a fourth diameter BRD4 of 4.25 millimeters). Also, in an embodiment, balloon 8810 may have a preinflated outer diameter (e.g., such as first diameter BRD1) of between one millimeter and three millimeters in diameter, and inflated outer diameter (e.g., such as fourth diameter BRD4) of between four millimeters and seven millimeters at an inflation pressure (e.g., such as fourth inflation pressure BRP4) of between three atmosphere and four atmosphere in pressure, while having an inflated axial length that increases with increasing inflation volume (e.g., such as third length BRL3 increasing to fourth length BRL4 with third inflation volume BRV3 increasing to fourth inflation volume BRV4) to allow the balloon to occlude a blood vessel (e.g., such as blood vessel 990) while the balloon inflated outer diameter (e.g., such as fourth diameter BRD4) maintains an inflation pressure (e.g., such as fourth inflation pressure BRP4) of between three atmosphere and four atmosphere pressure on an inner diameter of the blood vessel (e.g., such as on an inner diameter of blood vessel 990 at treatment region 996).

Furthermore, balloon 8810 may be designed to inflate by select increasing inflation volumes to a total inflation volume which is greater than, or oversized as compared to, an inner diameter of a blood vessel, such as by being greater than an inner diameter of a blood vessel by a selected diameter. Specifically, referring to FIGS. 67A and B, it is possible to inflate balloon 8810 to a plurality of selected increasing inflation volumes up to third volume BRV3 and then to increase the inflation volume to fourth volume BRV4 to target fifth diameter BRD5 which is greater than the inner diameter of blood vessel 990 by oversized diameters 8870 plus 8872. For example, oversized diameters 8870 plus 8872 may add to be a diameter distance in a range of between 0.1 millimeters and one millimeter in diameter distance, such as by totaling to be 0.25 millimeters in diameter.

Examples of balloon 8810 contemplated include a balloon having an inflated outer diameter (e.g., such as fourth diameter BRD4) of between 1.25 millimeters and 12 millimeters in diameter (e.g., such as if fourth diameter BRD4 were between four millimeters and seven millimeters in diameter), and an inflated length that increases in inflated length by a total length of up to 15 millimeters (e.g., such as by increasing by a total increased length of BRLI1 plus BRLI2). Specifically, in accordance with embodiments, balloon 8810 may having an inflated length that increases in inflated length by a total length that is inversely proportional to the preinflated length of the balloon. For instance, as shown in FIGS. 64A-67B, balloon 8810 may increase by a total increased length of BRLI1 plus BRLI2 of 0.5 mm for a balloon preinflated first length, BRL1 of eight mm (e.g., here, BRL4 is 8.5 mm), and increase by a total increased length of BRLI1 plus BRLI2 of 0.25 mm for a balloon preinflated first length, BRL1 of 10 mm (e.g., here, BRL4 is 10.25 mm) It is also contemplated that examples of balloon 8810 may have a wall thickness that decreases by between 10 percent and 75 percent in thickness, at an inflation pressure (e.g., such as fourth inflation pressure BRP4) of between three atmosphere and four atmosphere in pressure.

In a second example balloon 8810 may have first diameter BRD1 of 1.3 millimeters at first inflation pressure BRP1 below one atmosphere in pressure, and fourth diameter BRD4 between four millimeters and seven millimeters at fourth inflation pressure BRP4 of between three atmosphere and four atmosphere in pressure. Specifically, in this case, balloon 8810 may have an inner diameter of 0.044 inches and a wall thickness of 0.003 inches when deflated, such as when at first inflation volume BRV1.

In another instance, balloon 8810 may have first diameter BRD1 of 1.3 millimeters and be designed to expand to fifth diameter BRD5 of 14 millimeters when inflated to fourth inflation pressure BRP4 of between one and six atmosphere in pressure, without balloon 8810 bursting or permanently deforming. In other words, balloon 8810 may expand to several times its original diameter under low pressure (e.g., such as fourth inflation pressure BRP4 of less than six atmosphere in pressure) and then return to its original low profile dimension upon inflation volume release (e.g., such as by returning to first diameter BRD1 upon reducing inflation volume from fourth inflation volume BRV4 to first inflation volume BRV1). Thus, balloon 8810 may return to almost its original size upon or after deflation. For example, after inflation, balloon 8810 may return to an outer diameter that is within 10 percent of its preinflated diameter (e.g., such as within 10 percent of first diameter BRD1), an axial length within 10 percent of its preinflated axial length (e.g., such as within 10 percent of first length BRL1), and a wall thickness of within five percent of its preinflated wall thickness. Additionally, according to some embodiments, balloon 8810 may include a property such that during deflation it forms a plurality of decreasing radial outer diameters, such as by forming radial outer diameters third diameter BRD3, second diameter BRD2, and first diameter BRD1 during deflation from fourth inflation volume BRV4 back down to first inflation volume BRV1.

Furthermore, according to some embodiments, balloon 8810 may be made of or include a balloon material having one or more of a block copolymer of polyether and polyester (e.g., such as a polyester sold under the trademark Hytrel® of DUPONT COMPANY), a biocompatible polymer such as a polyether block amide resin (e.g., for instance, PEBAX® of ATOCHEM CORPORATION), a styrene isoprene styrene (SIS), styrene butadiene styrene (SBS), styrene ethylene butylene styrene (SEBS), polyetherurethane, ethyl propylene, ethylene vinyl acetate (EVA), ethylene methacrylic acid, ethylene methyl acrylate, and ethylene methyl acrylate acrylic acid. It is also contemplated that balloon 8810 may include a material from a material family of one of styrenic block copolymers and polyurethanes; or a melt processible polymer. Balloon 8810 may also include a low durometer material, such as a material to allow the walls or outer diameter of balloon 8810 to gently occlude a blood vessel during infusion of therapeutic agents such as stem cells, genes, adenovirus, progenitor cells, and other treatment agents as described herein.

It is to be appreciated that balloon 8810 may be formed by melt extruding a material, such as balloon material described above, into a tube to form a balloon, and then bonding the balloon or tube to a cannula, such as a catheter or cannula 8802. For example, a balloon or tube as described above can be bonded by laser, heat, shrink tube, or adhesive bonding to a catheter or cannula. Specifically, according to some embodiments, a tube or balloon may be shrink tube bonded to cannula 8802 such as at proximal attachment 8809 and distal attachment 8811 so that exterior surface of balloon 8810 forms symmetrical shapes with respect to an axis of cannula 8802 when balloon 8810 is inflated over a range of inflation volumes. For example, shrink tube bonding may be used to bond balloon 8810 to cannula 8802 so that when the balloon is inflated from first inflation volume BRV1 to fourth inflation volume BRV4, balloon 8810 forms a plurality of symmetrical shapes, such as first shape 8820, second shape 8822, third shape 8824, and fourth shape 8826 during inflation. More particularly, such shrink tube bonding may include an even or straight perpendicular radial bond of a balloon or balloon tube to a cannula with respect to an axis of the cannula to effect a symmetrical inflation of the balloon over a range of selected inflation volumes as mentioned herein. Hence, cannula 8802 may function as one or more of a guide catheter, a delivery catheter, and a guidewire catheter; while balloon 8810 may inflate to expand in size to an outer diameter in a range of between one millimeter and 15 millimeters in diameter, such as to occlude a blood vessel injuring treatment infusion to a treatment region of the blood vessel.

Figure 69A:
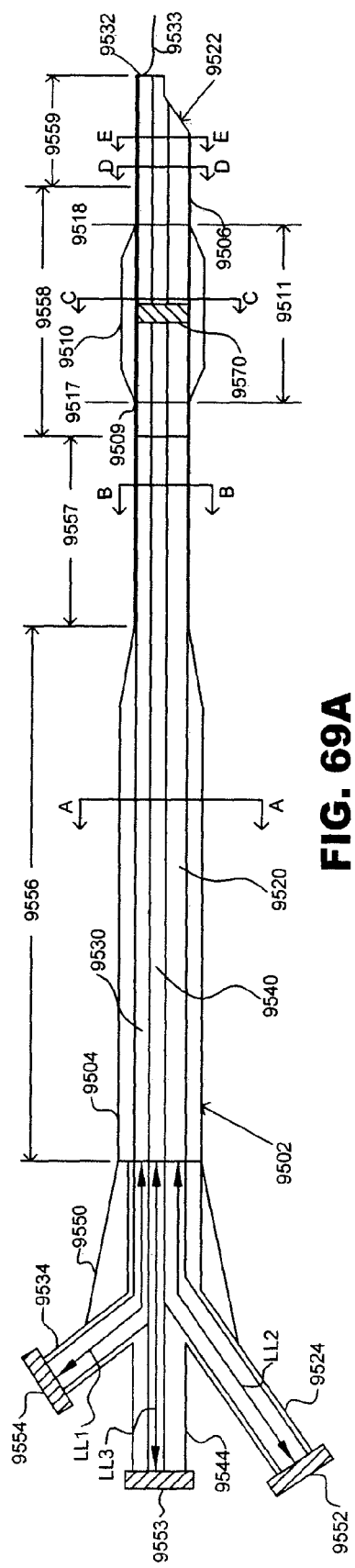
FIG. 69A is a side perspective view of a cannula having a balloon attached to its distal end and an infusion lumen and accessory lumen running through the cannula.

According to some embodiments, a balloon high compliance balloon, such as balloon 8810, may be heat bonded, laser bonded, shrink tube bonded, or attached with an adhesive to a cannula, such as cannula 8802 (e.g., or cannula 9502 as shown in FIGS. 69A-70 and described in accompanying text, or a catheter as describe herein). Specifically, a balloon (e.g., such as any balloon, occlusion device or filter device as described herein) may be shrink tube bonded to a cannula so that the balloon exterior surface inflates to symmetrical shape with respect to an axis of the cannula. For instance, shrink tube bonding may provide and even and straight bond of a balloon tube to a cannula with respect to an axis of the cannula to effect such symmetrical inflation of the balloon over a range of inflation volumes as mentioned herein.

Hence, a balloon may have a balloon outer diameter growth rate that changes in correlation to a percentage change in the inflation volume of gas or fluid (e.g., such as fluoroscopy contrast media) within the balloon. For instance, it is possible to design a high compliance balloon formed of a material and by a process as described herein, having a length of between two millimeters and 20 millimeters, and a double wall thickness between about 0.0003 inches and about 0.0038 inches, such that an outer diameter of the balloon can inflate from one millimeter when deflated to 18 millimeters when inflated without bursting or permanently deforming.

Figure 68:
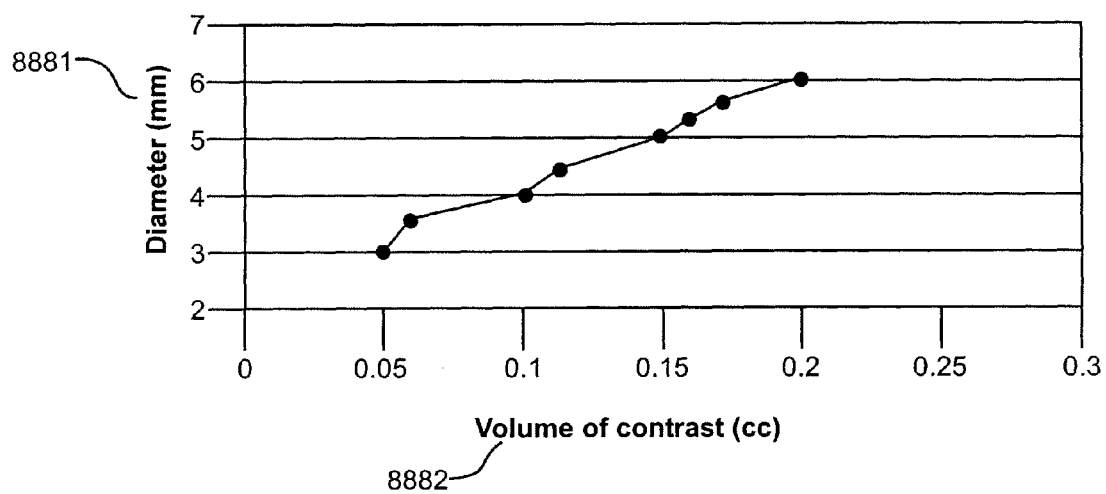
FIG. 68 is a graph showing the relationship between the outer diameter of a balloon and the volume of inflation contrast fluid injected into the balloon.

Specifically, a high compliance balloon formed of PEBAX 63D can be designed to have a deflated outer diameter and length to achieve a growth rate greater than about 40% while maintaining an inflation pressure that increases by less than five percent. For instance, FIG. 68 is a graph showing the relationship between the outer diameter of a balloon and the volume of inflation contrast fluid injected into the balloon. Here, FIG. 68 plots outer diameter of the balloon 8881 versus volume of inflation contrast fluid injected into the balloon 8882 for a 4.0 millimeter outer diameter by 10 millimeter long balloon of PEBAX 63D operating at an inflation pressure below four atmospheres.

Note that although FIGS. 64A-68 show and the related discussion describes inflating balloon 8810 with selected inflation volumes to occlude a blood vessel, it can be appreciated that a balloon (e.g., including balloon 8810) may be designed by a process or of the materials described herein and may have a dimension, characteristic, deflated outer diameter, or deflated length, such that the outer diameter of the balloon may be inflation pressure controlled. More particularly, a balloon may be designed by a process or of the materials described herein to have an outer diameter that can be controlled by controlling the amount of inflation pressure of a gas (e.g., such as air, carbon dioxide, or a gas having a fluoroscopy contrast agent) or a liquid (e.g., such as water, saline solution, or a fluid having a fluoroscopy contrast agent) used to inflate the balloon. Again, such a balloon may be used as an occlusion device.

Hence, a balloon (e.g., such as balloon 8810) can be used with a cannula or catheter (e.g., such as cannula 8802) that has a dimension suitable for percutaneous advancement through a blood vessel to infuse a treatment agent (e.g., such as biological agents) into a treatment region, such as arterial vessels or venous vessels. For example, FIG. 69A is a side perspective view of a cannula having a balloon attached to its distal end and an infusion lumen and accessory lumen running through the cannula. FIG. 69A shows apparatus 9500 having cannula 9502 with proximal end 9504 and distal end 9506. Cannula 9502 may be a cannula or catheter such as a cannula similar to cannula 710 or any of the various other guide, delivery, or guidewire catheters or cannulas described herein. For instance, cannula 9502 may be include materials as described above for catheter 302 or 512, such as may one or more of a synthetic or natural latex or rubber, such as a polymer material; a polyetheramide; a plasticiser free thermoplastic elastomer; a thermoplastic blend; a block copolymer of polyether and polyester; a biocompatible polymer such as a polyether block amide resin; a polycarbonate or acrylonitrile bubadiene styrene (ABS); a bio-compatible polymer such as a polyether block amide resin; a styrene isoprene styrene (SIS), a styrene butadiene styrene (SBS), a styrene ethylene butylene styrene (SEBS), a polyetherurethane, an ethyl propylene, an ethylene vinyl acetate (EVA), an ethylene methacrylic acid, an ethylene methyl acrylate, an ethylene methyl acrylate acrylic acid, a material from a material family of one of styrenic block copolymers and polyurethanes, a melt processable polymer, a low durometer material, and nylon.

Balloon 9510 is axially connected to exterior surface 9508 of cannula 9502 at proximal coupling 9509 and distal coupling 9511, at or adjacent distal end 9506. Balloon 9510 may be a balloon, occlusion device, or filter device such as balloon 2647, 3147, 3522, 3947, 2547, 3047, 3604, 3704, 3804, 4004, 308, 2204, 2250, 2112, 314, 4520, 4620, 4820, 8810, or other balloons or occlusion devices. For example, balloon 9510 may be a balloon including a property such that when inflated to a selected inflation volume the balloon will expand in size to an outer diameter sufficient to occlude a blood vessel as described herein. In one example, balloon 9510 may be a high-compliance balloon made of a low durometer material or it may function similarly to balloon 8810 as described herein.

In addition, cannula 9502 may have infusion lumen 9520 extending from proximal end 9504 to distal end 9506 and exiting infusion opening 9522 distal to balloon 9510. Furthermore, cannula 9502 may also include accessory lumen 9530 extending from proximal end 9504 to distal end 9506 and exiting accessory opening 9532 distal to balloon 9510.

Thus, according to some embodiments, infusion lumen 9520 or accessory lumen 9530 may be adapted to have a guidewire, such as guidewire 9533 disposed therethrough to guide cannula 9502 through a blood vessel (e.g., such as blood vessel 990) to a treatment region (e.g., such as treatment region 996). For instance, infusion lumen 9520 or accessory lumen 9530 may be adapted to have a guidewire disposed therethrough to guide cannula 9502 to a location in a blood vessel with respect to delivery catheter 310 as shown and described with respect to FIG. 3, cannula 720 as shown and described with respect to FIGS. 7-19, or cannula 9902-9904 as shown and described with respect to FIGS. 86-89. More particularly cannula 9502 may have a dimension or profile compatible with or suitable to be received within, or be slidably disposed within a guide catheter (e.g., such as a guide catheter or cannula as described herein, including guide catheter 302) having an outer diameter in a range of between 5 French and 9 French. It is also contemplated that cannula 9502 may have a dimension suitable for percutaneous advancement through a blood vessel such as blood vessel 990.

FIG. 69B is a cross section view of first section 9556 of apparatus 9500 of FIG. 69A from perspective "A". FIG. 69B shows cannula 9502 having outer diameter COD1 less than 0.09 inches. It is also contemplated that cannula 9502 may include a shaft having an outer diameter which is less than 0.06 inches in diameter. FIG. 69B also shows accessory lumen 9530 having inner diameter ALID1 and infusion lumen 9520 having inner diameter ILID1. According to some embodiments inner diameter ALID1 may be less than inner diameter ILID1. In addition, it is contemplated that infusion lumen 9520 may have inner diameter ILID1 greater than 0.01 inches in diameter.

Also, accessory lumen 9530 may have an inner diameter that is greater than between 0.01 inches and 0.5 inches in diameter, such as an inner diameter capable of accommodating a guidewire having a diameter of at least 0.01 inches. Furthermore, lumen 9530 may be used to infuse a treatment agent to a treatment region, or to aspirate fluids from a treatment region (e.g., see hole 988 of FIG. 9 and accompanying text).

It is also contemplated that accessory lumen 9530 may have a dimension suitable to allow for several usages including continuous guidewire access during an infusion process to maintain the location of cannula 9502, to monitor pressure distal to balloon 9510, to allow for accessibility of other accessories to a location distal to balloon 9510. For example, accessory lumen 9530 may allow for accessibility of a flow and pressure wire to measure distal flow and pressure, or other types of sensor wires to make measurements in a location of a blood vessel distal to balloon 9510. Specifically, accessory lumen 9530 may have a dimension suitable to allow a device to be connected to a proximal end of the accessory lumen, such as at proximal access lumen port 9554, or for a device to be disposed through accessory lumen 9530 to measure one of chronic renal failure (CRF), electrocardiogram (EKG), oxygen level, pressure, flow, blood sampling, or temperature, such as at treatment region 996. Moreover, it is contemplated that accessory lumen 9530 may be used to measure or to receive a device to measure various other physiological parameters, such as at treatment region 996 distal to balloon 9510.

According to some embodiments infusion lumen 9520 or accessory lumen 9530 may each include a surrounding material, sleeve, cannula or lumen, such as by being constructed with composite tube. For example, the composite tube may include a braid or coil reinforced polyamide or polymer tube.

Thus, infusion lumen 9520 or accessory lumen 9530 may include a reinforced tube, to prevent catheter or lumen (e.g., such as lumen 9502) kinking. Note, that composite accessory or infusion lumen such as described above with respect to balloon section 9511, third section 9558 and fourth section 9559 also help maintain lumen roundness.

Infusion lumen 9520 or accessory lumen 9530 may be adapted to receive a guidewire or have a guidewire disposed therein and exiting a proximal opening at proximal end 9506 (e.g., such as opening 9532 or opening 9522), so that cannula 9502 can be used in an over-the-wire fashion, or have the guidewire removed therefrom. It is also considered that infusion lumen 9520 or accessory lumen 9530 may have a proximal opening, such as port 9554 or 9552 located proximal to balloon 9510 and within 35 centimeters of the distal end of cannula 9502 such that cannula 9502 can be used in rapid exchange fashion.

FIG. 69C is a cross sectional view of second section 9557 of apparatus 9500 of FIG. 69A from perspective "B". FIG. 69C shows second section 9557 of cannula 9502 having width CW1 between 0.03 inches and 0.05 inches, such as a width of 0.04 inches. FIG. 69C also shows cannula 9502 having height CHI between 0.04 inches and 0.06 inches, such as a height of 0.055 inches.

FIG. 69D is a cross sectional view of balloon section 9511 of FIG. 69A from perspective "C". FIG. 69D shows balloon 9510 including a property such that when inflated to inflation volume BIV1, such as a selected inflation volume, the balloon will expand in size to outer diameter BOD1 sufficient to occlude a blood vessel. For example, balloon 9510 may include a property such that the balloon has inflation pressure BPI1 of less than five atmospheres in pressure at inflation volume BIV1.

Moreover, according to some embodiments balloon 9510 may have a property such that when inflated to a plurality of increasing inflation volumes, the balloon forms a plurality of increasing radial outer diameters, and has an inflation pressure that increases by less than five percent in pressure over the range of the increasing inflation volumes. For example, FIG. 70 is a cross sectional view of the balloon section of FIG. 69A from perspective "C", with the balloon inflated to a second volume that is less than that shown in FIG. 69D. FIG. 70 shows balloon section 9511 after balloon 9510 inflated with inflation volume BIV2 which is less than volume BIV1 to form radial outer diameter BOD2 which is less than BOD1. Thus, although the inflation volume of balloon 9510 can be increased from inflation volume BIV2 to BIV1, the inflation pressure of balloon 9510 may increase from pressure BPI2 to pressure BPI1, where pressure BPI1 is less than 105% of BPI2 in pressure. For example, balloon 9510 may be a balloon that expands in size to an outer diameter, such as diameter BOD1, in a range of between one millimeter and 15 millimeters in diameter, controlled by volume injection, such as to inject volumes BIV2 and BIV1 of a gas or a fluid.

Cannula 9502 may further include balloon inflation lumen 9540 extending from proximal end 9504 to balloon 9510 and exiting and inflation opening (not shown) within balloon 9510. Balloon inflation lumen 9540 and the inflation opening may have a diameter sufficient to inflate and deflate balloon 9510 as described herein, such as by having a diameter of between 0.01 inches and 0.02 inches in diameter. Also, infusion lumen 9520 may have an inner diameter that is at least 0.015 inches in diameter. In addition, balloon inflation lumen 9540 may be connected to an inflation device or syringe to inflate balloon 9510 as described herein.

It is also to be appreciated that cannula 9502 may include additional cannula or lumen extending through cannula 9502, such as from proximal end 9504 to distal end 9506, or otherwise as described herein. Moreover, according to some embodiments, each of infusion lumen 9520, accessory lumen 9530, inflation lumen 9540, or other lumen described herein may include or have its own sleeving, cannula, or other surrounding material or structure having a dimension to fit within the surrounding cannula in which the lumen is disposed or extending through. For example, each of infusion lumen 9520, accessory lumen 9530, and inflation lumen 9540 may include an independent sleeve of material extending through cannula 9502 (e.g., such as by fitting within cannula 9502 and restricted to the dimension of cannula 9502 as described herein) and function with that sleeving.

In addition, as shown in FIG. 69A, accessory lumen 9530 may extend first length LL1, infusion lumen 9520 may extend second length LL2 and inflation lumen may extend third length LL3 in distance beyond or out of proximal end 9504, where at least one of the first length LL1, second length LL2, or third length LL3 is a different distance in length than at least one of the others. Also, it is to be appreciated that accessory lumen 9530 being of a dimension suitable to infuse a first volume of treatment agent to a treatment region (e.g., such as treatment region 996) and to ask for a second volume of blood and treatment agent from the treatment region. Similarly balloon inflation lumen 9540 may have a dimension suitable to inflate balloon 9510 with a volume of (e.g., such as volume BIV1) a gas or liquid to an inflation pressure (such as inflation pressure BPI1) of less than 6 atmospheres and maintain the inflation volume or inflation pressure for at least 4 minutes.

As shown in FIG. 69A cannula 9502 may have luer adaptor 9550 at or attached to proximal end 9504. Thus, accessory lumen 9530, infusion lumen 9520, or inflation lumen 9540 may extend through luer adaptor 9550 or be attached to luer adaptor 9550 at proximal end 9504. It is also considered that luer adaptor 9550 may include proximal end of access lumen 9534, proximal end of inflation lumen 9544, or proximal end of infusion lumen 9524. Correspondingly, proximal end of access lumen 9534 may end with proximal access lumen port 9554, proximal end of inflation lumen 9544 may end with balloon inflation port 9553. Luer adaptor 9550 may include a port, such as proximal access lumen, port 9554 to connect to a hemastatic valve. Furthermore, proximal end of inflation lumen 9524 may end with proximal infusion port 9552, such as a port having a spring loaded pressure seal. Also, balloon inflation port 9553 may be a port to have an inflation device or syringe attached thereto as described herein. Some embodiments of inflation device or syringes contemplated for use with apparatus 9500 are discussed herein with respect to apparatus 9700 and 9800 of FIGS. 75A-81. For instance, an inflation device or syringe attached to balloon inflation port 9553 may include a label on its surface such as to identify a purpose or information related to the device or syringe.

According to some embodiments luer adaptor may have a dimension suitable to allow a first volume of treatment agent to be infused to a treatment region, to allow a second volume of blood and treatment agent to be aspirated from the treatment region (e.g., see hole 988 of FIG. 9 and accompanying text), and to allow a volume of a gas or fluid to inflate balloon 9510 to a pressure, such as BPI1, of less than six atmospheres, and to maintain the inflation volume (e.g., such as BVI1) for at least four minutes.

FIG. 69E is a cross sectional view of third section 9558 of FIG. 69A from perspective "D". FIG. 69E shows third section 9558 of cannula 9502 having second width CW2 of between 0.035 inches and 0.055 inches, such as having a width of 0.048 inches. FIG. 69E also shows cannula 9502 having a second height CH2 of between 0.05 and 0.065 inches, such as a height of 0.057 inches. For instance, according to some embodiments, third section 9558 may be a section that extends from a proximal end of balloon 9510 to a distal end of balloon 9510, such as a balloon shaft. More particularly, third section 9558 may include balloon section 9511, and may have a profile that is taller or wider than second section 9557, such as a profile shown in FIG. 69E resulting from third section 9558 including balloon 9510.

FIG. 69F is a cross section view of fourth section 9559 of FIG. 69A from perspective "E". FIG. 69F shows fourth section 9559 having third width CW3 of between 0.03 inches and 0.045 inches, such as having a width of 0.037 inches. FIG. 69F also shows fourth section 9559 having third height CH3 of between 0.05 inches and 0.065 inches such as having a height of 0.057 inches. According to some embodiments, balloon inflation lumen 9540 does not extend into either third section 9558 or fourth section 9559.

For example, the distal end of cannula 9502 may have a soft tip having a plurality of compliant tubes, lumen, sub-cannula with extended portions extending past the distal end of the cannula, where the extended portions are bound together by a compliant material wrap. Specifically, for example, as shown in fourth section 9559 of FIGS. 69A and 69F, infusion lumen 9520 or accessory lumen 9530 may be joined to or joined by a soft tube made with a polymer material that is bondable to the infusion or accessory lumen tube. Moreover, the polymer may have a lower hardness Durometer than either the tube of infusion lumen 9520 or the tube of accessory lumen 9530. In addition, the soft section described above may be further wrapped with another soft jacket wrapping over the soft tubes to form the tip of cannula 9502. It is contemplated that all the joining and wrapping described above may be performed with laser bonding, heat melting, or adhesive gluing.

Also, according to some embodiments, cannula 9502 may have support mandrel 9560 disposed within the cannula and exiting or ending at proximal end 9504 and extending proximal to, within the length of, or distal to balloon 9510. Specifically, mandrel 9560 may extend to balloon 9510 such as shown by balloon section 9511 and may or may not extend past balloon 9510, such as shown by third cross section 958. Thus, mandrel 9560 may extend through third section 9558 to support apparatus 9500 through the third section, where exterior surface 9508 or cannula 9502 may not exist through the third section. It is also contemplated that support mandrel 9560 may have a partial length, such as beginning at proximal end 9504 or beginning distal to proximal end 9504 and extending to the midpoint between proximal end 9504 and distal end 9506, a point along first section 9556, or a point along second section 9557. In addition, as a marker band, shrink wrap, infused material, extruded material, laser-bonded material, heat-bonded material, or other material or wrap may be used to couple, attach, or connect mandrel 9560, accessory lumen 9530, or infusion lumen 9520 within balloon section 9511. For example, as described below, a radio-opaque marker band, material infused from third section 9558, or material that is included in third section 9558 may extend through a portion or all of balloon section 9511 to connect together or be a part of inflation lumen 9540, accessory lumen 9530, infusion lumen 9520, or support mandrel 9560.

It is also considered that where materials described above with respect to third section 9558 extend into balloon section 9511, materials included in or used to form fourth section 9559 may also exist or form components of the structure within balloon section 9511 or third section 9558 as described herein.

Moreover, according to some embodiments, mandrel 9560 may have various cross-sectional shapes, such as a circle, oval, square, rectangle, or other polygon or curved cross-sectional shape as mandrel 9560 extends through cannula 9502. For example, mandrel 9560 may have outer diameter MOD1 which is constant, or which reduces with extension of the mandrel from proximal end 9504 toward distal end 9506. For example, mandrel 9560 may have a constant outer diameter MOD1 of less than 0.017 inches in diameter. Alternately, mandrel 9560 may have proximal outer diameter MOD1 that begins with less than 0.017 inches at proximal end 9504 and steps down to a plurality of lesser outer diameters that end with a distal diameter of the MOD2 between 0.012 inches and 0.003 inches in diameter such as shown in FIG. 70.

In addition, it is contemplated that support mandrel 9560 may be anchored or attached to a proximal adaptor such as luer adaptor 9550, cannula 9502 at proximal end 9504, as well as cannula 9502 within the length of balloon 9510, such as where the balloon is connected to the exterior surface of the cannula. It is also contemplated that support mandrel 9510 may only be attached at one or none of the locations identified above.

Support mandrel 9560 may be used to add stiffness to or reinforce catheter 9520, such as to prevent the catheter from kinking. Support mandrel 9560 may include one or more of titanium, nickel-titanium (NiTi), stainless steel, a plastic, a polymer, a polyether block amide resin having a durometer hardness of about 50 to about 70 shore D, a polyimide, a polyethylene, or other suitable materials or metals, such as those having a sufficient stiffness to prevent the cannula from kinking. For example, support mandrel 9560 may extend from proximal end 9504 to a location distal to proximal coupling 9517 to prevent or reduce the possibility of cannula 9502 from kinking when the cannula is not supported by a guidewire, such as is a guidewire used during insertion of cannula 9502 is removed from accessory lumen 9530 and accessory lumen 9530 is used to monitor parameters at a treatment region.

Note that material coupling infusion lumen 9520, accessory lumen 9530, mandrel 9560, or inflation lumen 9540 in balloon section 9511 may also be coupled to or may include cannula 9502, such as in embodiments where cannula 9502 extends through balloon section 9511. It may be appreciated that one or more marker bands, polymer sheaths, on other materials may be mounted around all tubes, mandrel, lumens, or cannula running through balloon 9510, or can be mounted over single components thereof. Thus, if a marker band is mounted over a single component, a polymer sheath may be added to bundle together more than one of the components identified above, such as within the length of balloon 9510. Specifically, a polymer sheath may bundle together cannula 9502, inflation lumen 9540, mandrel 9560, or accessory lumen 9530 at a point along the length of balloon 9510 (e.g., such as where balloon 9510 is coupled to exterior surface 9508). According to an embodiment, balloon inflation lumen 9540 may extend through exterior surface 9508 and to balloon 9510, and marker band 9570 may be attached to cannula 9502 at the location that balloon inflation lumen 9540 exits to balloon 9510 at an inflation opening. Thus, placement of marker band 9570 may assist in bonding of balloon inflation lumen 9540 to cannula 9502, may create a more resilient bond, and may protect the inflation opening.

According to some embodiments, apparatus 9500 may include at least one radio-opaque marker band. For example, FIGS. 69A, 69D, and 70 show radio-opaque marker band 9570 around the exterior of accessory lumen 9530, infusion lumen 9520, and mandrel 9560 at midpoint 9516 of balloon 9510. Moreover, as described above, marker band 9570 may encircle a portion of balloon section 9511 that includes material infused there from or also included in third section 9558. In addition, it is to be appreciated that marker band 9570 may be around the exterior of cannula 9502 (e.g., if cannula 9502 extends through balloon section 9511), accessory lumen 9530, or infusion lumen 9520 at midpoint 9516 of the balloon, proximal end 9517 of the balloon or distal end 9518 of the balloon (e.g., proximal end 9517 and distal end 9518 may correspond to the "shoulder" where the balloon is coupled to the exterior surface of the cannula). Note that more than one marker band may be used such as at more than one of the locations identified above.

According to some embodiments, lengths, diameters, materials, and other characteristics of cannula 9502, infusion lumen 9520, accessory lumen 9530, inflation lumen 9540, mandrel 9560, balloon 9510, or other components mentioned with respect to FIGS. 69A-F and 70 may be selected so that apparatus 9500 may assist in or be used for treatment agent or cell infusion to treat acute myocardia infraction (AMI) or other forms of loss of heart function due to heart muscle damage.

Figure 71A:
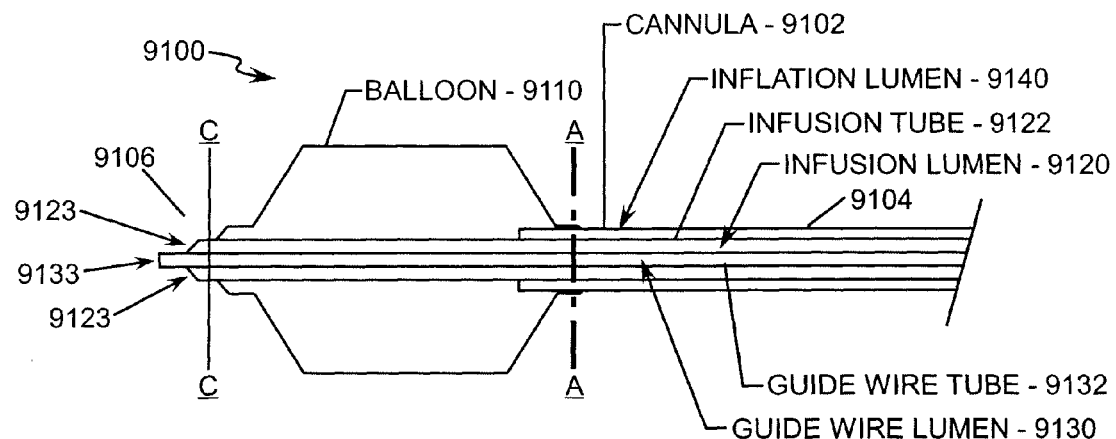
FIG. 71A is a cross-sectional view of a cannula and a balloon, where the cannula includes coaxially aligned lumens.
Figure 71B:
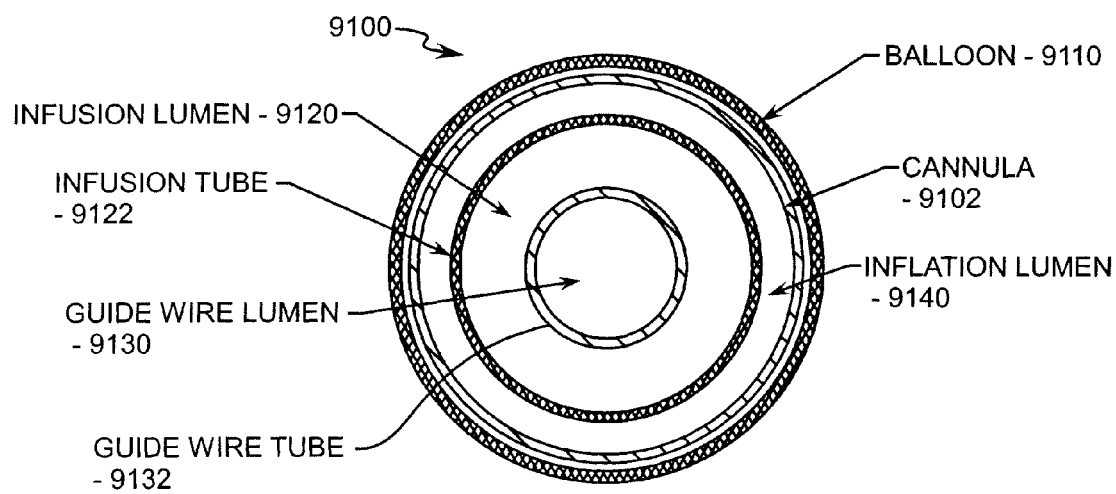
FIG. 71B is a cross-sectional view of the apparatus of FIG. 71A from perspective "A".

Another example of a cannula or catheter that has a dimension suitable for percutaneous advancement through a blood vessel to infuse a treatment agent (e.g., such as biological agents) into a treatment region, such as arterial vessels or venous vessels is a cannula having coaxial or co-linear lumen extending therethrough. For example, FIG. 71A is a cross-sectional view of a cannula and a balloon, where the cannula includes coaxially aligned lumens. As shown in FIG. 71A, apparatus 9100 has cannula 9102 having proximal end 9104 and distal end 9106 and balloon 9110 axially coupled to the exterior surface of the cannula at or adjacent distal end 9106, where balloon 9110 includes a property such that when inflated, the balloon may expand in size to an outer diameter sufficient to occlude a blood vessel. FIG. 71B is a cross-sectional view of apparatus 9100 of FIG. 71A from perspective "A". Cannula 9102 includes guidewire tube 9132 extending from proximal end 9104 to distal end 9106 and existing guidewire opening 9133. Guidewire tube 9132 is part of or includes guidewire lumen 9130.

Infusion tube 9122 is disposed around guidewire tube 9132 and extends from proximal end 9104 to distal end 9106 and exist infusion opening 9123. Also shown, infusion tube 9122 includes infusion lumen 9120. FIGS. 71A and B also show inflation lumen 9140 defined between infusion tube 9122 and cannula 9102. According to some embodiments, guidewire tube 9132, infusion tube 9122, and inflation lumen 9140 are coaxially aligned with an axis of cannula 9102 (e.g., such as shown in FIGS. 71A and B).

It is to be appreciated that inflation lumen 9140 extends to balloon 9110 and has a dimension suitable to inflate balloon 9110. Similarly, infusion tube 9122 has an outer diameter sufficient to infuse a treatment agent, such as treatment agents described herein, to a treatment region distal to balloon 9110. Next, guidewire tube 9132 has a sufficient outer diameter and be adapted to have a guidewire disposed therethrough to guide cannula 9102 through a blood vessel to a treatment region, such with respect to guiding cannula or catheters (e.g., such as cannula 9502) to a treatment region of a blood vessel.

As shown in FIG. 71B, cannula 9102 may have an exterior surface that forms a circular cross-section with respect to perspective "A" where balloon 9110 is axially coupled to the exterior surface of cannula 9102. Sealing on a round shaft allows for a more concentric balloon outer diameter profiles, such as elastomeric balloon inflation profiles. A concentrically inflated balloon profile puts can put an even stress or inflation pressure on the balloon wall to seal around or occlude a blood vessel more reliably and evenly. Similarly, it is contemplated that infusion tube 9122 may be coupled or attached to the exterior surface of guidewire tube 9132 at a location or along locations distal to balloon 9110, such as adjacent to or at the distal end of cannula 9102.

Figure 72A:
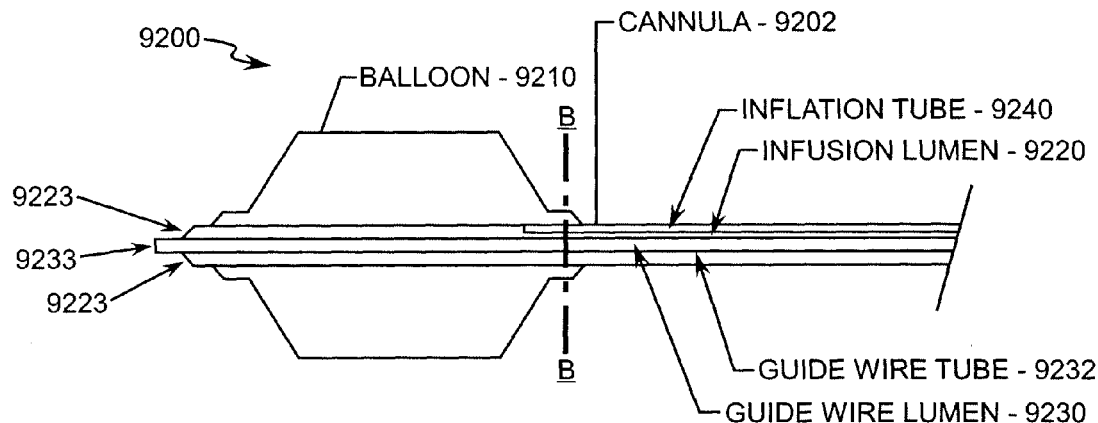
FIG. 72A is a cross-sectional view of a cannula and a balloon, where the cannula includes coaxially and co-linearly aligned lumens.
Figure 72B:
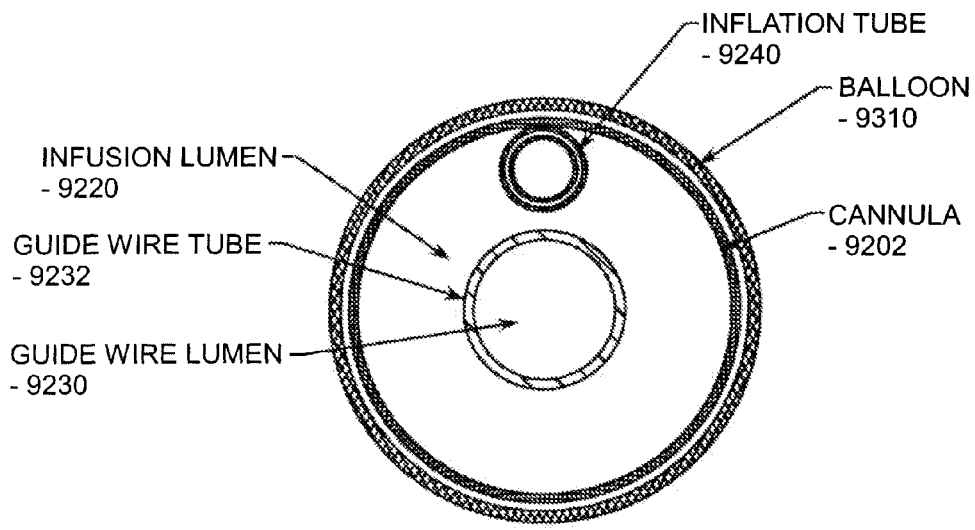
FIG. 72B is a cross-sectional view of the apparatus of FIG. 72A from perspective "B".

FIG. 72A is a cross-sectional view of a cannula and a balloon, where the cannula includes coaxially and co-linearly aligned lumens. As shown in FIG. 72A, apparatus 9200 has cannula 9202 having proximal end 9204 and distal end 9206 and balloon 9210 axially coupled to the exterior surface of the cannula at or adjacent distal end 9206, where balloon 9210 includes a property such that when inflated, the balloon may expand in size to an outer diameter sufficient to occlude a blood vessel. FIG. 72B is a cross-sectional view of apparatus 9200 of FIG. 72A from perspective "B". Cannula 9202 includes guidewire tube 9232 extending from proximal end 9204 to distal end 9206 and existing guidewire opening 9233. Guidewire tube 9232 is part of or includes guidewire lumen 9230.

FIGS. 72A and B also show infusion lumen 9220 defined between guidewire tube 9232 and cannula 9202. According to some embodiments, guidewire tube 9232 and infusion lumen 9220 are coaxially aligned with an axis of cannula 9202, such as shown in FIGS. 72A and B. Inflation tube 9240 is shown extending from proximal end 9204 to balloon 9210 and is co-linearly aligned with an axis of cannula 9202. It is contemplated that inflation tube 9240 may be attached or coupled to cannula 9202 such as by adhesive, heat bonding, or laser bonding. Thus, guidewire lumen 9330, guidewire tube 9332, and inflation lumen 9340 may be co-linearly aligned with an axis of cannula 9302.

It is to be appreciated that inflation tube 9240 extends to balloon 9210 and has a dimension suitable to inflate balloon 9210. Similarly, infusion lumen 9220 has an outer diameter sufficient to infuse a treatment agent, such as treatment agents described herein, to a treatment region distal to balloon 9210. Next, guidewire tube 9232 has a sufficient outer diameter and be adapted to have a guidewire disposed therethrough to guide cannula 9202 through a blood vessel to a treatment region, such with respect to guiding cannula or catheters to a treatment region of a blood vessel.

It is also contemplated that cannula 9202 may have an exterior surface that forms a circular cross-section with respect to perspective "A" where balloon 9210 is axially coupled to the exterior surface of cannula 9202. Similarly, it is contemplated that infusion tube 9222 may be coupled or attached to the exterior surface of guidewire tube 9232 at a location or along locations distal to balloon 9210, such as adjacent to or at the distal end of cannula 9202.

FIG. 73 is a cross-sectional view of a cannula and a balloon, where the cannula has coaxially and co-linearly aligned lumens. FIG. 73 shows apparatus 9300 having cannula 9302. Cannula 9302 includes guidewire tube 9332 forming guidewire lumen 9330 is coaxially aligned with infusion lumen 9320. FIG. 73 also shows inflation lumen 9340 formed within cannula 9302, and balloon 9310 axially coupled to the exterior surface of cannula 9302. Balloon 9310 may be a part of or correspond to a balloon such as described above with respect to balloon 9110. Similarly, infusion lumen 9320, guidewire tube 9332, guidewire lumen 9330, and cannula 9301 may have an outer diameter, dimension, or character to function similarly to their counterparts described above with respect to FIGS. 71A and B.

Moreover, according to some embodiments, none, any, or all of guidewire tube 9132, infusion tube 9122, inflation lumen 9140, guidewire tube 9232, infusion lumen 9220, inflation tube 9240, guidewire tube 9332, infusion lumen 9320, or inflation lumen 9340 may include or have its own sleeving, cannula, or other surrounding material or structure having a dimension to fit within the surrounding cannula in which the lumen is disposed or extending through, such with respect to lumen 9520 at FIGS. 69A-F.

Additionally, because of it's structure, apparatus 9100, 9200, and 9300 may track better in tortuous vasculature than cannula or catheters that do not have lumen coaxially or co-linearly located. In addition, a coaxial or co-linearly constructed catheters can be easier to fabricate. For instance, various processes may be used to form apparatus 9100, 9200, or 9300 of FIGS. 71A-73. For example, one or more materials may be melt-extruded to form a multi-lumen extruded cannula having a plurality of coaxially aligned tubes with respect to an axis of the cannula, where each coaxially aligned tube has an exterior surface with a circular cross-sectional shape with respect to the axis of the cannula. Then, a balloon may be axially sealed to the circular cross-sectional exterior surface of the cannula where the balloon includes a property such that when inflated, the balloon with expand in size to an outer diameter sufficient to occlude a blood vessel (e.g., such as described above with respect to balloon 9110).

A process for forming apparatus 9100, 9200, or 9300 of FIGS. 71A-73, as described above may also include melt-extruding at least one material to form a number of tubes where some of the tubes may be inserted into other tubes to form a multi-tube cannula having a number of coaxially aligned tubes or co-linearly aligned tubes with respect to an axis of the cannula, where each of the tubes has a circular cross-sectional shape with respect to an axis of the cannula. Then, a balloon (e.g., as described for balloon 9110) may be axially sealed to the circular cross-sectional exterior surface of the cannula.

Next, a process for forming apparatuses 9100, 9200, or 9300 of FIGS. 71A-73, as described above might include placing a mandrel having a crescent-shaped cross-section within an infusion tube, placing an inflation tube on a support mandrel next to the infusion tube, wrapping the infusion tube and the inflation tube in a jacket material, inserting the jacket material into a shrink tube, and heating the shrink tube sufficiently to melt a portion of the infusion tube and the inflation tube material so that those materials are redistributed to form a cannula having the infusion tube and inflation tube coaxially aligned with respect to an axis of the cannula.

It is also considered that a process for forming apparatus 9100, 9200, or 9300 of FIGS. 71A-73, as described above might include placing a round support mandrel within a portion of a guidewire tube and placing the guidewire tube within an infusion tube so the guidewire tube is coaxially aligned with the infusion tube. Note that it can be appreciated the guidewire tube and infusion tube may each have a circular cross-section with respect to an axis of the infusion tube. Next, two crescent-shaped mandrel may be placed between the guidewire tube and the infusion tube at or along a location where the support mandrel is within the guidewire tube. The two crescent-shaped mandrel may be located at opposing axial locations to form a construction. The construction described above then may be inserted into a shrink tube and heated (e.g., such as by thermal heat or laser energy) sufficiently to melt the infusion tube to a portion of the guidewire tube, to form one or more tack joints where the crescent mandrels do not support the infusion tube, and thus the infusion tube bonds to the guidewire tube.

For example, FIG. 74A is a cross-sectional view of the apparatus of FIG. 71A from perspective "C" before forming tack joints between the guidewire tube and the infusion tube. FIG. 74A shows the structure of apparatus 9100 having guidewire opening 9133 within guidewire tube 9132 and infusion tube 9122 around infusion opening 9123 and guidewire tube 9132. FIG. 74B is the structure of FIG. 74A after forming tack joints between the guidewire tube and the infusion tube. For instance, FIG. 74B is the structure shown of apparatus 9100 after tack joints 9470 and 9472 are formed such as by heat or laser energy as described above with respect to forming apparatus 9100, 9200, and 9300 of FIGS. 71A-73. Thus, after tack joints 9470 and 9472 are formed, FIG. 74B shows infusion openings 9423 formed between attached infusion tube sections 9420 and 9422, and guidewire tube 9132. Note that the structures and processes described above with respect to FIGS. 74A and B, such as forming tack joints, may also be applied to apparatus 9200 and 9300 of FIGS. 72A-73. Furthermore, the structure and processes described above with respect to FIGS. 72A-73 may also be applied to apparatus 9100 of FIGS. 71A and B.

Figure 75A:
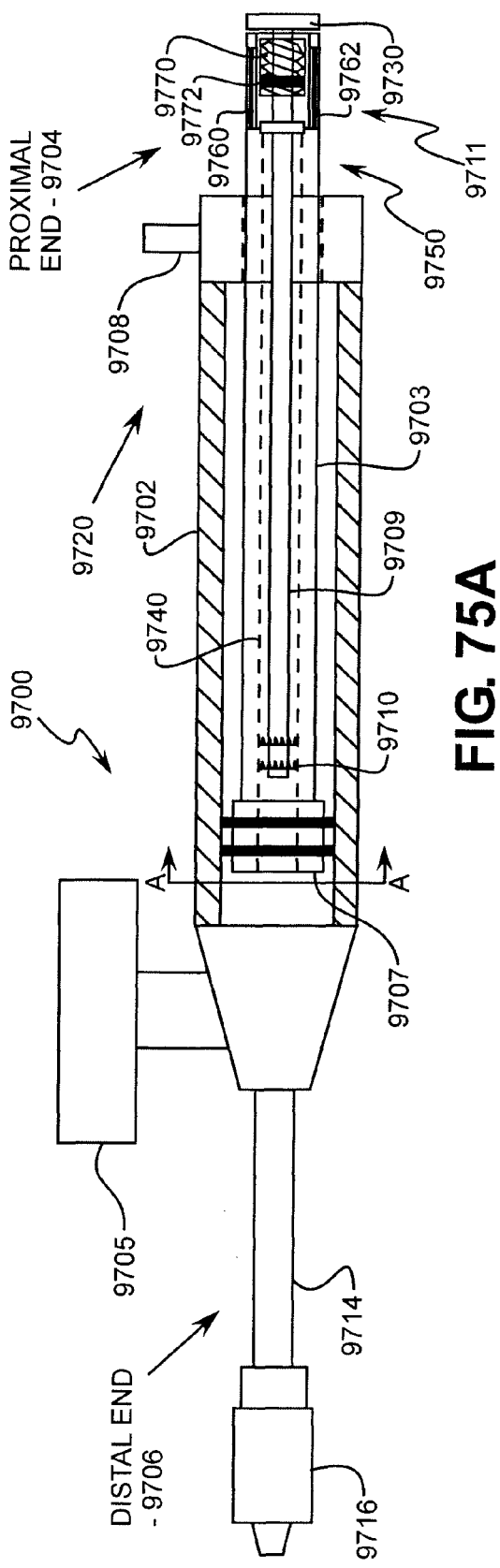
FIG. 75A is a cross sectional view of an apparatus to inflate a low volume balloon to occlude a blood vessel.
Figure 75B:
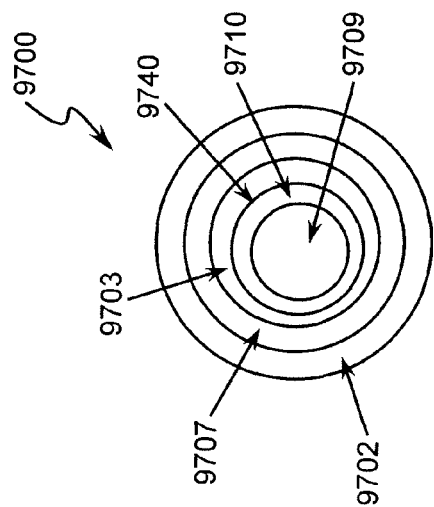
FIG. 75B is a cross-sectional view of the apparatus of FIG. 75A from perspective "A".

Some embodiments of inflation device or syringes contemplated for use with apparatus, cannula, and catheters, described herein (e.g., including apparatus 9100, 9200, 9300, 9500 of FIGS. 69A-74) for inflating or deflating balloons described herein (e.g., such as balloon 8810 and 9510 of FIGS. 64A-70) may include one or more inflation syringes. For example, FIG. 75A is a cross sectional view of an apparatus to inflate a low volume balloon to occlude a blood vessel. For example, apparatus 9700, as will be shown and described below in FIGS. 75A-80 may be used to inflate a balloon coupled to a distal end of a cannula having an inflation lumen extending from the balloon through a cannula and out a proximal exit in the cannula where the lumen will be coupled to apparatus 9700. FIG. 75A shows apparatus 9700 having large volume syringe 9720 and low volume syringe 9750 within an elongated hollow inner diameter of the plunger of large volume syringe 9720. FIG. 75B is a cross-sectional view of the apparatus of FIG. 75A from perspective "A".

Large volume syringe 9720 is shown having barrel 9702 which forms an elongated hollow body proximal end 9704, and distal end 9706. Barrel 9702 of apparatus 9700 is shown cut away in the travel region of the outer plunger 9703. Outer plunger 9703 incorporates one or more seals on piston 9707, which do not allow fluid/air flow between the outer diameter (OD) of the outer plunger 9703 and the inner diameter (ID) of barrel 9702 in the area where they form a seal. The lumen/ID of the barrel 9702 is in communication with the output extension tube 9714 and pressure gage 9705, such that as outer plunger 9703 is translated distally, fluid may be expelled out of the extension tube 9714 and the pressure applied to the fluid may be measured. The distal end of extension tube 9714 is terminated in a male Luer Lock connector 9716. Thus, large volume syringe 9720 has an opening in the distal end to couple to a proximal exit of a cannula, such as by coupling male Luer Lock connector 9716 to a lumen in a cannula. More particularly, embodiments of apparatus 9700 and 9800 may attach to delivery catheter 2620 or catheter system 3000, such as by coupling male Luer Lock connector 9716 to fitting 2640 as shown in FIGS. 26-29 or fitting 3040 as shown in FIG. 30.

The position of the outer plunger 9703 in the barrel 9702 may be locked into position or unlocked to move freely by actuating outer plunger lock 9708. Outer plunger lock 9708 is on the proximal end of the barrel 9702 and can have many configurations. The simplest configuration is a pressure/force engagement of the proximal portion of plunger 9703 with sufficient force and material coefficient of friction to hold plunger 9703 in place when the lock 9708 is engaged. For example, the basic mechanism can be the similar to lock/unlock mechanisms for use on balloon inflation devices, indeflators and syringes.

According to some embodiments, outer plunger 9703 is longitudinally slidable within barrel 9702 and has a first shaft with first piston 9707 disposed on the first shaft distal end. In accordance with embodiments, first piston 9707 and the shaft have elongated hollow inner diameter 9740 with inner plunger 9709 longitudinally slidable within the inner diameter. Inner plunger 9740 has a second shaft with second piston 9710 disposed on the second shaft distal end. Therefore, the inner diameter and second plunger define low volume syringe 9750 having a volume relatively substantially less than a volume of large volume syringe 9720.

For example, low volume syringe 9750 is may communicate with the draw volume of internal volume of large volume syringe 9720 in barrel 9702 distal to plunger 9707. For example, outer plunger 9703 is a hollow construction in which inner plunger 9709 resides. Inner plunger 9709 may contain seals 9710 which perform the same function for the inner plunger 9709 and the ID of the outer plunger 9703 as seals 9707 do for the outer plunger 9703 and the ID of the barrel 9702. In its most distal travel position, the distal end of the inner plunger 9709 aligns with or is very close to the distal end of the outer plunger 9703. If the distal position of the inner plunger 9709 is too far proximal of the distal end of the outer plunger 9703, then it is possible that air could get trapped in the ID of the outer plunger 9703 that is distal to the distal end of the inner plunger 9709. As previously explained, trapped air is not desirable and should be avoided in these applications. In one design, the ID of the barrel 9702 is designed such that it can accommodate a significant protrusion of the inner plunger 9709 distal to the distal end of the outer plunger 9703 and distal to the seals 9710.

Also, apparatus 9700 may include one or more lock mechanisms to lock the plunger of each syringe so that a user can selects whether the plunger is free or constrained to move in response to the rotation of its threads or a lock can be used to engage the plunger surface(s) with sufficient friction to prevent accidental plunger motion (in this case the threads aren't really needed to provide the mechanical advantage to more easily produce high pressures, since the pressures are to be low), the plunger handle configuration modified to make accidental motion less likely (i.e. from a "T" shape to a more round shape). As shown in FIG. 75A, low volume syringe 9750 may have its own associated translation and locking control. Specifically, large volume syringe 9720 may use outer plunger lock 9708 to releasably secure plunger 9703 to lock piston 9707 at various locations along barrel 9702. Correspondingly, low volume syringe 9750 may use inner plunger lock 9711 to releasably secure plunger 9709 to lock piston 9710 at various locations along inner diameter 9740. Thus, inner plunger lock 9711 is on the proximal end of the outer plunger 9703 and allows the locking and unlocking of the inner plunger 9709 position relative to the outer plunger 9703. Inner plunger lock 9711 may have a mechanism similar to that of the outer plunger lock 9708.

The maximum proximal travel position of the inner plunger is constrained to limit the amount of fluid that may be drawn into the ID of outer plunger 9703 (or alternatively or in addition to limit the minimum protrusion of the distal end of the inner plunger 9709 into the ID of barrel 9702). Many mechanisms are commonly used to accomplish this, the most common utilize OD or cross-section changes of the plunger 9709 (or the ID of the outer plunger 9703) to interfere with portions of the device that it must translate through, such as the lock 9711. (A similar method may be used to constrain the proximal travel of the outer plunger 9703.) The limiting of plunger 9703 or 9709 travel sets the fluid displacement allowed for that plunger. In a design for a compliant balloon, the displacement set for inner plunger 9709 is the maximum incremental injection that can be safely injected into the catheter to incrementally inflate the balloon or less. This is an important safety feature.

In addition, according to some embodiments, the proximal end of the outer plunger 9703 may contain a mechanism to allow the selection of different proximal travels of inner plunger 9709 and, thus allow a single inflation/deflation device to safely operate catheters with different inflation or deflation volumes. Alternately or in addition, the previously mentioned proximal travel limit (used to initially limit the inflation of a compliant balloon) may be removed (a distal limit may be added) and the inner plunger 9709 may subsequently be used to more rapidly inflate and deflate the balloon. Alternately or in addition, the proximal end of the outer plunger 9703 may contain a mechanism to control the translation of inner plunger. Such mechanisms can be incorporated as a part of the lock 9711 mechanism.

It can be appreciated that the translation control on the second plunger or other components of the device (i.e. the first plunger) may contain an indicator or marks that show the expected size of the balloon or the expected sizes of various balloon catheters or their expected deflation volumes. The translation control on the second plunger may contain a selection mechanism that limits the plunger translation to a safe maximum injection volume for the selected catheter.

More particularly, according to an embodiment, large volume syringe 9720 may have large drawing volume, such as between 10 cubic centimeters (cc) in volume and 30 cubic centimeters in volume; and low volume syringe 9750 may have substantially smaller drawing volume, such as between 0.2 cubic centimeters in volume and three cubic centimeters in volume to inject additional controlled volumes in increments of between 0.005 cubic centimeters in volume and 0.05 cubic centimeters in volume.

For example, in order to allow a balloon (e.g., such as a low pressure, high compliance, or low tension occlusion balloon with respect to balloons 4420, 8810, or 9510) to be conveniently and quickly deflated and then accurately re-inflated, apparatus 9700 may include latch mechanisms 9760 and 9762 to unlatch inner plunger lock 9711 from inner diameter 9740 so that piston 9710 can be moved towards proximal end 9704. Thus, when unlatched, piston 9710 may be moved towards proximal end 9704 of inner diameter 9740 to evacuate a selected volume of fluid from the balloon and into low volume syringe 9750. Furthermore, latch mechanisms 9760 and 9762 may be configured to latch inner plunge lock 9711 back to inner diameter 9740 so that piston 9710 can be moved towards distal end 9706 to return or deliver a selected volume of fluid to the balloon. More particularly, latching or re-latching inner plunger lock 9711 to inner diameter 9740 may return the same volume of fluid evacuated from a balloon and into low volume syringe 9750, as described above, when piston 9710 is moved towards the proximal end of hollow inner diameter 9740 and returned to its original position. Latch mechanisms 9760 and 9762 will be described further below with respect to FIGS. 76-80.

Inner plunger lock 9711 may also include an adjustment mechanism to adjust the position of piston 9710 to various locations along hollow inner diameter 9740. For example, inner plunger lock 9710 may include threaded cavity 9770 coupled to knob 9730 which is exterior to hollow inner diameter 9740. Thus, bolt 9772 may threadably engage threaded cavity 9770 and be coupled to plunger 9709 so that knob 9730 may be rotated to adjust a position of piston 9710 to various locations along inner diameter 9740. More particularly, knob 9730 may include indicia disposed about the knob to indicate a selected volume of fluid to be communicated to or from the balloon corresponding to the marked position on the knob, such that knob 9730 may be rotated to various marked positions to inflate the balloon with various selected volumes of an inflation gas or liquid. For instance, knob 9730 may be rotated from a first position to a balloon volume position to deliver a selected volume of fluid to the balloon. On the other hand, knob 9730 may be rotated from the balloon volume position back to the first position to evacuate the same selected volume of fluid from the balloon and into apparatus 9700.

It can be appreciated that piston 9710 or 9707 may each include one or more sealing members adapted to create a fluid seal between the piston and the elongated hollow in which the piston is slidably disposed (e.g., such as by including one or more elastic O-rings).

Figure 76:
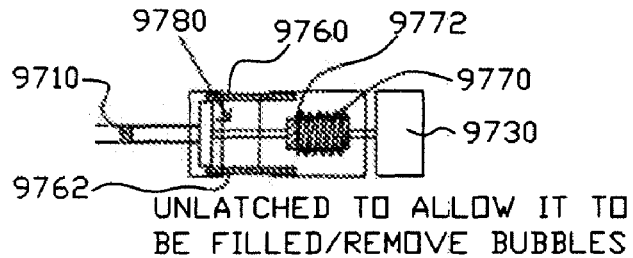
FIG. 76 shows the latch mechanisms of FIG. 75A in an unlatched position.

FIGS. 76-80 show latch mechanisms 9760 and 9762, and knob 9730 adjusted to various positions, such as positions they may be adjusted to during use of inner plunger lock mechanism 9711 or apparatus 9700. For instance, FIGS. 76-80 show what effect latching and unlatching mechanisms 9760 and 9762, or rotating knob 9730 to various positions have on the position of piston 9710. FIG. 76 shows the latch mechanisms of FIG. 75A in an unlatched position. FIG. 76 shows latch mechanisms 9760 and 9762 in an unlatched position to unlatch inner plunger lock 9711 from hollow inner diameter 9740. Latch mechanisms 9760 and 9762 may include retaining structure on their proximal and distal ends so that an unlatched position, such as shown in FIG. 76 cannot be exceeded and inner plunger lock 9711 cannot be separated from inner diameter 9740. FIG. 76 also shows gap 9780 between inner plunger lock 9711 and inner diameter 9740. Latch mechanisms 9760 and 9762 may be used to provide an unlatched position, such as shown in FIG. 76, so that low volume syringe 9750 may be filled with liquid or bubbles my be removed therefrom.

Figure 77:
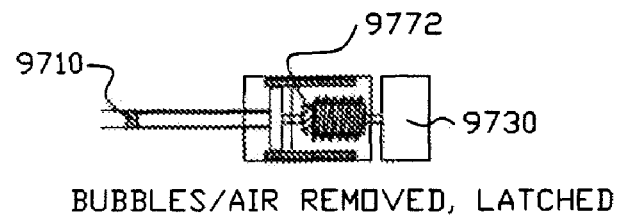
FIG. 77 shows the latch mechanisms of FIG. 76 relatched.

FIG. 77 shows the latch mechanisms of FIG. 76 relatched. FIG. 77 shows FIG. 76 after latch mechanisms 9760 and 9762 are used to reattach or latch inner plunger lock 9711 to inner diameter 9740. The latch positions shown in FIGS. 76 and 77 may be used to remove bubbles or air from low volume syringe 9750, such as by alternating between the latch positions shown in FIGS. 76 and 77 for latch mechanisms 9760 and 9762 to remove bubbles or air from low volume syringe 9750. After bubble/air removal, the latch position of latch mechanisms 9760 and 9762 may be returned to the latched position as shown in FIG. 77.

Figure 78:
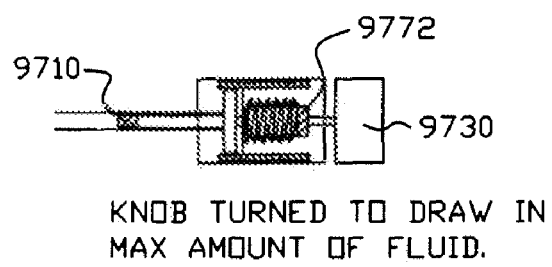
FIG. 78 shows FIG. 77 after the inflation volume adjustment knob has been rotated or turned to retain fluid.

FIG. 78 shows FIG. 77 after the inflation volume adjustment knob has been rotated or turned to retain fluid. FIG. 78 shows FIG. 77 after knob 9730 has been rotated or turned, such as to draw in or retain a maximum amount of fluid within low volume syringe 9750. As shown in FIG. 78, bolt portion 9772 is in a most proximal position, as to where bolt portion 9772 is in a most distal portion in FIG. 77. The travel of bolt portion 9772 may be limited such that the maximum fluid volume that may be retained (and then expelled into the balloon) is limited to an amount that limits the maximum outer diameter to which the balloon may be inflated. Thus, a limit to the travel of bolt portion 9772 may be selected (e.g., such as a safety feature) to prevent over-inflation/bursting of the balloon or over-stretching of the blood vessel to be occluded.

Figure 79:
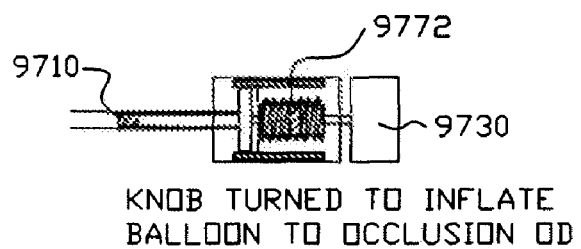
FIG. 79 shows FIG. 78 after the inflation volume adjustment knob has been rotated or turned to inflate the balloon with a selected inflation volume fluid.

FIG. 79 shows FIG. 78 after the inflation volume adjustment knob has been rotated or turned to inflate the balloon with a selected inflation volume fluid. FIG. 79 shows knob 9730 turned or rotated to inflate a balloon, such as to occlude a blood vessel. Note that FIG. 79 shows bolt portion 9772 between a minimum and maximum distal position along threaded cavity 9770, such as when knob 9730 is being rotated to various rotational positions as indicated by markings to provide selected volumes of fluid to the balloon.

Figure 80:
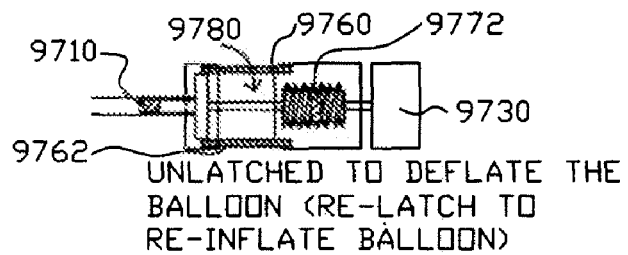
FIG. 80 shows FIG. 79 after unlatching inner the plunger lock to deflate the balloon.

FIG. 80 shows FIG. 79 after unlatching inner the plunger lock to deflate the balloon. FIG. 80 shows FIG. 79 after unlatching inner plunger lock 9711 from inner diameter 9740. For example, latch mechanisms 9760 and 9762 are in an unlatched position and allow for gap 9780. Thus, the configuration shown in FIG. 80 may be used after the balloon is inflated with a proper volume to occlude a blood vessel and it is desired to deflate the balloon to allow blood to perfuse back into a treatment region of the blood vessel, such as treatment region 996 of blood vessel 990. More particularly, after a blood vessel is sufficiently occluded and treatment agent is infused through a treatment region for a sufficient period of time, inner plunger lock 9711 may be unlatched from inner diameter 9740 so that plunger 10 may be pulled to a distal position to deflate the occluding balloon to allow blood to reflow through the portion of the blood vessel previously occluded.

After the position shown in FIG. 80, it is then possible to re-latch inner plunger lock 9711 to inner diameter 9740, such as by pushing knob 9730 forward to return apparatus 9700 to the position that is shown in FIG. 79. Thus, it is possible to alternate between the positions shown in FIG. 79 and FIG. 80 in order to inflate a balloon to a sufficient volume to occlude a blood vessel is described herein, then deflate the balloon sufficiently to allow blood flow through the blood vessel, and then re-inflate the balloon to the same volume of inflation fluid that the balloon was inflated with before deflation.

Thus, the apparatus and steps shown and described with respect to FIGS. 75A-80 provide a safe and predictable device and process for inflating, deflating, and re-inflating and a high compliance, low pressure, or low tension balloons for occlusion of a blood vessel. For instance, latch mechanisms 9760 and 9762 allow apparatus 9700 to be used to safely more rapidly inflate and deflate a low volume balloon after an initial inflation.

Figure 81:
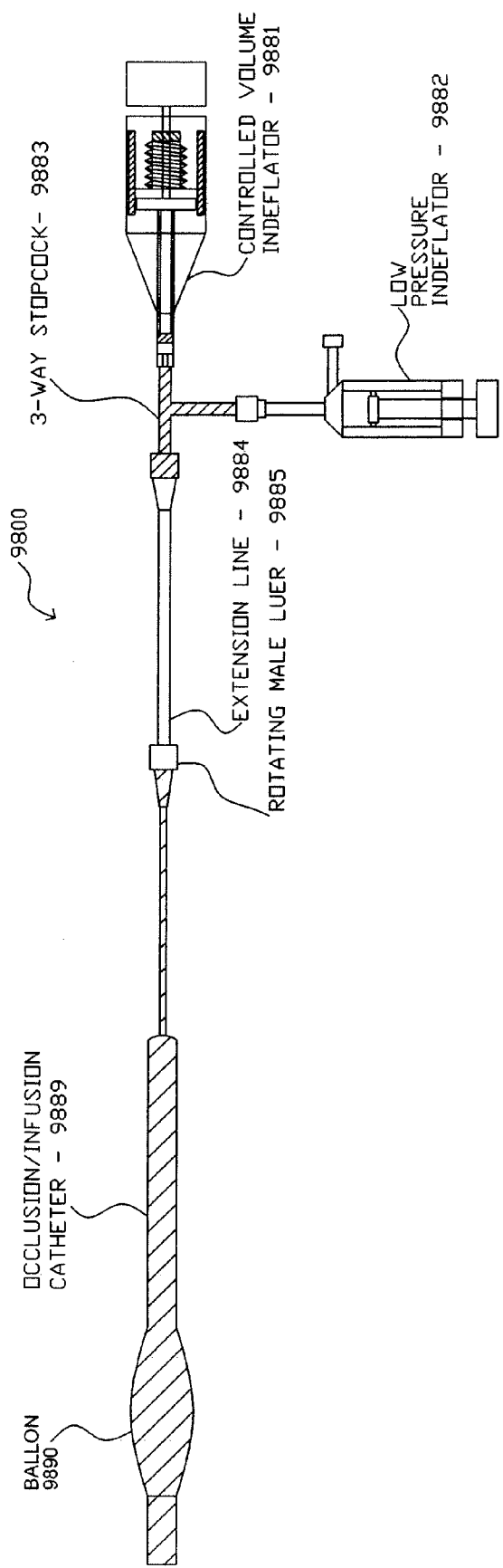
FIG. 81 shows an alternate embodiment of an apparatus to perform the functions of FIG. 75A-80.

FIG. 81 shows an alternate embodiment of an apparatus to perform the functions of FIGS. 75A-80. As shown in FIG. 81, apparatus 9800 has low pressure indeflator 9882 which may be a large volume syringe having a functionality similar to that described above with respect to large volume syringe 9720. FIG. 81 also shows controlled volume indeflator 9881, which may have a functionality similar to that described above with respect to low volume syringe 9750. Indeflator 9881 and 9882 are coupled to three-way stop cock 9883 which is in turn coupled to extension line 9884 and rotating male luer 9885. In turn, luer 9885 is coupled to occlusion/infusion catheter 9889. And balloon 9880 is coupled to catheter 9889. Thus, apparatus 9800 may provide a balloon inflation and deflation functionality similar to that described above with respect to apparatus 9700. Thus, in accordance with embodiments a balloon may be inflated by apparatus 9700 or 9800 having large volume syringe 9720 or low pressure indeflator 9882 which may be a high volume, low pressure syringe for initially inflating the balloon to a controlled or selected low pressure initial diameter. Then, the balloon may be further inflated by low volume syringe 9750 or controlled volume indeflator 9881 of apparatus 9700 or 9800, which may be a low volume syringe for further inflating the balloon with controlled volume increments (e.g., such as selected low volume increments of inflation fluid) to produce controlled diameter increase(s) up the an occlusion diameter.

It can be appreciated that apparatus 9700 or 9800 may be low pressure inflation/deflation device that requires only one operator and the normal stopcock connections, and still provide the ability to effectively evacuate the air, to inflate the balloon to its nominal out diameter (OD), to subsequently control the injected inflation volumes (for a compliant balloon) or the subsequent withdrawn volumes (to allow subsequent rapid balloon deflations and inflations) to the desired degree of precision, to lock the injected inflation volumes (so the device may be set aside) and unlock the injected inflation volumes (so the balloon may be deflated).

For example large volume syringe 9720 provides a large volume capacity to allow a vacuum/low pressure to be drawn on a device via normal Luer connected components that may leak a little air under dry/low pressure (relative to air pressure) conditions and to allow for any relatively low pressure/higher volume initial filling steps, while subsequently providing for very controlled/adjustable small volume injections and withdrawals. As such, large volume syringe 9720 can be used to remove air from a catheter and balloon, and subsequently inflate the balloon with contrast to a low pressure (to its beginning/initial OD or desired OD). Then, low volume syringe 9750 can be used to inflate the balloon (e.g., such as a balloon as described herein, including balloons 4420, 8810, and 9510) with additional controlled small volumes of contrast to be adjustably injected to bring the compliant balloon controllably up to the desired OD in steps to occlude a vessel or to withdraw/inject a controlled small volume of contrast to subsequently rapidly and safely deflate and re-inflate the balloon.

Apparatus 9700 or 9800 may be designed to effectively remove the air in a balloon and its inflation lumen so that only a small residual volume of air remains (air which will be replaced with the inflation fluid) to allow the balloon's OD to be effectively controlled by the volume of the injected fluid. One inflation fluid used is contrast. Contrast allows the balloon and its location to be very easily imaged by conventional fluoroscopy. As the OD of a compliant balloon is stepped up or a relatively non-compliant balloon is inflated to a low pressure, contrast may be injected proximal of the balloon into the vessel (normally via the guiding catheter) to assess whether the desired occlusion has been obtained or not.

It is also contemplated that apparatus 9700 or 9800 may be designed to have a relatively large drawing volume (usually in the 10-30 cc range) compared to the volume of air leaked, to maintain a sufficiently low pressure for effective air removal. Thus, using apparatus 9700 or 9800, it is possible to first inflate a compliant balloon to its nominal OD (its lowest OD) at a specified low pressure and then inject additional controlled volumes to produce the larger OD's. For instance, a balloon may be inflated with controlled volumes with increments on the order of 0.005 to 0.05 cc (or smaller) with a maximum total on the order of about 0.5 cc (or less) to control the balloon OD effectively.

Next a process for percutaneous advancing one or more cannula or catheters through a blood vessel to treat or infuse a treatment agent (e.g., such as biological agents) into a treatment region, such as arterial vessels or venous vessels is described.

For example, FIG. 82 is a flow diagram of a process for treating a treatment region of a blood vessel with one or more treatment agents or progenitor cells. At block 9610, a treatment region of a blood vessel is identified. For example, a treatment region may be similar to treatment region 996 of blood vessel 990; or may be a treatment zone of a blood vessel, a coronary vein, a coronary artery, or an infarct artery may be identified such as by releasing a marker into the blood vessel and marking ischemic signal at a location or region. Also, a treatment region includes those described above with respect to block 9610 as well as a location of a blood vessel, such as blood vessel 990, proximal to a treatment zone, such as a zone to be treated with a treatment agent (e.g., which may include progenitor cells).

Moreover, if sufficient ischemic signal does not exist before treatment of a blood vessel, it is possible to precondition a treatment region to allow for marking as described above. For example, at block 9620 ischemic preconditioning of a treatment region can be performed, such as by occluding a treatment region (e.g., such as treatment region 996 or a treatment region in the myocardium) for a period of time between 30 minutes and 180 minutes before releasing the marker fluid into the blood vessel. More particularly, a balloon or occlusion device may be inflated to block the blood vessel just above a targeted location of the vessel with respect to the direction of blood flow for a sufficient period of time to increase the ischemic signal from that location sufficiently for the marker to mark.

At block 9630 a cannula may be percutaneously advanced through a blood vessel. It is contemplated that the cannula may be a guide catheter, delivery catheter, guidewire, or other catheter or cannula (e.g., such as cannula 8802 or 9502). For example, the cannula may have a proximal end, a distal end, and a surface at or adjacent a distal end axially coupled to a balloon. For example, at block 9638, the cannula to be advanced through a blood vessel may include a lumen adapted to have a guidewire disposed therethrough so that a distal end of a guidewire (e.g., which may or may not have an occlusion balloon or balloon that may be inflated to an outer diameter greater than the inner diameter of the blood vessel at the location, such as to fix the guidewire distal end) may be advanced percutaneously through a blood vessel to or beyond a treatment region so that the cannula may be advanced over the guidewire, such as by inserting and sliding the guidewire lumen over the guidewire to advance the distal end of the cannula through the blood vessel and to the treatment region.

Specifically, a cannula such as 8802 or 9502 may be advanced through a blood vessel such as 990 and may have a balloon such as balloon 8810 or 9510 axially coupled to the cannulous exterior surface at or adjacent the distal end of the cannula. In one example, the cannula may have an outer diameter of less than 0.09 inches and include a lumen extending from the proximal end to the distal end of the cannula, where the lumen has an inner diameter greater than 0.010 inches.

At block 9640 it is determined whether the tip of the cannula or the balloon has been advanced to the treatment region. If at block 9640 the cannula or balloon is not at a treatment region, the process returns to block 9630 or the cannula or balloon may be advanced further. On the other hand, if at block 9640 the cannula or balloon is at a treatment region, the process continues to block 9650.

At block 9650 the balloon is inflated to occlude the blood vessel. For example, a balloon such as a balloon described above with respect to block 9630 may be inflated from a first diameter (e.g., such as first diameter BRD1 as described above) to a different second diameter (e.g., such as fourth diameter BRD4 as described above) that is at least equivalent to an inner diameter of a blood vessel to occlude the blood vessel at a treatment region (e.g., such as a treatment region as described above with respect to block 9610) for a first period of time. For example the balloon may be inflated by controlling a volume of a gas or a fluid injected into the balloon, such as to inflate the balloon to a plurality of increasing inflation volumes to form a plurality of increasing radial outer diameters. Moreover, it is contemplated that the increasing inflation volumes may be increased to a volume corresponding to a radial outer diameter of the balloon which is greater than the radial inner diameter of the blood vessel at a treatment region.

Furthermore, according to some embodiments, as described with respect to balloon 8810, the balloon may have a property such that when inflated to such a volume, the balloon has an inflation pressure that increases by less than five percent in pressure than the inflation pressure at one or more of the previous inflation volumes. For example, the balloon may be a high compliance balloon that increases in inflated axial length sufficiently to cause the balloon inflated outer diameter to maintain an inflation pressure that is within five percent of the previous pressure on the inner diameter of the blood vessel while the inflation volume is increased.

At block 9660 treatment agents are infused to the treatment region. For example, a treatment agent or a plurality of progenitor cells (e.g., such as progenitor cells suspended in a liquid) may be infused through a lumen extending from a proximal end to a distal end of the cannula and exit in outlet portal at the distal end of the cannula (e.g., such as by being infused through lumen 9520 and exiting outlet port 9522 distal to balloon 8810 or 9510 as described above). According to some embodiments the progenitor cells may be bone marrow derived progenitor cells such as those produced by: (1) harvesting bone marrow, (2) selecting stem cells from bone marrow, or (3) deriving cells from bone marrow aspirates. It is also contemplated that the progenitor cells may be blood derived progenitor cells, such as those produced by: (1) collecting venous blood, (2) purifying mononuclear cells, or (3) ex-vivo culturing of mononuclear cells. It is to be appreciated that the treatment region being treated may be in the blood vessel of the same person from which the progenitor cells are derived (e.g., the progenitor cells may be reinfused into the infarct artery of the person from which the bone marrow or blood derived progenitor cells are taken).

In addition, it is contemplated that block 9660 may include infusion and a therapeutic agent having one or more of cardiomyocytes, stem cells, progenitor cell, skeletal myocytes, smooth muscle cells, and endothelial cells, and growth factors such as IGF-I, HGF, VEGF, NGF, FGF, TGF-beta, and their isoforms.

In addition, infusing at block 9660 may include infusing treatment agent or progenitor cells at a low pressure and distal to the occluding balloon such that a flow of blood through the treatment region is precluded and does not wash the treatment agent away from the treatment region. For example, the occluding balloon may completely preclude blood flow through the treatment region, such as treatment region 996. Thus, an occluding balloon or device may block off blood flow from treatment region 996 to increase treatment agent residence time in treatment region 996, such as a capillary bed. Without such blood flow, the treatment agent residence time in the blood vessel allows for more treatment agent (e.g., such as stem cells) to adhere to the vessel wall and eventually migrate into target muscle, such as heart muscle. Also, infusing may include infusing a volume of between one milliliter and 10 milliliters of treatment agent or progenitor cells, such as by infusing a volume of between three milliliters and four milliliters of a progenitor cell suspension (e.g., such as 3.3 milliliters of progenitor cell suspension).

At block 9670 it is determined whether the first period of time has expired. According to some embodiments the first period of time may be a period of time between two minutes and five minutes, such as a period of three minutes in time. If at block 9670 the first period of time has not expired, more time is allowed to elapse, and additional treatment agent or progenitor cells may be infused. Also, if the first period of time has not expired, other processes or measurements may be performed, such as those described herein or desired during an infusion treatment. Specifically, measurement or procedures such as those described above with respect to accessory lumen 9530 may be performed during the first period of time.

In accordance with embodiments, one way to balance the benefit of having a long treatment agent or progenitor cell residence time at the treatment region with the risk of inducing ischemic damage to the target muscle during occlusion of the blood vessel is to provide for blood perfusion around or through the occluding device so that blood can still pass through the treatment region in a controlled amount or during a controlled time period during treatment of the treatment region.

For instance, If at block 9670 the first period of time has expired, the process continues to block 9675. At block 9675, liquid (e.g., such as blood or a treatment agent) is allowed to perfuse from a location in the blood vessel proximal to the balloon to the treatment region (or vice versa depending on the direction of blood flow). In other words, at block 9675, a liquid, such as blood or treatment agent, may be allowed to perfuse between a location in the blood vessel proximal to the balloon and the treatment region, such as by allowing the liquid to flow from a location proximal to the balloon to a location distal to the balloon, or vice versa. For example, the balloon may be deflated sufficiently to allow the blood vessel (such as blood vessel 990 at treatment region 996) to be open to a flow of fluid, such as blood. Thus, the balloon may be deflated (e.g., such with respect to balloon 8810 or 9510) to allow a reflow of blood through the treatment region, such as to minimize extensive ischemia. According to some embodiments, at block 9675 the balloon may be configured to be and may be sufficiently deflated to be subsequently reinflated after a second period of time. Moreover, at block 9675 the balloon may be deflated sufficiently to be retracted from the blood vessel, such as by being withdrawn by the cannula.

Alternatively or in addition to allowing perfusion at block 9675 by deflating the balloon, a liquid (e.g., such as blood or treatment agent) may be allowed to perfuse between a location in the blood vessel proximal to the balloon and the treatment region via a lumen extending through the cannula. For example, the cannula may include a lumen extending from a location proximal to the balloon to a location distal to the balloon and a proximal hole through the exterior surface of the cannula and to the lumen at a location proximal to the balloon as well as a hole through the exterior surface of the cannula and to the lumen at a location distal to the balloon. Thus, a lumen for perfusing liquid such as is described herein with respect to apparatus 9910, 9920, 9930, or 9940 may be used at block 9675.

Likewise, instead of or in addition to deflating the balloon, perfusion of a liquid (e.g., such as blood or treatment agent) at block 9675 may including retracting or pulling back a guidewire disposed through a guidewire lumen extending past at least one hole in the exterior of the cannula and to the guidewire lumen proximal to the balloon to allow liquid to perfuse between a location in the blood vessel proximal to the balloon and to a location distal to the balloon via a guidewire lumen opening in the distal end of the cannula. Specifically, for example, the cannula may include a guidewire lumen extending from a proximal end to a distal end of the cannula and exiting in opening in the cannula distal to the balloon, so that a distal end of a guidewire disposed through the guidewire lumen can be retracted to a location proximal to at least one hole through the exterior of the cannula and to the guidewire lumen, where the at least one hole is located proximal to the balloon. Furthermore, disembodiment also allows the distal end of the guidewire to be advanced to a location distal to the at least one hole through the exterior of the cannula to prohibit or reduce liquid perfusion between a location in the blood vessel proximal to the balloon and the treatment region, such as by blocking perfusion of the liquid between the blood vessel and the lumen. Specifically, the embodiment described above may be performed by an apparatus such as apparatus 9600 as described herein.

The ability to retract the distal end of the guidewire to allow perfusion and advance the distal end of the guidewire to reduce or prohibit perfusion is important since such an embodiment may provide a simple process for performing block 9675 as well as repeating blocks 9650 through 9685 one or more times. As with apparatus 9600, it is also worth noting that the plurality of holes through the cannula exterior described above can include various numbers and size and shape holes to allow the movement of the distal end of the guidewire to control an amount of liquid perfusion between a location of the blood vessel proximal to the balloon and the treatment region.

At block 9680 it is determined whether a second period of time, during which the liquid is allowed to perfuse, has expired. If at block 9680 the second period of time has not expired, further time may be allowed to elapse while the liquid is allowed to perfuse. For instance, the deflated occluding, the balloon may be further deflated, the balloon may be inflated to a diameter that does not occlude the blood vessel or other processes or measurements may be performed. For example, measurements or procedures, such as those described above with respect to accessory lumen 9530, may be performed during the second period of time. Similarly, during block 9680, perfusion may be allowed to continue as described above with respect to apparatus 9910, 9920, 9930, 9940, or 9600. According to some embodiments the second period of time may be a period of between two minutes and five minutes in time, such as a period of three minutes in time. Moreover, it is contemplated that the second period of time may be shorter than, equal to, or greater than the first period of time.

If at block 9680 the second period of time has expired, the process proceeds to block 9685. At block 9685 it is determined whether treatment is complete. For example, according to some embodiments treatment may include repetition of blocks 9650 through 9685 to infuse treatment agent or progenitor cells a number of times to the treatment region. Specifically, blocks 9650 through 9685 may be repeated 2, 3, 4, 5, 6, or more times to infuse treatment agent or progenitor cells at the treatment region. In one case, treatment region may be occluded (e.g., such as by inflating the balloon for a first period of time) (such as for three minutes) during which treatment agent or progenitor cells are infused to the treatment region, then blood or treatment agent may be allowed to perfuse into the treatment region (e.g., such as by deflating the balloon for a second period of time) (such as for three minutes). Thus, this occlusion/treatment and perfusion may be performed a total of three repetitions to infuse a total of 10 milliliters of progenitor cell suspension via three infusions of 3.3 milliliters each.

If at block 9685 treatment is completed the process may continue to block 9690. At block 9690 the occluding balloon may be deflated and the cannula may be retracted from the blood vessel, such as by withdrawing the deflated balloon using the cannula.

Note that it is contemplated that the process described above with respect to FIG. 82 may be controlled manually, automatically, or by a machine, such as by system controller 3080, or according to a treatment process for infusion of a treatment agent into an artery or vein of a patient using devices, apparatus, methods, or processes described herein (e.g., such as according to the process described with respect to FIG. 3, 19, 54, 55 or 63).

Now, specifically addressing three types of apparatus for allowing blood or treatment agent to perfuse between a location in the blood vessel proximal and distal to an occluding balloon, such as is described above with respect to block 9675. First, as mentioned at block 9675, the occluding balloon may be deflated sufficiently to allow the blood vessel (such as blood vessel 990 at treatment region 996) to be open to a flow of fluid, such as blood.

Second or in addition to allowing perfusion at block 9675 by deflating the balloon, blood or treatment agent may be allowed to perfuse between a location in the blood vessel proximal and distal to an occluding balloon by retracting or pulling back a guidewire disposed through a guidewire lumen extending past at least one hole in the exterior of the cannula proximal to the balloon to allow perfusion to a location distal to the balloon via a guidewire lumen opening in the distal end of the cannula.

Figure 83:
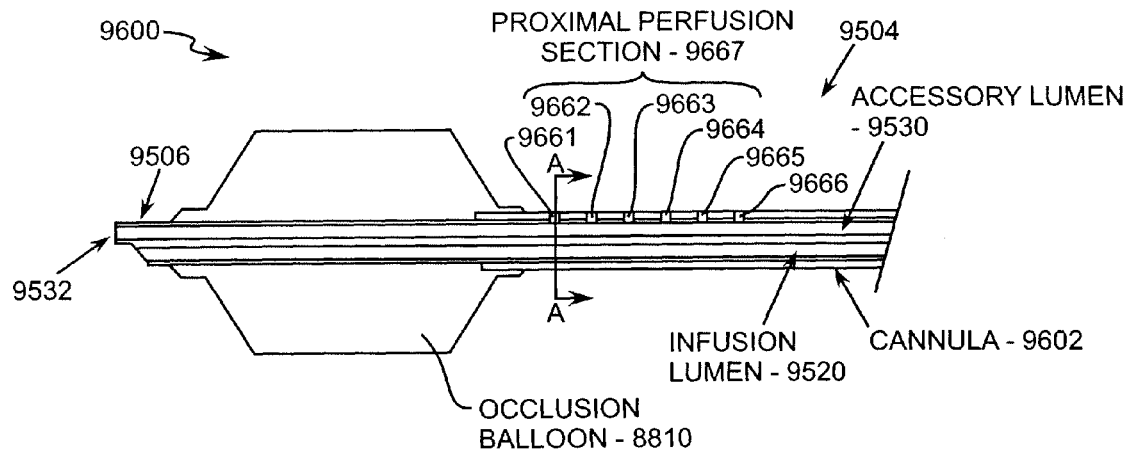
FIG. 83 is a cross-sectional view of an occlusion balloon attached to a cannula having holes through an exterior surface of the cannula proximate to the balloon, where the holes extend to a lumen in the cannula having an exit distal to the balloon.

Thus, according to some embodiments, liquid, blood, or treatment agent perfusion between the treatment region and a location proximal to the balloon, or from a location on one side of an occlusion device to a location on the other side of an occlusion device as described herein, may be achieved by including a liquid perfusion capability through the cannula. For example, perfusion from one side of an occluded site to the other side of an occluded site may be a constant flow, a controlled amount of flow, or a flow that may be adjusted to start or stop the flow or provide different flow rates as controlled by an operator. For instance, FIG. 83 is a cross-sectional view of an occlusion balloon attached to a cannula having holes through an exterior surface of the cannula proximate to the balloon, where the holes extend to a lumen in the cannula having an exit distal to the balloon. Thus, a cannula described with respect to FIG. 83 may be referred to as a blood perfusion catheter or a blood perfusion cannula. FIG. 83 shows apparatus 9600 that may be an apparatus similar to apparatus 9500 but including proximal perfusion of section 9667 having at least one hole through the exterior surface of cannula 9602 and to accessory lumen 9530 at a location proximal to balloon 8810 to allow perfusion of a liquid between a location in a blood vessel proximal to balloon 8810 and to a treatment region, such as a region of the blood vessel distal to balloon 8810. Specifically, FIG. 83 shows holes 9661, 9662, 9663, 9664, 9665, and 9666 at proximal perfusion section 9667 extending through cannula 9602 and to accessory lumen 9530.

Although FIG. 83 shows 6 holes through cannula 9602, it is contemplated that various numbers, sizes, and shapes of holes may be used at proximal perfusion section 9667. For example, between 4 and 8 holes may be used according to various embodiments. Moreover, any of the holes, a combination of any of the holes, or a combination of all of the holes may have a dimension to allow perfusion of blood or treatment agent between a location of the blood vessel proximal to balloon 8810 and accessory lumen 9530 or a location of a blood vessel distal to balloon 8810. For example, the holes may allow perfusion of blood at a flow rate between full flow sufficient to prevent an ischemic event in the blood vessel of a patient when all of the holes are open, and a flow of a fraction of full flow to reduce or minimize wash off or washing away of a treatment agent in an occluded area of the blood vessel. Specifically, the holes at proximal perfusion section 9667 and lumen 9530 may have a dimension to allow for a flow of liquid of between 10 cubic centimeters per minute and 80 cubic centimeters per minute of flow of liquid at balloon 8810 at a pressure of less than 240 mmHg at perfusion section 9667 (e.g., such as a high systolic blood pressure for a patient).

Figure 84:
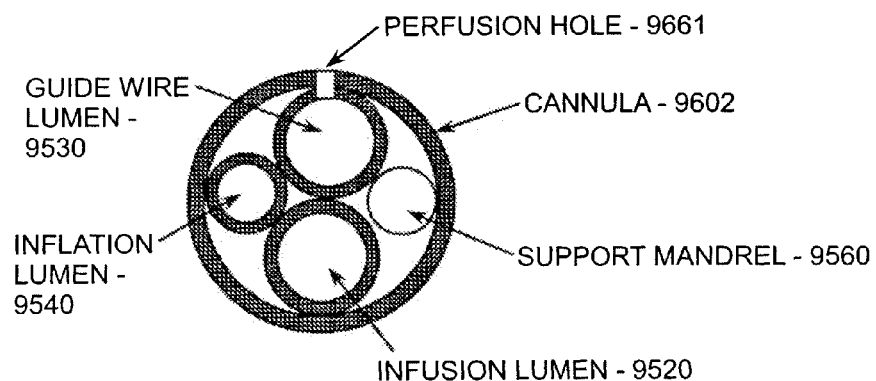
FIG. 84 is a cross-sectional view of FIG. 83 from perspective "A".

FIG. 84 is a cross-sectional view of FIG. 83 from perspective "A". FIG. 84 shows cannula 9602 having support mandrel 9560, infusion lumen 9520, inflation lumen 9540, and guidewire lumen 9530. Perfusion hole 9561 is shown through the exterior surface of cannula 9602 and to lumen 9530. Perfusion hole 9661 may represent any of the perfusion holes as described above with respect to holes at proximal perfusion section 9667. Also, note that according to some embodiments, lumen 9530 as described with respect to FIGS. 83 and 84 may have its own sleeving, cannula, or surrounding material or composite tube such with respect to lumen 9520 at FIGS. 69A-F. Thus, lumen 9530 is shown in FIG. 84 as being disposed within or including a tube of material surrounding that lumen (e.g., wherein that, too, may be formed such for forming a lumen or tube).

Holes, such as holes 9661 through 9666, at proximal perfusion section 9667 may be formed by inserting a reinforcing mandrel within lumen 9530 and drilling the holes such as by a mechanical drill using a drill bit or a laser drilling technology to produce the holes as described herein.

It is also contemplated that cannula 9602 may have one or more distal holes through the exterior surface of the cannula and to lumen 9530 at a location distal to balloon 8810 to allow or increase perfusion of liquid between a location in the blood vessel proximal to balloon 8810 and treatment region or a location in the blood vessel distal to balloon 8810. More particularly, blood flowing through lumen 9530 toward distal end 9506 may exit lumen 9530 through holes in cannula 9602 distal to balloon 8810 in addition to opening 9532. It is to be appreciated that distal holes through the surface of cannula 9602 distal to balloon 8810 may have a number, shape, and size or be formed as described above with respect to holes at proximal perfusion section 9667.

Figure 85:
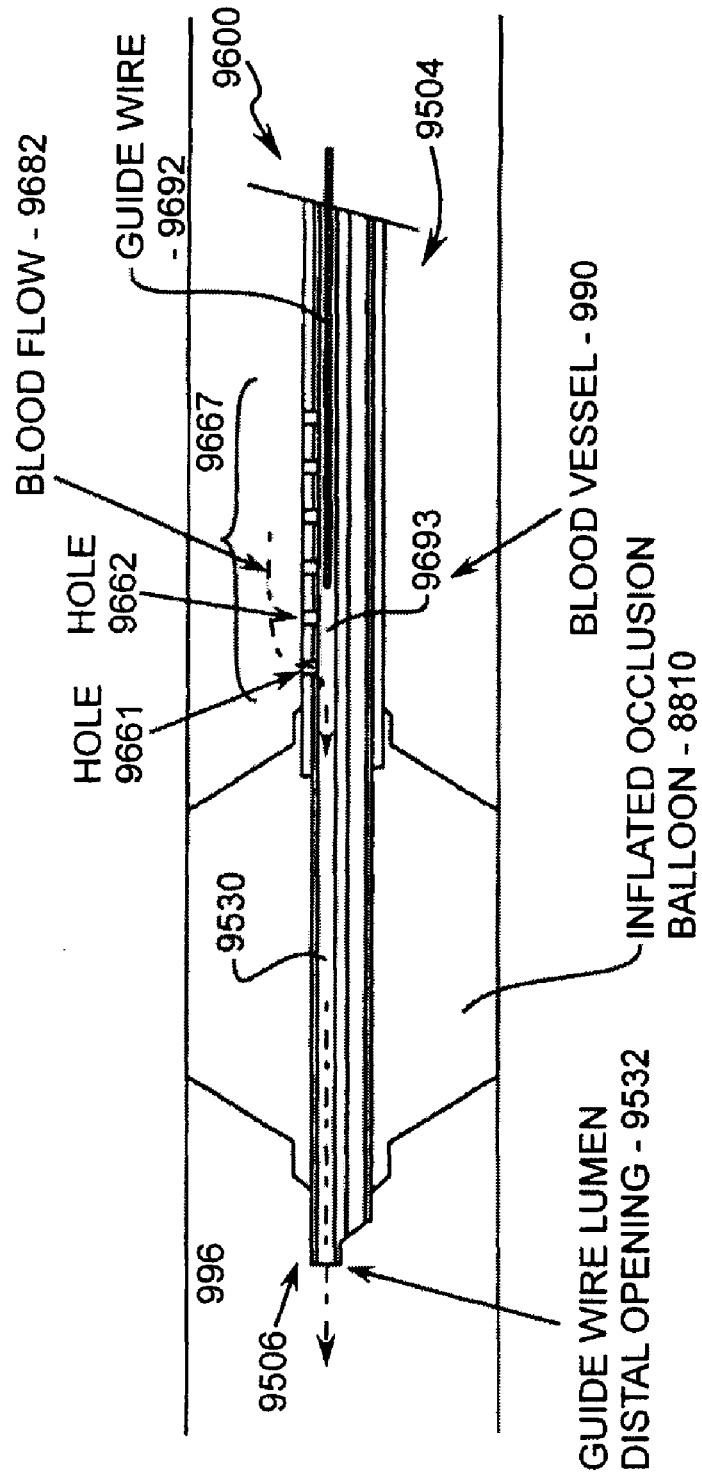
FIG. 85 is a cross-sectional view of the apparatus shown in FIG. 83 advanced to a treatment region of a blood vessel.

According to some embodiments, accessory lumen 9530 may be adapted to have a guidewire disposed therethrough to guide cannula 9602 to a treatment region, such with respect to lumen 9530 and a guidewire disposed therethrough. Additionally, lumen 9530 may be adapted or have a dimension such that a distal end of a guidewire disposed therethrough can be extended past to a location distal to, to a location along, or to a location proximal to proximal perfusion section 9667. Additionally, lumen 9530 may have an inner diameter and a guidewire disposed therein, may have an outer diameter sufficient that the guidewire or a distal end thereof occludes liquid from flowing through lumen 9530 or from perfusion between the holes at proximal perfusion section 9667 and lumen 9530. Such a relationship between the guidewire and lumen allows the guidewire to be slid past one or more of the holes towards distal end 9506 to control or stop the perfusion of liquid from an area of a blood vessel proximal to balloon 8810 and to a treatment region distal to balloon 8810. For example, FIG. 85 is a cross-sectional view of the apparatus shown in FIG. 83 advanced to a treatment region of a blood vessel. Thus, FIG. 85 shows apparatus 9600 advanced to a treatment region 996 of blood vessel 990, and having balloon 8810 inflated to occlude a flow of blood from flowing between a location proximal to balloon 8810 to treatment region 996.

Thus, apparatus 9600 and the process described with respect to FIG. 82 may provide several benefits. For example, it may provide adequate blood supply during self or treatment agent infusion so that a patient will not enter in ischemic condition by supplying adequate perfusion or flow of blood, such as a flow of approximately four cc/minute.

Thus, guidewire 9692 may have a dimension to be slidably adjustable to extend or retract distal end 9693 to a location past none or any of holes at proximal perfusion section 9667, such as to adjust an amount of liquid to perfuse between the location in the blood vessel proximal to balloon 8810 and lumen 9530. Specifically, FIG. 85 shows distal end 9693 extended distal to hole 9662 but proximal to hole 9661. Thus, blood flow 9682 may perfuse through hole 9661 into lumen 9530, out distal opening 9532 and to treatment region 996. However, liquid is occluded or prohibited or reduced from flowing through or perfusing between hole 9662 and lumen 9530 (fluid is similarly prohibited or reduced from perfusing through any of the other holes shown in proximal perfusion section 9667, other than hole 9661, and lumen 9530).

It is worth noting that by varying the size or shape of the holes in proximal perfusion section 9667, such as by increasing the radial size of the holes from most distal hole 9661 to a hole most proximal to proximal end 9504, it is possible to control the perfusion flow. Thus, larger holes towards proximal end 9504 and smaller holes towards distal end 9506 allow distal end 9693 of the guidewire to be slid to decrease the perfusion flow from full flow to a fraction of full flow such as a fraction between $1/10$ and $1/100$ of full flow (e.g., a fraction that may be dictated by the size of hole 9661). Note that although holes in proximal perfusion section 9667 are shown oriented longitudinally with respect to an axis of cannula 9602, it is contemplated that the holes may be oriented otherwise as long as they extend with a sufficient dimension to the lumen to allow for perfusion of liquid.

Another application for this apparatus or process is to provide intermittent blood flow between treatment agent infusions without deflating an occlusion balloon, such as balloon 8810. Thus, instead of deflating the balloon to allow blood perfusion or flow, the guidewire may be retracted past the holes at proximal perfusion section 9667 to allow for adequate blood perfusion or flow.

Moreover, since the apparatus and process allows for various amounts of liquid to perfuse, retraction or advancement of distal end 9693 can be adjusted in response to the status of or measurements taken with respect to a patient. For example, if a patient is in severe chest pain or needs additional blood or treatment agent flow into an occluded area of a blood vessel, guidewire 9692 can be retracted sufficiently or past proximal perfusion section 9667 to allow for a maximum blood flow, such as 40 cubic centimeters/minute. On the other hand, if the patient is only in slight discomfort, and does not require greater blood flow, a lower flow rate may be used by locating distal end 9693 to a midpoint or distal to a midpoint along proximal perfusion section 9667 (e.g., minimizing flow by placing distal end 9693 at such a location reduces treatment agent or cell wash off from a treatment region or treatment zone). Another application of the apparatus or process may be to continuously provide a perfusion flow rate that is a small fraction of the full flow rate during treatment agent or cell infusion for a prolonged occlusion. The low perfusion flow rate will have less impact on washing the treatment agent or cells away from the treatment region while providing some supply of blood to the treatment region or occluded region to allow for a longer infusion or treatment period.

Third, or in addition to allowing perfusion at block 9675 by deflating the balloon or via a perfusion lumen, blood or treatment agent may be allowed to perfuse between a location in the blood vessel proximal and distal to an occluding balloon via a separate perfusion lumen extending through the cannula the balloon is attached to and exiting a hole distal to the balloon and a hole proximal to the balloon.

Figure 86:
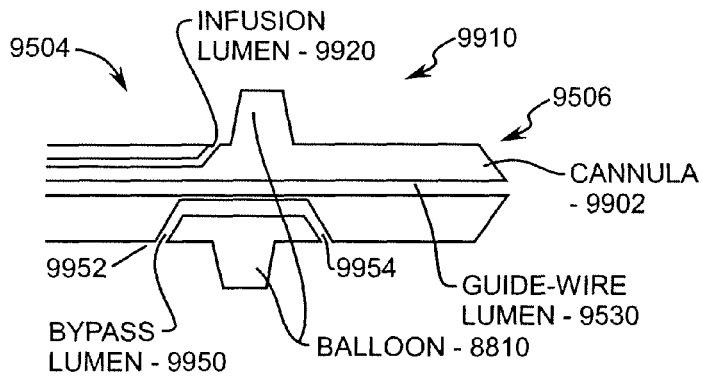
FIG. 86 is a cross-sectional view of a cannula having a balloon attached to its distal end and a bypass lumen extending from a hole distal to the balloon to a hole proximal to the balloon.

For example, according to some embodiments, a blood perfusion cannula may be used, such as a version of cannula 9502 or a similar or modified process to that described with respect to FIG. 82. For example, FIG. 86 is a cross-sectional view of a cannula having a balloon attached to its distal end and a bypass lumen extending from a hole distal to the balloon to a hole proximal to the balloon. FIG. 86 shows apparatus 9910 having cannula 9902 (e.g., such as a version of cannula 9502 described with respect to FIGS. 69A-F, and 70) with proximal end 9504 and distal end 9506, and balloon 8810 axially coupled to the exterior of cannula 9902 (e.g., such as by balloon 8810 being axially coupled similarly to as described above for FIGS. 69A-F, and 70 with respect to attachment of balloon 9510 to cannula 9502). FIG. 86 also shows guidewire lumen 9530 extending through cannula 9902 (e.g., such as by lumen 9530 extending similarly to for FIGS. 69A-F, and 70 with respect to guidewire lumen 9530 extending through cannula 9502). Next, FIG. 86 shows infusion lumen 9920 extending from proximal end 9504 to a location proximal to balloon 8810 (e.g., such as by lumen 9920 being a lumen and extending such as is described herein with respect to lumen 9520 extending through cannula 9502 for FIGS. 69A-F, and 70).

Notably, FIG. 86 shows bypass lumen 9550 extending from proximal hole 9952 proximal to balloon 8810 to distal hole 9954 distal to balloon 8810. Proximal hole 9952, lumen 9950, and distal hole 9954 may have a dimension suitable to allow for perfusion of liquid between a location in a blood vessel proximal to balloon 8810 and a location in the blood vessel distal to balloon 8810, such as a treatment region as described herein. For example, proximal hole 9952 and distal hole 9954 may be a hole such as is described herein with respect to hole 9661. Thus, proximal hole 9952 and distal hole 9954 may be oriented longitudinally with respect to an axis of cannula 9902. Also, lumen 9550, proximal hole 9952, and distal hole 9954 may have a dimension, such as a selected radius, or selected radii to control or adjust an amount of liquid to perfuse between a location distal to balloon 8810 and proximal to balloon 8810 such as to control an amount of blood or treatment agent perfusing between the locations to prevent an ischemic event in the blood vessel of a patient.

For instance, apparatus 9910 may be helpful to deliver a treatment agent such as a treatment agent described herein, including a drug, a peptide, growth factors, and other therapeutic agents (that may or may not be mixed with blood) to be delivered locally. For example, VEGF-1, an angiogenic growth factor, may be administered through infusion lumen 9920 to deliver treatment agent to a blood vessel location to mix well with blood proximal to balloon 8810, and then to flow mixed with the blood through bypass lumen 9950 at a controlled flow rate and to a region of a blood vessel distal to balloon 8810 to assist in more efficient absorption of the treatment agent by local tissues proximal to balloon 8810.

Figure 87:
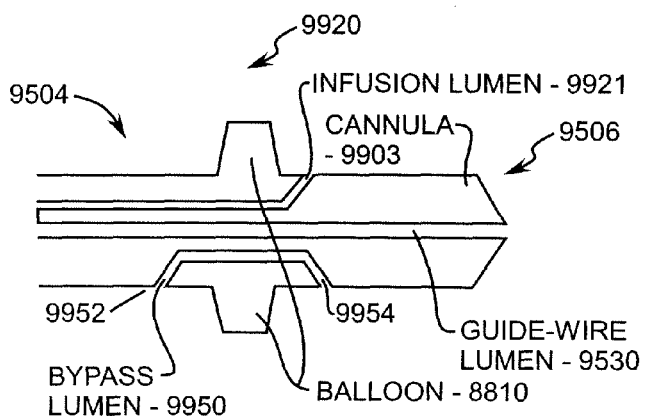
FIG. 87 shows the apparatus of FIG. 86 where the infusion lumen extends to a location distal to balloon 8810.

In another embodiment, FIG. 87 shows the apparatus of FIG. 86 where the infusion lumen extends to a location distal to balloon 8810. Specifically, FIG. 87 shows apparatus 9920 having infusion lumen 9921 extending from proximal end 9504 of cannula 9903 to an infusion exit through the exterior surface of the cannula at a location distal to balloon 8810 to deliver treatment agent to a blood vessel location distal to balloon 8810.

Thus, apparatus 9920 may be useful to deliver treatment agent such as genes, viral vectors, stem cells, and other therapeutic agents that require longer dwelling time at an infusion site to enhance delivery period. For example, to deliver autologous bone marrow mononuclear cells, apparatus 9920 may be used so that those treatment agents dwell in a blood vessel distal to balloon 8810 while that location of the blood vessel receives some blood flow as controlled by lumen 9950, proximal hole 9952, and distal hole 9954.

Figure 88:
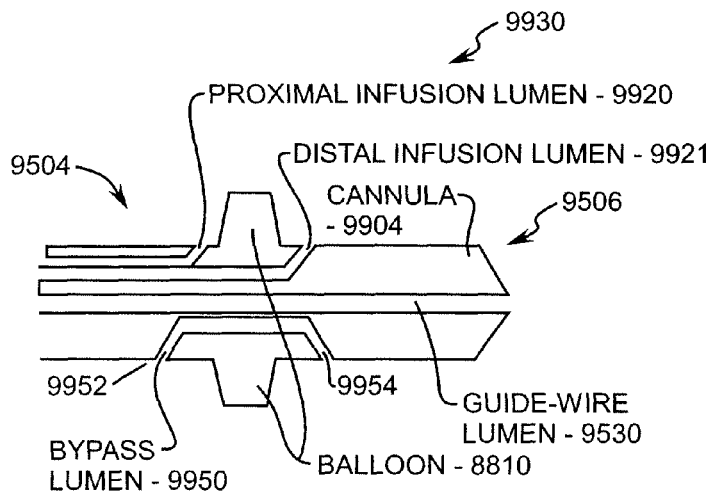
FIG. 88 is a cross-sectional view of a cannula having a balloon attached to its distal end, and infusion lumen to provide treatment agent to a location distal to the balloon, and a bypass lumen to allow for perfusion of liquid from the location distal to the balloon to the location proximal to the balloon.

Next, FIG. 88 is a cross-sectional view of a cannula having a balloon attached to its distal end, and infusion lumen to provide treatment agent to a location distal to the balloon, and a bypass lumen to allow for perfusion of liquid from the location distal to the balloon to the location proximal to the balloon. FIG. 88 shows apparatus 9930 having cannula 9904 (e.g., such as a cannula described herein with respect to cannula 9502 for FIGS. 69A-F, and 70). Cannula 9904 includes guidewire lumen 9530, infusion lumen 9920 and infusion lumen 9921. Cannula 9904 also includes bypass lumen 9950, proximal hole 9952 and distal hole 9954 to perfuse blood from a proximal location to a distal location of a blood vessel occluded by balloon 8810.

Thus, apparatus 9930 may be useful for a combination of therapies with multiple treatment or therapeutic agents. For example, in order to infuse a transfection agent before delivery liposome encapsulated therapeutic DNA, the transfection agent may be infused through proximal infusion lumen 9920 to allow for sufficient mixing and distribution of the agent with blood, and then liposomes may be infused through distal infusion lumen 9921 to treat a region of a blood vessel proximal to balloon 8810 with transfection agents for a sufficient period of time, and a region of the blood vessel distal to lumen 8810 with liposomes for a sufficient period of time. It is to be appreciated that a pressure sensing port may be added to cannula 9902, 9903, or 9904 to monitor or control the re-perfusion rate via the cannula.

Figure 89:
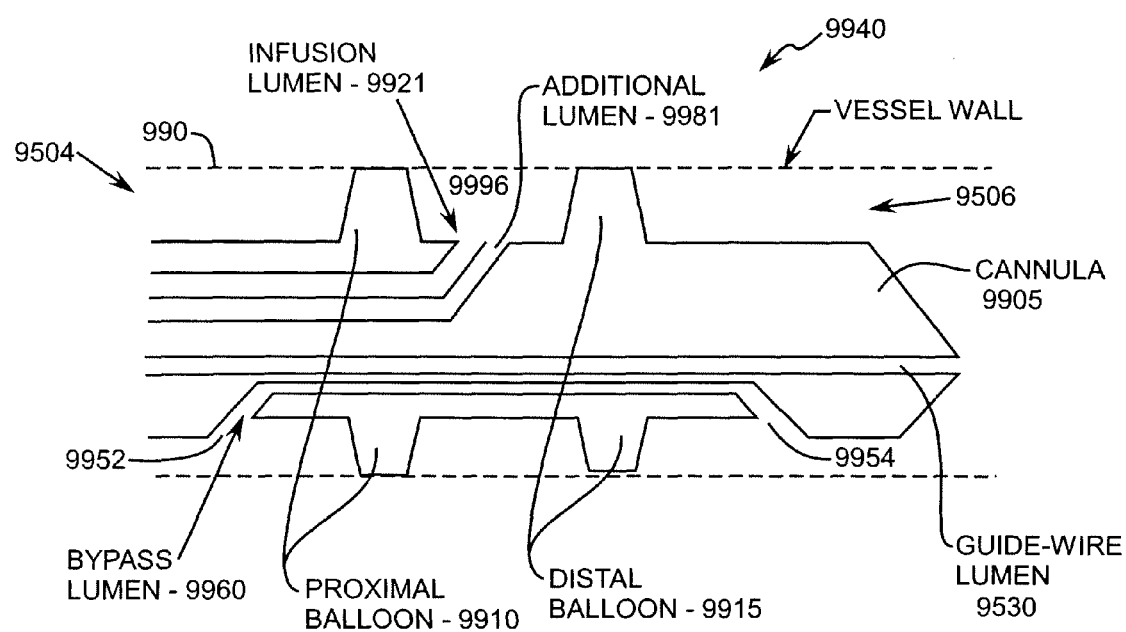
FIG. 89 is a cross-sectional view of a cannula having two balloons attached to its distal end, and infusion lumen exiting the cannula between the balloons, and a bypass lumen to allow perfusion between a location proximal to both balloons and a location distal to both balloons.

FIG. 89 is a cross-sectional view of a cannula having two balloons attached to its distal end, and infusion lumen exiting the cannula between the balloons, and a bypass lumen to allow perfusion between a location proximal to both balloons and a location distal to both balloons. FIG. 89 shows apparatus 9940 having cannula 9905 with proximal end 9504 and distal end 9506, proximal balloon 9910, and distal balloon 9915 occluding treatment region 9996 from a location of blood vessel 990 proximal to proximal balloon 9910 and a location of blood vessel 990 distal to distal balloon 9915. For example, proximal balloon 9910 and distal balloon 9915 may be a balloon such with respect to balloon 8810 to have a property such that when insulated to a selected inflation volume the balloons expand to an outer diameter sufficient to occlude blood vessel 990 to occlude treatment region 9996. Treatment region 9996 may be a treatment region with respect to treatment region 996.

FIG. 89 also shows infusion lumen 9921 and additional lumen 9981 extending from proximal end 9504 of cannula to exists through the exterior surface of cannula 9905 at locations between proximal balloon 9910 and distal balloon 9915. Infusion lumen 9921 may be an infusion lumen such as described with respect to infusion lumen 9920 or 9921 of FIGS. 86 and 87. Additional lumen 9981 may be a lumen similar to infusion lumen 9921 or may be a lumen to provide pressure sensing at treatment region 9996, such as is described herein. Note that treatment region 9996 may be described an inter-balloon occlusion infusion space.

Thus, apparatus 9940 creates an inter-balloon occlusion-infusion space to provide a more specific local delivery of treatment agent because treatment agents infused to treatment region 9996 are confined between proximal balloon 9910 and 9915 and will not be washed away by blood circulation.

In addition, FIG. 89 shows bypass lumen 9960 extending from proximal hole 9952 to distal hole 9954. Bypass lumen 9960 may function similarly to bypass lumen 9950 as described above with respect to FIG. 86. For example, bypass lumen 9960, proximal hole 9952, and distal hole 9954 may allow for perfusion of blood or treatment agent from a location proximal to balloon 9910 and balloon 9915 to a location distal to balloon 9910 and balloon 9915.

Specifically, apparatus 9940 allows perfusion of blood from one side of the balloons to the other side of the balloons at all times while treatment agent may be administered to treatment region 9996, such as to allow uninterrupted cardiac circulation through blood vessel 990. Moreover, apparatus 9940 may create a static environment between proximal balloon 9910 and distal balloon 9915 sufficient to reduce shear stress caused by circulation and to assist treatment agent attachment to the wall of blood vessel 990. Likewise, the wall tension to the walls of blood vessel 990, such as at treatment region 9996 created by both balloons may cause the wall to be more permeable to therapeutic agents.

It is also contemplated that cannula 9905 may include infusion lumen or pressure sensing lumen extending from proximal end 9504 of cannula 9905 to exit openings through the outer surface of cannula 9905 at locations proximal or distal to proximal balloon 9910 and distal balloon 9915. Note that in such a case, the wall tension created by both of the balloons may also make the wall of blood vessel 9900 proximal and distal to the balloons more permeable to therapeutic agents infused distal and proximal to the balloons.

Thus, it is considered that balloon 8810, other occlusion balloons described herein, other occlusion devices described herein, cannula or catheters described herein may be used to occlude a location or infuse treatment agent to a treatment region or a location of a blood vessel, such as an artery or a vein of a human being, such as those in the human heart.

Note that all embodiments of devices, catheter, balloon, cannula, lumen, filter devices, perfusion devices, apparatus, methods, or processes described herein are contemplated to include treatment of one or more human or animal blood vessels (e.g., including veins or arteries), intra-coronary veins, and intra-coronary arteries, such as by infusion of a therapeutic treatment agent including by retrograde infusion, intra-venous retrograde infusion, multiple catheter infusion, infusion involving multiple occlusion devices, multiple treatment agent infusion, and any combinations thereof.

Hence, such treatment may be used to treat or repair ischemic and recently infarcted (dead) tissue, such as that resulting from acute myocardial infarction (AMI) or heart disease. For example such treatment may provide intracoronary infusion of progenitor cells into an infarct artery within days after AMI to allow the treatment agent to access capillaries and transmigrate into adjacent infarct artery tissues.

It is also contemplated that both, intra-coronary veins and arteries could be treated or involved in treating a treatment region or treatment zone. In one case, intra-coronary veins and arteries are treated by retrograde insertion of a first catheter to perform multiple occlusion of intra-coronary veins to occlude around a treatment region, percutaneous insertion of a second catheter to perform occlusion of one or more coronary arteries occlude around the treatment region, and infusion of a treatment agent from the second catheter to treat the treatment region with respect to a multi-occlusion device or embodiment. It can be appreciated that this process may allow the treatment agent to access capillaries between the occlusions of the coronary veins and the coronary arteries.

In the preceding detailed description, reference to specific embodiments were described. It will, however, be evident that various modifications and changes may be made thereto without departing from the broader spirit and scope of the appended claims. The specification and drawings are, accordingly, to be regarded in an illustrative rather than a restrictive sense.

What is claimed is:

1. A method comprising:
   winding a plurality of layers of ePTFE onto a large mandrel;
   bonding a seam between two of a plurality of second ePTFE windings;
   fusing together the layers of ePTFE;
   heating the layers of ePTFE at a temperature of approximately 380 degrees celsius for a duration of between 20 minutes and 30 minutes;
   stretching the fused layers of ePTFE onto a small mandrel, wherein stretching comprises:
   putting the small mandrel within an inner diameter of fused ePTFE layers;
   stretching apart a distal end and a proximate end of the ePTFE sufficiently to stretch the inner diameter of fused ePTFE layers onto an outer diameter of the small mandrel;
   compacting the stretched fused layers of ePTFE axially;
   one of wrapping an outer diameter of the stretched fused layers of ePTFE with a polytetrafluoroethylene, and constraining the outer diameter of the stretched fused layers of ePTFE within a steel tube before compacting, and then sufficiently compacting axially inwards a distal end and a proximate end of the stretched fused layers of ePTFE, such that during inflation of the lined ePTFE balloon, the compacted stretched fused layers of ePTFE may not expand axially
   bonding a balloon liner to the compacted stretched fused layers of ePTFE to form a lined ePTFE balloon.

2. The method of claim 1 further comprising bonding an outer diameter of a balloon to the inner diameter of the plurality of fused layers of ePTFE.

3. The method of claim 1 wherein the step of winding a plurality of layers of ePTFE onto a large mandrel includes winding two or more layers of ePTFE over each other in concentric, overlaying, intersecting, or criss-cross patterns.

4. The method of claim 1 wherein the ePTFE winding is one or more strips or ribbons of ePTFE material greater in length than in width.

5. The method of claim 1 wherein the fused layers of ePTFE are porous.

6. The method of claim 5 wherein the fused layers of ePTFE do not stretch.

7. The method of claim 1 wherein the fused layers of ePTFE do not stretch.

8. The method of claim 7 wherein the fused layers of ePTFE are constructed such that the fused layer of ePTFE expand and contract radially without exhibiting substantial expansion or contraction axially.

9. The method of claim 8 wherein without exhibiting substantial expansion or contraction axially is defined as expanding or contracting axially in length by a distance of less than 5 percent of the outer diameter of the layers.

* * * * *